United States Patent [19]
Elliott et al.

[11] Patent Number: 5,750,510
[45] Date of Patent: May 12, 1998

[54] 3-DESCLADINOSE-2,3-ANHYDROERYTHROMYCIN DERIVATIVES

[75] Inventors: Richard L. Elliott, Grayslake; Yat Sun Or, Libertyville, both of Ill.; Daniel T. Chu, Santa Clara, Calif.; George W. Griesgraber; Jacob J. Plattner, both of Libertyville, Ill.; Daisy Pireh, Lincolnshire, Ill.

[73] Assignee: Abbott Laboratories, Abbott Park, Ill.

[21] Appl. No.: 832,741

[22] Filed: Apr. 4, 1997

[51] Int. Cl.$^6$ .................... A01N 43/04; C07H 17/08
[52] U.S. Cl. .................... 514/29; 536/7.1; 536/18.6
[58] Field of Search ................ 514/29; 536/7.1, 536/18.6

[56] References Cited

FOREIGN PATENT DOCUMENTS

| | | |
|---|---|---|
| 0487411 A | 5/1992 | European Pat. Off. . |
| 0559896 | 9/1993 | European Pat. Off. . |
| 0638585 | 2/1995 | European Pat. Off. . |
| 0676409 A | 10/1995 | European Pat. Off. . |

OTHER PUBLICATIONS

Journal of Antibiotics, vol. 43, No. 11 (1990), pp. 1508–1511, H. Susuki et al., "Biosynthesis of Mycinamicins by a Blocked Mutant of Micromonospora Griseorubida".
Journal of the Chemical Society Perkin Trans. I, No. 6 (1987), pp. 1189–1209, A.G. Fishman et al "Novel Semisynthetic Oxa and Alkyl Macrolike Antibacterials and Related Derivatives".
Chemical Abstract, vol. 120 (1994) 218423h.
Chemical Abstract, vol. 120 (1994) 77599f.
Chemical Abstract, vol. 122 (1995) 240349b.
Chemical Abstract, vol. 117 (1992) 251713p.

*Primary Examiner*—Gary L. Kunz
*Attorney, Agent, or Firm*—Mona Anand

[57] ABSTRACT

Novel 3-descladinose-2,3-anhydroerythromycin compounds and pharmaceutically acceptable salts and esters thereof having antibacterial activity.

44 Claims, No Drawings

3-DESCLADINOSE-2,3-ANHYDROERYTHROMYCIN DERIVATIVES

TECHNICAL FIELD

The present invention relates to novel semisynthetic macrolides having antibacterial activity and useful in the treatment and prevention of bacterial infections. More particularly, the invention relates to 3-descladinose-2,3-anhydroerythromycin derivatives, compositions containing such compounds and methods for using the same, as well as processes for making such compounds.

BACKGROUND OF THE INVENTION

Erythromycins A through D, represented by formula (E):

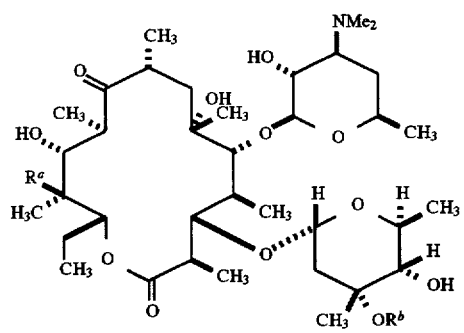

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Although Agouridas, et al. (U.S. Pat. No. 5,444,051, issued Aug. 22, 1995) have disclosed a 9-O-((2-methoxyethoxy)methyl)oxime of 2-deoxy-2,3-anhydro-3-O-des(2,6-dideoxy- 3-C-methyl-3-O-methyl-α-L-ribo-hexopyranosyl)-6-O-methyl-erythromycin, no utility nor method of preparation was disclosed.

We have, however, discovered novel 3-descladinose-2,3-anhydroerythromycin derivatives that possess significant activity against selected microorganisms.

Likewise, various C3-modified erythromycin compounds are known, but none possess the C2–C3 modifications of the present invention (see, for example, Agouridas, et al., European application EP 676409, published Oct. 11, 1995; Kashimura, et al., European application EP 559896, published Sep. 15, 1993; and Asaka, et al., PCT application WO 93/21200, published Oct. 28, 1993).

SUMMARY OF THE INVENTION

The present invention provides a novel class of 3-descladinose-2,3-anhydroerythromycin compounds which possess antibacterial activity.

In one aspect of the present invention are disclosed novel 3-descladinose-2,3-anhydroerythromycin compounds selected from the group consisting of:

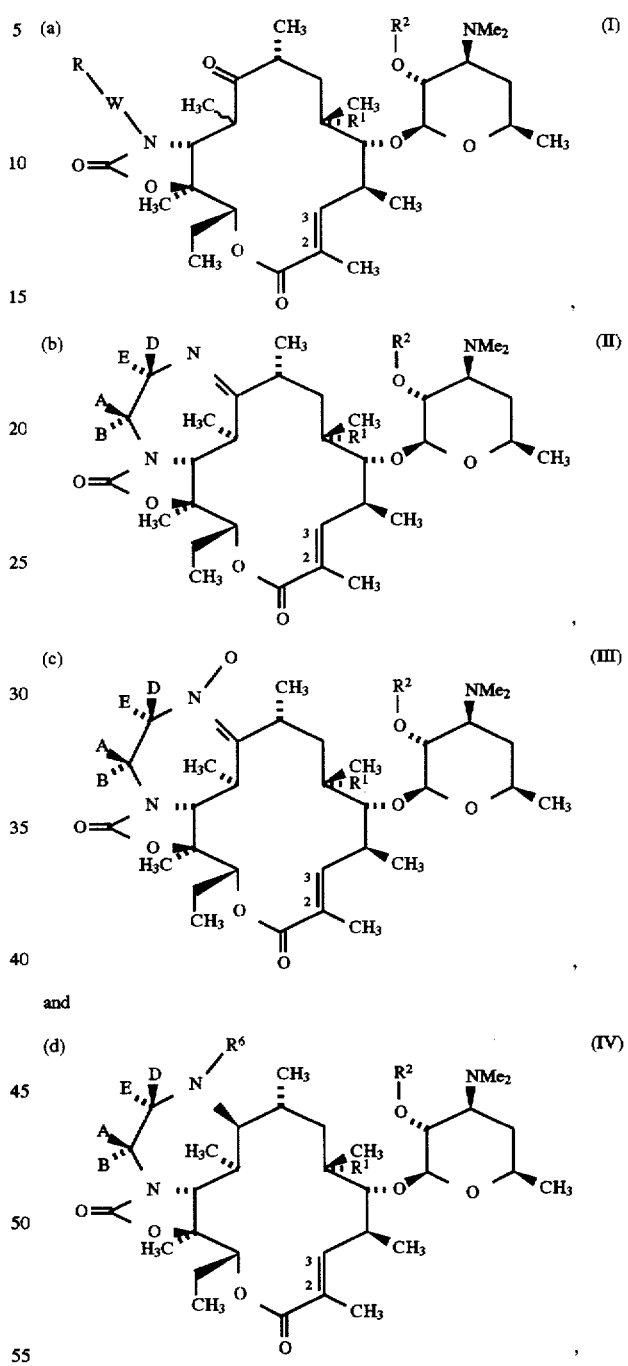

or pharmaceutically acceptable salts and esters thereof.
In formulas (I)–(IV) above,
$R^1$ is selected from the group consisting of:
(a) hydrogen;
(b) hydroxy;
(c) O—C$_1$-C$_{12}$-alkyl;
(d) O—CO—C$_1$-C$_6$-alkyl;
(e) O—CO—NH$_2$;
(f) O—CO—NH—CO—C$_1$-C$_2$-alkyl; and
(g) O—CO—NH—SO$_2$—C$_1$-C$_{12}$-alkyl;
$R^2$ is hydrogen or a hydroxy protecting group;

$R^6$ is hydrogen or $C_1-C_6$-alkyl;

R is selected from the group consisting of:

(a) hydrogen;

(b) $C_1-C_6$-alkyl optionally substituted with one or more substituents selected from the group consisting of:
  (i) aryl;
  (ii) substituted-aryl;
  (iii) heteroaryl;
  (iv) substituted-heteroaryl;
  (v) hydroxy;
  (vi) $C_1-C_6$-alkoxy;
  (vii) $NR^3R^4$, where $R^3$ and $R^4$ are independently selected from hydrogen and $C_1-C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1-C_6$-alkyl-)—, —N(aryl)—, —N(aryl-$C_1-C_6$-alkyl-)—, —N(substituted-aryl-$C_1-C_6$-alkyl-)—, —N(heteroaryl)—, —N(heteroaryl-$C_1-C_6$-alkyl-)—, —N(substituted-heteroaryl-$C_1-C_6$-alkyl-)—, —S— or —S(O)$_n$—, wherein n is 1 or 2;
  (viii) —CH$_2$—M—R$^5$, wherein M is selected from the group consisting of:
    (aa) —C(O)—NH—;
    (bb) —NH—C(O)—;
    (cc) —NH—
    (dd) —N=;
    (ee) —N(CH$_3$)—
    (ff) —O—
    (gg) —S(O)$_n$—, wherein n is 0, 1 or 2;
    (hh) —CO—O—
    (ii) —O—CO—
    (jj) —CO—; and
  $R^5$ is selected from the group consisting of:
    (aaa) $C_1-C_6$-alkyl, optionally substituted with a substituent selected from the group consisting of:
      (i) aryl;
      (ii) substituted-aryl;
      (iii) heteroaryl; and
      (iv) substituted-heteroaryl;
    (bbb) aryl;
    (ccc) substituted-aryl;
    (ddd) heteroaryl;
    (eee) substituted-heteroaryl; and
    (fff) heterocycloalkyl; and (c) $C_3-C_7$-cycloalkyl;

(d) aryl;

(e) substituted-aryl;

(f) heteroaryl;

(g) substituted-heteroaryl;

W is absent or selected from the group consisting of —O—, —NH—CO—, —N=CH—, —NH— and —N($C_1-C_6$-alkyl)—;

A, B, D and E are independently selected from the group consisting of:

(a) hydrogen;

(b) $C_1-C_6$-alkyl, optionally substituted with one or more substituents selected from the group consisting of:
  (i) aryl;
  (ii) substituted-aryl;
  (iii) heteroaryl;
  (iv) substituted-heteroaryl;
  (v) heterocycloalkyl;
  (vi) hydroxy;
  (vii) $C_1-C_6$-alkoxy;
  (viii) halogen consisting of Br, Cl, F or I; and
  (ix) $NR^3R^4$, where $R^3$ and $R^4$ are independently selected from hydrogen and $C_1-C_6$-alkyl, or $R^3$ and $R^4$ are taken with the nitrogen atom to which they are connected to form a 3- to 7-membered ring optionally containing a hetero function consisting of —O—, —NH—, —N($C_1-C_6$-alkyl-)—, —N(aryl-$C_1-C_6$-alkyl-)—, —N(substituted-aryl-$C_1-C_6$-alkyl-)—, —N(heteroaryl-$C_1-C_6$-alkyl-)—, —N(substituted-heteroaryl-$C_1-C_6$-alkyl-)—, —S— or —S(O)$_n$—, wherein n is 1 or 2;

(c) $C_3-C_7$-cycloalkyl;

(d) aryl;

(e) substituted-aryl;

(f) heteroaryl;

(g) substituted-heteroaryl;

(h) heterocycloalkyl; and (i) a group selected from option (b) above further substituted with —M—R$^5$, wherein M and R$^5$ are as defined above;

or any one pair of substituents, consisting of AB, AD, AE, BD, BE or DE, is taken together with the atom or atoms to which they are attached to form a 3- to 7-membered ring optionally containing a hetero function consisting of:
  —O—,
  —NH—,
  —N($C_1-C_6$-alkyl-)—,
  —N(aryl-$C_1-C_6$-alkyl-)—,
  —N(substituted-aryl-$C_1-C_6$-alkyl-)—,
  —N(heteroaryl-$C_1-C_6$-alkyl-)—,
  —N(substituted-heteroaryl-$C_1-C_6$-alkyl-)—,
  —S— or —S(O)$_n$—, wherein n is 1 or 2;
  —C(O)—NH—;
  —C(O)—NR$^5$—, wherein R$^5$ is as defined above;
  —NH—C(O)—;
  —NR$^5$—C(O)—, wherein R$^5$ is as defined above; and
  —C(=NH)—NH—.

The compounds and compositions of the present invention have antibacterial activity.

In another aspect of the present invention are disclosed pharmaceutical compositions for treating bacterial infections comprising a therapeutically effective amount of a compound of the invention in combination with a pharmaceutically acceptable carrier. Suitable carriers and methods of formulation are also disclosed.

Still another aspect of this invention is a method for treating bacterial infections comprising administering to a mammal in need of such treatment a pharmaceutical composition containing a therapeutically-effective amount of a compound of the invention.

In a further aspect of the invention are provided processes for the preparation of tricyclic macrolide derivatives of Formulas (I)–(IV) above.

In another aspect of the invention are provided novel compounds (cf. compound (4) of Scheme I) having use as intermediates in the preparation of compounds of Formulas (I)–(IV) above.

In still another aspect of the invention is a process for the preparation of a novel 3-descladinose-2,3-anhydroerythromycin intermediate compound having the Formula of Compound (4) of Scheme 1; $R^1$=OMe (cf. Scheme 1 below).

DETAILED DESCRIPTION OF THE INVENTION

In one preferred embodiment of the invention are compounds having the formula (I):

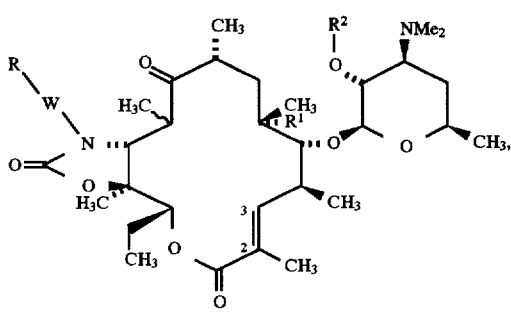

wherein $R^1$, $R^2$, R, and W are as defined above.

In a more preferred embodiment of the invention are compounds of formula (I) wherein W is absent or is an —NH— grouping.

In another preferred embodiment of the invention are compounds having the formula (II):

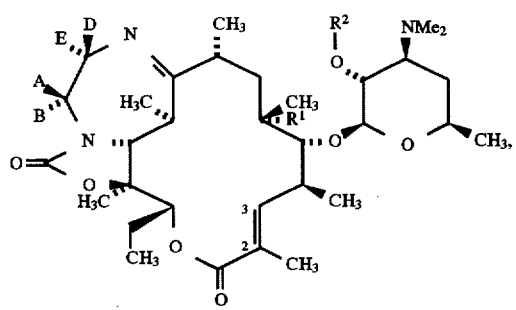

wherein $R^1$, $R^2$, A, B, D, and E are as defined above.

In a further embodiment of the invention are compounds having the formula (III):

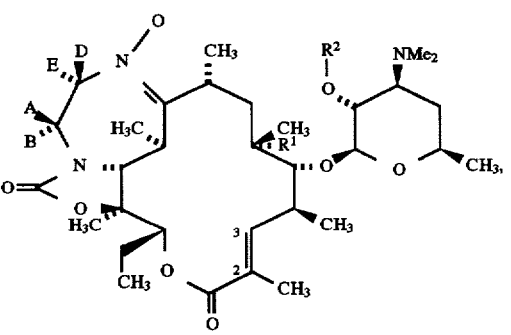

wherein $R^1$, $R^2$, A, B, D, and E are as defined above.

In still another embodiment of the invention are compounds having the formula (IV):

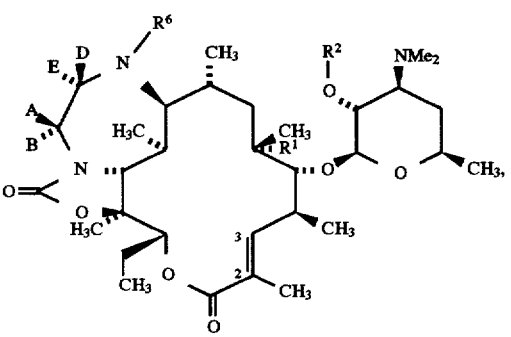

wherein $R^1$, $R^2$, $R^6$, A, B, D, and E are as defined above.
Representative compounds of the invention include:

Compound of Formula (I); $R^1$=H; $R^2$=H; W is absent; R=4-phenylbutyl;
Compound of Formula (I); $R^1$=methoxy; $R^2$=H; W is absent; R=4-phenylbutyl;
Compound of Formula (I); $R^1$=methoxy; $R^2$=H; W is absent; R=3-phenoxypropyl;
Compound of Formula (I); $R^1$=methoxy; $R^2$=H; W is absent; R=2-((phenylmethyl)amino)ethyl;
Compound of Formula (I); $R^1$=methoxy; $R^2$=H; W is absent; R=3-(N-methyl-N-phenylamino)propyl;
Compound of Formula (I); $R^1$=methoxy; $R^2$=H; W is absent; R=3-(4-chlorophenoxy)propyl;
Compound of Formula (II); $R^1$=methoxy; $R^2$=H; A=B=C=D=H;
Compound of Formula (I); $R^1$=methoxy; $R^2$=H; W is absent; R=3-(1-quinoyloxy)propyl;
Compound of Formula (I); $R^1$=methoxy; $R^2$=H; W is absent; R=4-(4-chlorophenyl)-3(Z)-butenyl;
Compound of Formula (I); $R^1$=methoxy; $R^2$=H; W is absent; R=2-phenylethyl;
Compound of Formula (I); $R^1$=methoxy; $R^2$=H; W is absent; R=2-(3,4-dichlorophenyl)ethyl;
Compound of Formula (1); $R^1$=methoxy; $R^2$=H; W is absent; R=phenylmethyl;
Compound of Formula (I); $R^1$=methoxy; $R^2$=H; W is —NH—; R=3-phenylpropyl;
Compound of Formula (I); $R^1$=methoxy; $R^2$=H; W is absent; R=3-(4-phenoxyphenyl)ethyl;
Compound of Formula (I); $R^1$=methoxy; $R^2$=H; W is absent; R=3-phenylpropyl;
Compound of Formula (I); $R^1$=methoxy; $R^2$=H; W is absent; R=2,2-diphenylethyl;
Compound of Formula (I); $R^1$=methoxy; $R^2$=H; W is absent; R=H;
Compound of Formula (IV); $R^1$=methoxy; $R^2$=H; A=B=C=D=H; R=H;
Compound of Formula (I); $R^1$=methoxy; $R^2$=H; W is —NH—; R=H; C10 methyl is epi-isomer;
Compound of Formula (I); $R^1$=methoxy; $R^2$=H; W is —NH—; R=H; C10 methyl is natural isomer;
Compound of Formula (I); $R^1$=methoxy; $R^2$=H; W is —NH—; R=(4-quinolinyl)propyl; C10 methyl is natural isomer;
Compound of Formula (I); $R^1$=methoxy; $R^2$=H; W is absent; R=3-(2-naphthyloxy)propyl;
Compound of Formula (I); $R^1$=-methoxy; $R^2$=H; W is absent; R=3-(3-pyridyloxy)propyl;
Compound of Formula (I); $R^1$=methoxy; $R^2$=H; W is absent; R=3-(2-pyridyloxy)propyl;
Compound of Formula (I); $R^1$=OH; $R^2$=H; W is absent; R=4-phenylbutyl;
Compound of Formula (I); $R^1$=$OCONH^2$; $R^2$=H; W is absent; R=4-phenylbutyl;
Compound of Formula (I); $R^1$=OCONHCO-methyl; $R^2$=H; W is absent;
R=4-phenylbutyl;
Compound of Formula (I); $R^1$=$OCONHSO^2$-methyl; $R^2$=H; W is absent; R=4-phenylbutyl;
Compound of Formula (I); $R^1$=OMe; $R^2$=H; W is absent; R=phenyl;
Compound of Formula (I); $R^1$=OMe; $R^2$=H; W is absent; R=3-pyridyl;
Compound of Formula (I); $R^1$=OMe; $R^2$=H; W is —O—; R=H;
Compound of Formula (I); $R^1$=OMe; $R^2$=H; W is —O—; R=Me;
Compound of Formula (I); $R^1$=OMe; $R^2$=H; W is —NH—CO—; R=phenyl;

Compound of Formula (II); $R^1$=OMe; $R^2$=H; A=benzyl; B,D,E=H;

Compound of Formula (II); $R^1$=OMe; $R^2$=H; A,D=3,4-pyrrolidinyl; B,E=H;

Compound of Formula (III); $R^1$=OMe; $R^2$=H; A,B,D,E=H;

Compound of Formula (IV); $R^1$=OMe; $R^2$=H; A=benzyl; B,D,E=H; R=H;

Compound of Formula (IV); $R^1$=OMe; $R^2$=H; A,D=3,4-pyrrolidinyl; B,E=H; R=H;

Compound of Formula (IV); $R^1$=OMe; $R^2$=H; A,B,D,E=H, R=$CH_2CH_2CH_2C_6H_5$;

Compound of Formula (IV); $R^1$=OMe; $R^2$=H; A,B,D,E=H, R=2,4-dinitrobenzene;

Compound of Formula (IV); $R^1$=OMe; $R^2$=H; A,B,D,E=H, R=4-quinolyl;

Compound of Formula (I); $R^1$=methoxy; $R^2$=H; W is absent; R=(4H-4-oxo-1-quinolyl)propyl;

Compound of Formula (I); $R^1$=methoxy; $R^2$=H; W is absent; R=2-(4-nitrophenyl)ethyl;

Compound of Formula (I); $R^1$=methoxy; $R^2$=H; W is absent; R=2-(4-aminophenyl)ethyl;

Compound of Formula (I); $R^1$=methoxy; $R^2$=H; W is absent; R=3-ethoxypropyl;

Compound of Formula (I); $R^1$=methoxy; $R^2$=H; W is absent; R=isopropyl;

Compound of Formula (I); $R^1$=methoxy; $R^2$=H; W is absent; R=2-(4-bromophenyl)ethyl;

Compound of Formula (I); $R^1$=methoxy; $R^2$=H; W is absent; R=2-(4-hydroxylphenyl)ethyl;

Compound of Formula (I); $R^1$=methoxy; $R^2$=H; W is absent; R=2-(4-fluorophenyl)ethyl;

Compound of Formula (I); $R^1$=methoxy; $R^2$=H; W is absent; R=2-(3-methoxyphenyl)ethyl;

Compound of Formula (1); $R^1$=methoxy; $R^2$=H; W is absent; R=3-vinyloxypropyl;

Compound of Formula (I); $R^1$=methoxy; $R^2$=H; W is absent; R=2-(3-trifluoromethyl)phenylethyl;

Compound of Formula (I); $R^1$=methoxy; $R^2$=H; W is absent; R=2-thienylethyl;

Compound of Formula (I); $R^1$=methoxy; $R^2$=H; W is absent; R=2-(3,4-dibenzyloxyphenyl)ethyl;

Compound of Formula (I); $R^1$=methoxy; $R^2$=H; W is absent; R=2-(4-methylphenyl)ethyl;

Compound of Formula (I); $R^1$=methoxy; $R^2$=H; W is absent; R=allyl;

Compound of Formula (I); $R^1$=methoxy; $R^2$=H; W is absent; R=1,3-dihydroxypropyl;

Compound of Formula (I); $R^1$=methoxy; $R^2$=H; W is absent; R=1,3-dihydroxypropyl (10-epi;

Compound of Formula (I); $R^1$=-methoxy; $R^2$=H; W is absent; R=3-hydroxypropyl;

Compound of Formula (I); $R^1$=methoxy; $R^2$=H; W is absent; R=3-hydroxypropyl (10-epi);

Compound of Formula (I); $R^1$=methoxy; $R^2$=H; W is absent; R=propyl;

Compound of Formula (I); $R^1$=methoxy; $R^2$=H; W is absent; R=isobutyl;

Compound of Formula (I); $R^1$=methoxy; $R^2$=H; W is absent; R=2-(benzoylamino)ethyl;

Compound of Formula (I); $R^1$=methoxy; $R^2$=H; W is absent; R=3-(benzoylamino)propyl;

Compound of Formula (I); $R^1$=methoxy; $R^2$=H; W is absent; R=3-(acetylamino)propyl;

Compound of Formula (I); $R^1$=methoxy; $R^2$=H; W is absent; R=H (10-epi);

Compound of Formula (I); $R^1$=methoxy; $R^2$=H; W is absent; R=3-phenylpropyl (10-epi);

Compound of Formula (I); $R^1$=methoxy; $R^2$=H; W is absent; R=3-(4-phenoxyphenyl)ethyl (10-epi);

Compound of Formula (I); $R^1$=-methoxy; $R^2$=H; W is —NH—; R=3-(4-chlorophenyl)propyl;

Compound of Formula (I); $R^1$=methoxy; $R^2$=H; W is —NH—; R=3-(3-chlorophenyl)propyl;

Compound of Formula (I); $R^1$=methoxy; $R^2$=H; W is —NH—; R=3-(2-chlorophenyl)propyl;

Compound of Formula (I); $R^1$=methoxy; $R^2$=H; W is —NH—; R=3-(2,4-dichlorophenyl)propyl;

Compound of Formula (I); $R^1$=methoxy; $R^2$=H; W is —NH—; R=3-(4-hydroxyphenyl)propyl;

Compound of Formula (I); $R^1$=methoxy; $R^2$=H; W is —NH—; R=3-(3-hydroxyphenyl)propyl;

Compound of Formula (I); $R^1$=methoxy; $R^2$=H; W is —NH—; R=3-(2-hydroxyphenyl)propyl;

Compound of Formula (1); $R^1$=methoxy; $R^2$=H; W is —NH—; R=3-(4-methoxyphenyl)propyl;

Compound of Formula (I); $R^1$=methoxy; $R^2$=H; W is —NH—; R=3-(4-nitrophenyl)propyl;

Compound of Formula (I); $R^1$=methoxy; $R^2$=H; W is —NH—; R=3-(3-nitrophenyl)propyl;

Compound of Formula (I); $R^1$=-methoxy; $R^2$=H; W is —NH—; R=3-(2-nitrophenyl)propyl;

Compound of Formula (I); $R^1$=methoxy; $R^2$=H; W is —NH—; R=3-((4-(acetylamino)phenyl)propyl;

Compound of Formula (I); $R^1$=methoxy; $R^2$=H; W is —NH—; R=trans-3-phenylprop-2-enyl;

Compound of Formula (I); $R^1$=methoxy; $R^2$=H; W is —NH—; R=2-phenylethyl;

Compound of Formula (I); $R^1$=methoxy; $R^2$=H; W is —NH—; R=phenylmethyl;

Compound of Formula (I); $R^1$=methoxy; $R^2$=H; W is —NH—; R=(3-indolyl)methyl;

Compound of Formula (I); $R^1$=methoxy; $R^2$=H; W is —NH—; R=(4-methoxyphenyl)methyl;

Compound of Formula (I); $R^1$=methoxy; $R^2$=H; W is —NH—; R=(4-acetylaminophenyl)methyl;

Compound of Formula (I); $R^1$=methoxy; $R^2$=H; W is —NH—; R=(4-chlorophenyl)methyl;

Compound of Formula (I); $R^1$=methoxy; $R^2$=H; W is —NH—; R=(4-dimethylaminophenyl)methyl;

Compound of Formula (I); $R^1$=methoxy; $R^2$=H; W is —NH—; R=trans-3-(4-nitrophenyl)prop-2-enyl;

Compound of Formula (I); $R^1$=methoxy; $R^2$=H; W is —NH—; R=(4-nitrophenyl)methyl;

Compound of Formula (I); $R^1$=methoxy; $R^2$=H; W is —NH—; R=(3,4-dihydroxyphenyl)methyl;

Compound of Formula (I); $R^1$=methoxy; $R^2$=H; W is —NH—; R=(2,5-dihydroxyphenyl)methyl;

Compound of Formula (I); $R^1$=methoxy; $R^2$=H; W is —NH—; R=(2-hydroxy-5-nitrophenyl)methyl;

Compound of Formula (I); $R^1$=methoxy; $R^2$=H; W is —NH—; R=(4-hydroxymethylphenyl)methyl;

Compound of Formula (I); $R^1$=methoxy; $R^2$=H; W is —NH—; R=trans-3-(5-nitro-2-furanyl)prop-2-enyl;

Compound of Formula (I); $R^1$=methoxy; $R^2$=H; W is —NH—; R=(4-hydroxyphenyl)methyl;

Compound of Formula (I); $R^1$=methoxy; $R^2$=H; W is —NH—; R=(3-hydroxyphenyl)methyl;

Compound of Formula (I); $R^1$=-methoxy; $R^2$=H; W is —NH—; R=(2-hydroxyphenyl)methyl;

Compound of Formula (I); $R^1$=methoxy; $R^2$=H; W is —NH—; R=(4-trifluoromethylphenyl)methyl;

Compound of Formula (I); $R^1$=methoxy; $R^2$=H; W is —NH—; R=(4-cyanophenyl)methyl;

Compound of Formula (I); $R^1$=methoxy; $R^2$=H; W is —NH—; R=(2-pyridyl)methyl;

Compound of Formula (I); $R^1$=methoxy; $R^2$=H; W is —NH—; R=(3-pyridyl)methyl;

Compound of Formula (I); $R^1$=methoxy; $R^2$=H; W is —NH—; R=(4-pyridyl)methyl;

Compound of Formula (I); $R^1$=methoxy; $R^2$=H; W is —NH—; R=(2-hydroxy-1-naphthyl)methyl;

Compound of Formula (I); $R^1$=methoxy; $R^2$=H; W is —NH—; R=(4-dimethylamino-1-naphthyl)methyl;

Compound of Formula (I); $R^1$=methoxy; $R^2$=H; W is —NH—; R=(4-(methylthio)phenyl)methyl;

Compound of Formula (I); $R^1$=methoxy; $R^2$=H; W is —NH—; R=(4-phenoxyphenyl)methyl;

Compound of Formula (I); $R^1$=methoxy; $R^2$=H; W is —NH—; R=3-(4-fluorophenyl)propyl;

Compound of Formula (I); $R^1$=methoxy; $R^2$=H; W is —NH—; R=(trans-3-(4-nitrophenyl)prop-2-enyl;

Compound of Formula (I); $R^1$=methoxy; $R^2$=H; W is —NH—; R=(4-aminophenyl)methyl;

Compound of Formula (I); $R^1$=methoxy; $R^2$=H; W is —NH—; R=3-(4-aminophenyl)propyl;

Compound of Formula (I); $R^1$=methoxy; $R^2$=H; W is —NH—; R=3-(3-aminophenyl)propyl;

Compound of Formula (I); $R^1$=-methoxy; $R^2$=H; W is —NH—; R=3-(2-aminophenyl)propyl;

Compound of Formula (I); $R^1$=methoxy; $R^2$=H; W is —NH—; R=trans-3-(4-acetylaminophenyl)prop-2-enyl;

Compound of Formula (I); $R^1$=methoxy; $R^2$=H; W is —NH—; R=trans-3-(4-(4-nitrobenzoylamino)phenyl)prop-2-enyl;

Compound of Formula (I); $R^1$=methoxy; $R^2$=H; W is —NH—; R=3-(2-benztriazolyl)propyl;

Compound of Formula (I); $R^1$=methoxy; $R^2$=H; W is —NH—; R=3-(1-benztriazolyl)propyl;

Compound of Formula (I); $R^1$=methoxy; $R^2$=H; W is —NH—; R=3-(4-phenylimidazolyl)propyl;

Compound of Formula (I); $R^1$=methoxy; $R^2$=H; W is —NH—; R=3-(1-anhydro-1-cladinosyl)propyl;

Compound of Formula (I); $R^1$=methoxy; $R^2$=H; W is —NH—; R=3-phenylpropyl (10(-epi);

Compound of Formula (I); $R^1$=methoxy; $R^2$=H; W is —NH—; R=isopropyl;

Compound of Formula (I); $R^1$=methoxy; $R^2$=H; W is —NH—; R=1,3-diphenyl-2-propyl; and Compound of Formula (I); $R^1$=methoxy; $R^2$=H; W is —NH—; R=3-pentyl.

The present invention provides a process for the preparation of a compound having the Formula (I):

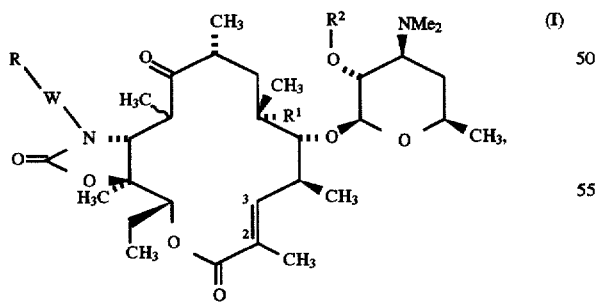

wherein
$R^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl;

$R^2$ is hydrogen or a hydroxy protecting group;

R is selected from the group consisting of:
(a) hydrogen;
(b) $C_1$–$C_6$-alkyl optionally substituted with one or more substituents selected from the group consisting of:
 (i) aryl;
 (ii) substituted-aryl;
 (iii) heteroaryl;
 (iv) substituted-heteroaryl;
 (v) hydroxy;
 (vi) $C_1$–$C_6$-alkoxy;
 (vii) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring optionally containing a hetero function consisting of —O—, —NH—, —N($C_1$–$C_6$-alkyl-)—, —N(aryl-$C_1$–$C_6$-alkyl-)—, —N(substituted-aryl-$C_1$–$C_6$-alkyl-)—, —N(heteroaryl-$C_1$–$C_6$-alkyl-)—, —N(substituted-heteroaryl-$C_1$–$C_6$-alkyl-)—, —S— or —S(O)$_n$—, wherein n is 1 or 2;
 (viii) —$CH_2$—M—$R^5$, wherein M is selected from the group consisting of:
  (aa) —C(O)—NH—;
  (bb) —NH—C(O)—;
  (cc) —NH—;
  (dd) —N=;
  (ee) —N($CH_3$)—
  (ff) —O—
  (gg) —S(O)$_n$—, wherein n is 0, 1 or 2;
  (hh) —CO—O—
  (ii) —O—CO—
  (jj) —CO—; and $R^5$ is selected from the group consisting of:
 (aaa) $C_1$–$C_6$-alkyl, optionally substituted with a substituent selected from the group consisting of:
  (i) aryl;
  (ii) substituted-aryl;
  (iii) heteroaryl; and
  (iv) substituted-heteroaryl;
 (bbb) aryl;
 (ccc) substituted-aryl;
 (ddd) heteroaryl;
 (eee) substituted-heteroaryl; and
 (fff) heterocycloalkyl; and
(c) $C_3$–$C_7$-cycloalkyl;
(d) aryl;
(e) substituted-aryl;
(f) heteroaryl;
(g) substituted-heteroaryl; and
W is absent;

the method comprising:

(a) treating a compound having the formula:

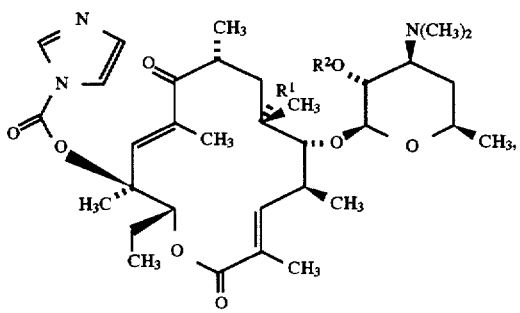

wherein $R^1$ is selected from the group consisting of hydrogen, protected hydroxy, O—CO—$C_1$-$C_6$-alkyl, O—$C_1$-$C_{12}$-alkyl, O—CO—$NH_2$, O—CO—NH—CO—$C_1$-$C_{12}$-alkyl, and O—CO—NH—$SO_2$—$C_1$-$C_{12}$-alkyl; and $R^2$ is a hydroxy protecting group, with a primary amine $RNH_2$, wherein R is as defined above, in a suitable organic solvent at room temperature to reflux temperature for about 4 to about 48 hours, extracting, optionally deprotecting, and isolating the desired compound.

In a preferred embodiment of the process immediately above R is hydrogen, $C_1$-$C_6$-alkyl, $C_3$-$C_7$-cycloalkyl, aryl, substituted-aryl, heteroaryl or substituted-heteroaryl, and the solvent is selected from the group consisting of methylene chloride, tetrahydrofuran, N-methyl-pyrrolidinone, diethyl ether, bis-methoxymethyl ether, dimethyl formamide, acetonitrile, acetone and aqueous mixtures thereof.

The present invention also provides an alternate process for the preparation of a compound having the Formula (I):

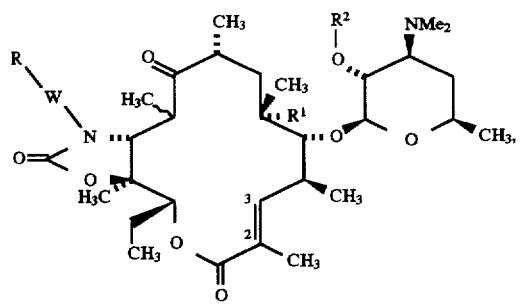

wherein
$R^1$ is selected from the group consisting of:
(a) hydrogen;
(b) hydroxy;
(c) O—$C_1$-$C_{12}$-alkyl;
(d) O—CO—$C_1$-$C_6$-alkyl;
(e) O—CO—$NH_2$;
(f) O—CO—NH—CO—$C_1$-$C_{12}$-alkyl; and
(g) O—CO—NH—$SO_2$—$C_1$-$C_{12}$-alkyl;
$R^2$ is hydrogen or a hydroxy protecting group;
R is selected from the group consisting of:
(a) hydrogen;
(b) $C_1$-$C_6$-alkyl optionally substituted with one or more substituents selected from the group consisting of:
  (i) aryl;
  (ii) substituted-aryl;
  (iii) heteroaryl;
  (iv) substituted-heteroaryl;
  (v) hydroxy;
  (vi) $C_1$-$C_6$-alkoxy;
  (vii) $NR^3R^4$, where $R^3$ and $R^4$ are independently selected from hydrogen and $C_1$-$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$-$C_6$-alkyl-)—, —N(aryl)—, —N(aryl-$C_1$-$C_6$-alkyl-)—, —N(substituted-aryl-$C_1$-$C_6$-alkyl-)—, —N(heteroaryl)—, —N(heteroaryl-$C_1$-$C_6$-alkyl-)—, —N(substituted-heteroaryl-$C_1$-$C_6$-alkyl-)—, —S— or —S(O)$_n$—, wherein n is 1 or 2;
  (viii) —$CH_2$—M—$R^5$, wherein M is selected from the group consisting of:
    (aa) —C(O)—NH—;
    (bb) —NH—C(O)—;
    (cc) —NH—
    (dd) —N=;
    (ee) —N($CH_3$)—
    (ff) —O—
    (gg) —S(O)$_n$—, wherein n is 0, 1 or 2;
    (hh) —CO—O—
    (ii) —O—CO—
    (jj) —CO—; and
  $R^5$ is selected from the group consisting of:
    (aaa) $C_1$-$C_6$-alkyl, optionally substituted with a substituent selected from the group consisting of:
      (i) aryl;
      (ii) substituted-aryl;
      (iii) heteroaryl; and
      (iv) substituted-heteroaryl;
    (bbb) aryl;
    (ccc) substituted-aryl;
    (ddd) heteroaryl;
    (eee) substituted-heteroaryl; and
    (fff) heterocycloalkyl; and
(c) $C_3$-$C_7$-cycloalkyl;
(d) aryl;
(e) substituted-aryl;
(f) heteroaryl;
(g) substituted-heteroaryl; and
W is selected from the group consisting of —NH—CO—, —N=CH—, —NH— and —N(($C_1$-$C_6$-alkyl)—;
the method comprising:
(a) treating a compound having the formula:

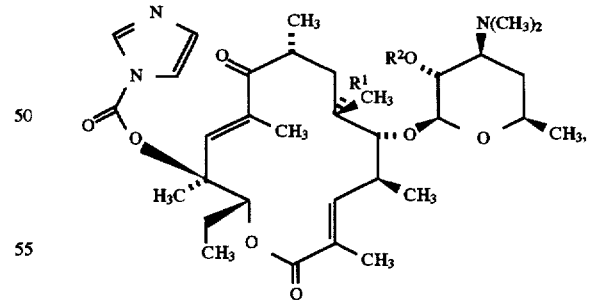

wherein $R^1$ is selected from the group consisting of hydrogen, protected hydroxy, O—CO—$C_1$-$C_6$-alkyl, O—$C_1$-$C_{12}$-alkyl, O—CO—$NH_2$, O—CO—NH—CO—$C_1$-$C_{12}$-alkyl, or O—CO—NH—$SO_2$—$C_1$-$C_{12}$-alkyl; and $R^2$ is a hydroxy protecting group, with a reagent selected from the group consisting of hydrazine and a substituted hydrazine in a suitable organic solvent at room temperature to reflux for about 4 to about 48 hours to afford the desired compound;

(b) optionally acylating the compound of Formula (I) obtained in step (a) wherein W is —NH— and R is H with an acylating agent to afford a compound of Formula (I) wherein W is —NH—CO—;

(c) optionally condensing the compound of Formula (I) obtained in step (a) wherein W is —NH— and R is H with an aldehyde to afford a compound of Formula (I) wherein W is —N=CH—;

(d) optionally reducing the compound of Formula (I) obtained in step (c) wherein W is —N=CH— with a reducing agent to afford a compound of Formula (I) wherein W is —NH—;

(e) and extracting, optionally deprotecting, and isolating the desired compound.

A preferred embodiment of the process immediately above is the one wherein the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF, and aqueous acetone.

In one embodiment of the process immediately above the product is a compound of Formula (I) wherein W is —NH— and R is H, and the hydrazine reagent is hydrazine.

In another embodiment of the process immediately above the product is a compound of Formula (I) wherein W is —N($C_1$–$C_6$-alkyl)—, the hydrazine reagent is a substituted hydrazine $RR^4NNH_2$, wherein R is as defined for Formula (I) and $R^4$ is $C_1$–$C_6$-alkyl.

In still another embodiment of the process immediately above the product is a compound of Formula (I) wherein W is —NH—CO—, the hydrazine reagent is hydrazine, and the product obtained in step (a) having the Formula (I) wherein W is —NH— and R is H is treated with an R-acyl acylating agent, wherein R is as defined for Formula (I). In a preferred embodiment the acylating agent is selected from the group consisting of an acid chloride, an acid fluoride, an acid anhydride, a carboxylic acid in the presence of carbonyldiimidazole, and a carboxylic acid in the presence of 1-(3-dimethylaminopropyl)-3-ethylcarbodiimide hydrochloride.

In yet another embodiment of the process immediately above the product is a compound of Formula (I) wherein W is —N=CH—, the hydrazine reagent is hydrazine, and the product obtained in step (a) having the Formula (I) wherein W is —NH— and R is H is treated with an aldehyde having the formula R—CHO, wherein R is as defined for Formula (I).

In an additional embodiment of the process immediately above the product is a compound of Formula (I) wherein W is —NH— and R is not H, the hydrazine reagent is hydrazine, the product obtained in step (a) having the Formula (I) wherein W is —NH— and R is H is treated with an aldehyde having the formula R—CHO, wherein R is as defined for Formula (I), and the product obtained in step (c) having the Formula (I) wherein W is —N=CH— is treated with a reducing agent. In a preferred embodiment of this process the reducing agent is selected from the group consisting of sodium cyanoborohydride, sodium borohydride, sodium triacetoxyborohydride, borane-tetrahydrofuran complex, and borane-piperidine complex.

The present invention further provides a process for the preparation of a compound having the Formula (I):

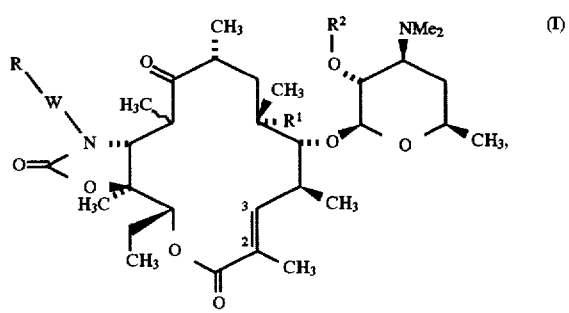

wherein
$R^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_{d\,2}$—$C_1$–$C_{12}$-alkyl;
$R^2$ is hydrogen or a hydroxy protecting group;
R is selected from the group consisting of:
(a) hydrogen;
(b) $C_1$–$C_6$-alkyl optionally substituted with one or more substituents selected from the group consisting of:
 (i) aryl;
 (ii) substituted-aryl;
 (iii) heteroaryl;
 (iv) substituted-heteroaryl;
 (v) hydroxy;
 (vi) $C_1$–$C_6$-alkoxy;
 (vii) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)-, —N(heteroalkyl)—, —N(heteroaryl-$C_1$–$C_6$-alkyl-)—, —N(substituted-heteroaryl-$C_1$–$C_6$-alkyl-)—, —S— or —S(O)$_n$—, wherein n is 1 or 2;
 (viii) —$CH_2$—M—$R^5$,
 wherein M is selected from the group consisting of:
  (aa) —C(O)—NH—;
  (bb) —NH—C(O)—;
  (cc) —NH—
  (dd) —N=;
  (ee) —N($CH_3$)—
  (ff) —O—
  (gg) —S(O)$_n$—, wherein n is 0, 1 or 2;
  (hh) —CO—O—
  (ii) —O—CO—
  (jj) —CO—; and
 $R^5$ is selected from the group consisting of:
  (aaa) $C_1$–$C_6$-alkyl, optionally substituted with a substituent selected from the group consisting of:
   (i) aryl;
   (ii) substituted-aryl;
   (iii) heteroaryl; and
   (iv) substituted-heteroaryl;
  (bbb) aryl;
  (ccc) substituted-aryl;

(ddd) heteroaryl;
(eee) substituted-heteroaryl; and
(fff) heterocycloalkyl; and
(c) $C_3$–$C_7$-cycloalkyl;
(d) aryl;
(e) substituted-aryl;
(f) heteroaryl;
(g) substituted-heteroaryl; and
W is —O—;
the method comprising:
(a) treating a compound having the formula:

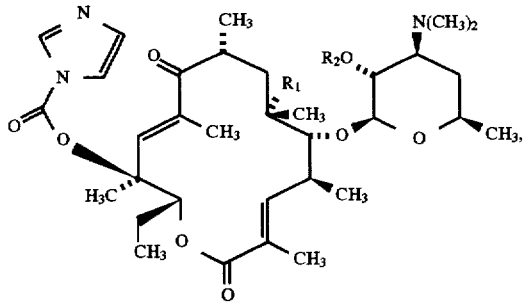

wherein $R^1$ is selected from the group consisting of hydrogen, protected hydroxy, O—$C_1$–$C_{12}$-alkyl, O—CO—$C_1$–$C_6$-alkyl, O—CO—$NH_2$, O—CO—NH—CO—$C_1$–$C_{12}$-alkyl, or O—CO—NH—$SO_2$—$C_1$–$C_{12}$-alkyl; and $R^2$ is a hydroxy protecting group, with a hydroxylamine reagent selected from the group consisting of unsubstituted hydroxylamine and an O—$C_1$–$C_6$-alkylated hydroxylamine in a suitable organic solvent at room temperature to reflux for about 4 to about 48 hours, to give the desired compound;

(b) optionally treating the product obtained in step (a) having the Formula (I) wherein W is —O— and R is H with a suitable base and an appropriate electrophile having the formula R-L, wherein R is selected from the group consisting of $C_1$–$C_6$-alkyl, $C_3$–$C_7$-cycloalkyl, aryl, substituted-aryl, heteroaryl and a substituted-heteroaryl group, wherein these terms are as defined for compounds of Formula (I) above and L is suitable leaving group, to give the desired compound of formula (I) wherein W is —O— and R is selected from the group consisting of $C_1$–$C_6$-alkyl, $C_3$–$C_7$-cycloalkyl, aryl, substituted-aryl, heteroaryl and a substituted-heteroaryl group; and (c) extracting, optionally deprotecting, and isolating the desired compound.

In one embodiment of the process immediately above the product is a compound of Formula (I) wherein W is —O— and R is H and the hydroxylamine reagent is unsubstituted hydroxylamine.

In one embodiment of the process immediately above the product is a compound of Formula (I) wherein W is —O— and R is O—$C_1$–$C_6$-alkyl and the hydroxylamine reagent is an O—$C_1$–$C_6$-alkylated hydroxylamine.

In still another embodiment of the process immediately above the final product is a compound of Formula (I) wherein W is —O— and R=$C_1$–$C_6$-alkyl, the hydroxylamine reagent is unsubstituted hydroxylamine, and the intermediate product having the Formula (I) wherein W=O and R is H is treated with a suitable base and an alkyl halide.

In still another embodiment of the process immediately above the final product is a compound of Formula (I) wherein W is —O— and R is selected from the group consisting of $C_3$–$C_7$-cycloalkyl, aryl, substituted-aryl, heteroaryl and a substituted-heteroaryl group, and the intermediate product having the Formula (I) wherein W is —O— and R is H is treated with a suitable base and an electrophile having the formula R-L, wherein R is as defined above and L is a suitable leaving group. In a preferred embodiment of this process the base is selected from the group consisting of sodium hydride, potassium hydride, lithium hydride, lithium diethylamide, and butyllithium, and L is selected from the group consisting of halide, methanesulfonyl and p-toluenesulfonyl.

The present invention also provides a process for the preparation of a compound having the Formula (II):

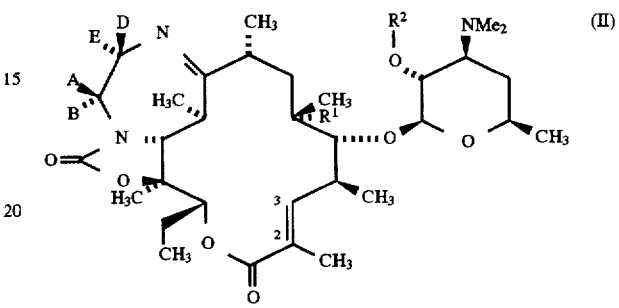

wherein
$R^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl;
$R^2$ is hydrogen or a hydroxy protecting group;
A, B, D and E are independently selected from the group consisting of:
(a) hydrogen;
(b) $C_1$–$C_6$-alkyl, optionally substituted with one or more substituents selected from the group consisting of:
(i) aryl;
(ii) substituted-aryl;
(iii) heteroaryl;
(iv) substituted-heteroaryl;
(v) heterocycloalkyl;
(vi) hydroxy;
(vii) $C_1$–$C_6$-alkoxy;
(viii) halogen consisting of Br, Cl, F or I; and
(ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)—, —N(heteroaryl-$C_1$–$C_6$-alkyl-)—, —N(substituted-heteroaryl-$C_1$–$C_6$-alkyl-)—, —S— or —S(O)$_n$—, wherein n is 1 or 2;
(c) $C_3$–$C_7$-cycloalkyl;
(d) aryl;
(e) substituted-aryl;
(f) heteroaryl;
(g) substituted-heteroaryl;
(h) heterocycloalkyl; and (i) a group selected from option (b) above further substituted with —M—

R⁵, wherein M is selected from the group consisting of
(aa) —C(O)—NH—;
(bb) —NH—C(O)—;
(cc) —NH—
(dd) —N(CH₃)—
(ee) —O—
(ff) —S(O)$_n$—, wherein n is 0, 1 or 2;
(gg) —C(=NH)—NH—;
(hh) —CO—O—
(ii) —O—CO—
(jj) —CO—;

and R⁵ is selected from the group consisting of:
(aaa) $C_1$–$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;
(eee) substituted-heteroaryl; and
(fff) heterocycloalkyl;

or any one pair of substituents, consisting of AB, AD, AE, BD, BE or DE, is taken together with the atom or atoms to which they are attached to form a 3- to 7-membered ring optionally containing a hetero function consisting of:

—O—,
—NH—,
—N($C_1$–$C_6$-alkyl-)—,
—N(aryl-$C_1$–$C_6$-alkyl-)—,
—N(substituted-aryl-$C_1$–$C_6$-alkyl-)—,
—N(heteroaryl-$C_1$–$C_6$-alkyl-)—,
—N(substituted-heteroaryl-$C_1$–$C_6$-alkyl-)—,
—S— or —S(O)$_n$—, wherein n is 1 or 2;
—C(O)—NH—;
—C(O)—NR⁵—, wherein R⁵ is as defined above;
—NH—C(O)—;
—NR⁵—C(O)—, wherein R⁵ is as defined above; and
—C(=NH)—NH—;

the method comprising:

(a) treating a compound having the formula:

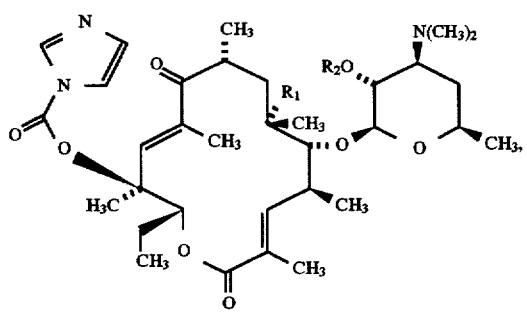

wherein R¹ is selected from the group consisting of hydrogen, protected hydroxy, O—$C_1$–$C_{12}$-alkyl, O—O—$C_1$–$C_6$-alkyl, O—CO—NH₂, O—CO—NH—CO—$C_1$–$C_{12}$-alkyl, or O—CO—NH—SO₂—$C_1$–$C_{12}$-alkyl; and R² is a hydroxy protecting group, with a compound having the formula:

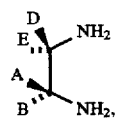

wherein A, B, D, and E are as defined for compounds of Formula (II) above, in a suitable solvent at room temperature to reflux temperature for about 4 to about 48 hours to give the bicyclic intermediate compound having the formula:

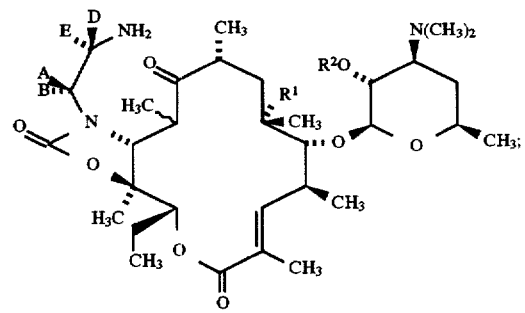

(b) deprotecting said bicyclic intermediate compounds to give the second intermediate compounds having the formula:

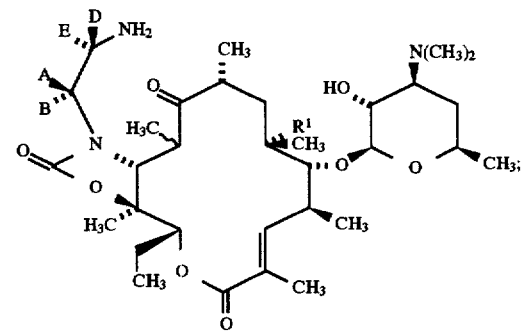

(c) cyclizing said second intermediate compounds by treatment with dilute concentration of a strong acid in a suitable organic solvent for a period of from about 4 hours to about 10 days at a temperature from ambient to reflux temperature of the solvent to give the desired compounds; and (d) extracting, optionally deprotecting, and isolating the desired compound.

A preferred embodiment of the process immediately above is the one wherein in step (a) the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF, and aqueous acetone; and in step (c) the solvent is selected the group consisting of methanol, ethanol, propanol, iso-propanol, butanol, iso-butanol and t-butanol.

The present invention provides an alternate process for the preparation of a compound having the Formula (II):

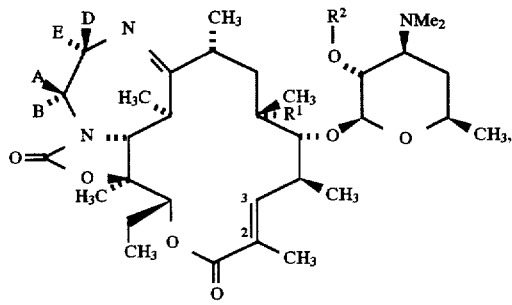

wherein A, B, D, E, $R^1$ and $R^2$ are as defined for Formula (II) above, the method comprising:

(a) treating a compound having the formula:

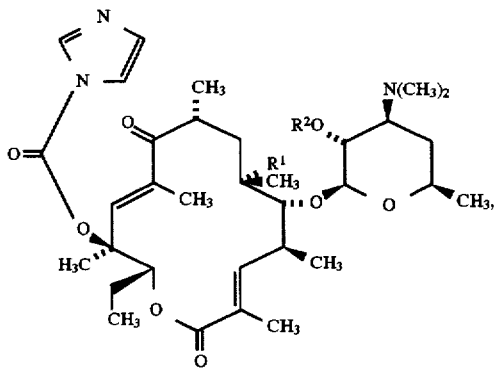

wherein $R^1$ is selected from the group consisting of hydrogen, protected hydroxy, O—$C_1$-$C_{12}$-alkyl, O—CO—$C_1$-$C_6$-alkyl, O—CO—$NH_2$, O—CO—NH—CO-$C_1$-$C_{12}$-alkyl, or O-CO-NH—$SO_2$—$C_1$-$C_{12}$-alkyl; and $R^2$ is a hydroxy protecting group, with a compound having the formula:

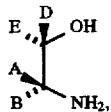

wherein A, B, D, and E are as defined above, in a suitable solvent at 0°–70° C. for about 4 to about 48 hours to give a bicyclic intermediate compound having the formula:

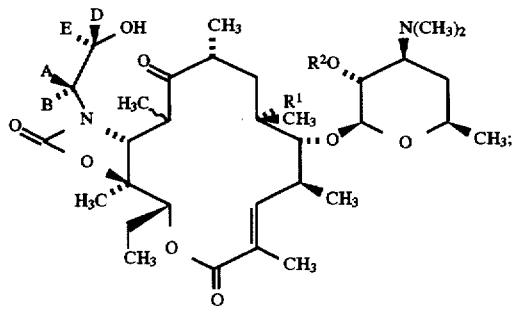

(b) treating the bicyclic intermediate compound from step (a) with triphenylphosphine and diphenylphosphoryl azide-diethylazodicarboxylate in tetrahydrofuran under Mitsunobu reaction conditions to prepare the second intermediate azide compound having the formula:

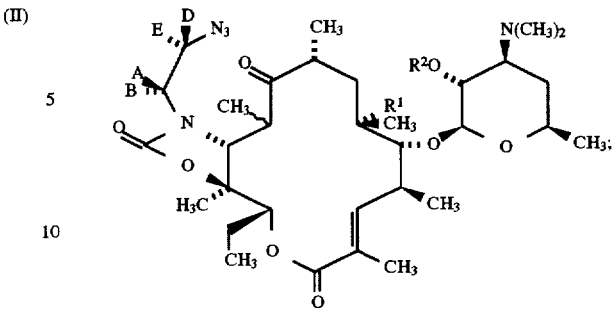

(c) reducing the second intermediate azide compound to prepare the third intermediate compound having the formula:

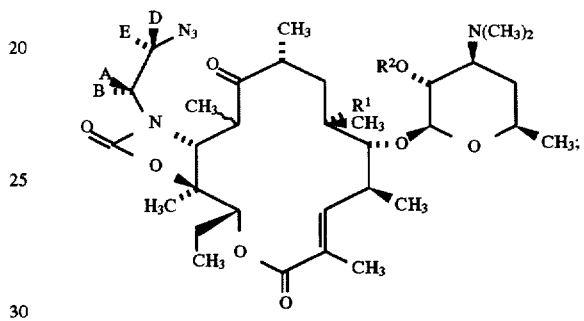

(d) cyclizing said third intermediate compound by treatment with a dilute concentration of a strong acid at ambient temperature to reflux temperature for about 4 hours to about 10 days in a aqueous alcohol solvent to give the desired compounds; and (e) extracting, optionally deprotecting, and isolating the desired compound.

In a preferred embodiment of the process described immediately above in step (a) the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF and aqueous acetone; in step (c) the reducing agent is selected from the group consisting of triphenylphosphine-water, hydrogen with a catalyst, sodium borohydride, and dialkylaluminum hydride; and in step (d) the solvent is selected the group consisting of methanol, ethanol, propanol, iso-propanol, butanol, iso-butanol and t-butanol.

In an alternate embodiment of the alternate process described immediately above, step (b) thereof is replaced with two steps consisting of:

(b') reacting the hydroxy group of the bicyclic intermediate compound with a sulfonating agent selected from the group consisting of sulfonyl chloride, alkyl sulfonic anhydride, aryl sulfonic anhydride, and trifluoromethane-sulfonic anhydride, in an aprotic solvent at −78° C. to room temperature to give an intermediate compound wherein the hydroxyl group has been replaced with a sulfonate ester moiety; and (b") reacting the sulfonate ester of step (b') with an alkali metal azide in an aprotic solvent at from about 0° C. to about 100° C. to give the second intermediate azide compound.

The present invention also provides a process for the preparation of a compound having the Formula (III):

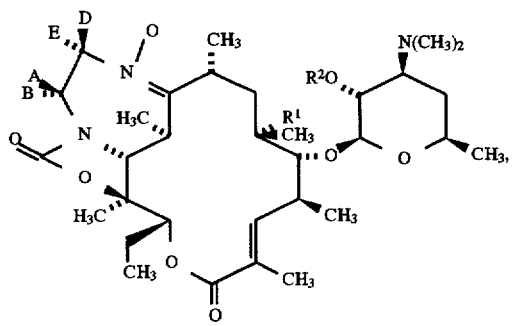

(III)

wherein

A, B, D and E are independently selected from the group consisting of:

(a) hydrogen;
(b) $C_1$–$C_6$-alkyl, optionally substituted with one or more substituents selected from the group consisting of:
  (i) aryl;
  (ii) substituted-aryl;
  (iii) heteroaryl;
  (iv) substituted-heteroaryl;
  (v) heterocycloalkyl;
  (vi) hydroxy;
  (vii) $C_1$–$C_6$-alkoxy;
  (viii) halogen consisting of Br, Cl, F or I; and
  (ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, -N(heteroaryl)—, —N(heteroaryl-$C_1$–$C_6$-alkyl-)—, —N(substituted-heteroaryl-$C_1$–$C_6$-alkyl-)—, —S— or —S(O)$_n$—, wherein n is 1 or 2;
(c) $C_3$–$C_7$-cycloalkyl;
(d) aryl;
(e) substituted-aryl;
(f) heteroaryl;
(g) substituted-heteroaryl;
(h) heterocycloalkyl; and
(i) a group selected from option (b) above further substituted with —M—$R^5$, wherein M is selected from the group consisting of
  (aa) —C(O)—NH—;
  (bb) —NH—C(O)—;
  (cc) —NH—
  (dd) —N($CH_3$)—
  (ee) —O—
  (ff) —S(O)$_n$—, wherein n is 0, 1 or 2; and
  (gg) —C(=NH)—NH—;

and $R^5$ is selected from the group consisting of:
  (aaa) $C_1$–$C_6$-alkyl, optionally substituted with a substituent selected from the group consisting of:
    (i) aryl;
    (ii) substituted-aryl;
    (iii) heteroaryl; and
    (iv) substituted-heteroaryl;
  (bbb) aryl;
  (ccc) substituted-aryl;
  (ddd) heteroaryl;
  (eee) substituted-heteroaryl; and
  (fff) heterocycloalkyl;

or any one pair of substituents, consisting of AB, AD, AE, BD, BE or DE, is taken together with the atom or atoms to which they are attached to form a 3- to 7-membered ring optionally containing a hetero function consisting of:

—O—,
—NH—,
—N($C_1$–$C_6$-alkyl-)—,
—N(aryl-$C_1$–$C_6$-alkyl-)—,
—N(substituted-aryl-$C_1$–$C_6$-alkyl-)—,
—N(heteroaryl-$C_1$–$C_6$-alkyl-)—,
—N(substituted-heteroaryl-$C_1$–$C_6$-alkyl-)—,
—S— or —S(O)$_n$—, wherein n is 1 or 2;
—C(O)—NH—;
—C(O)—$NR^5$—, wherein $R^5$ is as defined above;
—NH—C(O)—;
—$NR^5$—C(O)—, wherein $R^5$ is as defined above; and
—C(=NH)—NH—;

$R^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl; and $R^2$ is hydrogen or a hydroxy-protecting group; the method comprising:

(a) reacting a compound having the formula (II):

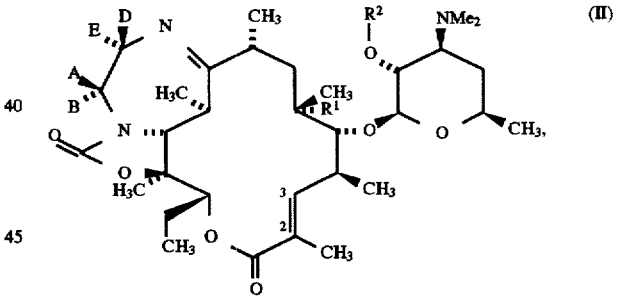

(II)

wherein $R^1$ is as above or is a hydroxy protecting group and $R^2$, A, B, D, and E are as defined above, with a suitable oxidizing agent to oxidize the imine nitrogen to the nitrone and the nitrogen atom on the desosamine moiety to the N-oxide to give an N-oxidized intermediate; and (b) treating the N-oxidized intermediate with a reducing agent to reduce the desosamine N-oxide, and extracting, optionally deprotecting, and isolating the desired compound.

A preferred embodiment of the process described immediately above is the one wherein in step (a) the oxidizing agent is selected from the group consisting of hydrogen peroxide and a carboxylic peracid; and in step (b) the reducing agent is selected from the group consisting of triphenylphosphine and hydrogen in the presence of a catalyst.

The invention further provides a process for the preparation of a compound having the Formula (IV):

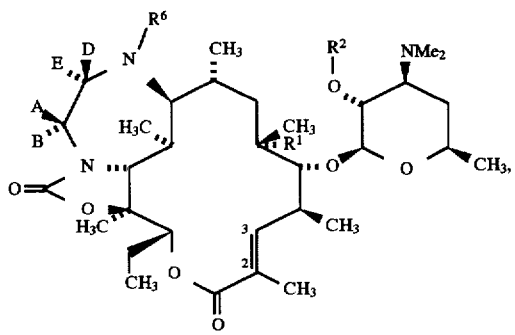

(IV)

wherein

A, B, D and E are independently selected from the group consisting of:
(a) hydrogen;
(b) $C_1$–$C_6$-alkyl, optionally substituted with one or more substituents selected from the group consisting of:
  (i) aryl;
  (ii) substituted-aryl;
  (iii) heteroaryl;
  (iv) substituted-heteroaryl;
  (v) heterocycloalkyl;
  (vi) hydroxy;
  (vii) $C_1$–$C_6$-alkoxy;
  (viii) halogen consisting of Br, Cl, F or I; and
  (ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)—, —N(heteroaryl-$C_1$–$C_6$-alkyl-)—, —N(substituted-heteroaryl-$C_1$–$C_6$-alkyl-)—, —S— or —S(O)$_n$—, wherein n is 1 or 2;
(c) $C_3$–$C_7$-cycloalkyl;
(d) aryl;
(e) substituted-aryl;
(f) heteroaryl;
(g) substituted-heteroaryl;
(h) heterocycloalkyl; and
(i) a group selected from option (b) above further substituted with —M—

$R^5$, wherein M is selected from the group consisting of:
  (aa) —C(O)—NH—;
  (bb) —NH—C(O)—;
  (cc) —NH—
  (dd) —N($CH_3$)—
  (ee) —O—
  (ff) —S(O)$_n$—, wherein n is 0, 1 or 2; and
  (gg) —C(=NH)—NH—;

and $R^5$ is selected from the group consisting of:
  (aaa) $C_1$–$C_6$-alkyl, optionally substituted with a substituent selected from the group consisting of:
    (i) aryl;
    (ii) substituted-aryl;
    (iii) heteroaryl; and
    (iv) substituted-heteroaryl;
  (bbb) aryl;
  (ccc) substituted-aryl;
  (ddd) heteroaryl;
  (eee) substituted-heteroaryl; and
  (fff) heterocycloalkyl;

or any one pair of substituents, consisting of AB, AD, AE, BD, BE or DE, is taken together with the atom or atoms to which they are attached to form a 3- to 7-membered ring optionally containing a hetero function consisting of
—O—,
—NH—,
—N($C_1$–$C_6$-alkyl-)—,
—N(aryl-$C_1$–$C_6$-alkyl-)—,
—N(substituted-aryl-$C_1$–$C_6$-alkyl-)—,
—N(heteroaryl-$C_1$–$C_6$-alkyl-)—,
—N(substituted-heteroaryl-$C_1$–$C_6$-alkyl-)—,
—S— or —S(O)$_n$—, wherein n is 1 or 2;
—C(O)—NH—;
—C(O)—$NR^5$—, wherein $R^5$ is as defined above;
—NH—C(O)—;
—$NR^5$—C(O)—, wherein $R^5$ is as defined above; and
—C(=NH)—NH—;

$R^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl; and
$R^2$ is hydrogen or a hydroxy-protecting group;
$R^6$ is hydrogen or $C_1$–$C_6$-alkyl; the method comprising:
(a) reacting a compound having the formula:

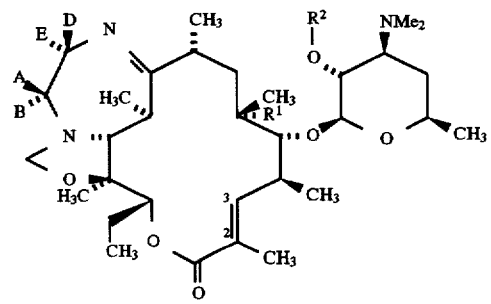

wherein $R^1$ is as above or is a hydroxy protecting group and $R^2$, A, B, D, and E are as defined above with a reducing agent in a suitable organic solvent to afford the desired compound wherein $R^6$ is H;

(b) optionally reductively alkylating the amino the product of step (a) with a reducing reagent in the presence of a $C_1$–$C_6$-alkyl-group precursor to afford the desired compound wherein $R^6$ is $C_1$–$C_6$-alkyl; and (c) extracting, optionally deprotecting, and isolating the desired compound.

A preferred embodiment of the process described immediate above is the one wherein in step (a) and in optional step (b) the reducing agent is selected from the group consisting of sodium cyanoborohydride, sodium borohydride, sodium triacetoxyborohydride, borane-tetrahydrofuran complex, and borane-piperidine complex.

The invention also provides for a novel intermediate compound having the formula:

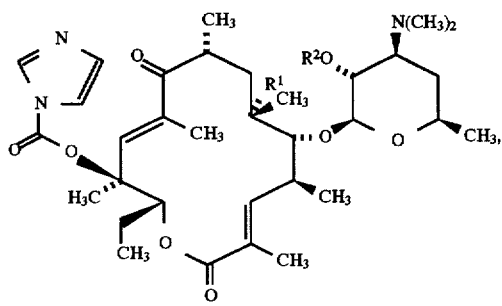

wherein $R^1$ is selected from the group consisting of:

(a) hydrogen;

(b) protected hydroxy;

(c) O—$C_1$-$C_{12}$-alkyl;

(d) O—CO—$C_1$-$C_6$-alkyl;

(e) O—CO—$NH_2$;

(f) O—CO—NH—CO—$C_1$-$C_{12}$-alkyl; and (g) O—CO—NH—$SO_2$—$C_1$-$C_{12}$-alkyl; and $R^2$ is hydrogen or a hydroxy-protecting group.

A preferred embodiment of the intermediate compound is that wherein $R^1$ is O—$C_1$-$C_{12}$-alkyl.

A more preferred embodiment of the intermediate compound is that wherein $R^1$ is methoxy.

The present invention also provides a process for the preparation of a compound having the formula:

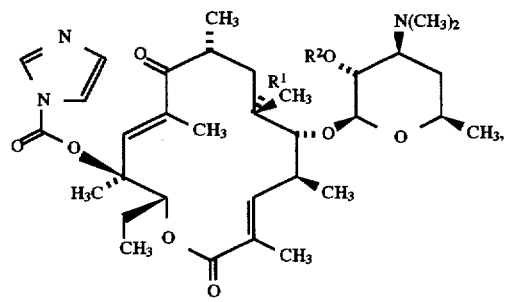

wherein $R^1$ is selected from the group consisting of:

(a) hydrogen;

(b) protected hydroxy;

(c) O—$C_1$-$C_{12}$-alkyl;

(d) O—CO—$C_1$-$C_6$-alkyl;

(e) O—CO—$NH_2$;

(f) O—CO—NH—CO—$C_1$-$C_{12}$-alkyl; and (g) O—CO—NH—$SO_2$—$C_1$-$C_{12}$-alkyl; and $R^2$ is hydrogen or a hydroxy-protecting group; the method comprising:

(a) treating an erythromycin A compound having the formula:

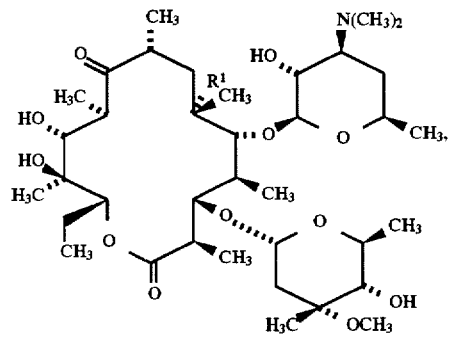

wherein $R^1$ is as defined above, with dehydrating reagents consisting of an organocarbonate in the presence of base at reflux temperature in an aprotic solvent to form an intermediate compound having the formula:

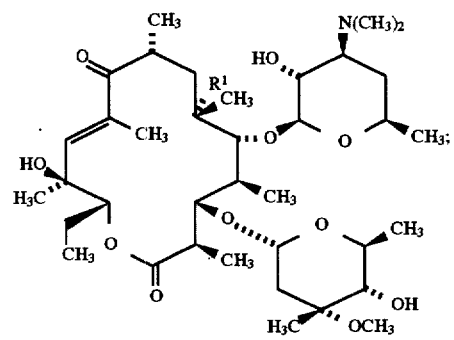

(b) hydrolytically removing the cladinose moiety from the intermediate compound of step (a) by treatment in an aqueous alcohol suspension with a dilute concentration of a strong acid at ambient temperature for about 0.5 to about 24 hours, extracting and optionally isolating the compound having the formula:

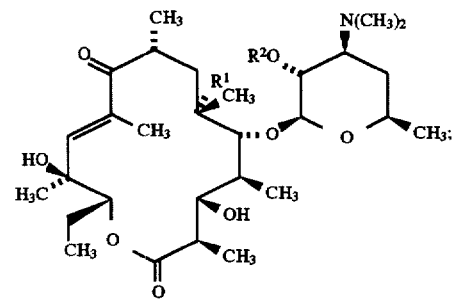

(c) treating the compound of step (b) with a suitable hydroxy group protecting reagent in an aprotic solvent, and extractively isolating the compound wherein $R^2$ is a hydroxy protecting group;

(d) treating a solution of the compound of step (c) with a sulfonylating agent at from about 0° C. to ambient temperature for about 1 to about 24 hours, and extractively isolating the compound having the formula:

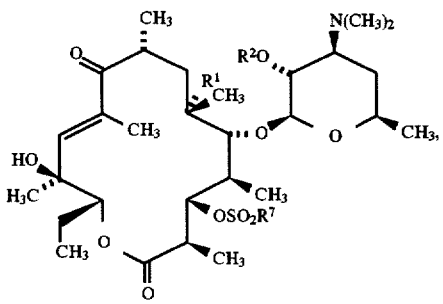

wherein $R^7$ is alkyl or aryl;

(e) dehydrating the compound of step (d) with a hydride base in the presence of carbonyldiimidazole in an aprotic solvent at a temperature from about —20° C. to about 70° C. for from about 0.5 hours to about 10 days, and extracting, optionally deprotecting, and isolating the desired compound.

In a preferred embodiment of the process immediately above, in step (a) the dehydrating reagents consist of an organocarbonate compound selected from the group consisting of ethylene carbonate, propylene carbonate, trimethylene carbonate, dipropyl carbonate, dibenzyl carbonate, isobutyl carbonate, dimethyl carbonate and diethyl carbonate, in the presence of a base selected from the group consisting of triethylamine, diisopropylethylamine, pyridine, 2,6-dimethylpyridne, 1,8-diazabicyclo[5.4.0] undec-7-ene, N-methylmorpholine, N-methylpyrrolidine, N-methylpiperidine, sodium carbonate, potassium carbonate, sodium bicarbonate and potassium carbonate; in step (b) the alcohol is chosen from the group consisting of methanol, ethanol, propanol, iso-propanol, butanol, iso-butanol and t-butanol, and the acid is selected from the group consisting of hydrochloric acid, sulfuric acid, dichloroacetic acid and trichloroacetic acid; in step (c) the hydroxy group protecting reagent is selected from the group consisting of acetyl chloride, acetic anhydride, benzoic anhydride, benzyl chloroformate, trimethylsilyl chloride and triethylsilyl chloride, and the aprotic solvent is selected from the group consisting of methylene chloride, chloroform, dimethylformamide, tetrahydrofuran, N-methylpyrrolidinone and mixtures thereof; in step (d) the sulfonylating agent is selected from the group consisting of methanesulfonyl anhydride, methanesulfonyl chloride, ethanesulfonyl chloride and p-toluenesulfonyl chloride, and the base is selected from the group defined in step (a) above; in step (e) the hydride base is selected from the group consisting of sodium hydride, potassium hydride and lithium hydride and the aprotic solvent is as defined for step (c).

In a more preferred embodiment of the process immediately above $R^1$ is H and steps (d) and (e) are replaced with a single step (d') consisting of:

(d') treatment of the compound from step (c) with sodium hexamethyldisilazane at from about –50° to about –28° C. under an inert atmosphere followed by addition of carbonyldiimidazole at from about 0° C. to about ambient temperature for about 15 minutes to about 6 hours, and extracting, optionally deprotecting, and isolating the desired compound.

The present invention also provides an alternate process for the preparation of a novel 3-descladinose-2,3-anhydroerythromycin intermediate compound having the formula:

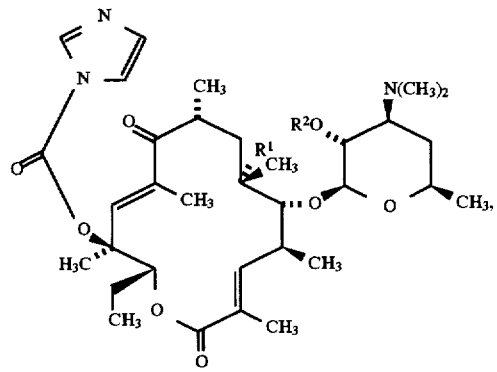

wherein $R^1$ is selected from the group consisting of:
(a) hydrogen;
(b) protected hydroxy;
(c) O—$C_1$-$C_{12}$-alkyl;
(d) O—CO—$C_1$—$C_6$-alkyl;
(e) O—CO—$NH_2$;
(f) O—CO—NH—CO—$C_1$-$C_{12}$-alkyl; and
(g) O—CO—NH—$SO_2$—$C_1$-$C_{12}$-alkyl; and
$R^2$ is hydrogen or a hydroxy-protecting group; the method comprising:

(a) hydrolytically removing the cladinose moiety from an erythromycin A compound having the formula:

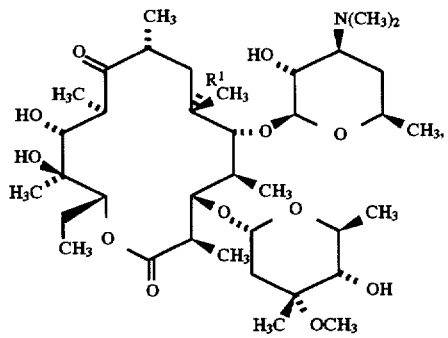

wherein $R^1$ is as described above by treatment in an aqueous alcohol suspension with a dilute concentration of a strong acid at ambient temperature for about 0.5 to about 24 hours, extracting and optionally isolating the first intermediate compound having the formula:

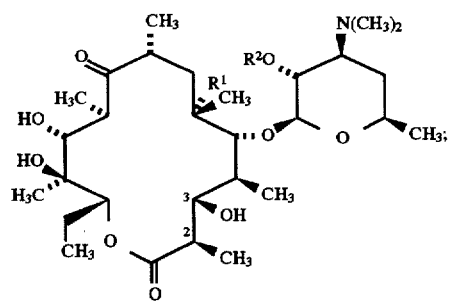

(b) optionally treating the first intermediate compound with a suitable hydroxy group protecting reagent, and extractively isolating the second intermediate compound having the formula of the compound of step (a) wherein $R^2$ is a hydroxy-protecting group;

(c) treating the second intermediate compound with an excess of a carbonylating reagent and isolating by aqueous work up the third intermediate compound having the formula:

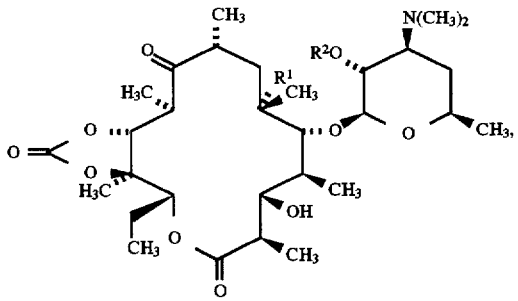

wherein $R^1$ may not be hydrogen but is otherwise as defined above;

(d) treating the third intermediate compound with a sulfonylating agent at from about 0° C. to ambient temperature for about 1 to about 24 hours, and extractively isolating the fourth intermediate compound having the formula:

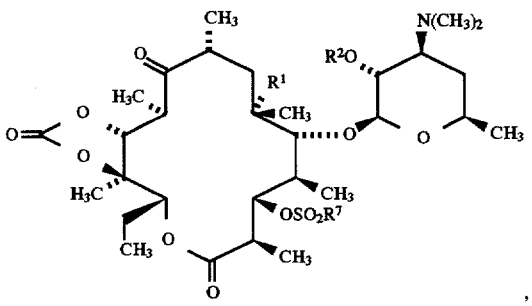

wherein
$R^7$ is alkyl or aryl;

(e) treating the fourth intermediate compound with a base, extracting and optionally isolating the to afford the fifth intermediate compound having the formula:

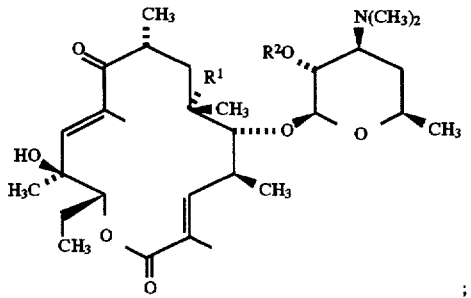

(f) treating the fifth intermediate compound with a hydride base and carbonyldiimidazole in an aprotic solvent at a temperature from about —20° C. to about 70° C. for from about 0.5 hours to about 10 days, and extracting, optionally deprotecting, and isolating the desired compound.

In a preferred embodiment of the process immediately above in step (a) the alcohol is chosen from the group consisting of methanol, ethanol, propanol, iso-propanol, butanol, iso-butanol and t-butanol, and the acid is selected from the group consisting of hydrochloric acid, sulfuric acid, dichloroacetic acid and trichloroacetic acid; in step (b) the hydroxy group protecting reagent is selected from the group consisting of acetyl chloride, acetic anhydride, benzoic anhydride, benzyl chloroformate, trimethylsilyl chloride and triethylsilyl chloride, and the aprotic solvent is selected from the group consisting of methylene chloride, chloroform, dimethylformamide, tetrahydrofuran, N-methylpyrrolidinone and mixtures thereof; in step (c) the carbonylating reagent is selected from the group consisting of phosgene, diphosgene and triphosgene; in step (d) the sulfonylating agent is selected from the group consisting of methanesulfonyl anhydride, methanesulfonyl chloride, ethanesulfonyl chloride and p-toluenesulfonyl chloride; in step (e) the base is selected from the group consisting of triethylamine, diisopropylethylamine, pyridine, 2,6-dimethylpyridne, 1,8-diazabicyclo[5.4.0]undec-7-ene, N-methylmorpholine, N-methylpyrrolidine, N-methylpiperidine, sodium carbonate, potassium carbonate, sodium bicarbonate and potassium carbonate; in step (f) the hydride base is selected from the group consisting of sodium hydride, potassium hydride and lithium hydride.

In a more preferred embodiment of the process immediately above, in step (b) the hydroxy protecting reagent is benzoic anhydride and $R^2$ is benzoyl, and steps (c), (d) and (e) are replaced with a single step (c') consisting of:

(c') treatment of the compound from step (b) with sodium hexamethyldisilazane at from about −50 to about −28° C. under an inert atmosphere followed by addition of carbonyldiimidazole at from about 0° C. to about ambient temperature for about 15 minutes to about 6 hours, and extracting, optionally deprotecting, and isolating the desired compound.

Definitions

The terms "$C_1$-C-alkyl", "$C_1$-$C_6$-alkyl", "$C_1$-$C_{12}$-alkyl" or "$C_1$-$C_{18}$-alkyl" as used herein refer to saturated, straight- or branched-chain hydrocarbon radicals containing between one and three, one and six, one and twelve, or one and eighteen carbon atoms, respectively. Examples of $C_1$-$C_3$ alkyl radicals include methyl, ethyl, propyl and isopropyl, examples of $C_1$-$C_6$-alkyl radicals include, but are not limited to, methyl, ethyl, propyl, isopropyl, n-butyl, tert-butyl, neopentyl and n-hexyl, examples of $C_1$-$C_{12}$-alkyl radicals include all of the preceding examples and n-heptyl, octyl, n-decyl, n-undecyl and n-dodecyl, for example, and examples of $C_1$-$C_{18}$-alkyl radicals include all of the preceding examples and n-triadecane, n-tetradecane, n-pentadecane, n-hexadecane, n-heptadecane, and n-octadecane, for example.

The term "$C_1$-$C_6$-alkoxy" as used herein refers to an $C_1$-$C_6$-alkyl group, as previously defined, attached to the parent molecular moiety through an oxygen atom. Examples of $C_1$-$C_6$-alkoxy, but are not limited to, methoxy, ethoxy, propoxy, isopropoxy, n-butoxy, tert-butoxy, neopentoxy and n-hexoxy.

The term "$C_1$-$C_3$-alkyl-amino" as used herein refers to one or two $C_1$-$C_3$-alkyl groups, as previously defined, attached to the parent molecular moiety through a nitrogen atom. Examples of $C_1$-$C_3$-alkyl-amino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, ethers such as diethyl ether and bis-methoxymethyl ether, as well as various other compounds like dimethyl formamide, acetonitrile, acetone and ethyl acetate. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick, et al., Vol. 11, in the Techniques of Chemistry Series, John Wiley & Sons, N.Y., 1986.

The term "aryl" as used herein refers to unsubstituted carbocyclic aromatic groups including, but not limited to, phenyl, 1- or 2-naphthyl and the like.

The term "$C_3$-$C_5$-cycloalkyl- and $C_3$-$C_7$-cycloalkyl" as used herein refers to carbocyclic groups of 3 to 5 or 3 to 7 carbons, respectively, for example, cyclopropyl, cyclobutyl, cyclopentyl, cyclohexyl, and cycloheptyl.

The terms "$C_1$-$C_3$-alkyl-$C_3$-$C_5$-cycloalkyl", as used herein refers to a $C_3$-$C_5$-cycloalkyl radical, as defined above, attached to a $C_1$-$C_3$-alkyl radical by replacement of a hydrogen atom on the latter.

The terms "halo" and "halogen" as used herein refer to an atom selected from fluorine, chlorine, bromine and iodine.

The term "halo-$C_1$-$C_3$-alkyl" as used herein refers to a $C_1$-$C_3$-alkyl group as defined above wherein 1, 2 or 3 hydrogen atoms thereon are independently replaced by a halogen atom.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "heterocycloalkyl" as used herein, refers to a non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

"Hydroxy-protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, acyl substituted with an aromatic group and the like.

A the term "protected-hydroxy" refers to a hydroxy group protected with a hydroxy protecting group, as defined above, including benzoyl, acetyl, trimethylsilyl, triethylsilyl, methoxymethyl groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick, et al., Vol. 11, in the Techniques of Chemistry Series, John Wiley & Sons, N.Y., 1986.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl-amino, formyl, carboxy, alkoxycarbonyl, $C_1$-$C_3$-alkyl-CO—O—, $C_1$-$C_3$-alkyl-CO—NH—, or carboxamide; except that tetrafluorophenyl and pentafluorophenyl are also included within the definition of "substituted aryl".

The term "substituted heteroaryl" as used herein refers to a heteroaryl group as defined herein substituted by independent replacement of one, two or three of the hydrogen atoms thereon with Cl, Br, F, I, OH, $C_1$-$C_3$-alkyl, $C_1$-$C_6$-alkoxy, methoxymethoxy, amino, or $C_1$-$C_3$-alkyl-amino, or may also refer to a mono-oxo substituted heteroaryl compound, such as 4-oxo-1H-quinoline, for example.

The term "substituted heterocycloalkyl" as used herein, refers to a heterocycloalkyl group, as defined above, substituted by independent replacement of one, two or three of the hydrogen atoms thereon with Cl, Br, F, I, OH, cyano, mercapto, nitro, $C_1$-$C_3$-alkyl, halo-$C_1$-$C_3$-alkyl, $C_1$-$C_6$-alkoxy, thio-$C_1$-$C_6$-alkoxy, methoxymethoxy, amino, $C_1$-$C_3$-alkyl-amino, di($C_1$-$C_3$-alkyl-)amino, carboxaldehydo, carboxy, alkoxycarbonyl, $C_1$-$C_3$-alkyl-CO—O—, $C_1$-$C_3$-alkyl-CO—NH—, or carboxamide.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butryates, acrylates and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Abbreviations

Abbreviations which have been used in the descriptions of the scheme and the examples that follow are: 9-BBN for 9-borabicyclo[3.3.1]nonane; AIBN for azobisisobutyronitrile; Bu$_3$SnH for tributyltin hydride; CDI for carbonyldiimidazole; DBU for 1,8-diazabicyclo[5.4.0]undec-7-ene; DEAD for diethylazodicarboxylate; DMAP for 4-dimethylaminopyridine; DMF for dimethyl formamide; DPPA for diphenylphosphoryl azide; EtOAc for ethyl acetate; MeOH for methanol; NaHMDS for sodium hexamethyldisilazane; NaN(TMS)$_2$ for sodium bis(trimethylsilyl) amide; NMMO for N-methylmorpholine N-oxide; TEA for triethylamine; THF for tetrahydrofuran; TPP for triphenylphosphine.

Synthetic Methods

The compounds and processes of the present invention will be better understood in connection with the following synthetic schemes which illustrate the methods by which the compounds of the invention may be prepared. The groups A, B, D, E, $R^1$ and $R^2$ are as defined above unless otherwise noted below.

not limited to, hydrochloric acid, sulfuric acid, dichloroacetic acid, trichloroacetic acid and the like. The reaction may be accomplished with a suspension of the reagents in aqueous alcohol, such as for example, methanol, ethanol, propanol, iso-propanol, butanol, iso-butanol and t-butanol, for example. The reaction mixture is then neutralized with an alkali metal base, the product is extracted with a suitable

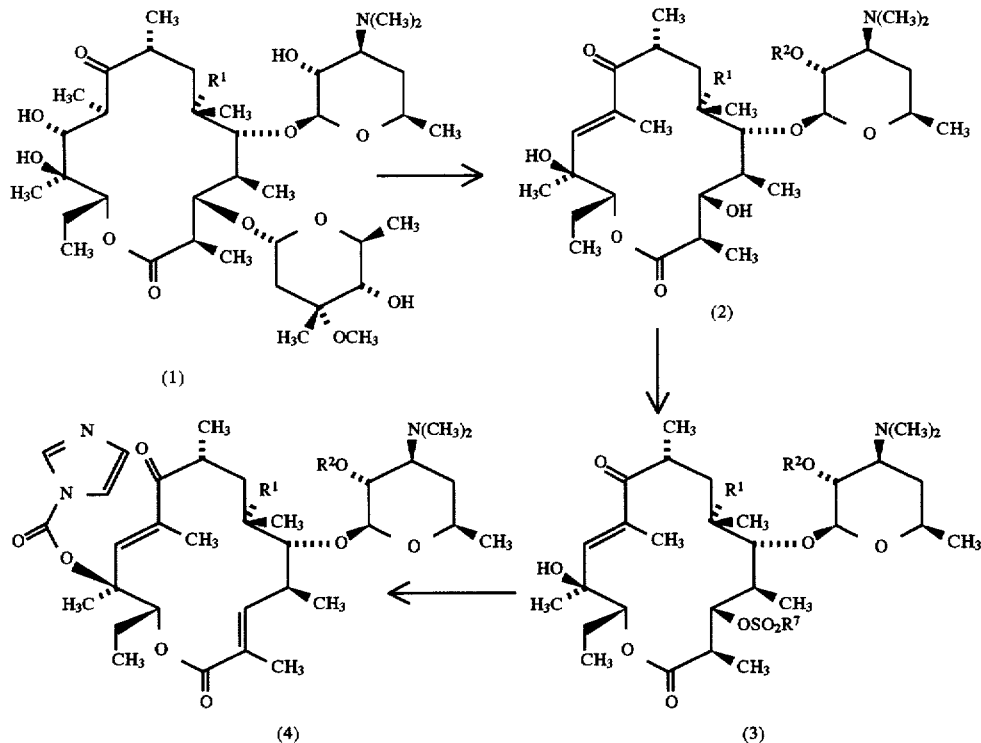

Scheme 1
Preparation of Intermediate Compound (4)

In accordance with Scheme I is prepared an intermediate compound 12-O-acylimidazolide-2,3 anhydroerythromycin compound (4) used as a starting material in Schemes 3–5 below. An erythromycin A compound (I) (wherein $R^1$ is hydrogen, protected hydroxy, O—$C_1$-$C_{12}$-alkyl, O—CO—$C_1$-$C_6$-alkyl, O—CO—$NH_2$, O—CO—NH—CO—$C_1$-$C_{12}$-alkyl, or O—CO—NH—$SO_2$—$C_1$-$C_{12}$-alkyl, and $R^2$=H or a hydroxy protecting group) is dehydrated at the 11-hydroxy position to form an intermediate compound (1a, not shown) having a C10-C11 double bond. The dehydration may be accomplished by treatment of compound (I) at reflux temperature in an aprotic solvent with an organocarbonate in the presence of base. Suitable organocarbonate compounds include, but are not limited to, ethylene carbonate, propylene carbonate, trimethylene carbonate, dipropyl carbonate, dibenzyl carbonate, isobutyl carbonate, dimethyl carbonate and diethyl carbonate. Suitable bases which may be utilized, include for example, triethylamine, diisopropylethylamine, pyridine, 2,6-dimethylpyridne, 1,8-diazabicyclo[5.4.0] undec-7-ene, N-methylmorpholine, N-methylpyrrolidine, N-methylpiperidine, sodium carbonate, potassium carbonate, sodium bicarbonate and potassium carbonate.

The cladinose sugar moiety is then removed from intermediate compound (1a) by the reaction with a dilute concentration of a strong acid at ambient temperature for about 0.5 to about 24 hours. Suitable strong acids include, but are organic solvent, such as ether, ethyl acetate or methylene chloride, for example, and the organic layer washed and dried. The compound is optionally isolated, but preferably is carried forward in solution.

The 2'-hydroxyl group is then protected by reaction with a suitable hydroxy group protecting reagent (cf. T. W. Greene and P. G. M. Wuts, *Protective Groups in Organic Synthesis*, 2nd ed., John Wiley & Son, Inc., 1991) such as acetyl chloride, acetic anhydride, benzoic anhydride, benzyl chloroformate, trimethylsilyl chloride or triethylsilyl chloride in an aprotic solvent that does not adversely affect the reaction, preferably methylene chloride, chloroform, dimethylformamide, tetrahydrofuran, N-methylpyrrolidinone or a mixture thereof, in the presence of a base such as triethylamine, with stirring at ambient temperature for 0.5 to 24 hours, for example. Preferably, a trialkylsilyl chloride or acetic anhydride is the protecting reagent. Extractive workup as before affords the desired 2'-protected macrolide of the formula (2) wherein $R^1$ is as above and $R^2$ is a hydroxy protecting group. When $R^1$ is a protected hydroxy group, it is preferred that the protecting group portion of it be the same as the $R^2$ protecting group.

Compounds of formula (2) are then reacted with a sulfonylating agent, such as methanesulfonyl anhydride, methanesulfonyl chloride, ethanesulfonyl chloride, or p-toluenesulfonyl chloride, in an aprotic solvent with stirring at from about 0° C. to ambient temperature for about 1 to about 24 hours. The crude product is isolated via an extractive workup similar to that described above to afford the desired 3-O-methanesulfonylated macrolide of the formula (3), wherein $R^7$ is an alkyl or aryl residue, such as methyl, ethyl or p-tolyl.

Treatment of compound (3) with a hydride base in the presence of carbonyldiimidazole in an aprotic solvent gives, after an extractive workup, the desired 12-O-acylimidazolide-2,3 anhydro macrolide (4). The hydride base may be, for example, sodium hydride, potassium hydride, or lithium hydride, and the aprotic solvent may be one as defined above. The reaction may require cooling or heating, depending on the conditions used. The reaction temperature may be from about −20° C. to about 70° C., and preferably from about 0° C to about room temperature. The reaction may require about 0.5 hours to about 10 days, and preferably about 1–5 days, to complete.

In an alternate process for compounds wherein $R^1$ is H, it is possible replace the sulfonylating and dehydrating steps described above with two different steps: first treatment with NaHMDS at from about −50° to to about −28° C. under an inert atmosphere followed by addition of carbonyldimidazole at from about 0° C. to about ambient temperature for about 15 minutes to about 6 hours, or until the reaction is complete. The compound (4) is obtained after quenching of the reaction and extraction of the product.

Scheme 2 provides for an alternate method of synthesis of the macrolide compound (4). Hydrolytic removal of the cladinose moiety from compound (1), wherein $R^1$ is as defined in Scheme I and $R^2$ is H is accomplished by the procedure described for Scheme 1, followed by protection of the 2'-hydroxyl group, also by the procedure of Scheme 1, affords the macrolide compound (5). When $R^1$ is a protected hydroxy group, it is preferred that the protecting group portion of it be the same as the $R^2$ protecting group.

Subsequent treatment of compound (5) with an excess of carbonylating reagent, such as phosgene, diphosgene, or triphosgene, for example, in an aprotic solvent followed by aqueous workup yields the 11,12-carbonate (5a, not shown) in which the 3-hydroxy group is unprotected.

Sulfonylation of the 3-hydroxy group of compound (5a) by procedures similar to those described above for macrolide compound (3) in Scheme I affords the desired compound (6) wherein $R^7$ is as defined in Scheme 1.

Treatment of compound (6) with a base in an aprotic solvent affords the diene macrolide (7). Suitable bases which may be utilized, include for example, triethylamine, diisopropylethylamine, pyridine, 2,6-dimethylpyridne, 1,8-diazabicyclo[5.4.0]undec-7-ene, N-methylmorpholine, N-methylpyrrolidine, N-methylpiperidine, sodium carbonate, potassium carbonate, sodium bicarbonate and potassium carbonate. Compound (7) can be treated with a hydride base and carbonyldiimidazole in an aprotic solvent to give the key intermediate macrolide (4).

In an alternate procedure for Scheme 2 wherein compound (1) is the 6-deoxy-erythromycin A compound ($R^1$ is H), removal of the cladinose residue from compound (1) and protection of the 2'-hydroxyl group to give the macrolide compound (5), wherein $R^1$ is H and $R^2$ is benzoyl follows the methods described above. However, the compound (5), wherein $R^1$ is H and $R^2$ is benzoyl may then be treated directly with an excess of sodium hexamethyldisilazane at −28° to −50° C. under an inert atmosphere, then with carbonyldiimidazole at 0° C. or at ambient temperature stirring for 15 minutes to 6 hours or until the reaction is complete to obtain the compound (4).

Scheme 2

Alternate Preparation of Intermediate Compound (4)

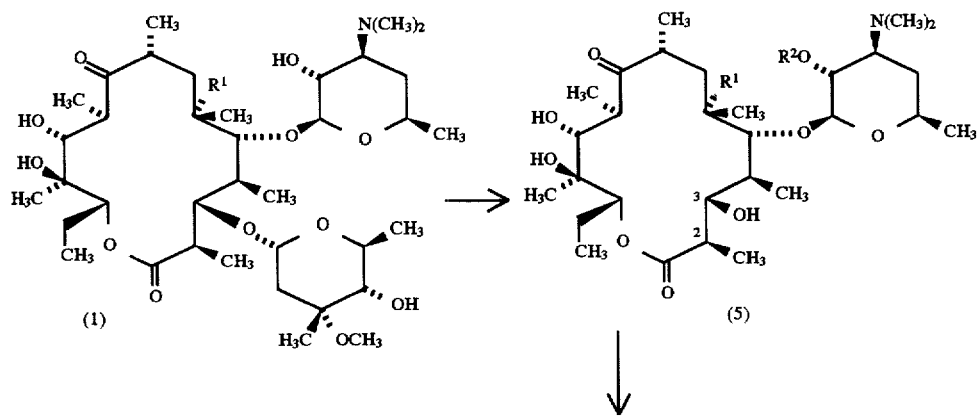

Scheme 2
Alternate Preparation of Intermediate Compound (4)
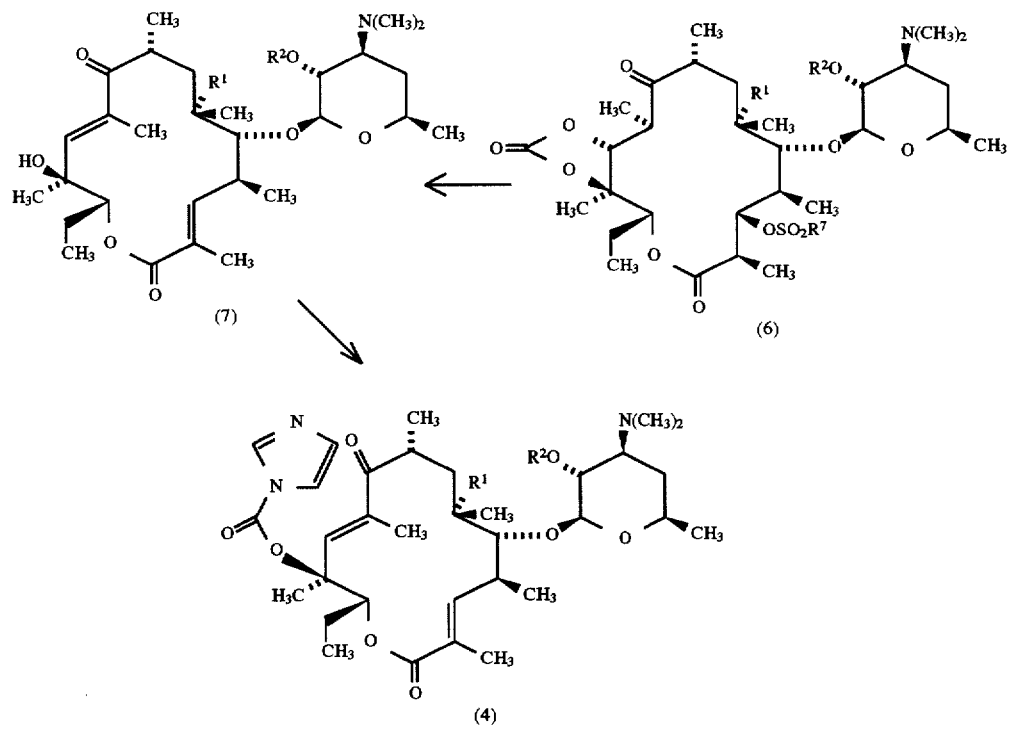
Scheme 3
Preparation of compounds of Formulas (I) and (II)
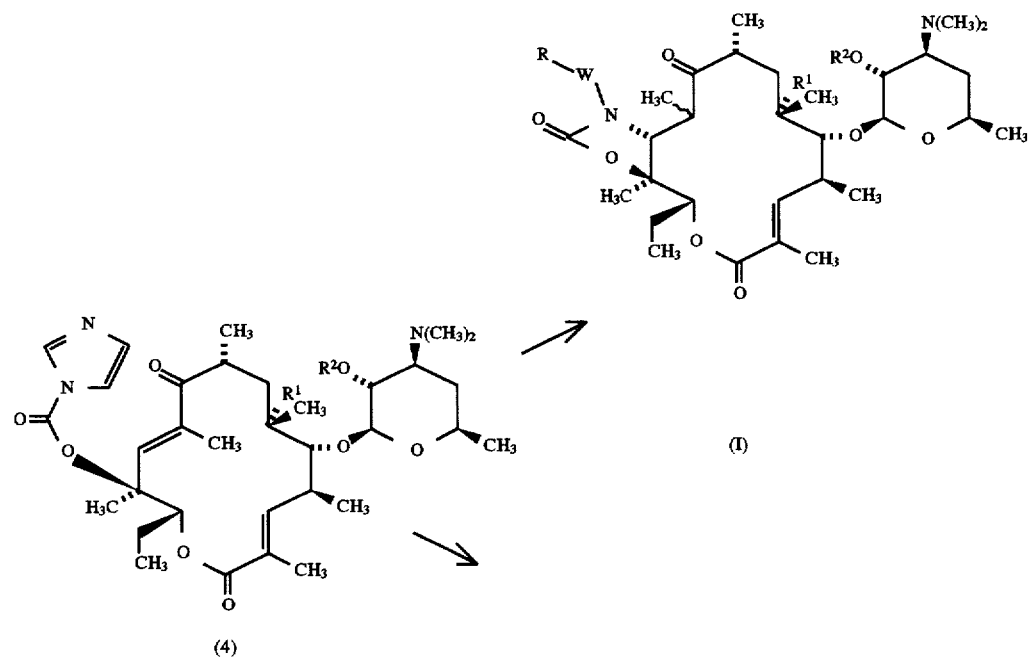

-continued
Scheme 3
Preparation of compounds of Formulas (I) and (II)

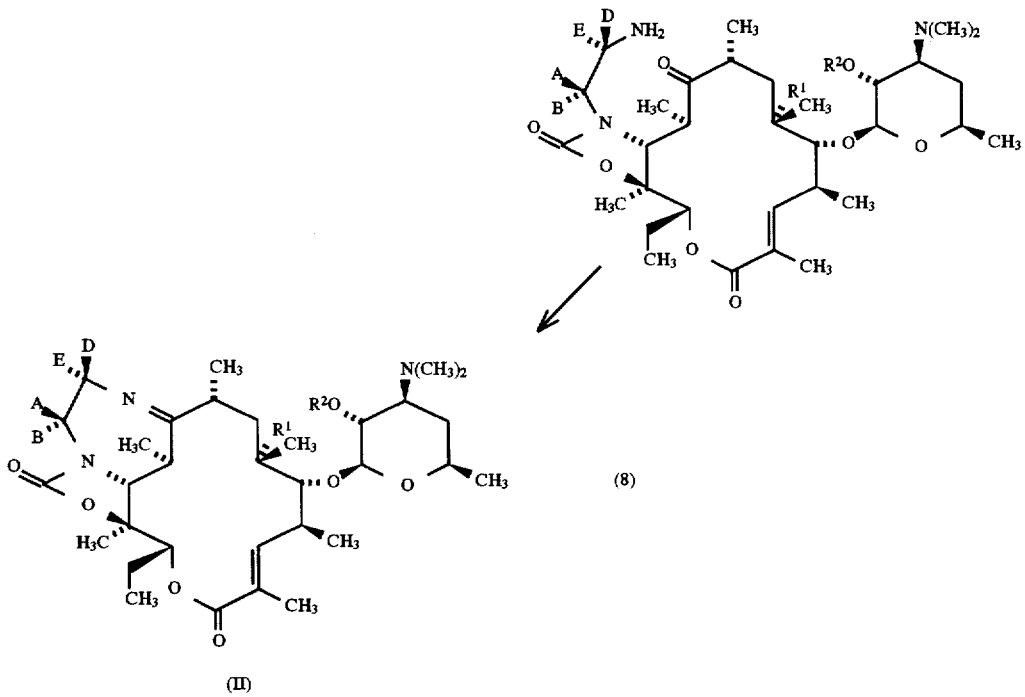

(II)

In accordance with Scheme 3 compound (4), wherein $R^1$ and $R^2$ are as defined in Scheme 1, is converted to desired compounds of the invention having Formulas (I) or (II).

To prepare a compound of Formula (I) wherein W is absent, compound (4) is reacted with a primary amine $RNH_2$ in a suitable solvent at room temperature to reflux temperature for about 4 to about 48 hours. Suitable solvents include alcohols such as methanol, ethanol, propanol, isopropanol, butanol, t-butanol, and the like, aprotic solvents such as methylene chloride, tetrahydrofuran, N-methylpyrrolidinone, diethyl ether, bis-methoxymethyl ether, dimethyl formamide, and acetone, for example, as well as aqueous mixtures thereof. Preferred solvents are aqueous acetonitrile, aqueous DMF, and aqueous acetone.

In the primary amine $RNH_2$ and in the resulting compound of Formula (I), R may be hydrogen, $C_1$–$C_6$-alkyl, $C_3$–$C_7$-cycloalkyl, aryl, substituted-aryl, heteroaryl or substituted-heteroaryl. When R is a $C_1$–$C_6$-alkyl substituent, the alkyl group may be optionally substituted with one or more substituents such as aryl, substituted-aryl, heteroaryl, substituted-heteroaryl, hydroxy, $C_1$–$C_6$-alkoxy, $NR^3R^4$, wherein $R^3$ and $R^4$ are independently selected from hydrogen and $C_1$–$C_6$-alkyl, or $NR^3R^4$, wherein $R^3$ and $R^4$ are taken with the nitrogen atom to which they are connected to form a 3- to 7-membered ring.

In the instance wherein the $NR^3R^4$ substituent is a 5- to 7-membered ring, the ring may optionally contain a hetero function consisting of —O—, —NH—, —N($C_1$–$C_6$-alkyl-)—, —N(aryl)—, —N(aryl-$C_1$–$C_6$-alkyl-)—, —N(substituted-aryl-$C_1$–$C_6$-alkyl-)—, —N(heteroaryl)—, —N(heteroaryl-$C_1$–$C_6$-alkyl-)—, —N(substituted-heteroaryl-$C_1$–$C_6$-alkyl-)—, —S— or —S(O)$_n$—, wherein n is 1 or 2. Additionally, when R is $C_1$–$C_6$-alkyl it may bear an optional substituent of the formula —$CH_2$—M—$R^5$, wherein M may be —C(O)—NH—, —NH—C(O)—, —NH—, —N═, —N($CH_3$)—, —O—, —S(O)$_n$—, wherein n is 0, 1 or 2, —CO—O—, —O—CO—, or —CO—; and $R^5$ may be aryl, substituted-aryl, heteroaryl, substituted-heteroaryl, heterocycloalkyl, or a $C_1$–$C_6$-alkyl optionally bearing one or more substituents such as aryl, substituted-aryl, heteroaryl, or substituted-heteroaryl. Chromatographic treatment of the crude reaction product affords both the natural and epi isomers at position C-10 of the molecule.

To prepare a compound wherein W is —NH—, compound (4) is reacted with a hydrazine reagent such as unsubstituted hydrazine or a substituted hydrazine in a solvent such as described immediately above to afford the desired compound of Formula (I). The natural and C-10 epimers of these compounds may be isolated from the reaction mixture.

Thus, treatment of compound (4) with unsubstituted hydrazine affords the compound of Formula (I) wherein W is —NH— and R is H.

Also, treatment of (4) with a substituted hydrazine $RR^4NNH_2$, wherein R is as defined for Formula (I) and $R^4$ is $C_1$–$C_6$-alkyl, gives the compounds of Formula (I) wherein W is —N($C_1$–$C_6$-alkyl)—.

Optionally, the compound of Formula (I) wherein W is —NH— and R is H can be treated with an R-acyl acylating agent, wherein R is as defined for Formula (I), to afford a compound of Formula (I) wherein W is —NH—CO—. The acylating agents can be, for example, an acid chloride, an acid fluoride, an acid anhydride, or a carboxylic acid in the presence of a carbodiimide coupling reagent such as carbonyldiimidazole or 1-(3-dimethylaminopropyl)-3-ethylcarbodiimide hydrochloride, for example, wherein R is as defined above.

Optionally, the compound of Formula (I) wherein W is —NH— and R is H can be treated with an aldehyde R—CHO, wherein R is as defined for Formula (I), to afford a compound of Formula (I) wherein W is —N═CH—.

Optionally, the compounds of Formula (I) wherein W is —N═CH— can be reduced to yield additional compounds of Formula (I) above, wherein W is —NH— using reducing reagents such as sodium cyanoborohydride, sodium borohydride, sodium triacetoxyborohydride, borane-tetrahydrofuran complex, and borane-piperidine complex, for example.

Also shown in Scheme 3 is the procedure by which compounds of Formula (I) wherein W is —O— and R is H or O—$C_1$–$C_6$-alkyl may be prepared. Under reaction conditions similar to those shown above for hydrazine reagents, treatment of compound (4) with unsubstituted hydroxylamine or an O—$C_1$–$C_6$-alkylated hydroxylamine affords the desired compound.

For example, treatment of compound (4) with an excess of hydroxylamine affords the compound of formula (I) wherein W is —O— and R is H.

Treatment of compound (4) with an O—$C_1$–$C_6$-alkylated hydroxylamine affords the desired compound of Formula (I) wherein W is —O— and R is $C_1$–$C_6$-alkyl.

Optionally, it is possible to further treat the compound of Formula (I) wherein W is —O— and R is H with a suitable base and an appropriate electrophile to prepared a compound wherein W is —O— and R is $C_1$–$C_6$-alkyl, $C_3$–$C_7$-cycloalkyl, aryl, substituted-aryl, heteroaryl or a substituted-heteroaryl group, wherein these terms are as defined for compounds of Formula (I) above. The base may be an alkali metal hydride or an organo-alkali metal compound, including but not limited to sodium hydride, potassium hydride, lithium hydride, lithium diethylamide, and butyllithium. The electrophile is a compound having the formula R-L, wherein R is as defined immediately above, and L is halide or another suitable leaving group, such as a methanesulfonyl or p-toluenesulfonyl moiety.

Optional deprotection of any of the compounds wherein W is —O— may be accomplished by standard methods as described by Wuts and Greene (op. cit.).

Compounds of Formula (II) may also be synthesized as outlined in Scheme 3. Thus, a starting material compound of formula (4) is reacted with a 1,2-diamine compound with a compound having the formula:

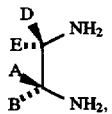

wherein A, B, D, and E are as defined above, in a suitable solvent at room temperature to reflux temperature for about 4 to about 48 hours to give the bicyclic compound of formula (8). The 1,2-diamine compound may have substituents A, B, D and E, as defined above for the compounds of Formula (II), but with $C_2$ or Cs symmetry or A=B=H. Suitable solvents include alcohols such as methanol, ethanol, propanol, isopropanol, butanol, t-butanol, and the like, aprotic solvents such as methylene chloride, tetrahydrofuran, N-methylpyrrolidinone, diethyl ether, bis-methoxymethyl ether, dimethyl formamide, and acetone, for example, as well as aqueous mixtures thereof. Preferred solvents are aqueous acetonitrile, aqueous DMF, and aqueous acetone.

The 2'-hydroxy protecting group on compound (8) is then removed by standard methods as described by Wuts and Greene (op. cit.). When $OR^2$ is an ester, for example, such as acetate or benzoate, the compound is preferably deprotected by treatment with methanol or ethanol. When $R^2$ is a trialkylsilyl group, the compound may be deprotected by treatment with fluoride in THF or acetonitrile. The reaction time required may be from about 1 to about 24 hours.

The deprotected compound of formula (8) wherein $R^2$ is H is then cyclized to give compounds of Formula (II) by treatment with a dilute concentration of a strong acid at ambient temperature to reflux temperature for about 4 hours to about 10 days in a suitable organic solvent. Suitable acids include, but are not limited to, hydrochloric acid, sulfuric acid, dichloroacetic acid, trichloroacetic acid and the like. The reaction may be accomplished with a suspension of the reagents in aqueous alcohol, such as for example, methanol, ethanol, propanol, iso-propanol, butanol, iso-butanol and t-butanol, for example.

Optional deprotection may be accomplished by standard methods as described by Wuts and Greene (op. cit.).

Scheme 4 illustrates an alternate preparation for compounds of formula (II). Starting material (4) is reacted with a compound having the formula:

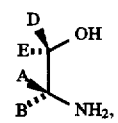

wherein A, B, D, and E are as defined above, in a suitable solvent at 0°–70 ° C. for about 4 to about 48 hours to give compound (9) where Y=OH. Suitable solvents are those such as methanol, ethanol, propanol, isopropanol, butanol, t-butanol, methylene chloride, tetrahydrofuran, N-methylpyrrolidinone, diethyl ether, bis-methoxymethyl ether, dimethyl formamide, acetone, aqueous acetonitrile, aqueous DMF, and aqueous acetone, for example.

Scheme 4
Alternate Preparation of compounds of Formula (II)

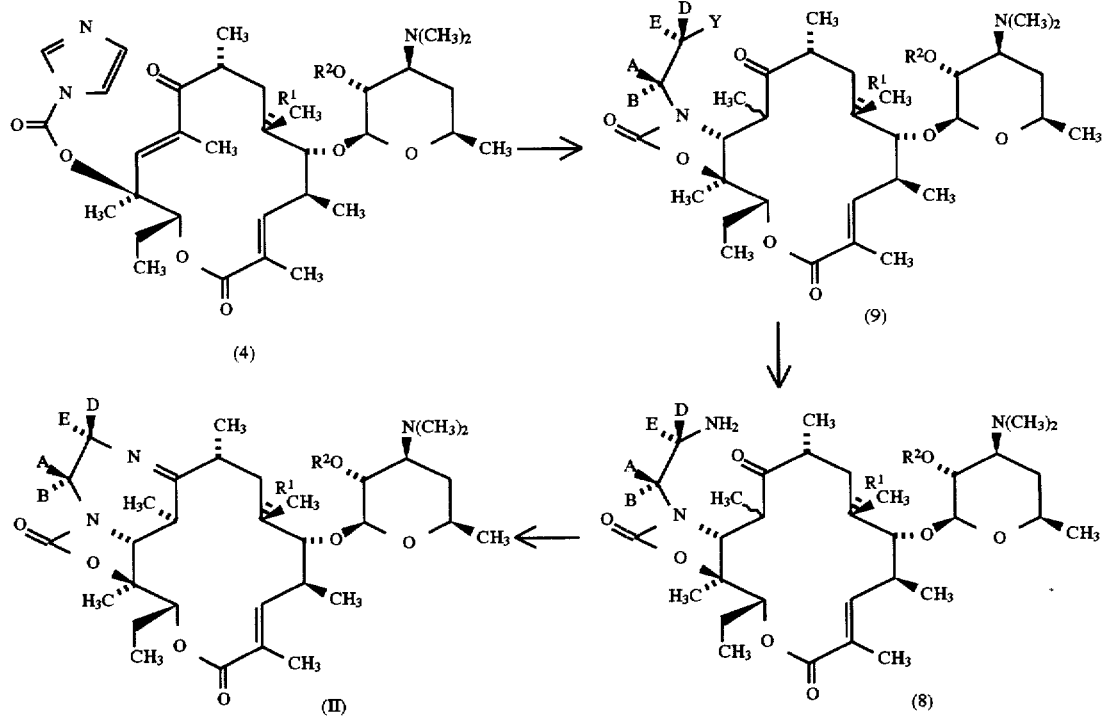

The azido intermediate, compound (9) Y=N₃, is prepared by Mitsunobu reaction by treating compound (9) wherein Y=OH with triphenylphosphine and diphenylphosphoryl azide-DEAD in tetrahydrofuran under Mitsunobu reaction conditions. Compound (9) wherein Y=N₃ is then deprotected by standard methods as described by Wuts and Greene (op. cit.). When OR² is an ester, for example, such as acetate or benzoate, the compound may be preferably deprotected by treatment with methanol or ethanol. When R² is a trialkylsilyl group, the compound may be deprotected by treatment with fluoride in THF or acetonitrile, for example.

The azido intermediate, compound (9) wherein Y=N₃, is then reduced to the amino compound (9) wherein Y=NH₂. Preferable reducing reagents are triphenylphosphine-water, hydrogen with a catalyst, sodium borohydride, or dialkylaluminum hydride.

Compound (9) wherein Y=NH₂ is then cyclized to prepare the compound of Formula (II) by treatment with a dilute concentration of a strong acid at ambient temperature to reflux temperature for about 4 hours to about 10 days in a suitable organic solvent.

Suitable acids include, but are not limited to, hydrochloric acid, sulfuric acid, dichloroacetic acid, trichloroacetic acid and the like. The reaction may be accomplished with a suspension of the reagents in aqueous alcohol, such as for example, methanol, ethanol, propanol, iso-propanol, butanol, iso-butanol and t-butanol, for example. This treatment also removes protecting groups at positions R¹ and R².

Alternately, the hydroxy group (Y=OH) in compound (9) may be activated by treatment with a sulfonating agent, such as sulfonyl chloride, alkyl or aryl sulfonic anhydride or trifluoromethanesufonic anhydride, in an aprotic solvent (e.g., diethyl ether, dichloromethane, tetrahydrofuran, chloroform, pyridine or a mixture thereof) to give the compound (9) wherein Y is a sulfonate ester. The reaction requires cooling or heating, depending on the conditions used. The reaction temperature is preferably −100° C. to 10° C.

The reaction may require 20 minutes to 24 hours to complete. The sulfonate ester activated hydroxy group in (9) (e.g. Y=—OSO₂CF₃) is then converted to an azide to give the second intermediate azide compound (9, Y=N₃) by reacting with an alkali metal azide, such as lithium azide or sodium azide, in the same solvent defined above. The reaction temperature is preferably about 0° C. to about 100° C. The azido compound is then converted to compound (8) according to the procedures described above.

As outlined in Scheme 5 below, the tricyclic macrolides of formula (II), wherein substituents A, B, D and E are as defined above, can be further transformed into macrolides having the formulas (III) and (IV). Treatment of the imine nitrogen atom of compound (II) with a suitable oxidizing agent, such as hydrogen peroxide or a carboxylic peracid, oxidizes the imine nitrogen to the nitrone and the nitrogen atom on the desosamine moiety to the N-oxide, to give an N-oxidized intermediate which is directly treated with a reducing agent such as triphenylphosphine or hydrogen in the presence of a catalyst, for example, to reduce the desosamine N-oxide, to give the desired compound of formula (III). Optional deprotection may be accomplished by standard methods as described by Wuts and Greene (op. cit.).

Macrolides of the formula (II) can also be treated with reducing agents such as sodium cyanoborohydride at pH 4–5 or sodium borohydride in a suitable organic solvent to yield the tricyclic amine of the formula (IVa), which is a compound of formula (IV) wherein R⁶ is H. Compounds of the formula (IVa) can be further transformed into compounds of type (IVb), which are compounds of formula (IV) wherein R⁶ is C₁–C₆-alkyl, via reductive alkylation of the amine with a reducing reagent, preferably sodium cyanoborohydride, sodium borohydride, sodium triacetoxyborohydride, borane-tetrahydrofuran complex, or borane-piperidine complex, in the presence of a $C_1$–$C_6$-alkyl-group precursor. Optional deprotection may be accomplished by standard methods as described by Wuts and Greene (op. cit.).

EXAMPLES

The procedures described above for preparing the compounds of the present invention will be better understood in connection with the following examples, which are intended as an illustration of and not a limitation upon the scope of the invention. Various changes and modifications to the dis-

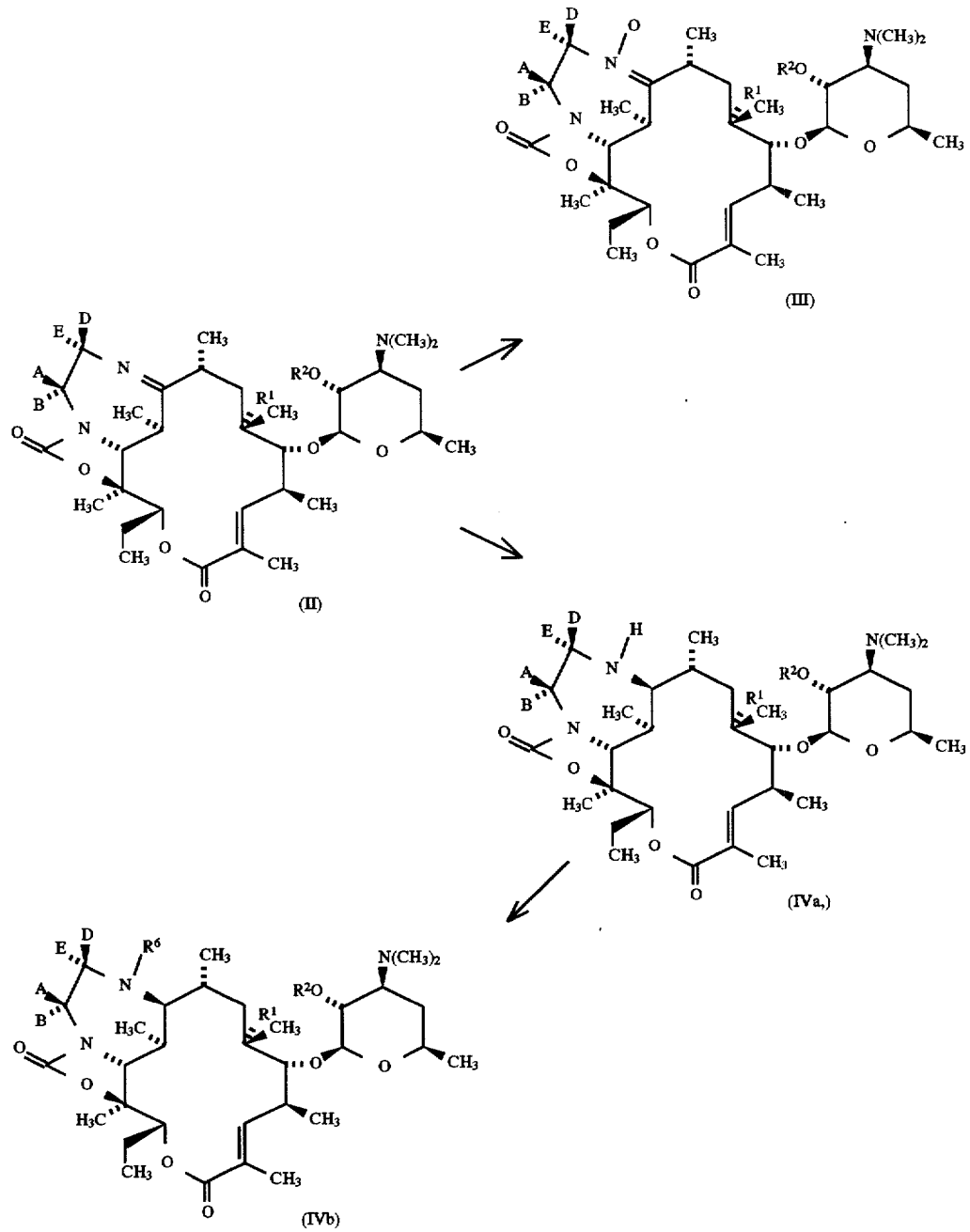

Scheme 5
Preparation of compounds (III) and (IV)

The compounds and processes of the present invention will be better understood in connection with the following examples, which are intended as an illustration of and not a limitation upon the scope of the invention.

closed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The NMR data for the central portion of the erythromycin compounds exemplified below are given in Table 1, which is placed after Example 133.

Example 1

Preparation Of Intermediate Compound (3)
(Scheme 1), $R^1$=OMe

Step 1a. Compound of Formula (2) Scheme 1, $R^1$=OMe: $R^2$=H

A suspension of Clarithromycin (MW=747.97, 98.48 g, 131.69 mmol, obtained from Abbott Laboratories), ethylene carbonate (50 mL) and triethylamine (200 mL) was refluxed for 29 hours, additional ethylene carbonate (~30 mL) was added, and the reaction mixture refluxed for an additional 18 hours. The triethylamine was removed in vacuo, 2% aqueous HCl (600 mL) and EtOH (50 mL) were added (pH=1-2), and the mixture was stirred at room temperature for 24 hours. Subsequent basification with 10% aqueous NaOH to pH ~12-14 yielded a precipitate. The aqueous layer was decanted, and the precipitate was taken up in EtOAc (500 mL), which was washed with 200-mL portions of saturated aqueous $NaHCO_3$, $H_2O$ and brine. The solution was dried ($MgSO_4$) and concentrated to afford the crude product as a light brown foam. Decolorization with charcoal and silica gave 65.94 g of the title compound (87%). MS m/z 572 $(M+H)^+$.

Step 1b. Compound of Formula (3) ($R^1$=OMe; $R^2$=$CH_3CO$)

A solution of the compound from step 1a (25.00 g, 43.72 mmol), acetic anhydride (8.25 mL, 87.45 mmol) and triethylamine (12.18 mL, 87.45 mmol) in $CH_2C_{12}$ (250 mL) was stirred at room temperature for 7 hours. Then the organic layer was washed with 100 mL portions of saturated aqueous $NaHCO_3$ (2 x), $H_2O$ (1 x), brine (1 x), dried ($MgSO_4$), and concentrated to afford the crude product as a brown foam (26.88 g, quantitative crude yield). MS m/z 614 $(M+H)^+$.

Step 1c. Compound of Formula (3) ($R^1$=OMe: $R^2$=$CH_3CO$)

A solution of the compound from step 1b (26.84 g, 43.72 mmol) and methanesulfonic anhydride (9.14 g, 52.47 mmol) in pyridine (40 mL) was stirred at room temperature for 24 hours. Then the pyridine was removed in vacuo, and the resulting solid was washed with 300-mL portions of saturated aqueous $NaHCO_3$ (2 x), $H_2O$ (1 x), and hexane (1 x) to afford the crude product as a brown solid (27.65 g, 91% crude yield). MS m/z 692(M+H)+.

Step 1d. Compound of Formula (4) ($R^2$=$CH_3CO$: $R^1$=OMe)

A solution of the compound from step 1c (5.00 g, 7.22 mmol) in a mixture of DMF (45 mL) and THF (15 mL) was treated with CDI (5.86g, 36.1 mmoL) followed by NaH (1.15 g, 60 wt %, 28.9 mmoL) at 0° C. under $N_2$. The cooling bath was removed, and the reaction mixture was stirred at room temperature for 2 hours. The reaction mixture was then slowly quenched into a mixture of saturated aqueous $NaHCO_3$ (150 mL) and EtOAc (300 mL). The layers were separated, and the aqueous layer was washed with an additional portion of EtOAc (150 mL), then the combined organic layer was washed with 150-mL portions of $H_2O$ (3 x) and brine (3x) and dried ($MgSO_4$). The solvent was removed to afford the crude product as a white solid (5.28 g, theory=4.98 g). MS m/z 590 $(M-112)^+$.

Example 2

Compound of Formula (I): $R^1$=H $R^2$=H: W is absent: R=4-phenylbutyl

Step 2a. Compound (5) (Scheme 2), $R^1$=H: $R^2$=H

6-Deoxyerythromycin A (50 g, 72 mmol, obtained from by the procedures of McAlpine, et al., 30th Interscience Conference on Antimicrobial Agents, Atlanta, US, (1990), Abstract No. 810 and Webber, et al., Science 252: 114–117 (1991)) was suspended in 570 mL of water and 145 mL of 1N HCl was added. The compound went into solution within a few minutes, and the solution was stirred at room temperature for 16 hours. The reaction mixture was made basic by addition of 145 mL of 1N NaOH, and the resulting precipitate was removed by filtration. This material was resuspended in water and refiltered. $CHCl_3$ (400 mL) was added, and to the resulting emulsion was added 200 mL of saturated brine and 200 mL of $NaHCO_3$. The organic layer was separated, and the emulsion was re-extracted with three additional portions of $CHCl_3$. The extracts were combined and dried over $Na_2SO_4$. The solvent was removed and the residue dried under high vacuum to afford 24 g of crude product.

Step 2b. Compound (5) (Scheme 1). $R^1$=H; $R^2$=benzoyl

The compound from step 2a (24 g, 44 mmol) was dissolved in dry methylene chloride (200 mL), triethylamine (122 mL, 88 mmol) and benzoyl anhydride (20 g, 88 mmol) were added, and the mixture was stirred under $N_2$ for 15 hours. The reaction was quenched by addition of 200 mL of saturated $NaHCO_3$ solution, and the resulting mixture was extracted with methylene chloride (2×100 mL). The extracts were combined, washed with water and brine, and dried over $Na_2SO_4$. The solvent was removed, and the residue was flash chromatographed on silica gel, eluting with 1:1 to 3:1 ethyl acetate:hexane to afford the title compound (4.06 g).

Step 2c. Compound (4) (Scheme 2): $R^1$=H, $R^2$=benzoyl

The compound from step 2b (541 mg, 0.816 mmol) was dissolved in X mL of THF under nitrogen, and the solution was cooled to −40° C. in an acetone/dry ice bath. NaHMDS (1.6 mL, 1.6 mmol) was added dropwise with stirring over a 3 minute period. The reaction mixture was stirred for 10 minutes, then CDI (560 mg, 3.46 mmol, dissolved in 12 mL of THF) was added over a 15 minute interval. The reaction mixture was stirred for 5 hours at ambient temperature, then cooled to 0° C. and quenched with 25 mL of 5% aqueous $KH_2PO_4$ solution. The mixture was extracted with ethyl acetate (2×40 mL), and the extract was washed with brine and dried over $Na_2SO_4$. The solvent was removed, and the residue was flash chromatographed on silica gel, eluting with 1:1 to 0:1 hexane/acetone to afford 230 mg of the title compound.

Step 2d. Compound (I) (Scheme 3); $R^1$=H: $R^2$=benzoyl: W is absent: R=4-phenylbutyl The compound from step 2c (180 mg, 0.250 mmol) was dissolved in 0.9 mL of acetonitrile and 0.1 mL of water. To this solution was added 4-phenylbutylamine (0.300 mL, 1.90 mmoL, Aldrich), and the reaction mixture was stirred at 50° C. under nitrogen for 5.5 hours. The reaction mixture was cooled to room temperature and diluted with 30 mL of methylene chloride. The solution was washed with 5% aqueous $KH_2PO_4$ solution and brine and dried over $Na_2SO_4$. The solvent was removed, and the residue was flash chromatographed on silica gel, eluting with 15 to 20 % acetone/hexane to afford 73 mg of the title compound.

Step 2e. Compound of Formula (I): $R^1$=H; $R^2$=H, W is absent; R=4-phenylbutyl The compound from step 2d (70 mg) was dissolved in 5 mL of methanol, and the solution was stirred at room temperature for 14 hours. The solvent was removed, and the residue was flash chromatographed on silica gel, eluting with 5% methanol in methylene chloride to afford the title compound. MS m/z 699 (M+H)$^+$. Anal.Calcd. for C$_{40}$H$_{62}$N$_2$O$_9$: C, 68.74; H, 8.94; N, 4.01; Found: C, 68.57; H, 8.91; N, 3.88.

Example 3

Compound of Formula (1); R$^1$=-methoxy; R$^2$=H; W is absent; R=4-phenylbutyl

Step 3a. Compound of Formula (I); R$^1$=methoxy; R$^2$=acetyl; W is absent, R=4-phenylbutyl The title compound of Example 1 (231 mg, 0.334 mmol) and 4-phenylbutylamine (0.177 mL, 1.105 mmol, Aldrich) were dissolved in 3 mL of DMF, and the solution was stirred at room temperature for 24 hours. The solution was diluted with ethyl acetate (40 mL), washed with 30 mL portions of water and brine, then dried over MgSO$_4$. The solvent was removed. The residue was flash chromatographed on silica gel, eluting with hexane—25% acetone/hexane, to afford the title compound (147 mg, 57% yield). MS m/z 771 (M+H)$^+$.

Step 3b. Compound of Formula (I); R$^1$=methoxy; R$^2$=H; W is absent; R=4-phenylbutyl The compound from step 3a (140 mg) was dissolved in 5 mL of methanol, and the solution was stirred at room temperature for 40 hours. The solvent was removed, and the residue was flash chromatographed on silica gel, eluting with 0–4 % methanol in methylene chloride to afford the title compound (50 mg, 37% yield). MS m/z 729 (M+H)$^+$.

Anal.Calcd. for C$_{41}$H$_{64}$N$_2$O$_9$: C, 67.55; H, 8.85; N, 3.84; Found: C, 67.17; H, 8.95; N, 3.66.

Example 4

Compound of Formula (I); R$^1$=methoxy; R$^2$=H; W is absent R=3-phenoxypropyl

Step 4a. ompound of Formula (I); R$^1$=methoxy; R$^2$=acetyl: W is absent, R=3-phenoxypropyl The title compound of Example 1 (1.00 g, 1.45 mmol) was dissolved in 3 mL of acetonitrile, 3-phenoxypropylamine (1.1 g, 7.28 mmol, prepared in a manner similar to that described by K. Smith, et al., *J. Chem. Soc. Petkin Trans. I,* (1988) 77–83) and 0.3 mL of water were added, and the reaction mixture was stirred for 21 hours. The solution was diluted with ethyl acetate (100 mL), washed with 5% aqueous KH$_2$PO$_4$, water and brine, then dried over Na$_2$SO$_4$. The solvent was removed. The residue was flash chromatographed on silica gel, eluting with 1:2 acetone/hexane, to afford the title compound (490 mg). MS m/z 773 (M+H)$^+$.

Step 4b. Compound of Formula (I); R$^1$=methoxy; R$^2$=H, W is absent; R=3-phenoxypropyl The compound from step 4a (400 mg) was dissolved in 20 mL of methanol, and the solution was stirred at room temperature for 27 hours. The solvent was removed, and the residue was flash chromatographed on silica gel, eluting with 4% methanol in methylene chloride containing 0.1% NH$_4$OH to afford the title compound (237 mg). MS m/z 731 (M+H)+. Anal.Calcd. for C$_{40}$H$_{62}$N$_2$O$_{10}$: C, 65.73; H, 8.55; N, 3.83; Found: C, 65.47; H, 8.71; N, 3.66.

Example 5

Compound of Formula (I); R$^1$=methoxy; R$^2$=H; W is absent; R=2-((phenylmethyl)amino)ethyl Step 5a. Compound of Formula (I); R$^1$=methoxy; R$^2$=acetyl; W is absent, R=2-((phenylmethyl)amino)ethyl The title compound of Example 1 (500 mg, 0.724 mmol) was added to a solution of N-benzylethylenediamine (0.5 g, 3.33 mmol, Eastman) in 1.5 mL of acetonitrile and 0.15 mL of water, and the reaction mixture was stirred for 40 hours. The solution was diluted with methylene chloride, washed with 5% aqueous KH$_2$PO$_4$, water and brine, then dried over Na$_2$SO$_4$. The solvent was removed. The residue was flash chromatographed on silica gel, eluting with 3% methanol in methylene chloride containing 0.1% NH$_4$OH, to afford the title compound (151 mg). MS m/z 772 (M+H)$^+$.

Step 5b. Compound of Formula (I); R$^1$=methoxy; R$^2$=H, W is absent; R=2-((phenylmethyl)amino)ethyl The compound from step 5a (145 mg) was dissolved in 10 mL of methanol, and the solution was stirred at room temperature for 27 hours. The solvent was removed, and the residue was flash chromatographed on silica gel, eluting with 3.5–5% methanol in methylene chloride containing 0.1% NHO$_4$H to afford the title compound (118 mg). The NMR was consistent with the C-10 epimeric form of this compound. MS m/z 730 (M+H)$^+$. Anal.Calcd. for C$_{40}$H$_{63}$N$_3$O$_9$: C, 65.82; H, 8.70; N, 5.76; Found: C, 65.58; H, 8.66; N, 5.76.

Example 6

Compound of Formula (1); R$^1$=methoxy; R$^2$=H: W is absent: R=3-(N-methyl—N-phenylamino) propyl Step 6a. Compound of Formula (I); R$^1$=methoxy; R$^2$=acetyl: W is absent: R=3-(N-methyl—N-phenylamino)propyl The title compound of Example 1 (500 mg, 0.724 mmol) was dissolved in 1.5 mL of acetonitrile, N-(3-aminopropyl) —N-methylaniline (0.50 g, 3.05 mmol, TCI) and 0.15 mL of water were added, and the reaction mixture was stirred for 16 hours. The solution was diluted with ethyl acetate (50 mL). This solution was then washed with 5% aqueous KH$_2$PO$_4$, water and brine, and dried over Na$_2$SO$_4$. The solvent was removed, and the residue was flash chromatographed on silica gel, eluting with 2.5% methanol/methylene chloride, to afford the title compound (410 mg). MS m/z 786 (M+H)$^+$.

Step 6b. Compound of Formula (1); R$^1$=methoxy; R$^2$=H: W is absent: R=3-(N-methyl—N-phenylamino) propyl The compound from step 6a (398 mg) was dissolved in 10 mL of methanol, and the solution was stirred at room temperature for 16 hours. The solvent was removed, and the residue was flash chromatographed on silica gel, eluting with 4% methanol in methylene chloride containing 0.2% NH$_4$OH to afford the title compound (205 mg), which was recrystallized from hexane/ethyl acetate (120 mg). mp 155°–156° C. MS m/z 744 (M+H)$^+$. Anal.Calcd. for C$_{41}$H$_{65}$N$_3$O$_9$: C, 66.19; H, 8.81; N, 5.65; Found: C, 66.38; H, 8.87; N, 5.49.

Example 7

Compound of Formula (I); R$^1$=methoxy; R$^2$=H: W is absent: R=3-(4-chlorophenoxy)propyl Step 7a. Compound of Formula (I); R$^1$=methoxy; R$^2$=acetyl, W is absent: R=3-(4-chlorophenoxy)propyl The title compound of Example 1 (500 mg, 0.726 mmol) was dissolved in 3 mL of acetonitrile, 3-(4-chlorophenoxy) propylamine (470 mg, 2.53 mmol, prepared in a manner similar to that described by K. Smith, et al., J. Chem. Soc. Perkin Trans. I, (1988) 77–83) and 0.3 mL of water were added, and the reaction mixture was stirred for 19 hours. The solution was diluted with ethyl acetate (100 mL). This solution was washed with 5% aqueous $KH_2PO_4$, water and brine, then dried over $Na_2SO_4$. The solvent was removed. The residue was flash chromatographed on silica gel, eluting with 3% methanol in methylene chloride containing 0.1% $NH_4OH$, to afford the title compound (328 mg). MS m/z 807 $(M+H)^+$.

Step 7b. Compound of Formula (I); $R^1$=methoxy; $R^2$=H; W is absent, R=3-(4-chlorophenoxy)propyl The compound from step 7a (322 mg) was dissolved in 100 mL of methanol, and the solution was stirred at room temperature for 21 hours. The solvent was removed, and the residue was flash chromatographed on silica gel, eluting with 4% methanol in methylene chloride containing 0.1% $NH_4OH$ to afford the title compound (162 mg), which was recrystallized from hexane/ethyl acetate. mp 183.5°–185° C. MS m/z 765 $(M+H)^+$. Anal.Calcd. for $C_{40}H_{61}ClN_2O_{10}$: C, 62.77; H, 8.03; N, 3.66; Found: C, 62.78; H, 8.17; N, 3.53.

Example 8

Compound of Formula (II), $R^1$=methoxy; $R^2$=H; A=B=C=D=H

Step 8a. Compound of Formula (I); W absent; $R^1$=methoxy; $R^2$=acetyl; A=B=C=D=H The title compound of Example 1 (2.0 g, 7.899 mmol) was dissolved in 5 mL of DMF, ethylenediamine (2 mL, Aldrich) was added, and the reaction mixture was stirred for 22.5 hours. The solution was diluted with ethyl acetate (60 mL), and this solution was washed with water and brine, then dried over $MgSO_4$. The solvent was removed to afford the title compound, which was used without further purification. MS m/z 682.

Step 8b. Compound of Formula (II): $R^1$=methoxy; $R^2$=H; A=B=C=D=H

A solution of the compound from step 8a, dissolved in 6 mL of methanol, was stirred at room temperature for 19 hours. This residue was purified by chromatography on silica gel, eluting with 5% methanol/1% triethylamine/ $CHCl_3$. The material was rechromatographed eluting with 5% methanol/$CHCl_3$ to afford the title compound (138 mg). mp 183.5°–185° C. MS m/z 622 (M+H)+. Anal.Calcd. for $C_{33}H_{55}N_3O_8 \cdot H_2O$: C, 61.95; H, 8.98; N, 6.57; Found: C, 62.22; H, 8.83; N, 6.50.

Example 9

Compound of Formula (I); $R^1$=methoxy: $R^2$=H; W is absent; R=3-(8-quinoyloxy)propyl Step 9a. Compound of Formula (I); $R^1$=methoxy; $R^2$=acetyl: W is absent; R=3-(8-quinoyloxy)propyl The title compound of Example 1 (508 mg, 0.737 mmol) was dissolved in 3 mL of 10% aqueous acetonitrile containing 3-(1-naphthyloxy)propylamine (500 mg, 2.5 mmol, prepared in a manner similar to that described by K. Smith, et al., J. Chem. Soc. Perkin Trans. 1, (1988) 77–83). The reaction mixture was stirred for 21.5 hours, then diluted with ethyl acetate (100 mL), washed with 5% aqueous $KH_2PO_4$, water and brine, then dried over $Na_2SO_4$. After removal of solvent the residue was flash chromatographed on silica gel, eluting with 3% methanol in methylene chloride containing 0.1% $NH_4OH$, to afford the title compound (495 mg). MS m/z 824 $(M+H)^+$.

Step 9b. Compound of Formula (I); $R^1$=methoxy; $R^2$=H: W is absent; R=3-(8-quinoyloxy)propyl The compound from step 9a (485 mg) was dissolved in 20 mL of methanol, and the solution was stirred at room temperature for 18 hours. The solvent was removed, and the residue was flash chromatographed on silica gel, eluting with 5% methanol in methylene chloride containing 0.1% $NH_4OH$ to afford the title compound (218 mg), which was recrystallized from hexane/ethyl acetate. mp 168°–170° C. MS m/z 782 $(M+H)^+$. Anal.Calcd. for $C_{43}H_{63}N_3O_{10}$: C, 66.05; H, 8.12; N, 5.37; Found: C, 66.02; H, 8.21; N, 5.28.

Example 10

Compound of Formula (I); $R^1$=methoxy; $R^2$=H; W is absent: R=4-(4-chlorophenyl)-3(Z)-butenyl Step 10a. Compound of Formula (1); $R^1$=methoxy; $R^2$=acetyl, W is absent: R=4-(4-chlorophenyl)-3-butenyl The title compound of Example 1 (750 mg) was dissolved in 4 mL of 10% aqueous acetonitrile containing 4-(4-chlorophenyl)-3-buteneamine (0.5 mL, prepared in a manner similar to that described by D. Olsen, et al., J. Org. Chem. (1980) 45, 4049–4052), and the reaction mixture was stirred for 12 hours. The solution was diluted with ethyl acetate (100 mL), washed with saturated aqueous $NH_4Cl$ and brine, then dried over $Na_2SO_4$. The solvent was removed, and the residue was flash chromatographed on silica gel, eluting with 2.5% methanol in methylene chloride containing 0.1% $NH_4OH$, to afford the title compound (513 mg).

Step 10b. Compound of Formula (I); $R^1$=methoxy; $R^2$=H: W is absent, R=4-(4-chlorophenyl)-3-butenyl The compound from step 10a (513 mg) was dissolved in 50 mL of methanol, and the solution was stirred at room temperature for 1 hours. The solvent was removed, and the residue was flash chromatographed on silica gel, eluting with 3.5% methanol in methylene chloride containing 0.1% $NH_4OH$ to afford the title compound (200 mg), which was recrystallized from hexane/ethyl acetate (120 mg). mp 180°–182.5° C. MS m/z 761 $(M+H)^+$. Anal.Calcd. for $C_{41}H_{61}ClN_2O_9$: C, 64.68; H, 8.08; N, 3.68; Found: C, 64.75; H, X.14; N, 3.45.

Example 11

Compound of Formula (II) $R^1$=methoxy; $R^2$=H: W is absent; R=2-phenylethyl

Step 11a. Compound of Formula (I); $R^1$=methoxy; $R^2$=acetyl: W is absent: R=2-phenylethyl The title compound of Example I (500 mg, 0.724 mmol) was dissolved in 3 mL of 10% aqueous acetonitrile containing 2-phenylethylamine (0.5 mL, 3.62 mmol, Aldrich), and the reaction mixture was stirred for 16 hours. The solution was diluted with ethyl acetate (100 mL), and this solution was washed with saturated aqueous 5% aqueous $KH_2PO_4$, water and brine, then dried over $Na_2SO_4$. The solvent was removed, and the residue was taken directly to the next step.

Step 11b. Compound of Formula (I); $R^1$=methoxy $R^2$=H: W is absent, R=2-phenylethyl The compound from step 11a was dissolved in 10 mL of methanol, and the solution was stirred at room temperature for 18 hours. The solvent was removed, and the residue was flash chromatographed on silica gel, eluting with 4% methanol in methylene chloride containing 0.1% $NH_4OH$ to afford the title compound. MS m/z 701 (M+H)+. Anal.Calcd.

$C_{39}H_{60}N_2O_9$: C, 66.83; H, 8.62; N, 3.99; Found: C, 66.80; H, 8.58; N, 3.97.

Example 12

Compound of Formula (I); $R^1$=methoxy; $R^2$=H: W is absent; R=2-(3,4-dichlorophenyl)ethyl Step 12a. Compound of Formula (I); $R^1$=methoxy; $R^2$=acetyl; W is absent; R=2-(3,4-dichlorophenyl)

The title compound of Example 1 (500 mg, 0.724 mmol) was dissolved in 5 mL of 10% aqueous acetonitrile containing 2-(3,4-dichlorophenyl)ethyl amine (0.7 g, 3.62 mmol, Aldrich), and the reaction mixture was stirred for 72 hours. The solution was diluted with ethyl acetate (100 mL), and this solution was washed with saturated aqueous 5% aqueous $KH_2PO_4$, water and brine, then dried over $Na_2SO_4$. The solvent was removed, and the residue was taken directly to the next step.

Step 12b. Compound of Formula (I); $R^1$=methoxy; $R^2$=H; W is absent: R=2-(3,4-dichlorophenyl)ethyl The compound from step 12a was dissolved in 10 mL of methanol, and the solution was stirred at room temperature for 16 hours. The solvent was removed, and the residue was flash chromatographed on silica gel, eluting with 4% methanol in methylene chloride containing 0.1% $NH_4OH$ to afford the title compound. MS m/z 769 (M+H)+. Anal.Calcd. for $C_{39}H_{59}Cl_2N_2O_9$: C, 60.85; H, 7.59; N, 3.63; Found: C, 60.22; H, 7.19; N, 3.63.

Example 13

Compound of Formula (I); $R^1$=methoxy: $R^2$=H: W is absent; R=phenylmethyl

Step 13a. Compound of Formula (I); R=-methoxy; $R^2$=acetyl: W is absent: R=phenylmethyl The title compound of Example 1(500 mg, 0.724 mmol) was dissolved in 5 mL of 10% aqueous acetonitrile containing benzylamine (0.4 g, 3.62 mmol, Aldrich), and the reaction mixture was stirred for 16 hours. The solution was diluted with ethyl acetate (100 mL), and this solution was washed with saturated aqueous 5% aqueous $KH_2PO_4$, water and brine, then dried over $Na_2SO_4$. The solvent was removed, and the residue was taken directly to the next step.

Step 13b. Compound of Formula (I); $R^1$=methoxy; $R^2$=H; W is absent; R=phenylmethyl The compound from step 13a was dissolved in 10 mL of methanol, and the solution was stirred at room temperature for 18 hours. The solvent was removed, and the residue was flash chromatographed on silica gel, eluting with 4% methanol in methylene chloride containing 0.1% $NH_4OH$ to afford the title compound (83mg). MS m/z 6 (M+H)+. Anal.Calcd. for $C_{38}H_{58}CN_2O_9$: C,66.44; H, 8.51; N,4.07; Found: C, 66.23; H, 8.19 ; N, 4.21.

Example 14

Compound of Formula (I): $R^1$=methoxyl $R^2$=H: W is —NH-, R=3-phenylpropyl

Step 14a. Compound (I) of Scheme 1: $R^1$=methoxy; $R^2$=H: W is —NH—; R=H

The title compound of Example 1 (2.0 g, 2.90 mmol) was dissolved in 10 mL of DMF, hydrazine (0.225 mL, 7.18 mmol, Aldrich) was added, and the reaction mixture was stirred for 0.5 hours. The solution was diluted with methylene chloride (125 mL), and this solution was washed with saturated aqueous 5% aqueous $KH_2PO_4$, water and brine, then dried over $Na_2SO_4$. The solvent was removed, and the residue was dissolved in methanol and allowed to stand for 16 hours. The solvent was removed, and the residue was flash chromatographed on silica gel, eluting with 2.5% methanol in t-butyl methyl ether containing 0.5% $NH_4OH$, to afford the mixture of compounds. The solvent was removed, and the residue was again flash chromatographed on silica gel, however eluting with 5% methanol in methylene chloride containing 0.1% $NH_4OH$ to 10% methanol in methylene chloride containing 0.2% $NH_4OH$ to give the title compound (0.19 g). MS m/z 612 (M+H)+.

Step 14b. Compound of Formula (I); $R^1$=methoxy: $R^2$=H; W is —N=—R=phenylethyl-CH=

The compound from step 14a was dissolved in toluene (5 mL), 3-phenylpropanal (0.200 mL, Aldrich) and 4A molecular sieves were added, and the reaction mixture was stirred for 48 hours. An additional portion of 3-phenylpropanal was added, and the reaction mixture was stirred for an additional 6 hours. The mixture was filtered, the solvent was removed, and the residue was flash chromatographed on silica gel, eluting with 4% methanol/methylene chloride containing 0.1 % $NH_4OH$ to give the title compound (181 mg). MS m/z 728 (M+H)+.

Step 14c. Compound of Formula (I); $R^1$=methoxy: $R^2$=H: W is —NH—; R=3-phenylpropyl The compound from step 14b (170 mg, 0.234 mmol) was dissolved in 5 mL of methanol, $NaBH_3CN$ (30 mg, 0.47 mmol) was added, and the solution was stirred at room temperature for 4.5 hours. Saturated aqueous $NaHCO_3$ was added, and the mixture was extracted with methylene chloride. The extract was washed with saturated aqueous $NaHCO_3$, water and brine, then dried over $Na_2SO_4$. The solvent was removed, and the residue was flash chromatographed on silica gel, eluting with 5% methanol in methylene chloride containing 0.1% $NH_4OH$ to afford the title compound (135 mg). MS m/z 730 (M+H)+. Anal.Calcd. for $C_4OH_{63}N_3O_9$: C, 65.82; H, 8.70; N, 5.76; Found: C, 65.97:, H, 8.79; N, 5.64.

Example 15

Compound of Formula (I); $R^1$=methoxy; $R^2$=H; W is absent: R=3-(4-phenoxyphenyl)ethyl Step 15a. Compound of Formula (I); $R^1$=methoxy; $R^2$=acetyl; W is absent; R=3-(4-phenoxyphenyl)propyl The title compound of Example 1 (0.4 mg, 0.0.58 mmol) was dissolved in 5 mL of 10% aqueous acetonitrile containing 2-(4-(phenoxy)phenyl)ethylamine (0.618 g, 2.89 mmol, Trans World Chemicals), and the reaction mixture was stirred for 20 hours. The solution was diluted with ethyl acetate (100 mL), and this solution was washed with 5% $NaH_2PO_4$, water and brine, then dried over $Na_2SO_4$. The solvent was removed, and the residue was flash chromatographed on silica gel, eluting with 1–2% ethanol in chloroform to afford the title compound (270 mg), mixture of natural and epi isomers.

Step 15b. Compound of Formula (I); $R^1$=methoxy; $R^2$=H; W is absent; R=3-(4-phenoxyphenyl)ethyl The compound from step 15a (80 mg) was dissolved in 5 mL of methanol, and the solution was stirred at room temperature for 20 hours. The solvent was removed, and the residue was flash chromatographed on silica gel, eluting with 4% methanol in methylene chloride to afford the title compound (19 mg) as a mixture of natural and epi isomers. MS m/z 793 (M+H)+. Anal. Calcd. for $C_{45}H_{64}N_2O_{10}$: C, 68.15; H, 8.13; N, 3.53; C, 68.23; H, 8.15; N, 3.62.

Example 16

Compound of Formula (I); $R^1$=methoxy; $R^2$=H:
W is absent; R=3-phenylpropyl

Step 16a. Compound of Formula (I); $R^1$=methoxy; $R^2$=acetyl; W is absent; R=3-phenylpropyl The title compound of Example 1 (500 mg, 0.724 mmol) was dissolved in 5 mL of 10% aqueous acetonitrile containing 3-phenyl-1-propylamine (0.5 mL, 3.62 mmol, Aldrich), and the reaction mixture was stirred for 16 hours. The solution was diluted with methylene chloride, and this solution was washed with 5% aqueous $NaH_2PO_4$, water and brine, then dried over $Na_2SO_4$. The solvent was removed, and the residue was taken directly to the next step.

Step 16b. Compound of Formula (I); $R^1$=methoxy; $R^2$=-H; W is absent; R=-3-phenylpropyl The compound from step 16a was dissolved in 5 mL of methanol, and the solution was stirred at room temperature for 16 hours. The solvent was removed, and the residue was flash chromatographed on silica gel, eluting with 4% methanol in methylene chloride to afford the title compound mixture of natural and epi isomers). MS m/z 715 (M+H)$^+$. Anal. Calcd. for $C_{40}H_{62}N_2O_9$: C, 67.19; H, 8.74; N, 3.91; Found: C, 67.23: H, 8.70; N, 3.90.

Example 17

Compound of Formula (I): $R^1$=methoxy, $R^2$=H: W is absent, R=2,2-diphenylethyl Step 17a. Compound of Formula (I); $R^1$=methoxy; $R^2$=acetyl: W is absent; R=2,2-diphenylethyl The title compound of Example 1 (300 mg, 0.434 mmol) was dissolved in 5 mL of 10% aqueous acetonitrile containing 2,2-diphenylethylamine (420 mg 2.174 mmol, Aldrich), and the reaction mixture was stirred for 16 hours. The solution was diluted with methylene chloride, and this solution was washed with 5% aqueous $NaH_2PO_4$, water and brine, then dried over $Na_2SO_4$. The solvent was removed, and the residue was taken directly to the next step.

Step 17b. Compound of Formula (I); $R^1$=methoxy; $R^2$=-H: W is absent, R=-2,2-diphenylethyl The compound from step 17a was dissolved in 5 mL of methanol, and the solution was stirred at room temperature for 16 hours. The solvent was removed, and the residue was flash chromatographed on silica gel, eluting with 4% methanol in methylene chloride to afford the title compound (as a mixture of natural and epi isomers). MS m/z 778 (M+H)+.

Example 18

Compound of Formula (I): $R^1$=methoxy; $R^2$=H, W is absent, R=H

Step 18a. Compound of Formula (I); $R^1$=methoxy; $R^2$=acetyl: W is absent, R=H The title compound of Example 1 (300 mg, 0.434 mmol) was dissolved in acetonitrile, placed in a pressure bottle and $NH_3$ was introduced. The reaction mixture was stirred for 17 hours. The solution was diluted with methylene chloride, and this solution was washed with 5% aqueous $NaH_2PO_4$, water and brine, then dried over $Na_2SO_4$. The solvent was removed, and the residue was taken directly to the next step.

Step 18b. Compound of Formula (I): $R^1$=methoxy: $R^2$=H: W is absent: R=H

The compound from step 17a was dissolved in 5 mL of methanol, and the solution was stirred at room temperature for 16 hours. The solvent was removed, and the residue was flash chromatographed on silica gel, eluting with 4% methanol in methylene chloride to afford the title compound. MS m/z 597 (M+H)+. Anal. Calcd. for $C_{31}H_{52}N_2O_9$: C, 62.39; H, 8.78; N, 4.69; Found: C, 62.19; H, 8.77; N, 4.72.

Example 19

Compound of Formula (IV): $R^1$=methoxy: $R^2$=H: A=B=C=D=H: R=H

A sample of the compound of Example 8 (166 mg, 0.207 mmol) (Formula (II); $R^1$=methoxy; $R^2$=H; A=B=C=D=H) was dissolved in 6 mL of methanol and 0.5 mL of acetic acid. To this solution was added $NaBH_3CN$ (126 mg,2.0 mmol), and the mixture was stirred at room temperature for 5 hours. The reaction was diluted with methylene chloride, washed with saturated aqueous $NaHCO_3$, dried and concentrated. The residue was chromatographed on silica gel, eluting with 3–10% methanol/methylene chloride to give 63 mg of the title compound. MS m/z 624 (M+H)$^+$.

Example 20

Compound of Formula (I); $R^1$=methoxy; $R^2$=H: W is —NH-: R=H: C10 methyl is epi-isomer A sample of the compound from Example 14a (300 mg) was further purified by flash chromatography on silica gel, eluting with 10% methanol/t-butyl methyl ether, to separate the mixture into two fractions. Fraction A had the C10-methyl group of the opposite epimeric configuration compared to the orientation of the C10-methyl group in natural erythromycins and is characterized herein, and Fraction B is characterized in the following Example. Fraction A: MS m/z 612 (M+H)$^+$. Anal.Calcd. for $C_{31}H_{53}N_3O_9$: C, 60.86; H, 8.73; N, 6.87; Found: C, 60.94; H, 8.85; N, 6.50.

Example 21

Compound of Formula (I); $R^1$=methoxy; $R^2$=H: W is —NH—: R=H; C10 methyl is natural isomer Fraction B from Example 20, possessing the C10 methyl group in the orientation of the C10-methyl group in natural erythromycins, was characterized as follows. MS m/z 612 (M+H)$^+$. Fraction B: Anal.Calcd. for $C_{31}H_{53}N_3O_9$: C, 60.86; H, 8.73; N, 6.87; Found: C, 60.97; H, 8.74; N, 6.54.

Example 22

Compound of Formula (I); $R^1$=methoxy; $R^2$=H: W is —NH-: R=3-(4-quinolinyl)propyl; C10 methyl is natural isomer Step 22a. Ethyl 3-(4-quinolinyl)propenoate LiCl (972 mg, 22.9 mmol) and 60 mL of $CH_3CN$ were placed in a dry flask, and triethyl phosphonoacetate (4.55 mL, 22.9 mmol, Aldrich) and DBU (3.05 mL, 20.4 mmol) were added. The mixture was stirred until the reagents were dissolved, and quinoline-4-carboxyaldehyde (3.00 g, 19.1 mmol) was added. The reaction mixture was stirred under nitrogen for 6 hours, and the reaction was quenched by addition of 5% $KH_2PO_4$. The mixture was extracted with ether, and the organic extract was washed with water and brine then dried over $MgSO_4$. The solvent was removed, and the residue was flash chromatographed on silica gel, eluting with t-butyl methyl ether, to afford the title compound.

Step 22b. Ethyl 3-(4-quinolinyl)propionate

The compound from step 22a (2.60 g) was dissolved in 20 mL of methanol, and hydrogenated at 1 atm while stirring over Pd/C catalyst for 17 hours. The mixture was filtered, and the solvent was removed. The residue was flash chromatographed on silica gel, eluting with 50% ethyl acetate/hexane, to afford the title compound.

Step 22c. 3-(4-Ouinolinyl)propanal

The compound from step 22b (1.51 g, 6.59 mmol) was dissolved in 60 mL of toluene, and the solution was cooled to −78° C. DIBAL-H (13.2 mL, 13.2 mmol) was added, and the reaction mixture was stirred under nitrogen for 2 hours. The reaction was quenched by addition of water (0.25 mL) and acetic acid (1 mL) dissolved in 3 mL of ether. The mixture was allowed to warm to room temperature then filtered. The solvent was removed, and the residue (1.2 g) was flash chromatographed on silica gel, eluting with 7.5–100% ethyl acetate/hexane, to afford the title compound (0.79 g, oil).

Step 22d. Compound of Formula (I); $R^1$=methoxy; $R^2$=H; W is —N=CH—; R=(4-quinolinyl)—$CH_2$—$CH_2$—; $C_{10}$ methyl is natural isomer A sample of the compound of Example 21 (270 mg, 0.442 mmol) was added to a solution of the aldehyde compound of step 22c (0.50 g, 2.7 mmol) in 10 mL of toluene.

Molecular sieves (4Å) were added, and the mixture was stirred under nitrogen for 16 hours.

A small amount of p-toluenesulfonate•$H_2O$ (98 mg) was added, and the mixture was stirred for 26 hours. The mixture was filtered, the solvent was removed, and the residue was flash chromatographed on silica gel, eluting with 4–5% methanol/methylene chloride containing 0.1% $NH_4OH$, to afford the title compound (242 mg). MS m/z 779 (M+H)$^+$.

Step 22e. Compound of Formula (I); $R^1$=methoxy; $R^2$=H; W is —NH—; R=3-(4-quinolinyl)propyl; $C_{10}$ methyl is natural isomer A sample of the compound of step 22d (235 mg, 0.302 mmol) was dissolved in 10 mL of methanol and $NaBH_3CN$ (40 mg) was added as well as enough acetic acid to turn bromocresol green indicator yellow, and the reaction mixture was stirred for 5 hours. The reaction was quenched with saturated $NaHCO_3$, and the mixture was extracted with methylene chloride. The solution was washed with saturated $NaHCO_3$, water and brine, then dried over $Na_2SO_4$. The solvent was removed, and the residue was flash chromatographed on silica gel, eluting with 5% methanol/methylene chloride containing 0.2% $NH_4OH$, to afford the title compound (128 mg). Flash chromatography was repeated, eluting with 10% methanol/t-butyl methyl ether to give 108 mg of title compound MS m/z 781 (M+H)$^+$.

Example 23

Compound of Formula (I); $R^1$=methoxy; $R^2$=H: W is absent, R=3-(2-naphthyloxy)propyl

Step 23a. N-(3-(2-naphthyloxy)propyl)phthalimide

A mixture of N-(3-bromopropyl)phthalimide (8 g, 29.83 mmol, Aldrich), 2-naphthol (4.30 g, 29.83 mmol) and $K_2CO_3$ (20.61 g, 149 mmol) in acetone (150 mL) was heated at reflux for 16 hours. The resulting suspension was filtered, and the filtrate was concentrated to give the title compound (10.28 g).

Step 23b. 3-(2-naphthyloxy)-1-propylamine

A sample of the compound from step 23a (10.28 g, 31.06 mmol) was suspended in ethanol, hydrazine (1.07 mL, 34.16 mmol) was added, and the mixture was heated at reflux for 21 hours. The mixture was cooled to room temperature, and the ethanol was removed. The residue was dissolved in 1N HCl, and an attempt was made to extract the solution with ethyl acetate. A stubborn emulsion formed, which was broken by adding $K_2CO_3$ to pH 10. The layers separated, the ethyl acetate fraction was discarded, and the aqueous layer was extracted with methylene chloride. The solvent was dried and removed to afford the title compound.

Step 23c. Compound of Formula (I); $R^1$=methoxy; $R^2$=acetyl: W is absent: R=3-(2-naphthyloxy)propyl The title compound of Example 1 (500 mg, 0.724 mmol) and 3-(2-naphthyloxy)-1-propylamine from step 23b (720 mg, 3.62 mmol) were dissolved in 10 (mL of 10% aqueous acetonitrile, and the reaction mixture was stirred for 16 hours. The solution was diluted with methylene chloride, and this solution was washed with 5% aqueous $NaH_2PO_4$, water and brine, then dried over $Na_2SO_4$. The solvent was removed, and the residue was taken directly to the next step.

Step 23d. Compound of Formula (I); $R^1$=methoxy; $R^2$=H: W is absent: R=3-(2-naphthyloxy)propyl The compound from step 23c was dissolved in 5 mL of methanol, and the solution was stirred at room temperature for 16 hours. The solvent was removed, and the residue (640 mg) was flash chromatographed on silica gel, eluting with 4% methanol in methylene chloride containing 0.1% $NH_4OH$ to afford the title compound (180 mg). MS m/z 781 (M+H)$^+$. Anal. Calcd. for $C_{44}H_{64}N_2O_{10}$: C, 67.66; H, 8.25; N, 3.58; Found: C, 67.71); H, 8.25; N, 3.61.

Example 24

Compound of Formula (I); $R^1$=-methoxy; $R^2$=H: W is absent: R=3-(3-pyridyloxy)propyl

Step 24a. N-(3-(3-pyridyloxy)propyl)phthalimide

3-Hydroxypyridine(2.83 g, 29.83 mmol) was dissolved in DMF (70 mL), the solution was cooled in an ice bath. NaH (1.3 g, 32.81 mmol) and N-(3-bromopropyl)phthalimide (8 g, 29.83 mmol, Aldrich) were added, the ice bath was removed, and the reaction mixture was stirred for 64 hours. The reaction was diluted with $CH_2Cl_2$ and filtered through celite to give a 1:1 mixture of N- and O-alkylated products. Recrystallization from EtOH afforded a 4:1 mixture of N- and O-alkylated products. The mother liquor was taken up in water and extracted with $CH_2Cl_2$, then the organic layer washed with water (5x) to afford the desired N-(3-(3-pyridyloxy)propyl)phthalimide (8.6 g).

Step 24b. 3-(3-pyridyloxy)-1-propylamine

A sample of the compound from step 24a (8.6 g, 30.49 mmol) was suspended in ethanol, hydrazine (1.05 mL, 33.54 mmol) was added, and the mixture was heated at reflux for 16 hours. The mixture was cooled to room temperature, and the ethanol was removed. The residue was dissolved in 1N HCl, and an attempt was made to extract the solution with ethyl acetate. A stubborn emulsion formed, which was broken by adding $K_2CO_3$ to pH 10.

The layers separated, the ethyl acetate fraction was saved, and the aqueous layer was extracted with methylene chloride. The organic extracts were combined and concentrated to afford the title compound (0.42 g).

Step 24c. Compound of Formula (I); $R^1$=-methoxy; $R^2$=acetyl: W is absent: R=3-(3-pyridyloxy)propyl The title compound of Example 1 (420 mg, 0.57 mmol) and 3-(3-pyridyloxy)-1-propylamine from step 24b (420 mg, 2.78 mmol) were dissolved in 5 mL of 10% aqueous acetonitrile, and the reaction mixture was stirred for 16 hours. The solution was diluted with methylene chloride, and this solution was washed with 5% aqueous NaH$_2$PO$_4$, water and brine, then dried over Na$_2$SO$_4$. The solvent was removed, and the residue was taken directly to the next step.

Step 24d. Compound of Formula (I); R$^1$=methoxy; R$^2$=H: W is absent; R=3-(3-pyridyloxy)propyl The compound from step 24c was dissolved in 5 mL of methanol, and the solution was stirred at room temperature for 16 hours. The solvent was removed, and the residue (510 mg) was flash chromatographed on silica gel, eluting with 4–6% methanol in methylene chloride containing 0.1% NH$_4$OH to afford the title compound (100 mg). MS m/z 774 (M+H)$^+$.

Example 25

Compound of Formula (I); R$^1$=methoxy; R$^2$=H: W is absent; R=3-(2-pyridyloxy)propyl Step 25a. N-(3-(2-pyridyloxy)propyl)phthalimide A mixture of N-(3-hydroxypropyl)phthalimide (Aldrich, 8.00 g, 38.98 mmol), 2-chloropyridimide (3.68 mL, 38.98 mmol) and NaH (60% dispersion, 2.33 g, 58.47 mmol) in DMF (100 mL) was heated at 75° C. and stirred for 5 days. The reaction mixture was then diluted with CH$_2$Cl$_2$, filtered, and the filtrate concentrated to give the title compound (13 g).

Step 25b. 3-(2-pyridyloxy)-1-propylamine

A sample of the compound from step 25a (11 g, 39 mmol) was suspended in ethanol, hydrazine (1.3 mL, 42.9 mmol) was added, and the mixture was heated at reflux for 16 hours. The mixture was cooled to room temperature, and then 8.7 mL of 6N HCl was added. The mixture was then heated at reflux for 2 hours. The mixture was cooled to room temperature and concentrated. The residue was taken up in 1N NaOH, and the solution was extracted with ethyl acetate. The organic extracts were combined, washed with water and brine, dried over Na$_2$SO$_4$ and concentrated to afford the title compound.

Step 25c. Compound of Formula (I); R$^1$=methoxy; R$^2$=acetyl: W is absent: R=3-(3-pyridyloxy)propyl The title compound of Example 1 (420 mg, 0.57 mmol) and 3-(2-pyridyloxy)-1-propylamine from step 25b were dissolved in 5 mL of 10% aqueous acetonitrile, and the reaction mixture was stirred for 16 hours. The solution was diluted with methylene chloride, and this solution was washed with 5% aqueous NaH$_2$PO$_4$, water and brine, then dried over Na$_2$SO$_4$. The solvent was removed, and the residue was taken directly to the next step.

Step 25d. Compound of Formula (I); R$^1$=methoxy; R$^2$=H, W is absent; R=3-(3-pyridyloxy)propyl The compound from step 25c was dissolved in 5 mL of methanol, and the solution was stirred at room temperature for 16 hours. The solvent was removed, and the residue (51 mg) was flash chromatographed on silica gel, eluting with 4–6% methanol in methylene chloride containing 0.1% NH$_4$OH to afford the title compound (100 mg). MS m/z 732 (M+H)$^+$.

Example 26

Compound of Formula (I), R$^1$=OH: R$^2$=H: W is absent. R=4-phenylbutyl

Following the procedures of Example 1, except substituting erythromycin A for the 6-methoxyerythromycin A thereof and carrying the product forward according to the procedures of Example 3, the title compound is prepared.

Example 27

Compound of Formula (1). R$^1$=OCONH$_2$; R$^2$=H, W is absent; R=4-phenylbutyl

Following the procedures of Example 1, except substituting 6-O-carbamoylerythromycin A (prepared according to procedures described by E. G. Brain in European Patent Application EP 212169, published Apr. 1, 1987) for the 6-methoxyerythromycin A thereof and carrying the product forward according to the procedures of Example 3, the title compound is prepared.

Example 28

Compound of Formula (I); R$^1$=OCONHCO-methyl: R$^2$=H: W is absent: R=4-phenylbutyl Following the procedures of Example 1, except substituting 6-O-(N-acetyl)carbamoyl erythromycin A (prepared according to procedures described by E. G. Brain in European Patent Application EP 212169, published Apr. 1, 1987) for the 6-methoxyerythromycin A thereof and carrying the product forward according to the procedures of Example 3, the title compound is prepared.

Example 29

Compound of Formula (I); R$^1$=OCONHSO2-methyl: R$^2$=H: W is absent: R=4-phenylbutyl Following the procedures of Example 1, except substituting 6-O-(N-methanesulfonyl)carbamoylerythromycin A (prepared according to procedures described by E. G. Brain in European Patent Application EP 212169, published Apr. 1, 1987) for the 6-methoxyerythromycin A thereof and carrying the product forward according to the procedures of Example 3, the title compound is prepared.

Example 30

Compound of Formula (1): R$^1$=OMe, R$^2$=H: W is absent: R=phenyl

Following the procedures of Example 3, except substituting aniline for the 4-phenylbutylamine thereof, the title compound is prepared.

Example 31

Compound of Formula (I): R$^1$=OMe; R$^2$=H: W is absent: R=3-pyridyl

Following the procedures of Example 3, except substituting 3-aminopyridine for the 4-phenylbutylamine thereof, the title compound is prepared.

Example 32

Compound of Formula (I): R$^1$=OME; R$^2$=H: W is —O—; R=H

Following the procedure of Example 14a, except substituting hydroxylamine for the hydrazine of step 14a, the title compound is prepared.

Example 33

Compound of Formula (I): R$^1$=OMe; R$^2$=H; W is —O—: R=methyl

Following the procedure of Example 14a, except substituting methoxylamine for the hydrazine of step 14a, the title compound is prepared.

Example 34

Compound of Formula (I); $R^1$=OMe; $R^2$=H: W is —NH—CO—, R=phenyl

Treatment of the compound described in example 14a with benzoyl chloride in the presence of a suitable base such as triethylamine or pyridine followed by chromatographic separation of the product and removal of the 2'-protecting group as described in step 2e affords the title compound.

Example 35

Compound of Formula (II): $R^1$=OME; R2=H; A=benzyl; B=D=E=H

Following the procedures of Example X, except substituting 2-amino-3-phenyl-1-propanol for the ethylenediamine thereof, to give an intermediate compound (Compound 11 of Scheme 4, wherein Y is OH and A is benzyl), then the intermediate thus prepared is reacted with triphenylphosphine, DEAD and DPPA under Mitsunobu conditions to replace the hydroxyl group with an azido group, then the azido group is reduced to an amino group with triphenylphosphine and water, then the amino compound is refluxed with acetic acid and water to close the ring to give the title compound.

Example 36

Compound of Formula (II); $R^1$=OMe; $R^2$=H; A=D=3,4-pyrrolidinyl; B=E=H

Following the procedures of Example 8, except substituting cis-3,4-diaminopyrrolidine for the ethylenediamine thereof, the title compound is prepared.

Example 37

Compound of Formula (III) $R^1$=OMe; $R^2$=H; A=B=D=E=H

The title compound of Example 8 (Compound of Formula (II); $R^1$=methoxy; $R^2$=H; A=B=C=D=H) is treated with $H_2O_2$ to oxidize the imine nitrogen, and the intermediate compound is treated with triphenyl phosphine in water to reduce any of the byproduct (the dimethylamine N-oxide on the desosamine moiety) to afford the title compound.

Example 38

Compound of Formula (IV): $R^1$=OMe: $R^2$=H: A=benzyl: B=D=E=H: R=H

The title compound of Example 35 is treated with sodium cyanoborohydride at pH 4–5, under conditions similar to that described for example 19, to afford the title compound.

Example 39

Compound of Formula (IV); $R^1$=OMe; $R^2$=H: A=D=3,4-pyrrolidinyl; B=E=H: R=H

The title compound of Example 36 is treated with sodium cyanoborohydride at pH 4–5, under conditions similar to that described for example 19, to afford the title compound.

Example 40

Compound of Formula (IV): $R^1$=OMe; $R^2$=H: A=B=D=E=H, R=$CH_2CH_2CH_2C_6H_5$

The title compound of Example 19 is reductively alkylated by treatment with 3-phenylpropanal and sodium cyanoborohydride to afford the title compound.

Example 41

Compound of Formula (IV): $R^1$=OMe: $R^2$=H; A=B=D=E=H, R=2,4-dinitrobenzene

The title compound of Example 19 (wherein $R^2$=acetyl) is treated with R=2,4-dinitrofluorobenzene followed by removal of the 2'-protecting group as described in step 2,e affords the title compound.

Example 42

Compound of Formula (IV): $R^1$=OMe: $R^2$=H: A=B=D=E=H, R=4-quinolyl

The title compound of Example 19 (wherein $R^2$=acetyl) is treated with 4-bromoquinine, in the presence of a suitable catalyst such as CuBr, followed by removal of the 2'-protecting group as described in step 2e affords the title compound.

Example 43

Compound of Formula (I); $R^1$=methoxy; $R^2$=H: W is absent: R=3-(4H-4-oxo-1-quinolylypropyl Step 43a. N-(1-(3-aminopropyl)-1H-4-oxoquinolin-1-yl) phthalimide 4-Hydroxyquinoline (4.04 g, 27.9 mmol) and N-(3-bromopropyl)phthalimide (7.48 g, 27.9 mmol) were suspended in acetone (140 mL), and $K_2CO_3$ (20 g) was added. The mixture was stirred at reflux under $N_2$ for 51 hours, then cooled, diluted with methylene chloride and filtered. The solvents were removed, and the residue was crystallized from ethanol (5.8 g). Chromatographic separation on silica gel eluting with 5% methanol in chloroform gave the title compound (2.8 g), which was taken directly to the next step.

Step 43b. 1-(3-aminopropyl)-1H-4-oxoquinoline

The compound from step 43a was dissolved in ethanol (80 mL) and heated at reflux in the presence of 0.5 mL of hydrazine for 16 hours. The solution was cooled and concentrated. The residue was taken up in 80 mL of ethanol containing 1.5 mL of conc. HCl, and the solution was heated at reflux for 3 hours. The mixture was filtered, and the filter cake was extracted with methylene chloride and 1N NaOH. The layers were separated, and the organic layer was washed with brine, dried and concentrated to afford the title compound (280 mg).

Step 43c. Compound of Formula (I); $R^1$=methoxy; $R^2$=acetyl: W is absent: R=(4H-4-oxo-1-quinolyl)propyl The title compound of Example 1 (330 mg, 0.479 mmol) and 1-(3-aminopropyl)-1H-4-oxoquinoline from step 43b (330 mg) were dissolved in 4 mL of 10% aqueous acetonitrile, and the reaction mixture was stirred for 40 hours. The solution was diluted with methylene chloride, and this solution was washed with 5% aqueous $NaH_2PO_4$, water and brine, then dried over $Na_2SO_4$. The solvent was removed, and the residue was purified by flash chromatography on silica gel, eluting with 4% methanol in methylene chloride containing 0.1% $NH_4OH$.

Step 43d. Compound of Formula (I); $R^1$=methoxy; $R^2$=H; W is absent; R=(4H-4-oxo-1-quinolyl)propyl The compound from step 43c was dissolved in 10 mL of methanol, and the solution was held at room temperature for 16 hours. The solvent was removed, and the residue was flash chromatographed on silica gel, eluting with 10% methanol in methylene chloride containing 0.1% $NH_4OH$ to afford the title compound (98 mg). mp 214.5°–25.5° C. MS m/z 782 (M+H)+. Anal.Calcd. for $C_{43}H_{63}N_3O_{10}$: C, 65.82; H, 8.70; N, 5.76; Found: C, 65.97; H, 8.79; N, 5.64.

Examples 44–66

Following the procedures of Example 11, except substituting the $R^2$-reagent compound shown in the Table 1 below for the phenylethylamine of Example 11a, the compounds of Examples 44–66 were prepared.

TABLE 1

Examples 44–66

| Ex. No. | $R^2$-reagent compound | Title Compound |
|---|---|---|
| 44 | 2-(4-nitrophenyl)ethylamine | Compound of Formula (I); $R^1$ = methoxy; $R^2$ = H; W is absent; R = 2-(4-nitrophenyl)ethyl |
| 45 | 2-(4-aminophenyl)ethylamine | Compound of Formula (I); $R^1$ = methoxy; $R^2$ = H; W is absent; R = 2-(4-aminophenyl)ethyl |
| 46 | 3-ethoxypropylamine | Compound of Formula (I); $R^1$ = methoxy; $R^2$ = H; W is absent; R = 3-ethoxypropyl |
| 47 | isopropylamine | Compound of Formula (I); $R^1$ = methoxy; $R^2$ = H; W is absent; R = isopropyl |
| 48 | 2-(4-bromophenyl)ethylamine | Compound of Formula (I); $R^1$ = methoxy; $R^2$ = H; W is absent; R = 2-(4-bromophenyl)ethyl |
| 49 | 2-(4-hydroxylphenyl)ethylamine | Compound of Formula (I); $R^1$ = methoxy; $R^2$ = H; W is absent; R = 2-(4-hydroxylphenyl)ethyl |
| 50 | 2-(4-fluorophenyl)ethylamine | Compound of Formula (I); $R^1$ = methoxy; $R^2$ = H; W is absent; R = 2-(4-fluorophenyl)ethyl |
| 51 | 2-(3-methoxyphenyl)ethylamine | Compound of Formula (I); $R^1$ = methoxy; $R^2$ = H; W is absent; R = 2-(3-methoxyphenyl)ethyl |
| 52 | 3-vinyloxypropylamine | Compound of Formula (I); $R^1$ = methoxy; $R^2$ = H; W is absent; R = 3-vinyloxypropyl |
| 53 | 2-(3-trifluoromethyl)phenylethylamine | Compound of Formula (I); $R^1$ = methoxy; $R^2$ = H; W is absent; R = 2-(3-trifluoromethyl)phenylethyl |
| 54 | 2-thienylethylamine | Compound of Formula (I); $R^1$ = methoxy; $R^2$ = H; W is absent; R = 2-thienylethyl |
| 55 | 2-(3,4-dibenzyloxyphenyl)ethylamine | Compound of Formula (I); $R^1$ = methoxy; $R^2$ = H; W is absent; R = 2-(3,4-dibenzyloxyphenyl)ethyl |
| 56 | 2-(4-methylphenyl)ethylamine | Compound of Formula (I); $R^1$ = methoxy; $R^2$ = H; W is absent; R = 2-(4-methylphenyl)ethyl |
| 57 | N-allylamine | Compound of Formula (I); $R^1$ = methoxy; $R^2$ = H; W is absent; R = allyl |
| 58 | 1,3-dihydroxypropylamine | Compound of Formula (I); $R^1$ = methoxy; $R^2$ = H; W is absent; R = 1,3-dihydroxypropyl |
| 59 | 1,3-dihydroxypropylamine (10-epi) | Compound of Formula (I); $R^1$ = methoxy; $R^2$ = H; W is absent; R = 1,3-dihydroxypropyl (10-epi) |
| 60 | 3-hydroxypropylamine | Compound of Formula (I); $R^1$ = methoxy; $R^2$ = H; W is absent; R = 3-hydroxypropyl |
| 61 | 3-hydroxypropylamine (10-epi) | Compound of Formula (I); $R^1$ = methoxy; $R^2$ = H; W is absent; R = 3-hydroxypropyl (10-epi) |
| 62 | propylamine | Compound of Formula (I); $R^1$ = methoxy; $R^2$ = H; W is absent; R = propyl |
| 63 | isobutylamine | Compound of Formula (I); $R^1$ = methoxy; $R^2$ = H; W is absent; R = isobutyl |
| 64 | 2-(benzoylamino)ethylamine | Compound of Formula (I); $R^1$ = methoxy; $R^2$ = H; W is absent; R = 2-(benzoylamino)ethyl |
| 65 | 3-(benzoylamino)propylamine | Compound of Formula (I); $R^1$ = methoxy; $R^2$ = H; W is absent; R = 3-(benzoylamino)propyl |
| 66 | 3-(acetylamino)propylamine | Compound of Formula (I); $R^1$ = methoxy; $R^2$ = H; W is absent; R = 3-(acetylamino)propyl |

Example 67

Compound of Formula (I): $R^2$=methoxy: $R^2$=H: W is absent, R=H (10-epi)

This compound was separated by flash chromatography from the mixture of products generated in Example 18, step b. MS m/z 597 (M+H)$^+$.

Example 68

Compound of Formula (I); $R^1$=methoxy; $R^2$=H; W is absent; R=3-phenylproply (10-epi)

This compound was separated by flash chromatography from the mixture of products generated in Example 16, step b. MS m/z 715 (M+H)$^+$.

Example 69

Compound of Formula (1); $R^1$=methoxy; $R^2$=H; W is absent; R=3-(4-phenoxyphenyl)ethyl (10-epi)

This compound was separated by flash chromatography from the mixture of products generated in Example 15, step b. MS m/z 794 (M+H)$^+$.

Example 70

Compound of Formula (I); $R^1$=methoxy; $R^2$=H; W is absent; R=3-(4-chlorophenyl)propyl To a sample of the title compound of Example 21 (225 mg, 0.368 mmol) dissolved in methanol (4 mL) were added 3-(4-chlorophenyl)propionaldehyde (400 mg, 2.4 mmol, prepared according to the procedure of T. Jeffery, *J. Chem. Soc. Chem. Commun.*, 1984:1287) and sufficient acetic acid to change bromocresol green indicator from blue to yellow. To this solution was added sodium cyanoborohydride (160 mg, 2.5 mmol), and the mixture was stirred under nitrogen for about 20 hours, adjusting the pH with acetic acid as necessary. The reaction was quenched by addition of aqueous sodium bicarbonate, then the mixture was extracted with methylene chloride. The organic layer was washed with aqueous sodium bicarbonate and water, then dried over $Na_2SO_4$. The solvent was removed, and the residue was flash chromatographed on silica gel, eluting with 10% methanol in methylene chloride containing 0.1% $NH_4OH$ to afford the title compound (159 mg). MS m/z 764 (M+H)$^+$.

Examples 71–109

Following the procedure of Example 70, except replacing the 3-(4-chlorophenyl)propionaldehyde with the reagent aldehyde as indicated, the compounds of Examples 71–109 were prepared as shown in Table 2 below. The aldehydes of Examples 71–81 were prepared from precursor aryl iodides (commercially available) and allyl alcohol via a Heck-type reaction (T. Jeffrey, *J. Chem. Soc. Chem. Commun.*, 1984:1287). The aldehyde reagents of Examples 82–109 were obtained commercially.

TABLE 2

Examples 71–109

| Ex. No. | Aldehyde Reagent | Title Compound |
|---|---|---|
| 71 | 3-(3-chlorophenyl)-propionaldehyde | Compound of Formula (I); $R^1$ = methoxy; $R^2$ = H; W is —NH—; R = 3-(3-chlorophenyl)propyl |
| 72 | 3-(2-chlorophenyl)-propionaldehyde | Compound of Formula (I); $R^1$ = methoxy; $R^2$ = H; W is —NH—; R = 3-(2-chlorophenyl)propyl |
| 73 | 3-(2,4-dichlorophenyl)-propionaldehyde | Compound of Formula (I); $R^1$ = methoxy; $R^2$ = H; W is —NH—; R = 3-(2,4-dichlorophenyl)propyl |
| 74 | 3-(4-hydroxyphenyl)-propionaldehyde | Compound of Formula (I); $R^1$ = methoxy; $R^2$ = H; W is —NH—; R = 3-(4-hydroxyphenyl)propyl |
| 75 | 3-(3-hydroxyphenyl)-propionaldehyde | Compound of Formula (I); $R^1$ = methoxy; $R^2$ = H; W is —NH—; R = 3-(3-hydroxyphenyl)propyl |
| 76 | 3-(2-hydroxyphenyl)-propionaldehyde | Compound of Formula (I); $R^1$ = methoxy; $R^2$ = H; W is —NH—; R = 3-(2-hydroxyphenyl)propyl |
| 77 | 3-(4-methoxyphenyl)-propionaldehyde | Compound of Formula (I); $R^1$ = methoxy; $R^2$ = H; W is —NH—; R = 3-(4-methoxyphenyl)propyl |
| 78 | 3-(4-nitrophenyl)-propionaldehyde | Compound of Formula (I); $R^1$ = methoxy; $R^2$ = H; W is —NH—; R = 3-(4-nitrophenyl)propyl |
| 79 | 3-(3-nitrophenyl)-propionaldehyde | Compound of Formula (I); $R^1$ = methoxy; $R^2$ = H; W is —NH—; R = 3-(3-nitrophenyl)propyl |
| 80 | 3-(2-nitrophenyl)-propionaldehyde | Compound of Formula (I); $R^1$ = methoxy; $R^2$ = H; W is —NH—; R = 3-(2-nitrophenyl)propyl |
| 81 | 3-(4-(acetylamino)-phenyl)propionaldehyde | Compound of Formula (I); $R^1$ = methoxy; $R^2$ = H; W is —NH—; R = 3-((4-(acetylamino)phenyl)propyl |
| 82 | trans-cinnamaldehyde | Compound of Formula (I); $R^1$ = methoxy; $R^2$ = H; W is —NH—; R = trans-3-phenylprop-2-enyl |
| 83 | phenylacetaldehyde | Compound of Formula (I); $R^1$ = methoxy; $R^2$ = H; W is —NH—; R = phenylethyl |
| 84 | benzaldehyde | Compound of Formula (I); $R^1$ = methoxy; $R^2$ = H; W is —NH—; R = phenylmethyl |
| 85 | indole-3-carboxaldehyde | Compound of Formula (I); $R^1$ = methoxy; $R^2$ = H; W is —NH—; R = (3-indolyl)methyl |
| 86 | 4-methoxybenzaldehyde | Compound of Formula (I); $R^1$ = methoxy; $R^2$ = H; W is —NH—; R = (4-methoxyphenyl)methyl |
| 87 | 4-acetylamino-benzaldehyde | Compound of Formula (I); $R^1$ = methoxy; $R^2$ = H; W is —NH—; R = (4-acetylaminophenyl)methyl |
| 88 | 4-chlorobenzaldehyde | Compound of Formula (I); $R^1$ = methoxy; $R^2$ = H; W is —NH—; R = (4-chlorophenyl)methyl |
| 89 | 4-(dimethylamino)-benzaldehyde | Compound of Formula (I); $R^1$ = methoxy; $R^2$ = H; W is —NH—; R = (4-dimethylaminophenyl)methyl |
| 90 | trans-4-nitro-cinnamaldehyde | Compound of Formula (I); $R^1$ = methoxy; $R^2$ = H; W is —NH—; R = trans-3-(4-nitrophenyl)prop-2-enyl |
| 91 | 4-nitrobenzaldehyde | Compound of Formula (I); $R^1$ = methoxy; $R^2$ = H; W is —NH—; R = (4-nitrophenyl)methyl |
| 92 | 3,4-dihydroxy-benzaldehyde | Compound of Formula (I); $R^1$ = methoxy; $R^2$ = H; W is —NH—; R = (3,4-dihydroxyphenyl)methyl |
| 93 | 2,5-dihydroxy-benzaldehyde | Compound of Formula (I); $R^1$ = methoxy; $R^2$ = H; W is absent; R = (2,5-dihydroxyphenyl)methyl |
| 94 | 2-hydroxy-5-nitrobenzaldehyde | Compound of Formula (I); $R^1$ = methoxy; $R^2$ = H; W is —NH—; R = (2-hydroxy-5-nitrophenyl)methyl |
| 95 | terephthaldicar-boxaldehyde | Compound of Formula (I); $R^1$ = methoxy; $R^2$ = H; W is —NH—; R = (4-hydroxymethylphenyl)methyl |
| 96 | 5-nitrofuranacrolein | Compound of Formula (I); $R^1$ = methoxy; $R^2$ = H; W is —NH—; R = trans-3-(5-nitro-2-furanyl)prop-2-enyl |
| 97 | phthalicdicarboxaldehyde | Compound of Formula (I); $R^1$ = methoxy; $R^2$ = H; W is N; R = (—CH$_2$-(1,2-phenylene)-CH$_2$— |
| 98 | 4-hydroxybenzaldehyde | Compound of Formula (I); $R^1$ = methoxy; $R^2$ = H; W is —NH—; R = (4-hydroxyphenyl)methyl |
| 99 | 3-hydroxybenzaldehyde | Compound of Formula (I); $R^1$ = methoxy; $R^2$ = H; W is —NH—; R = (3-hydroxyphenyl)methyl |
| 100 | salicylaldehyde | Compound of Formula (I); $R^1$ = methoxy; $R^2$ = H; W is —NH—; R = (2-hydroxyphenyl)methyl |
| 101 | trifluoro-p-tolualdehyde | Compound of Formula (I); $R^1$ = methoxy; $R^2$ = H; W is —NH—; R = (4-trifluoromethylphenyl)methyl |
| 102 | 4-cyanobenzaldehyde | Compound of Formula (I); $R^1$ = methoxy; $R^2$ = H; W is —NH—; R = (4-cyanophenyl)methyl |
| 103 | 2-pyridinecar-boxaldehyde | Compound of Formula (I); $R^1$ = methoxy; $R^2$ = H; W is —NH—; R = (2-pyridyl)methyl |
| 104 | 3-pyridinecar-boxaldehyde | Compound of Formula (I); $R^1$ = methoxy; $R^2$ = H; W is —NH—; R = (3-pyridyl)methyl |
| 105 | 4-pyridinecar-boxaldehyde | Compound of Formula (I); $R^1$ = methoxy; $R^2$ = H; W is —NH—; R = (4-pyridyl)methyl |
| 106 | 2-hydroxy-1-naphthaldehyde | Compound of Formula (I); $R^1$ = methoxy; $R^2$ = H; W is —NH—; R = (2-hydroxy-1-naphthyl)methyl |
| 107 | 4-dimethylamino-1-naphthaldehyde | Compound of Formula (I); $R^1$ = methoxy; $R^2$ = H; W is —NH—; R = (4-dimethylamino-1-naphthyl)methyl |
| 108 | 4-(methylthio)-benzaldehyde | Compound of Formula (I); $R^1$ = methoxy; $R^2$ = H; W is —NH—; R = (4-(methylthio)phenyl)methyl |
| 109 | 4-phenoxybenzaldehyde | Compound of Formula (I); $R^1$ = methoxy; $R^2$ = H; W is —NH—; R = (4-phenoxyphenyl)methyl |

Example 110

Compound of Formula (I); $R^1$=methoxy; $R^2$=H; W is —NH—; R=3-(4-fluorophenyl)propyl Following the procedures of Example 22, except substituting 4-fluorobenzaldehyde for the quinoline-4-carboxyaldehyde of Example 22a, and carrying the product forward as in Example 22 steps b–d, the title compound was prepared. Anal.Calcd. for $C_{40}H_{62}FN_3O_9$: C, 64.23; H, 8.35; N, 5.62; Found: C, 64.27; H, 8.60; N, 5.51.

Example 111

Compound of Formula (I); $R^1$=methoxy; $R^2$=H; W is —NH—; R=(trans-3-(4-nitrophenyl)prop-2-enyl A sample of the title compound from Example 90 (R= (trans-3-(4-nitrophenyl)prop-2-enyl, 144 mg, 0.193 mmol) in 10 mL of methanol was added to a solution of acetyl chloride (0.300 mL, 4.2 mmol) in methanol (5 mL), then Zn dust (380 mg, 5.81 mmol) was added and the mixture was stirred from 16 hours. Saturated aqueous sodium carbonate and ethyl acetate were added, and the mixture was stirred for 15 minutes. The organic layer was separated, washed dried (NaSO4) and concentrated. The residue was purified by flash chromatography on silica gel, eluting with 5% methanol/ chloroform containing 0.1% ammonium hydroxide to give the title compound (85 mg): MS m/z 717 (M+H)$^+$; Anal. Calcd. for $C_{40}H_{62}N_4O_9$: C, 63.66; H, 8.44; N, 7.86; Found: C, 63.62; H, 8.66; N, 7.68.

Example 112

Compound of Formula (I); $R^1$=methoxy; $R^2$=H; W is —NH—; R=4-aminophenylmethyl Following the procedure of Example 111, except substituting the compound of Example 91 for the starting material of Example 111, the title compound was prepared. Anal. Calcd. for $C_{38}H_6N_4O_9$: C, 63.66; H, 8.44; N, 7.81; Found: C, 63.62; H, 8.66; N, 7.66.

Example 113

Compound of Formula (I); $R^1$=methoxy; $R^2$=H; W is —NH—; R=3-(4-aminophenyl)propyl Following the procedure of Example 111, except substituting the compound of Example 78 for the starting material of Example 111, the title compound was prepared. Anal. Calcd. for $C_{40}H_{64}N_4O_9$: C, 64.49; H, 8.66; N, 7.52; Found: C, 64.35; H, 8.86; N, 7.31.

Example 114

Compound of Formula (I); $R^1$=methoxy; $R^2$=H; W is —NH—; R=3-(3-aminophenyl)propyl Following the procedure of Example 111, except substituting the compound of Example 79 for the starting material of Example 111, the title compound was prepared. Anal. Calcd. for $C_{40}H_{64}N_4O_9$: C, 64.49; H, 8.66; N, 7.52; Found: C, 64.57; H, 8.87; N, 7.31.

Example 115

Compound of Formula (I); $R^1$=methoxy; $R^2$=H; W is —NH—; R=3-(2-aminophenyl)propyl Following the procedure of Example 111, except substituting the compound of Example 80 for the starting material of Example 111, the title compound was prepared. Anal. Calcd. for $C_{40}H_{64}N_4O_9$: C, 61.99; H, 8.06; N, 7.23; Found: C, 62.25; H, 7.87; N, 7.08.

Example 116

Compound of Formula (I); $R^1$=methoxy; $R^2$=H; W is —NH—; R=trans-3-(4-acetylaminophenyl)prop-2-enyl A sample of the compound of Example 111 was treated with acetyl chloride in methylene chloride at 0° C. for 3 hours to give the title compound. Anal.Calcd. for $C_{42}H_{64}N_4O_{10}$: C, 64.26; H, 8.22; N, 7.14; Found: C, 64.21; H, 8.36; N, 6.93.

Example 117

Compound of Formula (I); $R^1$=methoxy; $R^2$=H; W is —NH—; R=trans-3-(4-(4-nitrobenzoylamino) phenyl)prop-2-enyl A sample of the compound of Example 111 was treated with 4-nitrobenzoyl chloride in methylene chloride at 0° C. for 3 hours to give the title compound. Anal.Calcd. for $C_{47}H_{65}N_5O_{12}$: C, 63.23; H, 7.34; N, 7.85; Found: C, 63.35; H, 7.59; N, 7.60.

Example 118

Compound of Formula (I); $R^1$=methoxy; $R^2$=H; W is —NH—; R=3-(2-benztriazolyl)propyl Step 118a. 1-(2-(1,3-dioxolan-2-yl)ethyl)benztriazole and 2-(2-(1,3-dioxolan-2-yl)ethyl)benztriazole Benztriazole (2.02 g, 16.97 mmol) was added to a suspension of NaH (1 g, 20 mmol) in dry DMF (25 mL) at 0° C. To this mixture was added in portions, 2-(2-bromoethyl)-1,3-dioxolane, and the mixture was warmed to room temperature and stirred for 16 hours. Brine was added, and the mixture was extracted with ether. The ether extract was washed with brine, dried ($Na_2SO_4$) and concentrated. The residue was purified by flash chromatography on silica gel, eluting with 25% ethyl acetate/hexane to give the two isomeric products. MS m/z 220 (M+H)$^+$.

Step 118b. 3-(2-benztriazolyl)propanaldehyde

The 2-(2-(1,3-dioxolan-2-yl)ethyl)benztriazole isomer from step 118a (550 mg) was dissolved in acetone (25 mL), and 2N HCl (10 mL) was added. The mixture was heated at 40°–50° C. for 23 hours, then diluted with methylene chloride. The solution was washed with brine, then dried and concentrated to give the title compound: MS m/z 176 (M+H)$^+$.

Step 118c. Compound of Formula (I); $R^1$=methoxy; $R^2$=H; W is —NH—; R=3-(2-benztriazolyl)propyl Following the procedure of Example 70, except replacing the 3-(4-chlorophenyl)propionaldehyde thereof with the aldehyde from step 118b, the title compound was prepared. MS m/z 771 (M+H)$^+$.

Example 119

Compound of Formula (I); $R^1$=methoxy; $R^2$=H; W is —NH—; R=3-(1-benztriazolyl)propyl Step 119a. 3-(1-benztriazolyl)propanaldehyde The 2-(2-(1,3-dioxolan-2-yl)ethyl)benztriazole isomer from Example 118a (630 mg) was dissolved in acetone (25 mL), and 2N HCl (10 mL) was added. The mixture was heated at 40°–50° C. for 23 hours, then diluted with methylene chloride. The solution was washed with brine, then dried and concentrated to give the title compound: MS m/z 176 (M+H)$^+$.

Step 119b. Compound of Formula (I); $R^1$=methoxy; $R^2$=H; W is —NH—; R=3-(1-benztriazolyl)propyl Following the procedure of Example 70, except replacing the 3-(4-chlorophenyl)propionaldehyde thereof with the aldehyde from step 119a, the title compound was prepared. Anal.Calcd. for $C_{40}H_{62}N_6O_9$: C, 62.32; H, H, 8.11; N, 10.90; Found: C, 62.27; H, 8.21; N, 10.61.

Example 120

Compound of Formula (I); $R^1$=methoxy; $R^2$=H; W is —NH—; R=3-(4-phenylimidazolyl)propyl Step 120a. 1-(2-(1,3-dioxan-2-yl)ethyl)-4-phenylimidazole Following the procedure of Example 118 step a, except substituting 4-phenylimidazole (2.01 g, 13.96 mmol) for the benztriazole thereof, the title compound (2.15 g) was prepared. MS m/z 245 (M+H)$^+$.

Step 120b. 3-(4-phenylimidazolyl)propanaldehyde

Following the procedure of Example 118 step b, except substituting the compound of step 120a for the compound of 118a thereof, the title compound was prepared. MS m/z 201 (M+H)$^+$.

Step 120c. Compound of Formula (I); R¹=methoxy; R²=H; W is —NH—; R=3-(4-phenylimidazolyl)propyl Following the procedure of Example 70, except replacing the 3-(4-chlorophenyl)propionaldehyde thereof with the aldehyde from step 120b, the title compound was prepared. Anal.Calcd. for $C_{43}H_{65}N_5O_9$: C, 64.88; H, 8.23; N, 8.80; Found: C, 65.04; H, 8.35; N, 8.60.

Example 121

Compound of Formula (I); R¹=methoxy; R²=H; W is absent; R=3-(1-anhydro-1-cladinosyl)propyl Step 121a. 1-O-methyl-cladinose To a solution of cladinose (5.0 g) in methanol (200 mL) was added acetyl chloride (3 mL), and the mixture was stirred for 3 hours. The reaction was quenched with 5% aqueous sodium bicarbonate solution, then the mixture was extracted with methylene chloride. The organic layer was dried ($Na_2SO_4$) and concentrated to give the title compound.

Step 121b. 1-O-methyl-4-O-acetylcladinose

To a sample of 1-O-methyl-cladinose (2.85 g, 15.0 mmol) in methylene chloride (75 mL) cooled to 0° C. were added acetic anhydride (1.6 mL, 16.9 mmol), triethylamine (4.2 mL, 30.1 mmol) and DMAP (100 mg, 0.82 mmol), and the mixture was stirred at room temperature for 19 hours. The reaction was quenched with saturated aqueous sodium bicarbonate solution, then the mixture was extracted with methylene chloride. The organic layer was washed with water and brine, then dried ($Na_2SO_4$) and concentrated. The residue was flash chromatographed on silica gel, eluting with 25% ethyl acetate/hexane to give 3.28 g of the title compound.

Step 121c. 1-allyl-1-anhydro-4-O-acetylcladinose

To a solution of 1-O-methyl-4-O-acetylcladinose (2.68 g, 11.6 mmol) and allyltrimethylsilane (5.50 mL, Aldrich) in methylene chloride at −16° C. flushed with nitrogen was added boron trifluoride etherate (4.26 mL) over an 8 minute period. The mixture was stirred at −15° C. for 2 hours and at −5° C. for 2 hours, then the reaction was quenched with saturated aqueous sodium bicarbonate solution. The mixture was extracted with methylene chloride, and the organic layer was washed with water and brine, then dried ($Na_2SO_4$) and concentrated. The residue was flash chromatographed on silica gel, eluting with 20% ethyl acetate/hexane to give 1.17 g of the title compound.

Step 121d. 3-(1-dehydroxycladinosyl)propanol

To a solution of 1-allyl-1-anhydro-4-O-acetylcladinose (465 mg, 1.92 mmol) in dry THF was added 9-BBN (265 mg, 2.17 mmol), and the mixture was heated at reflux for 16 hours. An additional portion of 9-BBN (54 mg) was added, and the heating was continued for 2 hour hours. The mixture was cooled to room temperature, and 15% NaOH (0.7 mL) and 30% $H_2O_2$ (0.9 mL) were added while cooling in an ice bath. The mixture was extracted with ether, and the organic layer was washed with water and brine, then dried ($Na_2SO_4$) and concentrated (0.53 mg). The residue was stirred in methanol with 450 mg of potassium carbonate for 4 hours. Methylene chloride was added, and the layers were separated. The organic layer was washed with water and brine, then dried ($Na_2SO_4$) and concentrated. The residue was flash chromatographed on silica gel, eluting with ethyl acetate to give 196 mg of the title compound. MS m/z 219 (M+H)⁺.

Step 121e. 3-(1-anhydro-1-cladinosyl)propanaldehyde

To a solution of 3-(1-anhydrocladinosyl)propanol (190 mg, 0.872 mmol) in methylene chloride (3 mL) was added 0.5M aqueous KBr (0.18 mL) and 2,2,6,6-tetramethylpiperidine-N-oxide (3 mg), and the mixture was cooled to 0° C. Aqueous 0.35M NaOCl (3.0 mL) buffered with sodium bicarbonate was added, and the mixture was stirred rapidly for 45 minutes. Saturated aqueous sodium bicarbonate was added, and the mixture was extracted with methylene chloride. The organic layer was washed with water and brine, then dried ($Na_2SO_4$) and concentrated. The residue was flash chromatographed on silica gel, eluting with 1:1 ethyl acetate/hexane to give 96 mg of the title compound. MS m/z 234 (M+H)⁺.

Step 121f. Compound of Formula (I); R¹=methoxy; R²=H; W is —NH—; R=3-(1-anhydro-1-cladinosyl)propyl Following the procedure of Example 70, except replacing the 3-(4-chlorophenyl)propionaldehyde thereof with the 3-(1-dehydroxy-1-cladinosyl)propanaldehyde from step 121e, the title compound was prepared.

Example 122

Compound of Formula (I); R¹=methoxy; R²=H; W is —NH—; R=3-phenylpropyl (10-epi)

This compound was prepared as in Example 14, except using the 10-epi isomer. MS m/z 730 (M+H)⁺.

Example 123

Compound of Formula (I); R¹=methoxy; R²=H; W is —NH—; R=isopropyl

This compound was made in a manner similar to example 14b and 14c; using the product compound of step 14a and substituting acetone (Aldrich) for 3-phenylpropanal and substituting refluxing acetone instead of toluene for step 14b; and using MeOH/AcOH as solvent for the reduction step 14c. MS m/z 654 (M+H)⁺.

Example 124

Compound of Formula (I); R¹=methoxy; R²=H; W is —NH—; R=1,3-diphenyl-2-propyl

This compound was made in a manner similar to example 14b and 14c; using the product compound from step 14a and substituting 1,3-diphenylacetone (Aldrich) for 3-phenylpropanal and substituting refluxing methanol instead of toluene for step 14b; and using MeOH/AcOH as solvent for the reduction step 14c. MS m/z 806 (M+H)⁺.

Example 125

Compound of Formula (I); R¹=-methoxy; R²=H; W is —NH—; R=3-pentyl

This compound was made in a manner similar to example 14b and 14c; using the product compound from step 14a and substituting 3-pentanone (Aldrich) for 3-phenylpropanal and substituting refluxing methanol instead of toluene for step 14b; and using MeOH/AcOH as solvent for the reduction step 14c. MS m/z 682 (M+H)⁺.

Example 126

Compound of Formula (I); R¹=methoxy; R²=H; W is absent; R=2-(benzoylamino)ethyl

The compound was prepared from the title compound of Example 1 and N-benzoyl ethylenediamine according to the procedures of Example 3. MS m/z 744 (M+H)⁺.

Example 127

Compound of Formula (I); R¹=methoxy; R²=H; W is absent; R=2-((4-methoxybenzoyl)amino)ethyl The compound was prepared from the title compound of Example 1 and N-(4-methoxybenzoyl)ethylene diamine according to the procedures of Example 3. MS m/z 774 (M+H)⁺.

Example 128

Compound of Formula (I); $R^1$=methoxy; $R^2$=H; W is absent; R=4-hydroxybutyl

The compound was prepared from the title compound of Example 1 and 4-amino-1-butanol according to the procedures of Example 3. MS m/z 669 $(M+H)^+$.

Example 129

Compound of Formula (I); $R^1$=methoxy; $R^2$=H; W is absent; R=2-(piperidinyl)ethyl The compound was prepared from the title compound of Example 1 and 1-(2-aminoethyl)piperidine according to the procedures of Example 3. MS m/z 708 $(M+H)^+$.

Example 130

Compound of Formula (I); $R^1$=methoxy; $R^2$=H; W is absent; R=2-3-((4-methylbenzoyl)amino)propyl The compound was prepared from the title compound of Example 1 and N-(4-methylbenzoyl)propylene diamine according to the procedures of Example 3. MS m/z 772 $(M+H)^+$.

Example 131

Compound of Formula (I); $R^1$=methoxy; $R^2$=H; W is absent; R=2-3-((4-chlorobenzoyl)amino)propyl The compound was prepared from the title compound of Example 1 and N-(4-chlorobenzoyl)propylene diamine according to the procedures of Example 3. MS m/z 792 $(M+H)^+$.

Example 132

Compound of Formula (I); $R^1$=methoxy; $R^2$=H; W is absent; R=R=2-(pyrrolidinyl)ethyl The compound was prepared from the title compound of Example 1 and 1-(2-aminoethyl)pyrrolidine according to the procedures of Example 3. MS m/z 694 $(M+H)^+$.

Example 133

Compound of Formula (I); $R^1$=methoxy; $R^2$=H; W is absent; R=2-methoxyethyl

The compound was prepared from the title compound of Example 1 and 2-methoxyethylamine according to the procedures of Example 3. MS m/z 655 $(M+H)^+$.

TABLE 3

NMR Data For The C1 C15 Atoms Of The Erythromycin Molecule

| ERYTHRO NOLIDE Atom Number | Example 2 $^{13}$C NMR | Example 2 $^1$H NMR | Example 3 $^{13}$C NMR | Example 3 $^1$H NMR | Example 4 $^{13}$C NMR | Example 4 $^1$H NMR | Example 5 $^{13}$C NMR | Example 5 $^1$H NMR | Example 6 $^{13}$C NMR | Example 6 $^1$H NMR | Example 7 $^{13}$C NMR | Example 7 $^1$H NMR | Example 8 $^{13}$C NMR | Example 8 $^1$H NMR |
|---|---|---|---|---|---|---|---|---|---|---|---|---|---|---|
| 1 | 169.6 | | 169.2 | | 169.3 | | 171.5 | | 169.2 | | 169.3 | | 169.9 | |
| 2 | 128.0 | | 123.7 | | 123.6 | | 125.0 | | 123.6 | | 123.6 | | 122.6 | |
| 2 Me | 13.1 | 1.95 | 12.9 | 1.91 | 12.9 | 1.92 | 12.0 | 1.97 | 12.9 | 1.91 | 12.8 | 1.91 | 12.5 | 1.90 |
| 3 | 143.8 | 6.41 | 146.1 | 6.75 | 146.3 | 6.75 | 144.1 | 6.39 | 146.1 | 6.75 | 146.3 | 6.75 | 147.3 | 6.72 |
| 4 | 35.8 | 2.90 | 37.3 | 2.78 | 37.3 | 2.79 | 37.1 | 2.87 | 37.2 | 2.78 | 37.3 | 2.79 | 37.1 | 2.81 |
| 4 Me | 16.8 | 1.23 | 17.1 | 1.34 | 17.1 | 1.34 | 17.8 | 1.23 | 17.0 | 1.35 | 17.0 | 1.34 | 17.0 | 1.31 |
| 5 | 85.1 | 3.50 | 83.2 | 3.67 | 83.3 | 3.67 | 83.8 | 3.66 | 83.2 | 3.65 | 83.2 | 3.67 | 83.5 | 3.65 |
| 6 | 34.8 | 1.97 | 79.0 | | 79.0 | | 78.8 | | 79.0 | | 79.0 | | 79.3 | |
| 6 Me | 18.5 | 1.06 | 20.2 | 1.32 | 20.2 | 1.35 | 20.8 | 1.29 | 20.2 | 1.32 | 20.2 | 1.35 | 19.9 | 1.37 |
| O Me | | | 48.8 | 2.84 | 49.1 | 2.94 | 50.2 | 3.13 | 48.8 | 2.96 | 49.0 | 2.91 | 48.6 | 3.00 |
| 7 | 36.3 | 1.53, 1.01 | 40.0 | 1.68, 1.53 | 40.0 | 1.70, 1.55 | 41.9 | 2.17, 1.40 | 40.1 | 1.69, 1.54 | 40.0 | 1.69, 1.55 | 39.5 | 161, 1.37 |
| 8 | 43.4 | 2.53 | 44.7 | 2.66 | 44.7 | 2.69 | 41.2 | 2.77 | 44.7 | 2.68 | 44.7 | 2.68 | 42.6 | 2.80 |
| 8 Me | 15.3 | 1.11 | 18.1 | 1.15 | 18.1 | 1.16 | 19.9 | 1.01 | 18.1 | 1.17 | 18.1 | 1.17 | 18.6 | 1.07 |
| 9 | 214.7 | | 215.4 | | 215.3 | | 214.1 | | 215.4 | | 215.4 | | 181.2 | |
| 10 | 42.9 | 2.90 | 40.1 | 3.00 | 40.1 | 3.02 | 46.5 | 3.04 | 40.1 | 3.02 | 40.1 | 3.02 | 37.1 | 2.67 |
| 10 Me | 10.6 | 1.01 | 14.1 | 1.02 | 14.1 | 1.05 | 10.5 | 1.17 | 14.1 | 1.04 | 14.1 | 1.04 | 11.9 | 1.20 |
| 11 | 59.8 | 3.56 | 60.6 | 3.32 | 61.1 | 3.37 | 61.7 | 3.21 | 61 | 3.35 | 61.0 | 3.35 | 61.1 | 3.30 |
| 12 | 82.2 | | 83.0 | | 83.1 | | 84.3 | | 83.0 | | 83.2 | | 82.3 | |
| 12 Me | 14.6 | 1.44 | 14.5 | 1.47 | 14.5 | 1.49 | 16.5 | 1.63 | 14.6 | 1.49 | 14.5 | 1.49 | 13.6 | 1.51 |
| 13 | 77.6 | 4.94 | 77.7 | 4.71 | 77.6 | 4.74 | 78.2 | 4.97 | 77.7 | 4.71 | 77.5 | 4.73 | 78.7 | 4.68 |
| 14 | 21.4 | 1.93, 1.63 | 21.9 | 1.95, 1.58 | 21.9 | 1.95, 1.6 | 21.6 | 1.86, 1.61 | 22.0 | 1.96, 1.60 | 21.9 | 1.93, 1.60 | 21.8 | 1.93, 1.61 |
| 15 | 10.4 | 0.95 | 10.7 | 0.98 | 10.6 | 0.98 | 10.3 | 0.90 | 10.7 | 1.00 | 10.6 | 0.97 | 10.6 | 1.01 |

| ERYTHRO NOLIDE Atom Number | Example 9 $^{13}$C NMR | Example 9 $^1$H NMR | Example 10 $^{13}$C NMR | Example 10 $^1$H NMR | Example 11 $^{13}$C NMR | Example 11 $^1$H NMR | Example 12 $^{13}$C NMR | Example 12 $^1$H NMR | Example 13 $^{13}$C NMR | Example 13 $^1$H NMR | Example 14 $^{13}$C NMR | Example 14 $^1$H NMR | Example 15 $^{13}$C NMR | Example 15 $^1$H NMR |
|---|---|---|---|---|---|---|---|---|---|---|---|---|---|---|
| 1 | 169.3 | | 169.2 | | 169.3 | | 169.4 | | 168.8 | | 169.1 | | 169.3 | |
| 2 | 123.4 | | 123.7 | | 123.6 | | 123.5 | | 123.8 | | 123.9 | | 123.8 | |
| 2 Me | 12.9 | 1.90 | 12.9 | 1.90 | 13.0 | 1.93 | 12.9 | 1.92 | 13.0 | 1.87 | 13.0 | 1.94 | 13.0 | 1.94 |
| 3 | 146.3 | 6.75 | 146.1 | 6.72 | 146.2 | 6.78 | 146.5 | 6.76 | 145.6 | 6.70 | 145.9 | 6.79 | 146.2 | 6.78 |
| 4 | 37.3 | 2.78 | 37.3 | 2.77 | 37.3 | 2.82 | 37.4 | 2.79 | 37.1 | 2.74 | 37.2 | 2.79 | 37.4 | 2.81 |
| 4 Me | 17.0 | 1.33 | 17.1 | 1.34 | 17.1 | 1.36 | 17.1 | 1.35 | 17.0 | 1.33 | 17.0 | 1.37 | 17.1 | 1.36 |
| 5 | 83.1 | 3.65 | 83.0 | 3.63 | 83.2 | 3.69 | 83.2 | 3.69 | 82.9 | 3.58 | 83.1 | 3.70 | 83.3 | 3.69 |

TABLE 3-continued

NMR Data For The C1 C15 Atoms Of The Erythromycin Molecule

| | | | | | | | | | | | | | | | |
|---|---|---|---|---|---|---|---|---|---|---|---|---|---|---|---|
| 6 | 78.9 | | 78.9 | | 79.0 | | 79.1 | | 78.6 | | 78.9 | | 79.2 | | |
| 6 Me | 20.2 | 1.32 | 20.3 | 1.31 | 20.3 | 1.37 | 20.2 | 1.37 | 20.2 | 1.26 | 20.4 | 1.32 | 20.4 | 1.37 |
| O Me | 49.1 | 2.90 | 48.6 | 2.68 | 49.2 | 2.90 | 49.1 | 2.88 | 48.2 | 2.28 | 49.0 | 2.83 | 49.2 | 2.91 |
| 7 | 40.1 | 1.69, 1.55 | 40.1 | 1.67, 1.55 | 40.1 | 1.73, 1.57 | 40.0 | 1.71, 1.56 | 40.3 | 1.67, 1.53 | 40.0 | 1.71, 1.61 | 40.1 | 1.73, 1.60 |
| 8 | 44.7 | 2.67 | 44.8 | 2.65 | 44.8 | 2.71 | 44.7 | 2.71 | 45.0 | 2.66 | 44.3 | 2.71 | 44.8 | 2.71 |
| 8 Me | 18.1 | 1.16 | 18.2 | 1.15 | 18.2 | 1.19 | 18.2 | 1.19 | 18.3 | 1.17 | 18.2 | 1.18 | 18.2 | 1.19 |
| 9 | 215.4 | | 215.7 | | 215.6 | | 215.8 | | 215.3 | | 217.2 | | 215.6 | | |
| 10 | 40.1 | 3.02 | 40.0 | 3.01 | 40.2 | 3.06 | 40.1 | 3.04 | 40.3 | 3.1 | 40.7 | 3.08 | 40.2 | 3.06 |
| 10 Me | 14.2 | 1.05 | 14.2 | 1.03 | 14.3 | 1.07 | 14.3 | 1.06 | 14.4 | 1.11 | 14.5 | 1.07 | 14.2 | 1.07 |
| 11 | 61.4 | 3.40 | 60.8 | 3.32 | 61.1 | 3.41 | 61.2 | 3.35 | 61.1 | 3.42 | 57.9 | 3.49 | 61.2 | 3.41 |
| 12 | 83.1 | | 83.3 | | 83.0 | | 83.2 | | 83.1 | | 81.5 | | 83.1 | | |
| 12 Me | 14.6 | 1.49 | 14.5 | 1.48 | 14.7 | 1.51 | 14.6 | 1.49 | 15.0 | 1.54 | 14.7 | 1.50 | 14.7 | 1.51 |
| 13 | 77.7 | 4.75 | 77.6 | 4.71 | 77.7 | 4.71 | 77.9 | 4.66 | 77.9 | 4.77 | 77.8 | 4.76 | 77.9 | 4.72 |
| 14 | 22.0 | 1.95, 1.6 | 22.0 | 1.93, 1.59 | 22.0 | 1.93, 1.62 | 21.9 | 1.92, 1.58 | 22.4 | 1.99, 1.62 | 21.8 | 1.95, 1.58 | 22.1 | 1.94, 1.60 |
| 15 | 10.8 | 0.99 | 10.8 | 0.99 | 10.7 | 0.99 | 10.7 | 0.98 | 11.0 | 1.03 | 10.6 | 0.99 | 10.7 | 0.99 |

| | Chemical shift | | | | | | | | | | | | | |
|---|---|---|---|---|---|---|---|---|---|---|---|---|---|---|
| ERYTHRO | Example 16 | | Example 18 | | Example 19 | | Example 20 | | Example 21 | | Example 22 | | Example 23 | |
| NOLIDE Atom Number | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.3 | | 170.0 | | 170.9 | | 171.9 | | 169.6 | | 169.3 | | 168.9 | |
| 2 | 123.7 | | 122.1 | | 127.8 | | 124.1 | | 122.8 | | 124.1 | | 123.2 | |
| 2 Me | 12.9 | 1.92 | 12.5 | 1.87 | 12.7 | 1.93 | 11.7 | 1.97 | 12.5 | 1.90 | 13.1 | 1.94 | 12.8 | 1.88 |
| 3 | 146.2 | 6.75 | 147.1 | 6.62 | 145.2 | 6.71 | 144.5 | 6.35 | 146.6 | 6.70 | 146.0 | 6.79 | 146.7 | 6.81 |
| 4 | 37.3 | 2.81 | 36.9 | 2.81 | 36.9 | 2.91 | 36.8 | 2.89 | 37.2 | 2.80 | 37.3 | 2.79 | 36.6 | 2.74 |
| 4 Me | 17.1 | 1.35 | 16.9 | 1.29 | 19.9 | 1.25 | 17.4 | 1.24 | 16.8 | 1.32 | 17.2 | 1.37 | 16.6 | 1.31 |
| 5 | 83.3 | 3.66 | 83.8 | 3.57 | 86.0 | 3.81 | 83.8 | 3.65 | 83.1 | 3.65 | 83.2 | 3.69 | 82.6 | 3.71 |
| 6 | 79.1 | | 78.7 | | 80.7 | | 78.6 | | 78.8 | | 79.0 | | 78.6 | |
| 6 Me | 20.3 | 1.34 | 19.8 | 1.32 | 20.8 | 1.25 | 21.2 | 3.15 | 19.9 | 2.94 | 20.4 | 1.30 | 20.1 | 1.24 |
| O Me | 48.9 | 2.81 | 48.8 | 2.86 | 51.1 | 3.24 | 50.4 | 1.32 | 48.8 | 1.35 | 49.1 | 2.75 | 48.6 | 2.80 |
| 7 | 40.1 | 1.70, 1.55 | 40.5 | 1.73, 1.47 | 35.2 | 1.85, 1.04 | 42.6 | 2.22, 1.40 | 40.1 | 1.75, 1.52 | 40.1 | 1.68, 1.59 | 39.4 | 1.67, 1.00 |
| 8 | 44.7 | 2.69 | 44.2 | 2.62 | 35.2 | 1.79 | 41.0 | 2.73 | 44.3 | 2.72 | 44.5 | 2.71 | 44.6 | 2.55 |
| 8 Me | 18.2 | 1.17 | 17.5 | 1.15 | 20.9 | 94.0 | 19.9 | 1.00 | 17.7 | 1.18 | 18.3 | 1.20 | 17.6 | 1.16 |
| 9 | 215.4 | | 217.5 | | 72.1 | | 215.1 | | 216.9 | | 217.4 | | 215.3 | |
| 10 | 40.2 | 3.02 | 38.3 | 2.83 | 33.6 | 2.34 | 45.6 | 3.53 | 40.3 | 3.02 | 40.8 | 3.09 | 39.3 | 3.09 |
| 10 Me | 14.1 | 1.05 | 13.6 | 1.13 | 19.3 | 1.79 | 10.4 | 1.13 | 14.0 | 1.08 | 14.6 | 1.09 | 13.7 | 0.94 |
| 11 | 61.0 | 3.35 | 58.4 | 3.41 | 60.9 | 0.98 | 63.7 | 3.23 | 63.0 | 3.29 | 57.9 | 3.48 | 60.1 | 3.31 |
| 12 | 83.1 | | 84.5 | | 82.8 | 3.67 | 83.9 | | 81.8 | | 81.7 | | 82.9 | |
| 12 Me | 14.6 | 1.50 | 14.1 | 1.49 | 13.2 | | 14.0 | 1.69 | 14.0 | 1.48 | 14.7 | 1.51 | 14.1 | 1.49 |
| 13 | 77.8 | 4.75 | 79.1 | 4.78 | 76.2 | 1.40, 4.93 | 78.3 | 4.94 | 77.8 | 4.77 | 77.8 | 4.76 | 76.8 | 4.60 |
| 14 | 22.0 | 1.97, 1.62 | 22.1 | 1.92, 1.61 | 21 | 1.89, 1.58 | 21 | 1.85, 1.64 | 21.6 | 1.94, 1.59 | 21.9 | 1.94, 0.60 | 21.6 | 1.76, 1.59 |
| 15 | 10.7 | 1.00 | 10.7 | 1.02 | 10.5 | 0.94 | 10.4 | 0.96 | 10.5 | 0.99 | 10.7 | 0.97 | 10.7 | 0.88 |

| | Chemical shift | | | | | | | | | | | | | |
|---|---|---|---|---|---|---|---|---|---|---|---|---|---|---|
| ERYTHRO | Example 24 | | Example 43 | | Example 44 | | Example 45 | | Example 46 | | Example 47 | | Example 48 | |
| NOLIDE Atom Number | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.4 | | 169.5 | | 169.4 | | 169.3 | | 169.4 | | 169.6 | | 169.3 | |
| 2 | 123.6 | | 123.0 | | 123.6 | | 123.8 | | 123.7 | | 123.3 | | 123.8 | |
| 2 Me | 12.9 | 1.91 | 12.9 | 1.90 | 12.9 | 1.93 | 13 | 1.93 | 12.9 | 1.91 | 12.7 | 1.89 | 13.0 | 1.93 |
| 3 | 146.4 | 6.76 | 146.6 | 6.73 | 146.4 | 6.76 | 146.1 | 6.78 | 146.2 | 6.75 | 146.3 | 6.70 | 146.2 | 6.76 |
| 4 | 37.3 | 2.79 | 37.4 | 2.77 | 37.4 | 2.81 | 37.3 | 2.79 | 37.3 | 2.78 | 37.2 | 2.77 | 37.4 | 2.8 |
| 4 Me | 17.1 | 1.34 | 17.1 | 1.34 | 17.1 | 1.36 | 17.1 | 1.35 | 17.1 | 1.33 | 17.0 | 1.31 | 17.2 | 1.35 |
| 5 | 83.3 | 3.68 | 83.2 | 3.63 | 83.2 | 3.69 | 83.3 | 3.69 | 83.3 | 3.67 | 82.9 | 3.67 | 83.3 | 3.68 |
| 6 | 79.1 | | 79.2 | | 79.2 | | 79.1 | | 79.0 | | 79.0 | | 79.2 | |
| 6 Me | 20.3 | 1.35 | 20.2 | 2.66 | 20.3 | 1.37 | 20.3 | 1.36 | 20.3 | 1.33 | 20.1 | 1.34 | 20.3 | 1.36 |
| O Me | 49.1 | 2.94 | 48.9 | 1.27 | 49.1 | 2.88 | 49.1 | 2.9 | 49.1 | 2.93 | 48.7 | 2.91 | 49.2 | 2.87 |
| 7 | 40.0 | 1.71, 1.55 | 40.1 | 1.70, 1.55 | 40.1 | 1.73, 1.57 | 40.1 | 1.71, 1.57 | 40.1 | 1.67, 1.54 | 39.9 | 1.69, 1.49 | 40.1 | 1.69, 1.58 |
| 8 | 44.7 | 2.68 | 44.8 | 2.64 | 44.8 | 2.72 | 44.7 | 2.7 | 44.7 | 2.66 | 44.9 | 2.64 | 44.8 | 2.7 |
| 8 Me | 18.1 | 1.16 | 18.1 | 1.16 | 18.2 | 1.2.0 | 18.2 | 1.18 | 18.2 | 1.16 | 18.0 | 1.13 | 18.2 | 1.19 |
| 9 | 215.5 | | 215.7 | | 216.0 | | 215.4 | | 215.4 | | 215.9 | | 215.7 | |
| 10 | 40.1 | 3.02 | 40.1 | 3.04 | 40.1 | 3.06 | 40.3 | 3.04 | 40.2 | 2.99 | 39.6 | 2.92 | 40.3 | 3.04 |
| 10 Me | 14.1 | 1.05 | 14.1 | 1.04 | 14.3 | 1.07 | 14.2 | 1.05 | 14.1 | 1.02 | 14.4 | 1.10 | 14.2 | 1.06 |
| 11 | 61.2 | 3.35 | 61.0 | 3.32 | 61.3 | 3.37 | 61.2 | 3.41 | 61 | 3.32 | 62.4 | 3.17 | 61.2 | 3.37 |
| 12 | 83.3 | | 83.4 | | 83.3 | | 83 | | 83.1 | | 83.0 | | 83.1 | |
| 12 Me | 14.5 | 1.49 | 14.6 | 1.51 | 14.6 | 1.5.0 | 14.7 | 1.49 | 14.6 | 1.47 | 14.0 | 1.42 | 14.7 | 1.5 |
| 13 | 77.5 | 4.73 | 77.6 | 4.72 | 77.8 | 4.66 | 78.0 | 4.69 | 77.7 | 4.71 | 77.6 | 4.69 | 77.9 | 4.67 |
| 14 | 21.9 | 1.93, 1.59 | 22.0 | 1.97, 1.63 | 22.0 | 1.93, 1.58 | 22.1 | 1.93, 1.59 | 22.0 | 1.91, 1.58 | 21.7 | 1.92, 1.55 | 22.0 | 1.93, 1.58 |
| 15 | 10.7 | 0.97 | 10.8 | 1.00 | 10.7 | 0.98 | 10.7 | 0.99 | 10.8 | 0.97 | 10.8 | 0.97 | 10.7 | 0.98 |

TABLE 3-continued

NMR Data For The C1 C15 Atoms Of The Erythromycin Molecule

| ERYTHRO NOLIDE Atom Number | Example 49 | | Example 50 | | Example 51 | | Example 52 | | Example 53 | | Example 54 | | Example 55 | |
|---|---|---|---|---|---|---|---|---|---|---|---|---|---|---|
| | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR |
| 1 | 169.4 | | 169.3 | | 169.3 | | 169.4 | | 169.3 | | 169.3 | | 169.3 | |
| 2 | 123.7 | | 123.8 | | 123.8 | | 123.7 | | 123.6 | | 123.6 | | 123.7 | |
| 2 Me | 13.0 | 1.91 | 13.0 | 1.92 | 13.0 | 1.92 | 12.9 | 1.91 | 12.9 | 1.92 | 12.9 | 1.92 | 13.0 | 1.93 |
| 3 | 146.2 | 6.76 | 146.2 | 6.77 | 146.1 | 6.77 | 146.2 | 6.75 | 146.4 | 6.76 | 146.3 | 6.76 | 146.2 | 6.77 |
| 4 | 37.3 | 2.80 | 37.3 | 2.80 | 37.3 | 2.80 | 37.3 | 2.78 | 37.4 | 2.79 | 37.3 | 2.79 | 37.4 | 2.8 |
| 4 Me | 17.1 | 1.34 | 17.1 | 1.35 | 17.1 | 1.34 | 17.2 | 1.33 | 17.1 | 1.34 | 17.1 | 1.34 | 17.1 | 1.36 |
| 5 | 83.1 | 3.69 | 83.3 | 3.69 | 83.3 | 3.68 | 83.2 | 3.68 | 83.8 | 3.68 | 83.3 | 3.68 | 83.8 | 3.68 |
| 6 | 79.1 | | 79.2 | | 79.1 | | 79.1 | | 79.2 | | 79.1 | | 79.1 | |
| 6 Me | 20.3 | 1.34 | 20.3 | 1.36 | 20.3 | 1.35 | 20.3 | 1.34 | 20.2 | 1.36 | 20.3 | 1.36 | 20.3 | 1.37 |
| O Me | 49.2 | 2.88 | 49.2 | 2.88 | 49.2 | 2.89 | 49.1 | 2.92 | 49.1 | 2.87 | 49.2 | 2.91 | 49.2 | 2.86 |
| 7 | 40.1 | 1.69, 1.56 | 40.1 | 1.70, 1.57 | 40.1 | 1.70, 1.58 | 40.1 | 1.68, 1.53 | 40 | 1.71, 1.56 | 40.2 | 1.71, 1.55 | 40.1 | 1.72, 1.58 |
| 8 | 44.8 | 2.69 | 44.8 | 2.70 | 44.7 | 2.69 | 44.7 | 2.66 | 44.7 | 2.71 | 44.7 | 2.7 | 44.8 | 2.71 |
| 8 Me | 18.2 | 1.17 | 18.2 | 1.18 | 18.2 | 1.17 | 18.2 | 1.16 | 18.2 | 1.18 | 18.2 | 1.17 | 18.2 | 1.19 |
| 9 | 215.8 | | 215.6 | | 215.4 | | 215.7 | | 215.7 | | 215.5 | | 215.5 | |
| 10 | 40.3 | 3.04 | 40.2 | 3.05 | 40.3 | 3.04 | 40.2 | 3.00 | 40.2 | 3.04 | 40.2 | 3.03 | 40.2 | 3.05 |
| 10 Me | 14.2 | 1.04 | 14.2 | 1.05 | 14.2 | 1.05 | 14.1 | 1.03 | 14.2 | 1.07 | 14.2 | 1.06 | 14.2 | 1.07 |
| 11 | 61.2 | 3.40 | 61.2 | 3.39 | 61.2 | 3.40 | 61.1 | 3.32 | 61.4 | 3.37 | 61.3 | 3.38 | 61.2 | 3.40 |
| 12 | 83.2 | | 83.1 | | 83.1 | | 83.3 | | 83.2 | | 83.2 | | 83.1 | |
| 12 Me | 14.7 | 1.49 | 14.7 | 1.49 | 14.7 | 1.49 | 14.6 | 1.48 | 14.6 | 1.50 | 14.6 | 1.49 | 14.7 | 1.50 |
| 13 | 77.9 | 4.69 | 77.9 | 4.67 | 77.9 | 4.68 | 77.7 | 4.71 | 77.8 | 4.69 | 77.9 | 4.67 | 77.9 | 4.70 |
| 14 | 22.0 | 1.91, 1.58 | 22.0 | 2.30, 1.57 | 22.0 | 1.92, 1.58 | 22.0 | 1.93, 1.59 | 22.0 | 1.93, 1.59 | 22.0 | 1.92, 1.58 | 22.0 | 1.94, 1.60 |
| 15 | 10.7 | 0.97 | 10.7 | 0.97 | 10.7 | 0.97 | 10.7 | 0.97 | 10.6 | 0.98 | 10.7 | 0.98 | 10.7 | 0.99 |

| ERYTHRO NOLIDE Atom Number | Example 56 | | Example 67 | | Example 68 | | Example 69 | | Example 70 | | Example 71 | | Example 72 | |
|---|---|---|---|---|---|---|---|---|---|---|---|---|---|---|
| | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR |
| 1 | 169.3 | | 171.9 | | 168.4c | | 168.3c | | 169.2 | | 169.3 | | 169.3 | |
| 2 | 123.8 | | 124.1 | | 126.0 | | 126.7 | | 124.0 | | 124.1 | | 124.0 | |
| 2 Me | 13.0 | 1.93 | 11.7 | 1.95 | 12.7 | 1.72 | 12.7 | 1.79 | 13.0 | 1.95 | 13.1 | 1.94 | 13.1 | 1.94 |
| 3 | 146.1 | 6.78 | 144.3 | 6.33 | 145.5 | 6.31 | 145.7 | 6.40 | 145.9 | 6.79 | 146.0 | 6.79 | 146.1 | 6.80 |
| 4 | 37.3 | 2.80 | 36.7 | 2.88 | 36.3 | 2.60 | 36.3 | 2.67 | 37.2 | 2.79 | 37.4 | 2.79 | 37.4 | 2.79 |
| 4 Me | 17.1 | 1.35 | 17.3 | 1.22 | 17.9 | 1.11 | 17.9 | 1.19 | 17.0 | 1.38 | 17.1 | 1.38 | 17.2 | 1.37 |
| 5 | 83.3 | 3.69 | 83.6 | 3.63 | 84.8 | 3.64 | 84.9 | 3.73 | 83.0 | 3.70 | 83.2 | 3.71 | 83.3 | 3.71 |
| 6 | 79.1 | | 78.9 | | 80.6 | | 80.6 | | 78.9 | | 79.1 | | 79.1 | |
| 6 Me | 20.3 | 1.36 | 21.2 | 1.29 | 20.1 | 1.19 | 20.1 | 1.28 | 20.4 | 1.32 | 20.5 | 1.33 | 20.5 | 1.33 |
| O Me | 49.2 | 2.90 | 50.0 | 3.08 | 49.6 | 3.1 | 49.6 | 3.18 | 49.0 | 2.78 | 49.2 | 2.83 | 49.2 | 2.88 |
| 7 | 40.1 | 1.71, 1.58 | 42.7 | 2.16, 1.39 | 34.5 | 1.72, 1.33 | 34.5 | 1.79, 1.39 | 40.1 | 1.72, 1.60 | 40.1 | 1.71, 1.60 | 40.2 | 1.72, 1.60 |
| 8 | 44.7 | 2.70 | 41.0 | 2.65 | 39.1 | 2.70 | 39.1 | 2.79 | 44.4 | 2.71 | 44.4 | 2.71 | 44.4 | 2.72 |
| 8 Me | 18.2 | 1.18 | 19.8 | 0.98 | 19.6 | 1.08 | 19.7 | 1.21 | 18.2 | 1.19 | 18.3 | 1.19 | 18.4 | 1.19 |
| 9 | 215.5 | | 215.3 | | 213 | | 212.8 | | 217.3 | | 217.3 | | 217.3 | |
| 10 | 40.3 | 3.05 | 51.6 | 2.85 | 43.2 | 2.75 | 43.1 | 2.89 | 40.6 | 3.08 | 40.8 | 3.08 | 40.9 | 3.09 |
| 10 Me | 14.2 | 1.05 | 10.4 | 1.24 | 9.2 | 1.20 | -9.20 | 1.32 | 14.5 | 1.07 | 14.6 | 1.07 | 14.6 | 1.08 |
| 11 | 61.1 | 3.41 | 58.4 | 3.32 | 63.5 | 4.13 | 63.6 | 4.09 | 57.9 | 3.47 | 58.0 | 3.47 | 58.1 | 3.49 |
| 12 | 83.0 | | 86.9 | | 83.8 | | 83.9 | | 81.6 | | 81.7 | | 81.7 | |
| 12 Me | 14.7 | 1.49 | 16.7 | 1.7 | 24.3 | 1.60 | 24.0 | 1.53 | 14.7 | 1.50 | 14.8 | 1.50 | 14.8 | 1.51 |
| 13 | 77.9 | 4.69 | 78.4 | 4.99 | 75.9 | 4.72 | 75.9 | 4.78 | 77.7 | 4.74 | 77.9 | 4.75 | 77.9 | 4.76 |
| 14 | 22.1 | 1.93, 1.58 | 21.3 | 1.84, 1.66 | 23.9 | 1.87, 1.72 | 23.9 | 1.92, 1.79 | 21.8 | 1.95, 1.59 | 21.9 | 1.95, 1.58 | 21.9 | 1.95, 1.60 |
| 15 | 10.7 | 0.98 | 10.5 | 0.97 | 11.4 | 0.88 | 11.3 | 0.94 | 10.7 | 0.99 | 10.7 | 0.99 | 10.7 | 0.99 |

| ERYTHRO NOLIDE Atom Number | Example 73 | | Example 74 | | Example 75 | | Example 76 | | Example 77 | | Example 78 | | Example 79 | |
|---|---|---|---|---|---|---|---|---|---|---|---|---|---|---|
| | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR | $^{13}$C NMR | $^1$H NMR |
| 1 | 168.8 | | 169.3 | | 170.1 | | 169.4 | | 169.2 | | 169.2 | | 169.3 | |
| 2 | 123.7 | | 124.0 | | 123.8 | | 123.9 | | 124.0 | | 124.0 | | 124.1 | |
| 2 Me | 12.7 | 1.94 | 13.1 | 1.94 | 13.1 | 1.94 | 13.1 | 1.93 | 13.1 | 1.94 | 13.0 | 1.91 | 13.1 | 1.93 |
| 3 | 145.6 | 6.79 | 446.2 | 6.79 | 146.5 | 6.78 | 146.3 | 6.79 | 146.0 | 6.79 | 146.0 | 6.77 | 146.1 | 6.78 |
| 4 | 36.9 | 2.78 | 37.3 | 2.79 | 37.3 | 2.78 | 37.4 | 2.78 | 37.3 | 2.79 | 37.3 | 2.77 | 37.4 | 2.79 |
| 4 Me | 16.7 | 1.36 | 17.1 | 1.37 | 17.0 | 1.38 | 17.1 | 1.31 | 17.1 | 1.37 | 17.0 | 1.35 | 17.2 | 1.31 |
| 5 | 82.8 | 3.53 | 83.1 | 3.70 | 83.1 | 3.60 | 83.1 | 3.70 | 83.2 | 3.70 | 83.0 | 3.68 | 83.3 | 3.70 |
| 6 | 78.6 | | 79.0 | | 78.9 | | 79.0 | | 79.0 | | 79.0 | | 79.1 | |

TABLE 3-continued

NMR Data For The C1 C15 Atoms Of The Erythromycin Molecule

| | | | | | | | | | | | | | | |
|---|---|---|---|---|---|---|---|---|---|---|---|---|---|---|
| 6 Me | 20.1 | 1.33 | 20.5 | 1.32 | 20.4 | 1.28 | 20.4 | 1.30 | 20.5 | 1.32 | 20.4 | 1.30 | 20.5 | 1.32 |
| O Me | 48.8 | 2.84 | 49.2 | 2.84 | 49.0 | 2.66 | 49.3 | 2.80 | 49.1 | 2.82 | 49.0 | 2.77 | 49.2 | 2.84 |
| 7 | 39.7 | 1.79, 1.61 | 40.1 | 1.70, 1.57 | 40.2 | 1.69, 1.57 | 40.1 | 1.87, 1.71 | 40.1 | 1.71, 1.59 | 40.1 | 1.70, 1.57 | 40.1 | 1.72, 1.61 |
| 8 | 44.0 | 2.71 | 44.4 | 2.71 | 44.4 | 2.69 | 44.6 | 2.70 | 44.4 | 2.71 | 44.5 | 2.77 | 44.5 | 2.71 |
| 8 Me | 17.9 | 1.20 | 18.3 | 1.18 | 18.3 | 1.16 | 18.4 | 1.17 | 18.3 | 1.19 | 18.2 | 1.21 | 18.4 | 1.17 |
| 9 | 216.9 | | 217.4 | | 217.4 | | 217.2 | | 217.3 | | 217.5 | | 217.4 | |
| 10 | 40.4 | 3.08 | 40.8 | 3.07 | 40.7 | 3.07 | 40.5 | 3.09 | 40.8 | 3.07 | 40.6 | 3.07 | 40.8 | 3.11 |
| 10 Me | 14.2 | 1.07 | 14.6 | 1.07 | 14.6 | 1.07 | 14.7 | 1.07 | 14.6 | 1.07 | 14.5 | 1.05 | 14.6 | 1.07 |
| 11 | 57.6 | 3.47 | 58.0 | 3.48 | 58.3 | 3.46 | 57.4 | 3.46 | 58.0 | 3.43 | 57.8 | 3.43 | 58.0 | 3.46 |
| 12 | 81.2 | | 81.7 | | 81.3 | | 82.0 | | 81.6 | | 81.7 | | 81.7 | |
| 12 Me | 14.4 | 1.49 | 14.8 | 1.50 | 14.9 | 1.51 | 14.8 | 1.51 | 14.8 | 1.50 | 14.6 | 1.48 | 14.7 | 1.50 |
| 13 | 77.4 | 4.43 | 77.9 | 4.75 | 78.5 | 4.75 | 77.9 | 4.75 | 77.9 | 4.75 | 77.7 | 4.70 | 77.8 | 4.72 |
| 14 | 21.5 | 1.93, 1.58 | 21.9 | 1.94, 1.58 | 22.0 | 1.95, 1.60 | 21.9 | 1.95, 1.59 | 21.9 | 1.94, 1.58 | 21.8 | 1.91, 1.57 | 21.9 | 1.94, 1.59 |
| 15 | 10.3 | 0.98 | 10.7 | 0.99 | 10.9 | 1.02 | 10.8 | 0.99 | 10.7 | 0.99 | 10.7 | 0.95 | 10.7 | 0.98 |

| | Chemical shift | | | | | | | | | | | | | |
|---|---|---|---|---|---|---|---|---|---|---|---|---|---|---|
| ERYTHRO | Example 80 | | Example 81 | | Example 82 | | Example 83 | | Example 84 | | Example 85 | | Example 86 | |
| NOLIDE Atom Number | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.2 | | 169.3 | | 169.4 | | 169.2 | | 169.3 | | 169.4 | | 169.4 | |
| 2 | 123.9 | | 124.0 | | 123.8 | | 123.8 | | 124.2 | | 124.4 | | 124.2 | |
| 2 Me | 13.1 | 1.93 | 13.1 | 1.94 | 13.1 | 1.95 | 13.0 | 1.93 | 13.1 | 1.96 | 13.0 | 1.95 | 13.1 | 1.96 |
| 3 | 146.2 | 6.79 | 146.1 | 6.79 | 146.2 | 6.83 | 146.1 | 6.79 | 146.0 | 6.84 | 146.1 | 6.83 | 146.0 | 6.84 |
| 4 | 37.4 | 2.78 | 37.4 | 2.79 | 37.4 | 2.82 | 37.2 | 2.79 | 37.4 | 2.82 | 37.4 | 2.82 | 37.4 | 2.82 |
| 4 Me | 17.1 | 1.37 | 17.1 | 1.37 | 17.1 | 1.38 | 17.0 | 1.36 | 17.2 | 1.38 | 17.2 | 1.37 | 17.2 | 1.39 |
| 5 | 83.3 | 3.72 | 83.3 | 3.71 | 83.3 | 3.73 | 83.2 | 3.68 | 83.4 | 3.74 | 83.6 | 3.72 | 83.4 | 3.74 |
| 6 | 79.0 | | 79.1 | | 79.0 | | 78.9 | | 79.2 | | 79.2 | | 79.2 | |
| 6 Me | 20.5 | 1.34 | 20.5 | 1.33 | 20.5 | 1.37 | 20.4 | 1.31 | 20.8 | 1.37 | 20.9 | 1.34 | 20.8 | 1.37 |
| O Me | 49.3 | 2.90 | 49.2 | 2.86 | 49.5 | 3.02 | 49.1 | 2.79 | 49.6 | 2.99 | 49.5 | 2.93 | 49.6 | 3.00 |
| 7 | 40.2 | 1.71, 1.59 | 40.1 | 1.72, 1.64 | 40.1 | 1.73, 1.61 | 40.0 | 1.71, 1.59 | 40.1 | 1.74, 1.66 | 40.0 | 1.72, 1.66 | 40.1 | 1.74, 1.67 |
| 8 | 44.5 | 2.72 | 44.4 | 2.75 | 44.4 | 2.74 | 44.2 | 2.77 | 44.3 | 2.77 | 44.0 | 2.77 | 44.3 | 2.77 |
| 8 Me | 18.3 | 1.18 | 18.3 | 1.18 | 18.4 | 1.20 | 18.2 | 1.19 | 18.4 | 1.20 | 18.4 | 1.20 | 18.4 | 1.20 |
| 9 | 217.4 | | 217.2 | | 217.5 | | 217.1 | | 217.2 | | 217.0 | | 217.2 | |
| 10 | 40.7 | 3.08 | 40.8 | 3.08 | 40.8 | 3.09 | 40.8 | 3.08 | 41.1 | 3.11 | 41.3 | 3.10 | 41.1 | 3.10 |
| 10 Me | 14.7 | 1.09 | 14.5 | 1.07 | 14.8 | 1.08 | 14.4 | 1.07 | 14.4 | 1.09 | 14.3 | 1.10 | 14.4 | 1.08 |
| 11 | 57.9 | 3.49 | 58.1 | 3.48 | 57.8 | 3.51 | 58.4 | 3.53 | 58.6 | 3.61 | 59.0 | 3.68 | 58.5 | 3.60 |
| 12 | 81.7 | | 81.7 | | 81.8 | | 81.6 | | 81.6 | | 81.7 | | 81.6 | |
| 12 Me | 14.8 | 1.50 | 14.8 | 1.50 | 14.8 | 1.47 | 14.7 | 1.51 | 14.9 | 1.49 | 14.9 | 1.51 | 14.9 | 1.48 |
| 13 | 77.8 | 4.74 | 77.9 | 4.74 | 78.6 | 4.78 | 77.8 | 4.82 | 77.3 | 4.68 | 78.2 | 4.74 | 78.3 | 4.63 |
| 14 | 21.9 | 1.91, 1.57 | 21.9 | 1.83, 1.51 | 21.8 | 1.77, 148 | 21.8 | 1.97, 1.60 | 21.9 | 1.85, 1.53 | 21.9 | 1.92, 1.59 | 21.9 | 1.85, 1.53 |
| 15 | 10.7 | 0.97 | 10.7 | 0.98 | 10.4 | 0.74 | 10.7 | 1.01 | 10.7 | 0.92 | 10.7 | 0.97 | 10.7 | 0.93 |

| | Chemical shift | | | | | | | | | | | | | |
|---|---|---|---|---|---|---|---|---|---|---|---|---|---|---|
| ERYTHRO | Example 87 | | Example 88 | | Example 89 | | Example 90 | | Example 91 | | Example 92 | | Example 93 | |
| NOLIDE Atom Number | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.3 | | 169.4 | | 169.3 | | 169.5 | | 169.5 | | 169.5 | | 169.5 | |
| 2 | 124.0 | | 124.0 | | 124.2 | | 123.8 | | 124.0 | | 124.0 | | 123.9 | |
| 2 Me | 13.1 | 1.95 | 13.1 | 1.96 | 13.1 | 1.96 | 13 | 1.96 | 13.1 | 1.97 | 13.1 | 1.96 | 13.2 | 1.97 |
| 3 | 146.1 | 6.83 | 146.2 | 6.84 | 145.9 | 6.85 | 146.3 | 6.84 | 146.4 | 6.84 | 146.4 | 6.86 | 146.4 | 6.86 |
| 4 | 37.4 | 2.81 | 37.4 | 2.82 | 37.4 | 2.82 | 37.4 | 2.82 | 37.4 | 2.82 | 37.4 | 2.82 | 37.4 | 2.82 |
| 4 Me | 17.1 | 1.38 | 17.1 | 1.38 | 17.2 | 1.38 | 17.1 | 1.38 | 17.1 | 1.39 | 17.1 | 1.39 | 17.1 | 1.41 |
| 5 | 83.2 | 3.74 | 83.2 | 3.74 | 83.4 | 3.74 | 83.2 | 3.74 | 83.2 | 3.75 | 83.0 | 3.75 | 82.9 | 3.75 |
| 6 | 79.1 | | 79.2 | | 79.2 | | 79.1 | | 79.2 | | 79.1 | | 79.2 | |
| 6 Me | 20.7 | 1.37 | 20.7 | 1.36 | 20.8 | 1.37 | 20.5 | 1.37 | 20.6 | 1.38 | 20.7 | 1.36 | 20.5 | 1.38 |
| O Me | 49.6 | 2.98 | 49.5 | 2.98 | 49.6 | 3.00 | 49.5 | 3.02 | 49.6 | 3.00 | 49.7 | 2.98 | 49.8 | 3.04 |
| 7 | 40.1 | 1.73, 1.64 | 40.1 | 1.74, 1.64 | 40.1 | 1.74, 1.66 | 40 | 1.74, 1.61 | 40.0 | 1.75, 1.63 | 40.2 | 1.74, 1.65 | 40.5 | 1.76, 1.65 |
| 8 | 44.3 | 2.77 | 44.4 | 2.76 | 44.1 | 2.77 | 44.4 | 2.75 | 44.5 | 2.76 | 44.4 | 2.76 | 44.6 | 2.73 |
| 8 Me | 18.4 | 1.20 | 18.4 | 1.20 | 18.5 | 1.20 | 18.3 | 1.21 | 18.4 | 1.22 | 18.4 | 1.20 | 18.5 | 1.21 |
| 9 | 217.3 | | 217.5 | | 217.0 | | 217.6 | | 217.7 | | 217.4 | | 217.7 | |
| 10 | 41.0 | 3.10 | 40.9 | 3.11 | 40.7 | 3.10 | 40.6 | 3.10 | 40.8 | 3.13 | 40.8 | 3.11 | 40.5 | 3.07 |
| 10 Me | 14.6 | 1.08 | 14.6 | 1.08 | 14.4 | 1.08 | 14.7 | 1.08 | 14.6 | 1.09 | 14.7 | 1.06 | 14.9 | 1.07 |
| 11 | 58.4 | 3.60 | 58.2 | 3.57 | 58.7 | 3.62 | 57.5 | 3.49 | 58.0 | 3.54 | 58.5 | 3.60 | 57.9 | 3.54 |
| 12 | 81.7 | | 81.6 | | 81.6 | | 81.8 | | 81.7 | | 81.8 | | 82.0 | |
| 12 Me | 14.9 | 1.49 | 14.8 | 1.48 | 15.0 | 1.49 | 14.7 | 1.47 | 14.7 | 1.48 | 15.0 | 1.48 | 14.9 | 1.47 |
| 13 | 78.1 | 4.71 | 78.2 | 4.62 | 78.4 | 4.71 | 78.3 | 4.71 | 78.4 | 4.58 | 78.6 | 4.61 | 78.9 | 4.50 |
| 14 | 21.9 | 1.84, 1.54 | 21.8 | 1.83, 1.53 | 22.0 | 1.85, 1.53 | 21.7 | 1.74, 1.46 | 21.7 | 1.79, 1.51 | 22.0 | 1.80, 1.51 | 22.1 | 1.76, 1.47 |
| 15 | 10.7 | 0.94 | 10.6 | 0.91 | 10.7 | 0.94 | 10.5 | 0.70 | 10.7 | 0.88 | 10.7 | 0.91 | 10.7 | 0.90 |

TABLE 3-continued

NMR Data For The C1 C15 Atoms Of The Erythromycin Molecule

| ERYTHRO NOLIDE Atom Number | Example 94 | | Example 95 | | Example 96 | | Example 97 | | Example 98 | | Example 99 | | Example 100 | |
|---|---|---|---|---|---|---|---|---|---|---|---|---|---|---|
| | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.3 | | 169.3 | | 169.5 | | 170.2 | | 169.5 | | 169.6 | | 169.3 | |
| 2 | 123.5 | | 124.1 | | 124.0 | | 124.8 | | 124.0 | | 124.1 | | 123.5 | |
| 2 Me | 13.0 | 1.97 | 13.1 | 1.95 | 13.1 | 1.95 | 12.6 | 1.94 | 13.1 | 1.96 | 13.1 | 1.98 | 13.0 | 1.96 |
| 3 | 146.7 | 6.85 | 146.0 | 6.84 | 146.3 | 6.82 | 146.5 | 6.77 | 146.1 | 6.84 | 146.3 | 6.89 | 146.4 | 6.84 |
| 4 | 37.3 | 2.82 | 37.4 | 2.82 | 37.3 | 2.81 | 37.4 | 2.84 | 37.3 | 2.82 | 37.4 | 2.83 | 37.3 | 2.82 |
| 4 Me | 17.0 | 1.39 | 17.1 | 1.38 | 17.2 | 1.38 | 17.4 | 1.27 | 17.1 | 1.38 | 17.1 | 1.40 | 17.0 | 1.38 |
| 5 | 83.1 | 3.75 | 83.3 | 3.74 | 83.3 | 3.73 | 84.8 | 3.64 | 83.2 | 3.75 | 83.1 | 3.71 | 83.1 | 3.74 |
| 6 | 79.1 | | 79.1 | | 79.1 | | 79.8 | | 79.1 | | 79.2 | | 79.0 | |
| 6 Me | 20.3 | 1.37 | 20.7 | 1.36 | 20.5 | 1.36 | 21.1 | 1.24 | 20.7 | 1.36 | 20.7 | 1.37 | 20.3 | 1.38 |
| O Me | 49.6 | 3.08 | 49.5 | 2.97 | 49.5 | 2.98 | 48.9 | 2.88 | 49.6 | 3.00 | 49.7 | 3.00 | 49.5 | 3.05 |
| 7 | 40.2 | 1.76, 1.60 | 40.1 | 1.73, 1.65 | 40.0 | 1.73, 1.61 | 39.0 | 1.60, 1.56 | 40.3 | 1.73, 1.63 | 40.2 | 1.73, 1.66 | 40.2 | 1.77, 1.62 |
| 8 | 44.4 | 2.74 | 44.3 | 2.76 | 44.4 | 2.74 | 42.2 | 2.78 | 44.3 | 2.75 | 44.5 | 2.78 | 44.5 | 2.73 |
| 8 Me | 18.1 | 1.20 | 18.4 | 1.20 | 18.3 | 1.20 | 18.2 | 1.08 | 18.4 | 1.16 | 18.5 | 1.20 | 18.2 | 1.20 |
| 9 | 218.3 | | 217.3 | | 217.6 | | 213.8 | | 217.4 | | 217.3 | | 217.7 | |
| 10 | 40.5 | 3.12 | 41.0 | 3.09 | 40.7 | 3.10 | 42.2 | 2.86 | 41.0 | 3.05 | 40.9 | 3.13 | 40.5 | 3.07 |
| 10 Me | 14.5 | 1.06 | 14.5 | 1.08 | 14.6 | 1.08 | 12.3 | 1.20 | 14.5 | 1.07 | 14.6 | 1.06 | 14.7 | 1.07 |
| 11 | 58.6 | 3.45 | 58.8 | 3.55 | 58.0 | 3.47 | 55.9 | 3.66 | 58.4 | 3.60 | 58.4 | 3.61 | 58.5 | 3.54 |
| 12 | 82.8 | | 81.6 | | 81.9 | | 83.4 | | 81.8 | | 81.5 | | 82.3 | |
| 12 Me | 14.6 | 1.53 | 14.9 | 1.48 | 14.7 | 1.49 | 14.4 | 1.50 | 14.9 | 1.54 | 15.0 | 1.47 | 14.7 | 1.51 |
| 13 | 77.6 | 4.75 | 78.3 | 4.62 | 78.1 | 4.72 | 77.9 | 4.92 | 78.3 | 4.70 | 78.9 | 4.56 | 78.1 | 4.72 |
| 14 | 21.7 | 1.88, 1.58 | 21.9 | 1.84, 1.53 | 21.7 | 1.86, 1.53 | 21.5 | 1.95, 1.67 | 21.9 | 1.81 | 22.1 | 1.75, 1.48 | 21.8 | 1.87, 1.54 |
| 15 | 10.5 | 0.95 | 10.7 | 0.93 | 10.7 | 0.88 | 10.6 | 1.03 | 10.7 | 0.95 | 10.7 | 0.88 | 10.6 | 0.95 |

| ERYTHRO NOLIDE Atom Number | Example 101 | | Example 102 | | Example 103 | | Example 104 | | Example 105 | | Example 106 | | Example 107 | |
|---|---|---|---|---|---|---|---|---|---|---|---|---|---|---|
| | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.4 | | 169.5 | | 168.9 | | 169.3 | | 169.5 | | 169.3 | | 169.4 | |
| 2 | 124.1 | | 124.1 | | 124.0 | | 124.0 | | 124.1 | | 123.7 | | 124.3 | |
| 2 Me | 13.1 | 1.96 | 13.0 | 1.95 | 13.1 | 1.95 | 13.0 | 1.96 | 13.1 | 1.95 | 13.1 | 1.97 | 13.1 | 1.97 |
| 3 | 146.2 | 6.84 | 146.3 | 3.84 | 145.6 | 6.85 | 146.2 | 6.84 | 146.3 | 6.83 | 146.4 | 6.84 | 146.0 | 6.86 |
| 4 | 37.4 | 2.81 | 37.4 | 2.82 | 37.2 | 2.81 | 37.3 | 2.81 | 37.5 | 2.81 | 37.3 | 2.82 | 37.4 | 2.83 |
| 4 Me | 17.2 | 1.39 | 17.2 | 1.37 | 17.0 | 1.38 | 17.1 | 1.38 | 17.2 | 1.38 | 17.1 | 1.39 | 17.2 | 1.37 |
| 5 | 83.3 | 3.74 | 83.3 | 3.75 | 83.1 | 3.74 | 83.1 | 3.73 | 83.3 | 3.75 | 83.5 | 3.72 | 83.5 | 3.76 |
| 6 | 79.3 | | 79.3 | | 78.8 | | 79.1 | | 79.3 | | 79.1 | | 79.2 | |
| 6 Me | 20.7 | 1.37 | 20.6 | 1.37 | 20.5 | 1.34 | 20.6 | 1.38 | 20.7 | 1.35 | 20.4 | 1.38 | 20.8 | 1.37 |
| O Me | 49.6 | 2.99 | 49.5 | 2.98 | 49.5 | 2.98 | 49.5 | 3.00 | 49.6 | 2.97 | 49.4 | 3.04 | 49.6 | 2.98 |
| 7 | 40.1 | 1.72, 1.65 | 40.0 | 1.74, 1.63 | 40.2 | 1.76, 1.65 | 40.0 | 1.75, 1.63 | 40.1 | 1.74, 1.62 | 40.3 | 1.77, 1.65 | 40.1 | 1.71, 1.68 |
| 8 | 44.4 | 2.75 | 44.5 | 2.72 | 44.4 | 2.73 | 44.3 | 2.72 | 44.5 | 2.75 | 44.5 | 2.74 | 44.1 | 2.77 |
| 8 Me | 18.4 | 1.22 | 18.4 | 1.21 | 18.3 | 1.21 | 18.3 | 1.21 | 18.4 | | 18.2 | 1.20 | 18.5 | 1.19 |
| 9 | 217.5 | | 217.6 | | 217.3 | | 217.5 | | 217.6 | | 217.7 | | 217.0 | |
| 10 | 41.0 | 3.09 | 40.9 | 3.10 | 40.8 | 3.11 | 40.8 | 3.11 | 40.9 | 3.11 | 40.7 | 3.11 | 41.3 | 3.11 |
| 10 Me | 14.5 | 1.09 | 14.5 | 1.07 | 14.5 | 1.10 | 14.4 | 1.09 | 14.5 | 1.09 | 14.5 | 1.13 | 14.4 | 1.09 |
| 11 | 58.3 | 3.57 | 58.1 | 3.53 | 58.5 | 3.65 | 58.3 | 3.57 | 58.2 | 3.57 | 60.3 | 3.67 | 59.3 | 3.74 |
| 12 | 81.7 | | 81.7 | | 81.7 | | 81.7 | | 81.8 | | 82.7 | | 81.8 | |
| 12 Me | 14.8 | 1.48 | 14.8 | 1.47 | 14.8 | 1.49 | 14.7 | 1.49 | 14.8 | 1.48 | 14.8 | 1.55 | 15.0 | 1.52 |
| 13 | 78.2 | 4.57 | 78.1 | 4.55 | 78.0 | 4.63 | 77.9 | 4.68 | 78.1 | 4.58 | 78.0 | 4.82 | 78.3 | 4.90 |
| 14 | 21.8 | 1.80, 1.50 | 21.7 | 1.79, 1.49 | 21.9 | 1.84, 1.53 | 21.7 | 1.87, 1.57 | 21.8 | 1.79, 1.50 | 21.9 | 1.94, 1.61 | 22.0 | 1.96, 1.61 |
| 15 | 10.6 | 0.88 | 10.6 | 0.89 | 10.7 | 0.93 | 10.6 | 0.96 | 10.6 | 0.90 | 10.6 | 0.97 | 10.7 | 1.01 |

| ERYTHRO NOLIDE Atom Number | Example 108 | | Example 109 | | Example 110 | | Example 111 | | Example 112 | | Example 113 | | Example 114 | |
|---|---|---|---|---|---|---|---|---|---|---|---|---|---|---|
| | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.3 | | 169.3 | | 169.3 | | 169.4 | | 169.3 | | 169.1 | | 169.5 | |
| 2 | 124.1 | | 124.0 | | 124.1 | | 123.9 | | 124.1 | | 123.9 | | 124.0 | |
| 2 Me | 13.1 | 1.96 | 13.0 | 1.95 | 13.1 | 1.94 | 13.0 | 1.92 | 13.1 | 1.96 | 13.0 | 1.92 | 13.1 | 1.94 |
| 3 | 146.0 | 6.84 | 146.0 | 6.84 | 146.0 | 6.79 | 146.1 | 6.79 | 145.9 | 6.84 | 145.9 | 6.79 | 146.0 | 6.79 |
| 4 | 37.4 | 2.82 | 37.3 | 2.81 | 37.4 | 2.80 | 37.4 | 2.78 | 37.4 | 2.82 | 37.2 | 2.78 | 37.3 | 2.78 |
| 4 Me | 17.1 | 1.38 | 17.0 | 1.37 | 17.1 | 1.38 | 17.2 | 1.34 | 17.1 | 1.38 | 17.0 | 1.36 | 17.1 | 1.36 |
| 5 | 83.3 | 3.74 | 83.2 | 3.73 | 83.2 | 3.70 | 83.4 | 3.70 | 83.3 | 3.74 | 83.1 | 3.62 | 83.3 | 3.70 |
| 6 | 79.1 | | 79.1 | | 79.1 | | 79.1 | | 79.1 | | 78.9 | | 79.0 | |
| 6 Me | 20.7 | 1.36 | 20.6 | 1.36 | 20.5 | 1.32 | 20.6 | 1.36 | 20.7 | 1.37 | 20.4 | 1.31 | 20.5 | 1.32 |
| O Me | 49.5 | 2.99 | 49.5 | 2.98 | 49.1 | 2.80 | 49.5 | 2.97 | 49.6 | 2.99 | 49.0 | 2.83 | 49.2 | 2.83 |

TABLE 3-continued

NMR Data For The C1 C15 Atoms Of The Erythromycin Molecule

| | | | | | | | | | | | | | | |
|---|---|---|---|---|---|---|---|---|---|---|---|---|---|---|
| 7 | 40.0 | 1.73, 1.65 | 40.0 | 1.74, 1.64 | 40.1 | 1.71, 1.60 | 40.0 | 1.69, 1.58 | 40.1 | 1.73, 1.66 | 40.0 | 1.77, 1.63 | 40.1 | 1.81, 1.68 |
| 8 | 44.3 | 2.75 | 44.3 | 2.75 | 44.7 | 2.72 | 44.3 | 2.70 | 44.2 | 2.76 | 44.3 | 2.70 | 44.4 | 2.69 |
| 8 Me | 18.4 | 1.20 | 18.3 | 1.19 | 18.3 | 1.19 | 18.4 | 1.16 | 18.4 | 1.20 | 18.2 | 1.17 | 18.3 | 1.18 |
| 9 | 217.3 | | 217.3 | | 217.3 | | 217.3 | | 217.2 | | 217.2 | | 217.2 | |
| 10 | 41.0 | 3.10 | 40.9 | 3.11 | 40.8 | 3.08 | 40.9 | 3.05 | 41.1 | 3.09 | 40.7 | 3.06 | 40.9 | 3.06 |
| 10 Me | 14.5 | 1.07 | 14.4 | 1.07 | 14.6 | 1.07 | 14.7 | 1.03 | 14.5 | 1.08 | 14.5 | 1.05 | 14.6 | 1.07 |
| 11 | 58.4 | 3.59 | 58.3 | 3.60 | 58.1 | 3.47 | 58.0 | 3.47 | 58.5 | 3.60 | 57.9 | 3.47 | 58.1 | 3.49 |
| 12 | 81.6 | | 81.5 | | 81.6 | | 81.7 | | 81.5 | | 81.5 | | 81.6 | |
| 12 Me | 14.9 | 1.48 | 14.8 | 1.48 | 14.8 | 1.50 | 14.8 | 1.47 | 14.9 | 1.48 | 14.7 | 1.48 | 14.8 | 1.50 |
| 13 | 78.2 | 4.65 | 78.1 | 4.68 | 77.9 | 4.74 | 78.6 | 4.75 | 78.3 | 4.70 | 77.8 | 4.74 | 78.0 | 4.76 |
| 14 | 21.9 | 1.84, 1.51 | 21.8 | 1.84, 1.53 | 21.9 | 1.94, 1.59 | 21.8 | 1.74, 1.44 | 21.9 | 1.81, 1.54 | 21.8 | 1.93, 1.58 | 21.9 | 1.95, 1.58 |
| 15 | 10.6 | 0.92 | 10.6 | 0.91 | 10.7 | 0.99 | 10.4 | 0.73 | 10.7 | 0.94 | 10.6 | 0.98 | 10.7 | 0.99 |

| | Chemical shift | | | | | | | | | | | | | |
|---|---|---|---|---|---|---|---|---|---|---|---|---|---|---|
| ERYTHRO | Example 115 | | Example 116 | | Example 117 | | Example 118 | | Example 119 | | Example 120 | | Example 121 | |
| NOLIDE Atom Number | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 169.1 | | 169.4 | | 169.4 | | 169.2 | | 169.2 | | 169.3 | | 169.3 | |
| 2 | 123.8 | | 123.8 | | 123.7 | | 124.1 | | 123.9 | | 123.8 | | 123.8 | |
| 2 Me | 13.0 | 1.93 | 13.0 | 1.95 | 13.0 | 1.95 | 13.1 | 1.91 | 13.0 | 1.92 | 13.0 | 1.81 | 13.0 | 1.93 |
| 3 | 146.1 | 6.79 | 146.2 | 6.82 | 146.3 | 6.82 | 146.1 | 6.77 | 146.3 | 6.77 | 146.3 | 6.71 | 146.2 | 6.79 |
| 4 | 37.2 | 2.91 | 37.4 | 2.81 | 37.4 | 2.80 | 37.3 | 2.76 | 37.4 | 2.77 | 37.3 | 2.71 | 37.3 | 2.80 |
| 4 Me | 17.0 | 1.37 | 17.1 | 1.37 | 17.1 | 1.37 | 17.2 | 1.36 | 17.1 | 1.35 | 17.0 | 1.29 | 17.1 | 1.37 |
| 5 | 83.0 | 3.71 | 83.3 | 3.73 | 83.3 | 3.73 | 83.2 | 3.68 | 83.2 | 3.70 | 83.1 | 3.62 | 83.2 | 3.71 |
| 6 | 78.9 | | 79.0 | | 79.1 | | 79.1 | | 79.1 | | 78.9 | | 79.2 | |
| 6 Me | 20.3 | 1.32 | 20.5 | 1.36 | 20.5 | 1.36 | 20.5 | 1.28 | 20.4 | 1.30 | 20.3 | 1.21 | 20.5 | 1.34 |
| O Me | 49.1 | 2.86 | 49.6 | 3.01 | 49.6 | 3.02 | 49.2 | 2.78 | 49.3 | 2.83 | 49.1 | 2.70 | 49.1 | 2.92 |
| 7 | 40.0 | 1.61, 1.54 | 40.1 | 1.72, 1.61 | 40.1 | 1.73, 1.60 | 40.1 | 1.67, 1.56 | 40.1 | 1.71, 1.54 | 40.0 | 1.65, 1.49 | 40.1 | 1.72, 1.58 |
| 8 | 44.4 | 2.73 | 44.4 | 2.74 | 44.5 | 2.73 | 44.4 | 2.70 | 44.5 | 2.70 | 44.4 | 2.65 | 44.3 | 2.72 |
| 8 Me | 18.2 | 1.19 | 18.4 | 1.20 | 18.4 | 1.20 | 18.3 | 1.16 | 18.3 | 1.18 | 18.2 | 1.13 | 18.4 | 1.19 |
| 9 | 217.5 | | 217.5 | | 217.5 | | 217.2 | | 217.4 | | 217.5 | | 217.2 | |
| 10 | 40.5 | 3.10 | 40.7 | 3.09 | 40.6 | 3.05 | 40.8 | 3.08 | 40.6 | 3.10 | 40.5 | 3.03 | 40.9 | 3.07 |
| 10 Me | 14.6 | 1.09 | 14.8 | 1.07 | 14.7 | 0.93 | 14.5 | 1.08 | 14.6 | 1.08 | 14.6 | 1.02 | 14.6 | 1.07 |
| 11 | 57.5 | 3.48 | 57.8 | 3.50 | 57.7 | 3.48 | 58.2 | 3.46 | 57.7 | 3.45 | 57.6 | 3.33 | 58.3 | 3.49 |
| 12 | 81.6 | | 81.9 | | 82.2 | | 81.7 | | 81.8 | | 81.8 | | 81.6 | |
| 12 Me | 14.6 | 1.50 | 14.8 | 1.47 | 14.7 | 1.41 | 14.8 | 1.51 | 14.7 | 1.51 | 14.6 | 1.41 | 14.8 | 1.50 |
| 13 | 77.6 | 4.77 | 78.5 | 4.78 | 78.3 | 4.76 | 77.8 | 4.77 | 77.6 | 4.72 | 77.5 | 4.68 | 78.2 | 4.75 |
| 14 | 21.7 | 1.92, 1.57 | 21.8 | 1.73, 1.46 | 21.7 | 1.62, 1.43 | 21.9 | 1.97, 1.60 | 21.8 | 1.93, 1.60 | 21.7 | 1.90, 1.54 | 21.8 | 1.74, 1.59 |
| 15 | 10.6 | 0.98 | 10.5 | 0.74 | 10.5 | 0.78 | 10.7 | 1.01 | 10.7 | 0.96 | 10.7 | 0.98 | 10.7 | 0.99 |

| | Chemical shift | | | | | | | |
|---|---|---|---|---|---|---|---|---|
| ERYTHRO | Example 122 | | Example 123 | | Example 124 | | Example 125 | |
| NOLIDE Atom Number | $^{13}$C NMR | $^{1}$H NMR | $^{13}$C NMR | $^{1}$H NMR | $^{13}$C NMR | $^{1}$H NMR | $^{13}$C NMR | $^{1}$H NMR |
| 1 | 171.7 | | 169.2 | | 169.3 | | 169.2 | |
| 2 | 124.3 | | 124.2 | | 124.8 | | 124.6 | |
| 2 Me | 11.8 | 1.98 | 13.1 | 1.93 | 13.2 | 1.97 | 13.4 | 1.96 |
| 3 | 144.4 | 6.36 | 145.9 | 6.79 | 145.6 | 6.85 | 145.5 | 6.84 |
| 4 | 36.8 | 2.90 | 37.3 | 2.78 | 37.3 | 2.8 | 37.3 | 2.8 |
| 4 Me | 17.5 | 1.24 | 17.1 | 1.37 | 17.3 | 1.39 | 17.1 | 1.41 |
| 5 | 83.8 | 3.64 | 83.1 | 3.72 | 83.5 | 3.72 | 82.9 | 3.76 |
| 6 | 78.6 | | 79 | | 79.2 | | 79 | |
| 6 Me | 21.4 | 3.09 | 20.8 | 1.32 | 20.8 | 1.23 | 20.6 | 1.33 |
| O Me | 50.1 | 1.31 | 49 | 2.87 | 49.3 | 2.72 | 49.3 | 2.88 |
| 7 | 42.1 | 2.23, 1.39 | 40.1 | 1.71, 1.60 | 40 | 1.71, 1.63 | 40.3 | 1.75, 1.67 |
| 8 | 41.0 | 2.71 | 44.6 | 2.71 | 44.2 | 2.66 | 44.8 | 2.72 |
| 8 Me | 19.8 | 1.00 | 18.3 | 1.18 | 18.4 | 1.18 | 18.5 | 1.2 |
| 9 | 214.9 | | 217.1 | | 216.3 | | 217.2 | |
| 10 | 46.0 | 3.40 | 40.7 | 3.09 | 41.4 | 3.06 | 40.7 | 3.12 |
| 10 Me | 10.5 | 1.12 | 14.6 | 1.05 | 14.3 | 1.07 | 14.8 | 1.08 |
| 11 | 62.7 | 3.25 | 58.2 | 3.48 | 60.1c | 3.61 | 58.3 | 3.51 |
| 12 | 83.9 | | 81.5 | | 81.6 | | 81.4 | |
| 12 Me | 16.9 | 1.67 | 14.8 | 1.49 | 15.2 | 1.52 | 15 | 1.51 |
| 13 | 78.0 | 4.94 | 78.1 | 4.77 | 78.2 | 4.84 | 78.1 | 4.76 |
| 14 | 20.9 | 1.86, 1.65 | 22 | 1.95, 1.57 | 22.1 | 1.92, 1.60 | 22.1 | 1.96, 1.59 |
| 15 | 10.4 | 0.87 | 10.8 | 0.98 | 10.8 | 0.97 | 10.9 | 1.00 |

Biological Data

Example 44

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35°–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay with selected compounds, shown in Table 4 below, demonstrate the antibacterial activity of the compounds of the invention.

TABLE 4

| Antibacterial Activity (MIC's) Of Selected Compounds | | | | | | | |
|---|---|---|---|---|---|---|---|
| MICROORGANISM | Ery A [Ref. Std.] | Cmpd Of Ex 2 | Cmpd Of Ex 3 | Cmpd Of Ex 4 | Cmpd Of Ex 5 | Cmpd Of Ex 6 | Cmpd Of Ex 7 |
| STAPHYLOCOCCUS AUREUS ATCC 6538P | 0.2 | 12.5 | 0.39 | 0.39 | 6.2 | 6.2 | 0.78 |
| STAPHYLOCOCCUS AUREUS A5177 | 3.1 | 25 | 0.39 | 0.39 | — | — | — |
| STAPHYLOCOCCUS AUREUS A-5278 | >100 | 25 | 50 | 50 | >100 | >100 | 50 |
| STAPHYLOCOCCUS AUREUS CMX 642A | 0.39 | 12.5 | 0.39 | 0.39 | 12.5 | 0.78 | 0.78 |
| STAPHYLOCOCCUS AUREUS NCTC10649M | 0.39 | 3.1 | 0.2 | 0.39 | 25 | 1.56 | 0.39 |
| STAPHYLOCOCCUS AUREUS CMX 553 | 0.39 | — | 0.2 | 0.78 | — | — | — |
| STAPHYLOCOCCUS AUREUS 1775 | >100 | 25 | 50 | 50 | >100 | >100 | 25 |
| STAPHYLOCOCCUS EPIDERMIDIS 3519 | 0.2 | — | 0.39 | 0.39 | 12.5 | 1.56 | 0.78 |
| ENTEROCOCCUS FAECIUM ATCC 8043 | 0.1 | 3.1 | 0.2 | 0.1 | 6.2 | 0.2 | 0.1 |
| STREPTOCOCCUS BOVIS A-5169 | 0.01 | 0.2 | — | — | 0.1 | 0.1 | 0.01 |
| STREPTOCOCCUS AGALACTIAE CMX 508 | 0.02 | 0.2 | 0.1 | 0.05 | 0.78 | 0.2 | 0.02 |
| STREPTOCOCCUS PYOGENES EES61 | 0.02 | <=0.005 | 0.02 | 0.01 | — | — | — |
| STREPTOCOCCUS PYOGENES 930 | >100 | 25 | 12.5 | 25 | 50 | >100 | 12.5 |
| STREPTOCOCCUS PYOGENES PIU 2548 | 3.1 | 0.39 | 0.39 | 0.39 | 3.1 | 0.39 | 0.39 |
| MICROCOCCUS LUTEUS ATCC 9341 | 0.02 | 6.2 | 0.2 | 0.1 | 3.1 | 0.78 | 0.2 |
| MICROCOCCUS LUTEUS ATCC 4698 | 0.39 | 6.2 | 0.39 | 0.78 | — | — | — |
| ESCHERICHIA COLI JUHL | 50 | >100 | >100 | >100 | >100 | >100 | >100 |
| ESCHERICHIA COLI SS | 0.39 | >100 | 0.78 | 0.2 | — | — | — |
| ESCHERICHIA COLI DC-2 | 100 | >100 | 25 | 100 | — | — | — |
| CANDIDA ALBICANS CCH 442 | >100 | >100 | >100 | >100 | >100 | >100 | >100 |
| MYCOBACTERIUM SMEGMATIS ATCC 114 | 1.56 | 25 | 0.78 | 1.56 | 6.2 | 3.1 | 6.2 |
| N. ASTEROIDES ATCC 9970 | 0.1 | 6.2 | 0.78 | — | 6.2 | 3.1 | 0.78 |
| MICROORGANISM | Ery A (Ref. Std.) | Cmpd Of Ex 8 | Cmpd Of Ex 9 | Cmpd Of Ex 10 | Cmpd Of Ex 11 | Cmpd Of Ex 12 | Cmpd Of Ex 13 |
| STAPHYLOCOCCUS AUREUS ATCC 6538P | 0.2 | 0.78 | 1.56 | 0.39 | 0.39 | 0.39 | 0.78 |
| STAPHYLOCOCCUS AUREUS A5177 | 3.1 | 0.78 | — | — | 0.1 | 0.39 | 0.78 |
| STAPHYLOCOCCUS AUREUS A-5278 | >100 | >100 | >100 | 12.5 | 50 | 12.5 | >100 |
| STAPHYLOCOCCUS AUREUS CMX 642A | 0.39 | 0.39 | 1.56 | 0.39 | 0.39 | 0.39 | 0.78 |
| STAPHYLOCOCCUS AUREUS NCTC10649M | 0.39 | 0.2 | 1.56 | 0.2 | 0.2 | 0.39 | 0.78 |
| STAPHYLOCOCCUS AUREUS CMX 553 | 0.39 | 0.78 | 1.56 | 0.2 | 0.2 | 0.39 | 0.78 |
| STAPHYLOCOCCUS AUREUS 1775 | >100 | >100 | >100 | 12.5 | 50 | 12.5 | >100 |
| STAPHYLOCOCCUS EPIDERMIDIS 3519 | 0.2 | 0.78 | 1.56 | 0.39 | 0.1 | 0.39 | 0.78 |
| ENTEROCOCCUS FAECIUM ATCC 8043 | 0.1 | 0.1 | 0.05 | 0.05 | <0.005 | 0.1 | 0.2 |
| STREPTOCOCCUS BOVIS A-5169 | 0.01 | 0.02 | 0.02 | 0.02 | <0.005 | 0.01 | 0.05 |
| STREPTOCOCCUS AGALACTIAE CMX 508 | 0.02 | 0.1 | 0.05 | 0.02 | 0.01 | 0.02 | 0.2 |
| STREPTOCOCCUS PYOGENES EES61 | 0.02 | 0.02 | 0.05 | 0.39 | <0.005 | 0.02 | 0.2 |
| STREPTOCOCCUS PYOGENES 930 | >100 | >100 | 100 | 3.1 | 25 | 6.2 | 100 |
| STREPTOCOCCUS PYOGENES PIU 2548 | 3.1 | 0.2 | 0.2 | 0.2 | 0.01 | 0.2 | 0.2 |
| MICROCOCCUS LUTEUS ATCC 9341 | 0.02 | 0.1 | 0.1 | 0.1 | 0.01 | 0.1 | 0.2 |
| MICROCOCCUS LUTEUS ATCC 4698 | 0.39 | 0.39 | 0.78 | 0.39 | 0.1 | 0.39 | 0.78 |
| ESCHERICHIA COLI JUHL | 50 | >100 | 100 | >100 | >100 | >100 | >100 |
| ESCHERICHIA COLI SS | 0.39 | 0.02 | 1.56 | 3.1 | 0.2 | 0.78 | 0.78 |
| ESCHERICHIA COLI DC-2 | 100 | >100 | 100 | >100 | 100 | >100 | >100 |
| CANDIDA ALBICANS CCH 442 | >100 | >100 | >100 | 25 | 100 | 25 | >100 |
| MYCOBACTERIUM SMEGMATIS ATCC 114 | 1.56 | 12.5 | 12.5 | 0.78 | 0.39 | 0.39 | 3.1 |
| N. ASTEROIDES ATCC 9970 | 0.1 | 0.39 | 0.78 | 0.78 | 0.2 | 0.39 | 0.39 |

TABLE 4-continued

Antibacterial Activity (MIC's) Of Selected Compounds

| MICROORGANISM | Ery A (Ref. Std.) | Cmpd Of Ex 14 | Cmpd Of Ex 15 | Cmpd Of Ex 16 | Cmpd Of Ex 18 | Cmpd Of Ex 19 | Cmpd Of Ex 20 |
|---|---|---|---|---|---|---|---|
| *STAPHYLOCOCCUS AUREUS* ATCC 6538P | 0.2 | 0.1 | 3.1 | 3.1 | 1.56 | 12.5 | 50 |
| *STAPHYLOCOCCUS AUREUS* A5177 | 3.1 | 0.1 | 3.1 | 3.1 | 0.78 | 6.2 | 50 |
| *STAPHYLOCOCCUS AUREUS* A-5278 | >100 | 50 | 25 | 50 | >100 | >100 | >100 |
| *STAPHYLOCOCCUS AUREUS* CMX 642A | 0.39 | 0.1 | 3.1 | 3.1 | 1.56 | 25 | 50 |
| *STAPHYLOCOCCUS AUREUS* NCTC10649M | 0.39 | 0.1 | 3.1 | 3.1 | 1.56 | 12.5 | 50 |
| *STAPHYLOCOCCUS AUREUS* CMX 553 | 0.39 | 0.1 | 3.1 | 3.1 | 1.56 | 25 | 50 |
| *STAPHYLOCOCCUS AUREUS* 1775 | >100 | 50 | 12.5 | 50 | >100 | >100 | >100 |
| *STAPHYLOCOCCUS EPIDERMIDIS* 3519 | 0.2 | 0.1 | 3.1 | 3.1 | 1.56 | 25 | 100 |
| *ENTEROCOCCUS FAECIUM* ATCC 8043 | 0.1 | 0.02 | 0.78 | 1.56 | 0.2 | 3.1 | 12.5 |
| *STREPTOCOCCUS BOVIS* A-5169 | 0.01 | 0.005 | 0.39 | 0.2 | 0.05 | 0.39 | 3.1 |
| *STREPTOCOCCUS AGALACTIAE* CMX 508 | 0.02 | 0.005 | 0.39 | 0.78 | 0.05 | 0.78 | 12.5 |
| *STREPTOCOCCUS PYOGENES* EES61 | 0.02 | 0.005 | 0.78 | 0.78 | 0.05 | 0.78 | 6.2 |
| *STREPTOCOCCUS PYOGENES* 930 | >100 | 25 | 6.2 | 25 | >100 | >100 | >100 |
| *STREPTOCOCCUS PYOGENES* PIU 2548 | 3.1 | 0.2 | 1.56 | 0.78 | 0.2 | 1.56 | 12.5 |
| *MICROCOCCUS LUTEUS* ATCC 9341 | 0.02 | 0.01 | 0.39 | 0.78 | 0.39 | 1.56 | 12.5 |
| *MICROCOCCUS LUTEUS* ATCC 4698 | 0.39 | 0.02 | 3.1 | 1.56 | 0.78 | 6.2 | 50 |
| *ESCHERICHIA COLI* JUHL | 50 | 50 | >100 | >100 | >100 | >100 | >100 |
| *ESCHERICHIA COLI* SS | 0.39 | 0.01 | >100 | 12.5 | 0.78 | 25 | >100 |
| *ESCHERICHIA COLI* DC-2 | 100 | 25 | >100 | >100 | >100 | >100 | >100 |
| *CANDIDA ALBICANS* CCH 442 | >100 | 100 | >100 | >100 | >100 | >100 | >100 |
| *MYCOBACTERIUM SMEGMATIS* ATCC 114 | 1.56 | 0.39 | 3.1 | 12.5 | 25 | >100 | >100 |
| *N. ASTEROIDES* ATCC 9970 | 0.1 | 0.1 | 1.56 | 6.2 | 0.78 | 12.5 | >100 |

| MICROORGANISM | Ery A (Ref. Std.) | Cmpd Of Ex 21 | Cmpd Of Ex 22 | Cmpd Of Ex 23 | Cmpd Of Ex 24 | Cmpd Of Ex 43 | Cmpd Of Ex 44 |
|---|---|---|---|---|---|---|---|
| *STAPHYLOCOCCUS AUREUS* ATCC 6538P | 0.2 | 1.56 | 0.2 | 0.2 | 0.39 | 1.56 | 0.1 |
| *STAPHYLOCOCCUS AUREUS* A5177 | 3.1 | 1.56 | 0.1 | 0.39 | 0.39 | — | 0.1 |
| *STAPHYLOCOCCUS AUREUS* A-5278 | >100 | >100 | >100 | 25 | >100 | >100 | 50 |
| *STAPHYLOCOCCUS AUREUS* CMX 642A | 0.39 | 1.56 | 0.39 | 0.78 | 0.39 | 3.1 | 0.2 |
| *STAPHYLOCOCCUS AUREUS* NCTC10649M | 0.39 | 1.56 | — | 0.78 | 0.39 | 0.78 | 0.1 |
| *STAPHYLOCOCCUS AUREUS* CMX 553 | 0.39 | 1.56 | — | 0.78 | 0.39 | 1.56 | 0.05 |
| *STAPHYLOCOCCUS AUREUS* 1775 | >100 | >100 | >100 | 12.5 | >100 | >100 | 50 |
| *STAPHYLOCOCCUS EPIDERMIDIS* 3519 | 0.2 | 1.56 | 0.1 | 0.78 | 0.78 | 1.56 | 0.2 |
| *ENTEROCOCCUS FAECIUM* ATCC 8043 | 0.1 | 0.39 | 0.05 | 0.02 | 0.1 | 0.2 | 0.05 |
| *STREPTOCOCCUS BOVIS* A-5169 | 0.01 | 0.1 | 0.05 | 0.02 | 0.1 | 0.02 | 0.01 |
| *STREPTOCOCCUS AGALACTIAE* CMX 508 | 0.02 | 0.39 | 0.05 | 0.02 | 0.1 | 0.1 | 0.05 |
| *STREPTOCOCCUS PYOGENES* EES61 | 0.02 | 0.1 | 0.05 | 0.01 | 0.2 | 0.05 | 0.02 |
| *STREPTOCOCCUS PYOGENES* 930 | >100 | >100 | 100 | 3.1 | >100 | >100 | 25 |
| *STREPTOCOCCUS PYOGENES* PIU 2548 | 3.1 | 0.39 | 0.2 | 0.39 | 0.2 | 0.39 | 0.1 |
| *MICROCOCCUS LUTEUS* ATCC 9341 | 0.02 | 0.2 | 0.05 | 0.05 | 0.1 | 0.05 | 0.05 |
| *MICROCOCCUS LUTEUS* ATCC 4698 | 0.39 | 0.78 | 0.2 | 0.1 | 0.2 | 0.39 | 0.1 |
| *ESCHERICHIA COLI* JUHL | 50 | >100 | >100 | >100 | >100 | >100 | >100 |
| *ESCHERICHIA COLI* SS | 0.39 | 1.56 | 0.39 | 0.78 | 12.5 | 0.39 | 0.2 |
| *ESCHERICHIA COLI* DC-2 | 100 | >100 | >100 | >100 | >100 | >100 | >100 |
| *CANDIDA ALBICANS* CCH 442 | >100 | >100 | >100 | >100 | >100 | >100 | >100 |
| *MYCOBACTERIUM SMEGMATIS* ATCC 114 | 1.56 | 100 | >100 | 0.78 | 1.56 | 25 | 0.2 |
| *N. ASTEROIDES* ATCC 9970 | 0.1 | 0.78 | >100 | 0.39 | 0.1 | 1.56 | 0.1 |

| MICROORGANISM | Ery A (Ref. Std.) | Cmpd Of Ex 45 | Cmpd Of Ex 46 | Cmpd Of Ex 47 | Cmpd Of Ex 48 | Cmpd Of Ex 49 | Cmpd Of Ex 50 |
|---|---|---|---|---|---|---|---|
| *STAPHYLOCOCCUS AUREUS* ATCC 6538P | 0.2 | 1.56 | 1.56 | 12.5 | 0.39 | 0.78 | 0.39 |
| *STAPHYLOCOCCUS AUREUS* A5177 | 3.1 | 0.78 | 1.56 | 12.5 | 0.39 | 0.78 | 0.39 |
| *STAPHYLOCOCCUS AUREUS* A-5278 | >100 | >100 | >100 | >100 | 25 | >100 | 50 |
| *STAPHYLOCOCCUS AUREUS* CMX 642A | 0.39 | 1.56 | 1.56 | 12.5 | 0.78 | 0.78 | 0.39 |
| *STAPHYLOCOCCUS AUREUS* NCTC10649M | 0.39 | 1.56 | 1.56 | 12.5 | 0.39 | 0.78 | 0.39 |
| *STAPHYLOCOCCUS AUREUS* CMX 553 | 0.39 | 1.56 | 1.56 | 12.5 | 0.39 | 0.78 | 0.39 |
| *STAPHYLOCOCCUS AUREUS* 1775 | >100 | >100 | >100 | >100 | 12.5 | >100 | 50 |
| *STAPHYLOCOCCUS EPIDERMIDIS* 3519 | 0.2 | 1.56 | 3.1 | 12.5 | 0.78 | 0.78 | 0.39 |
| *ENTEROCOCCUS FAECIUM* ATCC 8043 | 0.1 | 0.2 | 0.1 | 1.56 | 0.2 | 0.2 | 0.2 |
| *STREPTOCOCCUS BOVIS* A-5169 | 0.01 | 0.05 | 0.1 | 0.39 | 0.05 | 0.02 | 0.005 |
| *STREPTOCOCCUS AGALACTIAE* CMX 508 | 0.02 | 0.1 | 0.1 | 1.56 | 0.05 | 0.02 | 0.02 |
| *STREPTOCOCCUS PYOGENES* EES61 | 0.02 | 0.05 | 0.1 | 1.56 | 0.05 | 0.05 | 0.02 |
| *STREPTOCOCCUS PYOGENES* 930 | >100 | >100 | >100 | >100 | 6.2 | >100 | 25 |
| *STREPTOCOCCUS PYOGENES* PIU 2548 | 3.1 | 0.2 | 0.39 | 1.56 | 0.39 | 0.39 | 0.39 |
| *MICROCOCCUS LUTEUS* ATCC 9341 | 0.02 | 0.2 | 0.78 | 3.1 | 0.1 | 0.1 | 0.05 |
| *MICROCOCCUS LUTEUS* ATCC 4698 | 0.39 | 0.39 | 1.56 | 6.2 | 0.39 | 0.39 | 0.2 |
| *ESCHERICHIA COLI* JUHL | 50 | >100 | >100 | >100 | >100 | >100 | >100 |
| *ESCHERICHIA COLI* SS | 0.39 | 0.78 | 1.56 | 25 | 3.1 | 0.78 | 0.78 |
| *ESCHERICHIA COLI* DC-2 | 100 | >100 | >100 | >100 | >100 | >100 | >100 |
| *CANDIDA ALBICANS* CCH 442 | >100 | >100 | >100 | >100 | >100 | >100 | >100 |

TABLE 4-continued

Antibacterial Activity (MIC's) Of Selected Compounds

| MICROORGANISM | | | | | | | |
|---|---|---|---|---|---|---|---|
| MYCOBACTERIUM SMEGMATIS ATCC 114 | 1.56 | 6.2 | 12.5 | >100 | 0.78 | 3.1 | 0.78 |
| N. ASTEROIDES ATCC 9970 | 0.1 | 0.39 | 1.56 | 6.2 | 0.78 | 0.39 | 0.39 |

| MICROORGANISM | Ery A (Ref. Std.) | Cmpd Of Ex 51 | Cmpd Of Ex 52 | Cmpd Of Ex 53 | Cmpd Of Ex 54 | Cmpd Of Ex 55 | Cmpd Of Ex 56 |
|---|---|---|---|---|---|---|---|
| STAPHYLOCOCCUS AUREUS ATCC 6538P | 0.2 | 0.39 | 3.1 | 0.39 | 0.39 | >100 | 0.39 |
| STAPHYLOCOCCUS AUREUS A5177 | 3.1 | 0.39 | 3.1 | 0.78 | 0.39 | 100 | 0.39 |
| STAPHYLOCOCCUS AUREUS A-5278 | >100 | 100 | >100 | 25 | 50 | >100 | 25 |
| STAPHYLOCOCCUS AUREUS CMX 642A | 0.39 | 0.39 | 3.1 | 0.78 | 0.78 | >100 | 0.39 |
| STAPHYLOCOCCUS AUREUS NCTC10649M | 0.39 | 0.39 | 3.1 | 0.78 | 0.39 | >100 | 0.39 |
| STAPHYLOCOCCUS AUREUS CMX 553 | 0.39 | 0.39 | 3.1 | 0.78 | 0.78 | 100 | 0.39 |
| STAPHYLOCOCCUS AUREUS 1775 | >100 | 100 | >100 | 25 | 50 | >100 | 25 |
| STAPHYLOCOCCUS EPIDERMIDIS 3519 | 0.2 | 0.39 | 3.1 | 0.78 | 0.39 | >100 | 0.39 |
| ENTEROCOCCUS FAECIUM ATCC 8043 | 0.1 | 0.1 | 0.39 | 0.2 | 0.1 | 12.5 | 0.2 |
| STREPTOCOCCUS BOVIS A-5169 | 0.01 | 0.005 | 0.05 | 0.05 | 0.01 | — | 0.005 |
| STREPTOCOCCUS AGALACTIAE CMX 508 | 0.02 | 0.01 | 0.1 | 0.05 | 0.05 | — | 0.05 |
| STREPTOCOCCUS PYOGENES EES61 | 0.02 | 0.01 | 0.1 | 0.05 | 0.05 | 6.2 | 0.05 |
| STREPTOCOCCUS PYOGENES 930 | >100 | 25 | >100 | 6.2 | 25 | — | 12.5 |
| STREPTOCOCCUS PYOGENES PIU 2548 | 3.1 | 0.39 | 0.39 | 0.78 | 0.2 | — | 0.39 |
| MICROCOCCUS LUTEUS ATCC 9341 | 0.02 | 0.02 | 0.39 | 0.2 | 0.1 | 6.2 | 0.05 |
| MICROCOCCUS LUTEUS ATCC 4698 | 0.39 | 0.2 | 0.78 | 0.78 | 0.2 | 25 | 0.2 |
| ESCHERICHIA COLI JUHL | 50 | >100 | >100 | >100 | >100 | >100 | >100 |
| ESCHERICHIA COLI SS | 0.39 | 1.56 | 0.56 | 6.2 | 0.78 | >100 | 1.56 |
| ESCHERICHIA COLI DC-2 | 100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 0.78 | 12.5 | 1.56 | 0.78 | 12.5 | 0.78 |
| N. ASTEROIDES ATCC 9970 | 0.1 | 0.39 | 0.78 | 0.78 | 0.2 | 12.5 | 0.78 |

| MICROORGANISM | Ery A (Ref. Std.) | Cmpd Of Ex 57 | Cmpd Of Ex 58 | Cmpd Of Ex 59 | Cmpd Of Ex 60 | Cmpd Of Ex 61 | Cmpd Of Ex 62 |
|---|---|---|---|---|---|---|---|
| STAPHYLOCOCCUS AUREUS ATCC 6538P | 0.2 | 12.5 | >100 | >100 | 12.5 | >100 | 12.5 |
| STAPHYLOCOCCUS AUREUS A5177 | 3.1 | 6.2 | >100 | >100 | 12.5 | >100 | 12.5 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 12.5 | >100 | >100 | 12.5 | >100 | 25 |
| STAPHYLOCOCCUS AUREUS NCTC10649M | 0.39 | 6.2 | >100 | >100 | 12.5 | >100 | 25 |
| STAPHYLOCOCCUS AUREUS CMX 553 | 0.39 | 12.5 | >100 | >100 | 12.5 | >100 | 25 |
| STAPHYLOCOCCUS AUREUS 1775 | >100 | >100 | >100 | >100 | >100 | >100 | >100 |
| STAPHYLOCOCCUS EPIDERMIDIS 3519 | 0.2 | — | >100 | >100 | 12.5 | >100 | 12.5 |
| ENTEROCOCCUS FAECIUM ATCC 8043 | 0.1 | 1.56 | 100 | >100 | 1.56 | >100 | 1.56 |
| STREPTOCOCCUS BOVIS A-5169 | 0.01 | 0.39 | 50 | >100 | 0.39 | 25 | 0.78 |
| STREPTOCOCCUS AGALACTIAE CMX 508 | 0.02 | 0.78 | 50 | >100 | 0.78 | 50 | 0.78 |
| STREPTOCOCCUS PYOGENES EES61 | 0.02 | 0.39 | 100 | >100 | 0.78 | >100 | 0.78 |
| STREPTOCOCCUS PYOGENES 930 | >100 | >100 | >100 | >100 | >100 | >100 | >100 |
| STREPTOCOCCUS PYOGENES PIU 2548 | 3.1 | 0.78 | 100 | >100 | 1.56 | 100 | 1.56 |
| MICROCOCCUS LUTEUS ATCC 9341 | 0.02 | 1.56 | 100 | >100 | 3.1 | >100 | 3.1 |
| MICROCOCCUS LUTEUS ATCC 4698 | 0.39 | 6.2 | >100 | >100 | 12.5 | >100 | 25 |
| ESCHERICHIA COLI JUHL | 50 | >100 | >100 | >100 | >100 | >100 | >100 |
| ESCHERICHIA COLI SS | 0.39 | 6.2 | >100 | >100 | 12.5 | >100 | 25 |
| ESCHERICHIA COLI DC-2 | 100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | >100 | >100 | >100 | >100 | >100 | >100 |
| N. ASTEROIDES ATCC 9970 | 0.1 | 3.1 | 100 | >100 | 6.2 | >100 | 3.1 |

| MICROORGANISM | Ery A (Ref. Std.) | Cmpd Of Ex 63 | Cmpd Of Ex 64 | Cmpd Of Ex 65 | Cmpd Of Ex 66 | Cmpd Of Ex 67 | Cmpd Of Ex 68 |
|---|---|---|---|---|---|---|---|
| STAPHYLOCOCCUS AUREUS ATCC 6538P | 0.2 | 25 | 3.1 | 25 | 25 | 25 | 25 |
| STAPHYLOCOCCUS AUREUS A5177 | 3.1 | 25 | 3.1 | 12.5 | 25 | >100 | 25 |
| STAPHYLOCOCCUS AUREUS A-5278 | >100 | >100 | >100 | >100 | >100 | >100 | 100 |
| STAPHYLOCOCCUS AUREUS CMX 642A | 0.39 | 25 | 6.2 | 25 | 25 | 25 | 25 |
| STAPHYLOCOCCUS AUREUS NCTC10649M | 0.39 | 25 | 3.1 | 12.5 | 25 | 25 | 25 |
| STAPHYLOCOCCUS AUREUS CMX 553 | 0.39 | 25 | 3.1 | 12.5 | 25 | 25 | 25 |
| STAPHYLOCOCCUS AUREUS 1775 | >100 | >100 | 100 | >100 | >100 | >100 | 100 |
| STAPHYLOCOCCUS EPIDERMIDIS 3519 | 0.2 | 12.5 | 3.1 | 12.5 | 25 | 25 | 25 |
| ENTEROCOCCUS FAECIUM ATCC 8043 | 0.1 | 3.1 | 1.56 | 0.39 | 3.1 | 12.5 | 3.1 |
| STREPTOCOCCUS BOVIS A-5169 | 0.01 | 0.78 | 0.2 | 0.39 | 0.39 | 1.56 | 0.78 |
| STREPTOCOCCUS AGALACTIAE CMX 508 | 0.02 | 0.78 | 0.78 | 0.39 | 1.56 | 3.1 | 3.1 |
| STREPTOCOCCUS PYOGENES EES61 | 0.02 | 1.56 | 0.1 | 0.39 | 1.56 | 12.5 | 1.56 |
| STREPTOCOCCUS PYOGENES 930 | >100 | >100 | >100 | >100 | >100 | >100 | 25 |
| STREPTOCOCCUS PYOGENES PIU 2548 | 3.1 | 1.56 | 3.1 | 1.56 | 3.1 | 6.2 | 6.2 |
| MICROCOCCUS LUTEUS ATCC 9341 | 0.02 | 3.1 | 0.78 | 1.56 | 3.1 | 12.5 | 3.1 |
| MICROCOCCUS LUTEUS ATCC 4698 | 0.39 | 25 | 3.1 | 3.1 | 6.2 | 12.5 | 6.2 |
| ESCHERICHIA COLI JUHL | 50 | >100 | >100 | >100 | >100 | >100 | >100 |
| ESCHERICHIA COLI SS | 0.39 | 25 | 6.2 | 3.1 | 3.1 | 12.5 | 50 |
| ESCHERICHIA COLI DC-2 | 100 | >100 | >100 | >100 | >100 | >100 | >100 |

TABLE 4-continued

Antibacterial Activity (MIC's) Of Selected Compounds

| MICROORGANISM | | | | | | | |
|---|---|---|---|---|---|---|---|
| CANDIDA ALBICANS CCH 442 | >100 | >100 | >100 | >100 | >100 | >100 | >100 |
| MYCOBACTERIUM SMEGMATIS ATCC 114 | 1.56 | >100 | 25 | 25 | >100 | >100 | 25 |
| N. ASTEROIDES ATCC 9970 | 0.1 | 3.1 | 3.1 | 3.1 | 50 | 6.2 | 12.5 |

| MICROORGANISM | Ery A (Ref. Std.) | Cmpd Of Ex 69 | Cmpd Of Ex 70 | Cmpd Of Ex 71 | Cmpd Of Ex 72 | Cmpd Of Ex 73 | Cmpd Of Ex 74 |
|---|---|---|---|---|---|---|---|
| STAPHYLOCOCCUS AUREUS ATCC 6538P | 0.2 | 25 | 0.1 | 0.39 | 0.2 | 0.39 | 0.2 |
| STAPHYLOCOCCUS AUREUS A5177 | 3.1 | 25 | 0.05 | 0.39 | 0.2 | 0.39 | 0.1 |
| STAPHYLOCOCCUS AUREUS A-5278 | >100 | 12.5 | 25 | 50 | 50 | 25 | >100 |
| STAPHYLOCOCCUS AUREUS CMX 642A | 0.39 | 50 | 0.1 | 0.39 | 0.2 | 0.2 | 0.2 |
| STAPHYLOCOCCUS AUREUS NCTC10649M | 0.39 | 6.2 | 0.1 | 0.39 | 0.39 | 0.2 | 0.1 |
| STAPHYLOCOCCUS AUREUS CMX 553 | 0.39 | 50 | 0.1 | 0.39 | 0.39 | 0.2 | 0.1 |
| STAPHYLOCOCCUS AUREUS 1775 | >100 | 12.5 | 25 | 50 | 50 | 25 | >100 |
| STAPHYLOCOCCUS EPIDERMIDIS 3519 | 0.2 | 12.5 | 0.05 | 0.39 | 0.2 | 0.78 | 0.2 |
| ENTEROCOCCUS FAECIUM ATCC 8043 | 0.1 | 3.1 | 0.01 | 0.1 | 0.05 | 0.2 | 0.05 |
| STREPTOCOCCUS BOVIS A-5169 | 0.01 | 0.78 | 0.01 | 0.02 | 0.02 | 0.1 | 0.01 |
| STREPTOCOCCUS AGALACTIAE CMX 508 | 0.02 | 0.78 | 0.02 | 0.05 | 0.05 | 0.1 | 0.02 |
| STREPTOCOCCUS PYOGENES EES61 | 0.02 | 1.56 | 0.02 | 0.05 | 0.005 | 0.1 | 0.005 |
| STREPTOCOCCUS PYOGENES 930 | >100 | 6.2 | 12.5 | 12.5 | 25 | 12.5 | >100 |
| STREPTOCOCCUS PYOGENES PIU 2548 | 3.1 | 3.1 | 0.02 | 0.39 | 0.2 | 0.78 | 0.39 |
| MICROCOCCUS LUTEUS ATCC 9341 | 0.02 | 3.1 | 0.02 | 0.1 | 0.05 | 0.1 | 0.05 |
| MICROCOCCUS LUTEUS ATCC 4698 | 0.39 | 6.2 | 0.05 | 0.2 | 0.39 | 0.78 | 0.2 |
| ESCHERICHIA COLI JUHL | 50 | >100 | 50 | >100 | — | >100 | >100 |
| ESCHERICHIA COLI SS | 0.39 | >100 | 0.05 | 1.56 | 1.56 | 3.1 | 0.39 |
| ESCHERICHIA COLI DC-2 | 100 | >100 | 100 | >100 | >100 | >100 | >100 |
| CANDIDA ALBICANS CCH 442 | >100 | >100 | 100 | 25 | 100 | 50 | >100 |
| MYCOBACTERIUM SMEGMATIS ATCC 114 | 1.56 | 3.1 | 0.39 | 1.56 | 0.78 | 1.56 | 3.1 |
| N. ASTEROIDES ATCC 9970 | 0.1 | 3.1 | 0.05 | 0.39 | 0.78 | 0.78 | 0.2 |

| MICROORGANISM | Ery A (Ref. Std.) | Cmpd Of Ex 75 | Cmpd Of Ex 76 | Cmpd Of Ex 77 | Cmpd Of Ex 78 | Cmpd Of Ex 79 | Cmpd Of Ex 80 |
|---|---|---|---|---|---|---|---|
| STAPHYLOCOCCUS AUREUS ATCC 6538P | 0.2 | 0.1 | 0.2 | 0.39 | 0.1 | 0.2 | 0.1 |
| STAPHYLOCOCCUS AUREUS A5177 | 3.1 | 0.1 | 0.2 | 0.39 | 0.1 | 0.2 | 0.01 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 0.1 | 0.2 | 0.39 | 0.1 | 0.2 | 0.1 |
| STAPHYLOCOCCUS AUREUS NCTC10649M | 0.39 | 0.1 | 0.2 | 0.39 | 0.1 | 0.2 | 0.1 |
| STAPHYLOCOCCUS AUREUS CMX 553 | 0.39 | 0.1 | 0.2 | 0.39 | 0.1 | 0.2 | 0.1 |
| STAPHYLOCOCCUS AUREUS 1775 | >100 | >100 | >100 | >100 | 100 | >100 | >100 |
| STAPHYLOCOCCUS EPIDERMIDIS 3519 | 0.2 | 0.1 | 0.2 | 0.39 | 0.1 | 0.2 | 0.1 |
| ENTEROCOCCUS FAECIUM ATCC 8043 | 0.1 | 0.01 | 0.01 | 0.1 | 0.05 | 0.05 | 0.01 |
| STREPTOCOCCUS BOVIS A-5169 | 0.01 | 0.005 | 0.005 | 0.05 | 0.02 | 0.01 | 0.005 |
| STREPTOCOCCUS AGALACTIAE CMX 508 | 0.02 | 0.01 | 0.005 | 0.05 | 0.02 | 0.005 | 0.01 |
| STREPTOCOCCUS PYOGENES EES61 | 0.02 | 0.01 | 0.005 | 0.05 | 0.01 | 0.005 | 0.005 |
| STREPTOCOCCUS PYOGENES 930 | >100 | >100 | >100 | 100 | 50 | 50 | 50 |
| STREPTOCOCCUS PYOGENES PIU 2548 | 3.1 | 0.1 | 0.2 | 0.39 | 0.39 | 0.2 | 0.1 |
| MICROCOCCUS LUTEUS ATCC 9341 | 0.02 | 0.01 | 0.01 | 0.1 | 0.05 | 0.01 | 0.005 |
| MICROCOCCUS LUTEUS ATCC 4698 | 0.39 | 0.1 | 0.2 | 0.39 | 0.1 | 0.1 | 0.1 |
| ESCHERICHIA COLI JUHL | 50 | 100 | >100 | >100 | >100 | >100 | >100 |
| ESCHERICHIA COLI SS | 0.39 | 0.1 | 0.78 | 0.78 | 0.78 | 1.56 | 0.2 |
| ESCHERICHIA COLI DC-2 | 100 | 100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 6.2 | 6.2 | 3.1 | 0.39 | 0.39 | 1.56 |
| N. ASTEROIDES ATCC 9970 | 0.1 | 0.01 | 0.01 | 0.39 | 0.1 | 0.05 | 0.05 |

| MICROORGANISM | Ery A (Ref. Std.) | Cmpd Of Ex 81 | Cmpd Of Ex 82 | Cmpd Of Ex 83 | Cmpd Of Ex 84 | Cmpd Of Ex 85 | Cmpd Of Ex 86 |
|---|---|---|---|---|---|---|---|
| STAPHYLOCOCCUS AUREUS ATCC 6538P | 0.2 | 0.39 | 0.39 | 0.78 | 0.39 | 0.39 | 0.2 |
| STAPHYLOCOCCUS AUREUS A5177 | 3.1 | 0.39 | 0.1 | 0.78 | 0.2 | 0.39 | 0.2 |
| STAPHYLOCOCCUS AUREUS A-5278 | >100 | >100 | 100 | >100 | >100 | >100 | |
| STAPHYLOCOCCUS AUREUS CMX 642A | 0.39 | 0.39 | 0.1 | 1.56 | 0.39 | 0.39 | 0.39 |
| STAPHYLOCOCCUS AUREUS NCTC10649M | 0.39 | 0.39 | 0.39 | 1.56 | 0.2 | 0.39 | 0.2 |
| STAPHYLOCOCCUS AUREUS CMX 553 | 0.39 | 0.39 | 0.1 | 1.56 | 0.39 | 0.39 | 0.39 |
| STAPHYLOCOCCUS AUREUS 1775 | >100 | >100 | 50 | >100 | >100 | >100 | >100 |
| STAPHYLOCOCCUS EPIDERMIDIS 3519 | 0.2 | 0.39 | 0.1 | 1.56 | 0.2 | 0.39 | 0.39 |
| ENTEROCOCCUS FAECIUM ATCC 8043 | 0.1 | 0.2 | 0.05 | 0.2 | 0.05 | 0.1 | 0.1 |
| STREPTOCOCCUS BOVIS A-5169 | 0.01 | 0.01 | 0.01 | 0.01 | 0.01 | 0.01 | — |
| STREPTOCOCCUS AGALACTIAE CMX 508 | 0.02 | 0.05 | 0.005 | 0.02 | 0.01 | 0.05 | 0.05 |
| STREPTOCOCCUS PYOGENES EES61 | 0.02 | 0.05 | 0.01 | 0.02 | 0.01 | 0.01 | 0.05 |
| STREPTOCOCCUS PYOGENES 930 | >100 | >100 | 6.2 | 50 | 100 | 100 | >100 |
| STREPTOCOCCUS PYOGENES PIU 2548 | 3.1 | 0.78 | 0.1 | 0.2 | 0.2 | 0.2 | 0.39 |
| MICROCOCCUS LUTEUS ATCC 9341 | 0.02 | 0.05 | 0.01 | 0.2 | 0.05 | 0.05 | 0.1 |
| MICROCOCCUS LUTEUS ATCC 4698 | 0.39 | 0.39 | 0.1 | 0.2 | 0.2 | 0.39 | 0.39 |
| ESCHERICHIA COLI JUHL | 50 | — | 25 | >100 | >100 | >100 | >100 |
| ESCHERICHIA COLI SS | 0.39 | 0.78 | 0.02 | 0.39 | 0.2 | 0.78 | 0.39 |

TABLE 4-continued

Antibacterial Activity (MIC's) Of Selected Compounds

| MICROORGANISM | | | | | | | |
|---|---|---|---|---|---|---|---|
| ESCHERICHIA COLI DC-2 | 100 | >100 | 50 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 25 | 0.2 | 12.5 | 0.78 | 3.1 | 3.1 |
| N. ASTEROIDS ATCC 9970 | 0.1 | 3.1 | 0.1 | 0.2 | 0.2 | 0.78 | 0.2 |

| MICROORGANISM | Ery A (Ref. Std.) | Cmpd Of Ex 87 | Cmpd Of Ex 88 | Cmpd Of Ex 89 | Cmpd Of Ex 90 | Cmpd Of Ex 91 | Cmpd Of Ex 92 |
|---|---|---|---|---|---|---|---|
| STAPHYLOCOCCUS AUREUS ATCC 6538P | 0.2 | 0.78 | 0.2 | 0.2 | 0.2 | 0.05 | 0.78 |
| STAPHYLOCOCCUS AUREUS A5177 | 3.1 | 0.78 | 0.2 | 0.2 | 0.2 | 0.05 | 0.78 |
| STAPHYLOCOCCUS AUREUS A-5278 | >100 | >100 | 100 | >100 | 100 | >100 | >100 |
| STAPHYLOCOCCUS AUREUS CMX 642A | 0.39 | 0.78 | 0.2 | 0.39 | 0.2 | 0.1 | 1.56 |
| STAPHYLOCOCCUS AUREUS NCTC10649M | 0.39 | 0.78 | 0.2 | 0.39 | 0.2 | 0.05 | 1.56 |
| STAPHYLOCOCCUS AUREUS CMX 553 | 0.39 | 0.78 | 0.2 | 0.39 | 0.2 | 0.05 | 1.56 |
| STAPHYLOCOCCUS AUREUS 1775 | >100 | >100 | 100 | >100 | 100 | >100 | >100 |
| STAPHYLOCOCCUS EPIDERMIDIS 3519 | 0.2 | 0.78 | 0.2 | 0.39 | 0.2 | 0.05 | 0.78 |
| ENTEROCOCCUS FAECIUM ATCC 8043 | 0.1 | 0.39 | 0.05 | 0.1 | 0.2 | 0.005 | 0.2 |
| STREPTOCOCCUS BOVIS A-5169 | 0.01 | 0.05 | 0.01 | 0.02 | 0.05 | 0.005 | 0.1 |
| STREPTOCOCCUS AGALACTIAE CMX 508 | 0.02 | 0.1 | 0.005 | 0.05 | 0.05 | 0.005 | 0.1 |
| STREPTOCOCCUS PYOGENES EES61 | 0.02 | 0.1 | 0.005 | 0.02 | 0.05 | 0.005 | 0.1 |
| STREPTOCOCCUS PYOGENES 930 | >100 | >100 | 25 | >100 | 50 | >100 | >100 |
| STREPTOCOCCUS PYOGENES PIU 2548 | 3.1 | 0.78 | 0.2 | 0.78 | 0.39 | 0.05 | 0.78 |
| MICROCOCCUS LUTEUS ATCC 9341 | 0.02 | 0.1 | 0.02 | 0.2 | 0.05 | 0.005 | 0.2 |
| MICROCOCCUS LUTEUS ATCC 4698 | 0.39 | 0.39 | 0.2 | 0.39 | 0.39 | 0.02 | 0.78 |
| ESCHERICHIA COLI JUHL | 50 | 100 | >100 | — | 100 | 12.5 | >100 |
| ESCHERICHIA COLI SS | 0.39 | 0.39 | 0.39 | 0.78 | 0.78 | 0.05 | 0.39 |
| ESCHERICHIA COLI DC-2 | 100 | >100 | >100 | >100 | >100 | 12.5 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 25 | 0.39 | 6.2 | 0.78 | 0.1 | 100 |
| N. ASTEROIDES ATCC 9970 | 0.1 | 3.1 | 0.2 | 0.78 | 0.05 | 0.005 | 3.1 |

| MICROORGANISM | Ery A (Ref. Std.) | Cmpd Of Ex 93 | Cmpd Of Ex 94 | Cmpd Of Ex 95 | Cmpd Of Ex 96 | Cmpd Of Ex 97 | Cmpd Of Ex 98 |
|---|---|---|---|---|---|---|---|
| STAPHYLOCOCCUS AUREUS ATCC 6538P | 0.2 | 3.1 | 0.1 | 0.2 | 0.02 | 100 | 0.2 |
| STAPHYLOCOCCUS AUREUS A5177 | 3.1 | 3.1 | — | 0.2 | 0.01 | 100 | 0.2 |
| STAPHYLOCOCCUS AUREUS A-5278 | >100 | >100 | >100 | >100 | 100 | >100 | >100 |
| STAPHYLOCOCCUS AUREUS CMX 642A | 0.39 | 3.1 | 0.1 | 0.2 | 0.02 | 100 | 0.2 |
| STAPHYLOCOCCUS AUREUS NCTC10649M | 0.39 | 3.1 | 0.1 | 0.2 | 0.02 | 100 | 0.2 |
| STAPHYLOCOCCUS AUREUS CMX 553 | 0.39 | 3.1 | 0.1 | 0.2 | 0.02 | 100 | 0.2 |
| STAPHYLOCOCCUS AUREUS 1775 | >100 | >100 | >100 | >100 | >100 | >100 | >100 |
| STAPHYLOCOCCUS EPIDERMIDIS 3519 | 0.2 | 3.1 | 0.1 | 0.2 | 0.01 | 100 | 0.2 |
| ENTEROCOCCUS FAECIUM ATCC 8043 | 0.1 | 0.39 | 0.05 | 0.02 | 0.005 | 6.2 | 0.01 |
| STREPTOCOCCUS BOVIS A-5169 | 0.01 | 0.05 | 0.01 | 0.01 | 0.005 | 1.56 | 0.01 |
| STREPTOCOCCUS AGALACTIAE CMX 508 | 0.02 | 0.1 | 0.01 | 0.01 | 0.005 | 1.56 | 0.01 |
| STREPTOCOCCUS PYOGENES EES61 | 0.02 | 0.1 | 0.01 | 0.01 | 0.005 | 3.1 | 0.01 |
| STREPTOCOCCUS PYOGENES 930 | >100 | >100 | >100 | >100 | 25 | >100 | >100 |
| STREPTOCOCCUS PYOGENES PIU 2548 | 3.1 | 0.78 | 0.2 | 0.2 | 0.02 | 3.1 | 0.1 |
| MICROCOCCUS LUTEUS ATCC 9341 | 0.02 | 0.2 | 0.01 | 0.1 | 0.005 | 3.1 | 0.01 |
| MICROCOCCUS LUTEUS ATCC 4698 | 0.39 | 6.2 | 0.1 | 0.2 | 0.02 | 50 | 0.2 |
| ESCHERICHIA COLI JUHL | 50 | >100 | >100 | >100 | >100 | >100 | 100 |
| ESCHERICHIA COLI SS | 0.39 | 3.1 | 0.39 | 0.2 | 0.78 | >100 | 0.1 |
| ESCHERICHIA COLI DC-2 | 100 | >100 | >100 | >100 | >100 | >100 | 100 |
| CANDIDA ALBICANS CCH 442 | >100 | >100 | >100 | >100 | >100 | >100 | >100 |
| MYCOBACTERIUM SMEGMATIS ATCC 114 | 1.56 | 50 | 0.78 | 100 | 1.56 | >100 | 25 |
| N. ASTEROIDES ATCC 9970 | 0.1 | 0.78 | 0.1 | 0.1 | 0.005 | 25 | 0.1 |

| MICROORGANISM | Ery A (Ref. Std.) | Cmpd Of Ex 99 | Cmpd Of Ex 100 | Cmpd Of Ex 101 | Cmpd Of Ex 102 | Cmpd Of Ex 103 | Cmpd Of Ex 104 |
|---|---|---|---|---|---|---|---|
| STAPHYLOCOCCUS AUREUS ATCC 6538P | 0.2 | 0.2 | 0.2 | 0.78 | 0.05 | 0.39 | 0.39 |
| STAPHYLOCOCCUS AUREUS A5177 | 3.1 | 0.1 | 0.2 | 0.78 | 0.02 | 0.39 | 0.39 |
| STAPHYLOCOCCUS AUREUS A-5278 | >100 | >100 | >100 | 100 | >100 | >100 | >100 |
| STAPHYLOCOCCUS AUREUS CMX 642A | 0.39 | 0.2 | 0.2 | 0.78 | 0.1 | 0.39 | 0.39 |
| STAPHYLOCOCCUS AUREUS NCTC10649M | 0.39 | 0.2 | 0.2 | 0.78 | 0.1 | 0.39 | 0.39 |
| STAPHYLOCOCCUS AUREUS CMX 553 | 0.39 | 0.2 | 0.2 | 0.78 | 0.39 | 0.39 | 0.39 |
| STAPHYLOCOCCUS AUREUS 1775 | >100 | >100 | >100 | 100 | 50 | >100 | >100 |
| STAPHYLOCOCCUS EPIDERMIDIS 3519 | 0.2 | 0.2 | 0.2 | 0.78 | 0.39 | 0.39 | 0.39 |
| ENTEROCOCCUS FAECIUM ATCC 8043 | 0.1 | 0.01 | 0.05 | 0.39 | 0.1 | 0.02 | 0.1 |
| STREPTOCOCCUS BOVIS A-5169 | 0.01 | — | 0.005 | — | 0.02 | 0.01 | 0.01 |
| STREPTOCOCCUS AGALACTIAE CMX 508 | 0.02 | — | 0.02 | — | 0.05 | 0.02 | 0.02 |
| STREPTOCOCCUS PYOGENES EES61 | 0.02 | 0.01 | 0.02 | 0.05 | 0.05 | 0.05 | 0.02 |
| STREPTOCOCCUS PYOGENES 930 | >100 | >100 | 100 | 25 | 12.5 | >100 | >100 |
| STREPTOCOCCUS PYOGENES PIU 2548 | 3.1 | 0.1 | 0.1 | 0.39 | 0.39 | 0.39 | 0.39 |
| MICROCOCCUS LUTEUS ATCC 9341 | 0.02 | 0.01 | 0.05 | 0.39 | 0.1 | 0.05 | 0.05 |
| MICROCOCCUS LUTEUS ATCC 4698 | 0.39 | 0.2 | 0.39 | 0.78 | 0.2 | 01.2 | 0.2 |
| ESCHERICHIA COLI JUHL | 50 | 100 | >100 | >100 | >100 | >100 | >100 |

TABLE 4-continued

Antibacterial Activity (MIC's) Of Selected Compounds

| | | | | | | | |
|---|---|---|---|---|---|---|---|
| ESCHERICHIA COLI SS | 0.39 | 0.1 | 0.39 | 3.1 | 1.56 | 0.39 | 0.2 |
| ESCHERICHIA COLI DC-2 | 100 | 100 | >100 | >100 | >100 | >100 | >100 |
| CANDIDA ALBICANS CCH 442 | >100 | >100 | >100 | >100 | 25 | >100 | >100 |
| MYCOBACTERIUM SMEGMATIS ATCC 114 | 1.56 | 3.1 | 1.56 | 1.56 | 1.56 | 3.1 | 12.5 |
| N. ASTEROIDES ATCC 9970 | 0.1 | 0.05 | 0.2 | 0.39 | 0.39 | 0.2 | 0.2 |

| MICROORGANISM | Ery A (Ref. Std.) | Cmpd Of Ex 105 | Cmpd Of Ex 106 | Cmpd Of Ex 107 | Cmpd Of Ex 108 | Cmpd Of Ex 109 | Cmpd Of Ex 110 |
|---|---|---|---|---|---|---|---|
| STAPHYLOCOCCUS AUREUS ATCC 6538P | 0.2 | 0.39 | 0.2 | 3.1 | 0.39 | 1.56 | 0.39 |
| STAPHYLOCOCCUS AUREUS A5177 | 3.1 | 0.2 | — | 3.1 | — | 1.56 | 0.2 |
| STAPHYLOCOCCUS AUREUS A-5278 | >100 | >100 | 100 | 100 | >100 | 25 | 50 |
| STAPHYLOCOCCUS AUREUS CMX 642A | 0.39 | 0.39 | 0.2 | 3.1 | 0.2 | 1.56 | 0.39 |
| STAPHYLOCOCCUS AUREUS NCTC10649M | 0.39 | 0.39 | 0.2 | 3.1 | 0.2 | 1.56 | 0.39 |
| STAPHYLOCOCCUS AUREUS CMX 553 | 0.39 | 0.39 | 0.2 | 3.1 | 0.39 | 1.56 | 0.39 |
| STAPHYLOCOCCUS AUREUS 1775 | >100 | >100 | 100 | 100 | >100 | 25 | 50 |
| STAPHYLOCOCCUS EPIDERMIDIS 3519 | 0.2 | 0.39 | 0.2 | 3.1 | 0.39 | 1.56 | 0.39 |
| ENTEROCOCCUS FAECIUM ATCC 8043 | 0.1 | 0.1 | 0.1 | 0.78 | 0.1 | 0.39 | 0.05 |
| STREPTOCOCCUS BOVIS A-5169 | 0.01 | — | 0.01 | 0.1 | 0.01 | 0.1 | 0.005 |
| STREPTOCOCCUS AGALACTIAE CMX 508 | 0.02 | — | 0.02 | 0.2 | 0.01 | 0.05 | |
| STREPTOCOCCUS PYOGENES EES61 | 0.02 | 0.05 | 0.005 | 0.1 | 0.01 | 0.1 | 0.01 |
| STREPTOCOCCUS PYOGENES 930 | >100 | >100 | 25 | 25 | 50 | 6.2 | 25 |
| STREPTOCOCCUS PYOGENES PIU 2548 | 3.1 | 0.2 | 0.2 | 0.78 | 0.39 | 0.39 | 0.39 |
| MICROCOCCUS LUTEUS ATCC 9341 | 0.02 | 0.05 | 0.02 | 0.39 | 0.02 | 0.2 | 0.05 |
| MICROCOCCUS LUTEUS ATCC 4698 | 0.39 | 0.39 | 0.1 | 0.78 | 0.2 | 0.78 | 0.2 |
| ESCHERICHIA COLI JUHL | 50 | >100 | >100 | >100 | >100 | >100 | >100 |
| ESCHERICHIA COLI SS | 0.39 | 0.1 | 1.56 | 6.2 | 0.39 | 12.5 | 0.39 |
| ESCHERICHIA COLI DC-2 | 100 | >100 | >100 | >100 | >100 | >100 | >100 |
| CANDIDA ALBICANS CCH 442 | >100 | >100 | >100 | 100 | >100 | >100 | 25 |
| MYCOBACTERIUM SMEGMATIS ATCC 114 | 1.56 | 6.2 | 0.39 | 12.5 | 0.78 | 3.1 | 0.78 |
| N. ASTEROIDES ATCC 9970 | 0.1 | 0.05 | 0.39 | 12.5 | 0.39 | 0.78 | 0.39 |

| MICROORGANISM | Ery A (Ref. Std.) | Cmpd Of Ex 111 | Cmpd Of Ex 112 | Cmpd Of Ex 113 | Cmpd Of Ex 114 | Cmpd Of Ex 115 | Cmpd Of Ex 116 |
|---|---|---|---|---|---|---|---|
| STAPHYLOCOCCUS AUREUS ATCC 6538P | 0.2 | 0.2 | 0.78 | 0.39 | 0.2 | 0.39 | 0.2 |
| STAPHYLOCOCCUS AUREUS A5177 | 3.1 | 0.2 | 0.78 | — | 0.2 | 0.39 | 0.2 |
| STAPHYLOCOCCUS AUREUS A-5278 | >100 | >100 | >100 | >100 | >100 | >100 | >100 |
| STAPHYLOCOCCUS AUREUS CMX 642A | 0.39 | 0.2 | 0.78 | 0.39 | 0.2 | 0.39 | 0.2 |
| STAPHYLOCOCCUS AUREUS NCTC10649M | 0.39 | 0.2 | 0.78 | 0.39 | 0.2 | 0.39 | 0.2 |
| STAPHYLOCOCCUS AUREUS CMX 553 | 0.39 | 0.2 | 0.78 | 0.39 | 0.2 | 0.39 | 0.2 |
| STAPHYLOCOCCUS AUREUS 1775 | >100 | >100 | >100 | >100 | >100 | >100 | >100 |
| STAPHYLOCOCCUS EPIDERMIDIS 3519 | 0.2 | 0.2 | 0.78 | 0.39 | 0.2 | 0.39 | 0.2 |
| ENTEROCOCCUS FAECIUM ATCC 8043 | 0.1 | 0.1 | 0.2 | 0.1 | 0.1 | 0.1 | 0.2 |
| STREPTOCOCCUS BOVIS A-5169 | 0.01 | 0.005 | 0.005 | 0.02 | 0.01 | 0.02 | 0.005 |
| STREPTOCOCCUS AGALACTIAE CMX 508 | 0.02 | 0.02 | 0.1 | 0.02 | 0.02 | 0.02 | 0.05 |
| STREPTOCOCCUS PYOGENES EES61 | 0.02 | 0.02 | 0.02 | 0.02 | 0.005 | 0.005 | 0.05 |
| STREPTOCOCCUS PYOGENES 930 | >100 | 100 | >100 | >100 | >100 | >100 | >100 |
| STREPTOCOCCUS PYOGENES PIU 2548 | 3.1 | 0.39 | 0.39 | 0.39 | 0.39 | 0.39 | 0.39 |
| MICROCOCCUS LUTEUS ATCC 9341 | 0.02 | 0.05 | 0.1 | 0.1 | 0.05 | 0.05 | 0.05 |
| MICROCOCCUS LUTEUS ATCC 4698 | 0.39 | 0.2 | 0.39 | 0.39 | 0.2 | 0.2 | 0.2 |
| ESCHERICHIA COLI JUHL | 50 | >100 | >100 | >100 | >100 | >100 | >100 |
| ESCHERICHIA COLI SS | 0.39 | 0.78 | 0.39 | 0.78 | 0.39 | 0.78 | 0.39 |
| ESCHERICHIA COLI DC-2 | 100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 6.2 | 25 | 12.5 | 3.1 | 3.1 | 12.5 |
| N. ASTEROIDES ATCC 9970 | 0.1 | 0.1 | 0.78 | 0.39 | 0.1 | 0.1 | 0.39 |

| MICROORGANISM | Ery A (Ref. Std.) | Cmpd Of Ex 117 | Cmpd Of Ex 118 | Cmpd Of Ex 119 | Cmpd Of Ex 120 | Cmpd Of Ex 121 | Cmpd Of Ex 122 |
|---|---|---|---|---|---|---|---|
| STAPHYLOCOCCUS AUREUS ATCC 6538P | 0.2 | 0.78 | 0.2 | 0.2 | 0.2 | 12.5 | 12.5 |
| STAPHYLOCOCCUS AUREUS A5177 | 3.1 | 0.78 | 0.2 | 0..1 | — | 12.5 | — |
| STAPHYLOCOCCUS AUREUS A-5278 | >100 | >100 | >100 | >100 | >100 | >100 | 25 |
| STAPHYLOCOCCUS AUREUS CMX 642A | 0.39 | 0.78 | 0.39 | 022 | 0.2 | 12.5 | 12.5 |
| STAPHYLOCOCCUS AUREUS NCTC10649M | 0.39 | 1.56 | 0.2 | 0.1 | 0.2 | 12.5 | 12.5 |
| STAPHYLOCOCCUS AUREUS CMX 553 | 0.39 | 1.56 | 0.2 | 0.1 | 0.2 | 12.5 | 12.5 |
| STAPHYLOCOCCUS AUREUS 1775 | >100 | >100 | >100 | >100 | >100 | >100 | 25 |
| STAPHYLOCOCCUS EPIDERMIDIS 3519 | 0.2 | 0.78 | 0.39 | 0.2 | 0.1 | 12.5 | 25 |
| ENTEROCOCCUS FAECIUM ATCC 8043 | 0.1 | 0.78 | 0.05 | 0.05 | 0.05 | 1.56 | 3.1 |
| STREPTOCOCCUS BOVIS A-5169 | 0.01 | 0.05 | 0.005 | 0.01 | 0.005 | 0.2 | 0.78 |
| STREPTOCOCCUS AGALACTIAE CMX 508 | 0.02 | 0.2 | 0.02 | 0.01 | 0.005 | 0.78 | 3.1 |
| STREPTOCOCCUS PYOGENES EES61 | 0.02 | 0.2 | 0.005 | 0.01 | 0.01 | 0.78 | 3.1 |
| STREPTOCOCCUS PYOGENES 930 | >100 | >100 | >100 | >100 | >100 | >100 | 25 |
| STREPTOCOCCUS PYOGENES PIU 2548 | 3.1 | 1.56 | 0.2 | 0.39 | 0.39 | 1.56 | 6.2 |
| MICROCOCCUS LUTEUS ATCC 9341 | 0.02 | 0.1 | 0.02 | 0.02 | 0.01 | 1.56 | 1.56 |
| MICROCOCCUS LUTEUS ATCC 4698 | 0.39 | 0.39 | 0.1 | 0.1 | 0.2 | 3.1 | 6.2 |

TABLE 4-continued

Antibacterial Activity (MIC's) Of Selected Compounds

| ESCHERICHIA COLI JUHL | 50 | >100 | >100 | >100 | >100 | >100 | >100 |
|---|---|---|---|---|---|---|---|
| ESCHERICHIA COLI SS | 0.39 | 6.2 | 0.78 | 0.2 | 0.2 | 6.2 | 25 |
| ESCHERICHIA COLI DC-2 | 100 | >100 | >100 | >100 | >100 | >100 | >100 |
| CANDIDA ALBICANS CCH 442 | >100 | >100 | >100 | >100 | >100 | >100 | >100 |
| MYCOBACTERIUM SMEGMATIS ATCC 114 | 1.56 | 12.5 | 1.56 | 6.2 | 1.56 | >100 | 6.2 |
| N. ASTEROIDES ATCC 9970 | 0.1 | 1.56 | 0.1 | 0.1 | 0.2 | 6.2 | 3.1 |

| MICROORGANISM | Ery A (Ref. Std.) | Cmpd Of Ex 123 | Cmpd Of Ex 124 |
|---|---|---|---|
| STAPHYLOCOCCUS AUREUS ATCC 6538P | 0.2 | 12.5 | 1.56 |
| STAPHYLOCOCCUS AUREUS A5177 | 3.1 | 12.5 | 1.56 |
| STAPHYLOCOCCUS AUREUS A-5278 | >100 | >100 | 12.5 |
| STAPHYLOCOCCUS AUREUS CMX 642A | 0.39 | 12.5 | 1.5 |
| STAPHYLOCOCCUS AUREUS NCTC10649M | 0.39 | 12.5 | 1.5 |
| STAPHYLOCOCCUS AUREUS CMX 553 | 0.39 | 12.5 | 1.56 |
| STAPHYLOCOCCUS AUREUS 1775 | >100 | >100 | 12 |
| STAPHYLOCOCCUS EPIDERMIDIS 3519 | 0.2 | 12.5 | 1.56 |
| ENTEROCOCCUS FAECIUM ATCC 8043 | 0.1 | 0.78 | 0.39 |
| STREPTOCOCCUS BOVIS A-5169 | 0.01 | 0.2 | 0.1 |
| STREPTOCOCCUS AGALACTIAE CMX 508 | 0.02 | 0.2 | 0.1 |
| STREPTOCOCCUS PYOGENES EES61 | 0.02 | 0.2 | 0.1 |
| STREPTOCOCCUS PYOGENES 930 | >100 | >100 | 6.2 |
| STREPTOCOCCUS PYOGENES PIU 2548 | 3.1 | 1.56 | 1.56 |
| MICROCOCCUS LUTEUS ATCC 9341 | 0.02 | 3.1 | 0.39 |
| MICROCOCCUS LUTEUS ATCC 4698 | 0.39 | 6.2 | 0.78 |
| ESCHERICHIA COLI JUHL | 50 | >100 | >100 |
| ESCHERICHIA COLI SS | 0.39 | 3.1 | 6.2 |
| ESCHERICHIA COLI DC-2 | 100 | >100 | >100 |
| CANDIDA ALBICANS CCH 442 | >100 | >100 | 25 |
| MYCOBACTERIUM SMEGMATIS ATCC 114 | 1.56 | >100 | 1.56 |
| N. ASTEROIDES ATCC 9970 | 0.1 | 0.78 | 1.56 |

What is claimed is:

1. A compound, or a pharmaceutically acceptable salt or ester thereof, selected from the group consisting of:

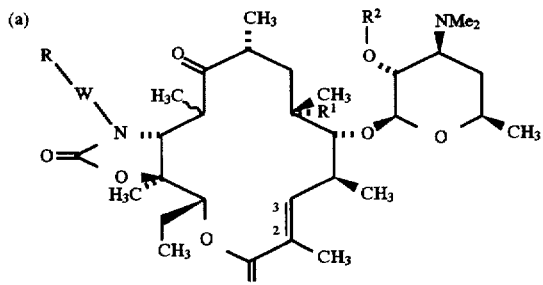

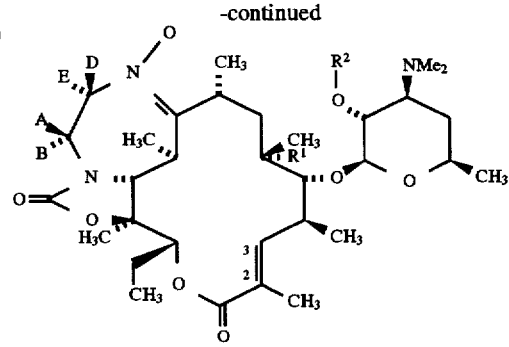

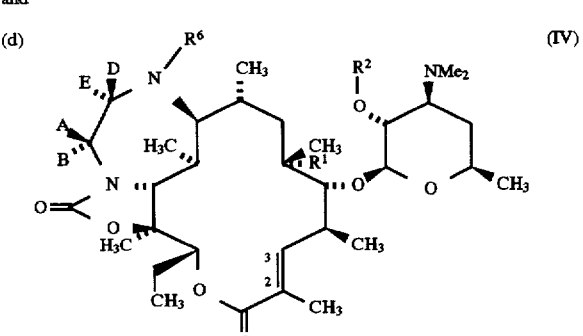

wherein, $R^1$ is selected from the group consisting of:

(a) hydrogen;
(b) hydroxy;
(c) O—$C_1$-$C_{12}$-alkyl;
(d) O—CO—$C_1$-$C_6$-alkyl;
(e) O—CO—$NH_2$;
(f) O—CO—NH—CO—$C_1$-$C_{12}$-alkyl; and
(g) O—CO—NH—$SO_2$—$C_1$-$C_{12}$-alkyl;

$R^2$ is hydrogen or a hydroxy protecting group;
$R^6$ is hydrogen or $C_1$-$C_6$-alkyl;
R is selected from the group consisting of:
  (a) hydrogen;
  (b) $C_1$-$C_6$-alkyl optionally substituted with one or more substituents selected from the group consisting of:
    (i) aryl;
    (ii) substituted-aryl;
    (iii) heteroaryl;
    (iv) substituted-heteroaryl;
    (v) hydroxy;
    (vi) $C_1$-$C_6$-alkoxy;
    (vii) $NR^3R^4$, where $R^3$ and $R^4$ are independently selected from hydrogen and $C_1$-$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$-$C_6$-alkyl-)-, —N(aryl)-, —N(aryl-$C_1$-$C_6$-alkyl-), —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, —S— or —S(O)$_n$—, wherein n is 1 or 2;
    (viii) —$CH_2$-M-$R^5$,
    wherein M is selected from the group consisting of:
      (aa) —C(O)—NH—;
      (bb) —NH—C(O)—;
      (cc) —NH—
      (dd) —N=;
      (ee) —N($CH_3$)—
      (ff) —O—
      (gg) —S(O)$_n$—, wherein n is 0, 1 or 2;
      (hh) —CO—O—
      (ii) —O—CO—
      (jj) —CO—; and
    $R^5$ is selected from the group consisting of:
      (aaa) $C_1$-$C_6$-alkyl, optionally substituted with a substituent selected from the group consisting of:
        (i) aryl;
        (ii) substituted-aryl;
        (iii) heteroaryl; and
        (iv) substituted-heteroaryl;
      (bbb) aryl;
      (ccc) substituted-aryl;
      (ddd) heteroaryl;
      (eee) substituted-heteroaryl; and
      (fff) heterocycloalkyl; and
  (c) $C_3$-$C_7$-cycloalkyl;
  (d) aryl;
  (e) substituted-aryl;
  (f) heteroaryl;
  (g) substituted-heteroaryl;

W is absent or selected from the group consisting of —O—, —NH—CO—, —N=CH—, —NH— and —N($C_1$-$C_6$-alkyl)-;

A, B, D and E are independently selected from the group consisting of:
  (a) hydrogen;
  (b) $C_1$-$C_6$-alkyl, optionally substituted with one or more substituents selected from the group consisting of:
    (i) aryl;
    (ii) substituted-aryl;
    (iii) heteroaryl;
    (iv) substituted-heteroaryl;
    (v) heterocycloalkyl;
    (vi) hydroxy;
    (vii) $C_1$-$C_6$-alkoxy;
    (viii) halogen consisting of Br, Cl, F or I; and
    (ix) $NR^3R^4$, where $R^3$ and $R^4$ are independently selected from hydrogen and $C_1$-$C_6$-alkyl, or $R^3$ and $R^4$ are taken with the nitrogen atom to which they are connected to form a 3- to 7-membered ring optionally containing a hetero function consisting of —O—, —NH—, —N($C_1$-$C_6$-alkyl-)-, —N(aryl-$C_1$-$C_6$-alkyl-)-, —N(substituted-aryl-$C_1$-$C_6$-alkyl-)-, —N(heteroaryl-$C_1$-$C_6$-alkyl-)-, —N(substituted-heteroaryl-$C_1$-$C_6$-alkyl-)-, —S— or —S(O)$_n$—, wherein n is 1 or 2;
  (c) $C_3$-$C_7$-cycloalkyl;
  (d) aryl;
  (e) substituted-aryl;
  (f) heteroaryl;
  (g) substituted-heteroaryl;
  (h) heterocycloalkyl; and
  (i) a group selected from option (b) above further substituted with -M-$R^5$, wherein M and $R^5$ are as defined above;
or
any one pair of substituents, consisting of AB, AD, AE, BD, BE or DE, is taken together with the atom or atoms to which they are attached to form a 3- to 7-membered ring optionally containing a hetero function consisting of:
  —O—,
  —NH—,
  —N($C_1$-$C_6$-alkyl-)-,
  —N(aryl-$C_1$-$C_6$-alkyl-)-,
  —N(substituted-aryl-$C_1$-$C_6$-alkyl-)-,
  —N(heteroaryl-$C_1$-$C_6$-alkyl-)-,
  —N(substituted-heteroaryl-$C_1$-$C_6$-alkyl-)-,
  —S— or —S(O)$_n$—, wherein n is 1 or 2;
  —C(O)—NH—;
  —C(O)—$NR^5$-, wherein $R^5$ is as defined above;
  —NH—C(O)—;
  —$NR^5$—C(O)—, wherein $R^5$ is as defined above; and
  —C(=NH)—NH—.

2. A compound according to claim 1 having the formula (I).

3. A compound according to claim 2, wherein W is absent or —NH—.

4. A compound according to claim 1 having the formula (II).

5. A compound according to claim 1 having the formula (III).

6. A compound according to claim 1 having the formula (IV).

7. A compound according to claim 1, or a pharmaceutically acceptable salt or ester thereof, which is:
Compound of Formula (I); $R^1$=H; $R^2$=H; W is absent; R=4-phenylbutyl;
Compound of Formula (I); $R^1$=methoxy; $R^2$=H; W is absent; R=4-phenylbutyl;

Compound of Formula (I); R¹=methoxy; R²=H; W is absent; R=3-phenoxypropyl;

Compound of Formula (I); R¹=methoxy; R²=H; W is absent; R=2-((phenylmethyl)amino)ethyl;

Compound of Formula (I); R¹=methoxy; R²=H; W is absent; R=3-(N-methyl-N-phenylamino)propyl;

Compound of Formula (I); R¹=methoxy; R²=H; W is absent; R=3-(4-chlorophenoxy)propyl;

Compound of Formula (II); R¹=methoxy; R²=H; A=B=C=D=H;

Compound of Formula (I); R¹=methoxy; R²=H; W is absent; R=3-(1-quinoyloxy)propyl;

Compound of Formula (I); R¹=methoxy; R²=H; W is absent; R=4-(4-chlorophenyl)-3(Z)-butenyl;

Compound of Formula (I); R¹=methoxy; R²=H; W is absent; R=2-phenylethyl;

Compound of Formula (I); R¹=methoxy; R²=H; W is absent; R=2-(3,4-dichlorophenyl)ethyl;

Compound of Formula (I); R¹=methoxy; R²=H; W is absent; R=phenylmethyl;

Compound of Formula (I); R¹=methoxy; R²=H; W is —NH—; R=3-phenylpropyl;

Compound of Formula (I); R¹=methoxy; R²=H; W is absent; R=3-(4-phenoxyphenyl)ethyl;

Compound of Formula (I); R¹=methoxy; R²=H; W is absent; R=3-phenylpropyl;

Compound of Formula (I); R¹=methoxy; R²=H; W is absent; R=2,2-diphenylethyl;

Compound of Formula (I); R¹=methoxy; R²=H; W is absent; R=H;

Compound of Formula (IV); R¹=methoxy; R²=H; A=B=C=D=H; R=H;

Compound of Formula (I); R¹=methoxy; R²=H; W is —NH—; R=H; C10 methyl is epi-isomer;

Compound of Formula (I); R¹=methoxy; R²=H; W is —NH—; R=H; C10 methyl is natural isomer;

Compound of Formula (I); R¹=methoxy; R²=H; W is —NH—; R=(4-quinolinyl)propyl; C10 methyl is natural isomer;

Compound of Formula (I); R¹=methoxy; R²=H; W is absent; R=3-(2-naphthyloxy)propyl;

Compound of Formula (I); R¹=methoxy; R²=H; W is absent; R=3-(3-pyridyloxy)propyl;

Compound of Formula (I); R¹=methoxy; R²=H; W is absent; R=3-(2-pyridyloxy)propyl;

Compound of Formula (I); R¹=OH; R²=H; W is absent; R=4-phenylbutyl;

Compound of Formula (I); R¹=OCONH2; R²=H; W is absent; R=4-phenylbutyl;

Compound of Formula (I); R¹=OCONHCO-methyl; R²=H; W is absent; R=4-phenylbutyl;

Compound of Formula (I); R¹=OCONHSO2-methyl; R²=H; W is absent; R=4-phenylbutyl;

Compound of Formula (I); R¹=OMe; R²=H; W is absent; R=phenyl;

Compound of Formula (I); R¹=OMe; R²=H; W is absent; R=3-pyridyl;

Compound of Formula (I); R¹=OMe; R²=H; W is —O—; R=H;

Compound of Formula (I); R¹=OMe; R²=H; W is —O—; R=Me;

Compound of Formula (I); R¹=OMe; R²=H; W is —NH——CO—; R=phenyl;

Compound of Formula (II); R¹=OMe; R²=H; A=benzyl; B,D,E=H;

Compound of Formula (II); R¹=OMe; R²=H; A,D=3,4-pyrrolidinyl; B,E=H;

Compound of Formula (III); R¹=OMe; R²=H; A,B,D,E=H;

Compound of Formula (IV); R¹=OMe; R²=H; A=benzyl; B,D,E=H; R=H;

Compound of Formula (IV); R¹=OMe; R²=H; A,D=3,4-pyrrolidinyl; (B,E=H; R=H;

Compound of Formula (IV); R¹=OMe; R²=H; A,B,D,E=H, R=CH₂CH₂CH₂C₆H₅;

Compound of Formula (IV); R¹=OMe; R²=H; A,B,D,E=H, R=2,4-dinitrobenzene;

Compound of Formula (IV); R¹=OMe; R²=H; A,B,D,E=H, R=4-quinolyl;

Compound of Formula (I); R¹=methoxy; R²=H; W is absent; R=(4H-4-oxo-1-quinolyl)propyl;

Compound of Formula (I); R¹=methoxy; R²=H; W is absent; R=2-(4-nitrophenyl)ethyl;

Compound of Formula (I); R¹=methoxy; R²=H; W is absent; R=2-(4-aminophenyl)ethyl;

Compound of Formula (I); R¹=methoxy; R²=H; W is absent; R=3-ethoxypropyl;

Compound of Formula (I); R¹=methoxy; R²=H; W is absent; R=isopropyl;

Compound of Formula (I); R¹=methoxy; R²=H; W is absent; R=2-(4-bromophenyl)ethyl;

Compound of Formula (I); R¹=methoxy; R²=H; W is absent; R=2-(4-hydroxylphenyl)ethyl;

Compound of Formula (I); R¹=methoxy; R²=H; W is absent; R=2-(4-fluorophenyl)ethyl;

Compound of Formula (I); R¹=methoxy; R²=H; W is absent; R=2-(3-methoxyphenyl)ethyl;

Compound of Formula (I); R¹=methoxy; R²=H; W is absent; R=3-vinyloxypropyl;

Compound of Formula (I); R¹=methoxy; R²=H; W is absent; R=2-(3-trifluoromethyl)phenylethyl;

Compound of Formula (I); R¹=methoxy; R²=H; W is absent; R=2-thienylethyl;

Compound of Formula (I); R¹=methoxy; R²=H; W is absent; R=2-(3,4-dibenzyloxyphenyl)ethyl;

Compound of Formula (I); R¹=methoxy; R²=H; W is absent; R=2-(4-methylphenyl)ethyl;

Compound of Formula (I); R¹=methoxy; R²=H; W is absent; R=allyl;

Compound of Formula (I); R¹=methoxy; R²=H; W is absent; R=1,3-dihydroxypropyl;

Compound of Formula (I); R¹=methoxy; R²=H; W is absent; R=1,3-dihydroxypropyl (10-epi);

Compound of Formula (I); R¹=methoxy; R²=H; W is absent; R=3-hydroxypropyl;

Compound of Formula (I); R¹=methoxy; R²=H; W is absent; R=3-hydroxypropyl (10-epi);

Compound of Formula (I); R¹=methoxy; R²=H; W is absent; R=propyl;

Compound of Formula (I); R¹=methoxy; R²=H; W is absent; R=isobutyl;

Compound of Formula (I); R¹=methoxy; R²=H; W is absent; R=2-(benzoylamino)ethyl;

Compound of Formula (I); R¹=methoxy; R²=H; W is absent; R=3-(benzoylamino)propyl;

Compound of Formula (I); R¹=methoxy; R²=H; W is absent; R=3-(acetylamino)propyl;

Compound of Formula (I); R¹=methoxy; R²=H; W is absent; R=H (10-epi);

Compound of Formula (I); R¹=methoxy; R²=H; W is absent; R=3-phenylpropyl (10-epi);

Compound of Formula (I); R¹=methoxy; R²=H; W is absent; R=3-(4-phenoxyphenyl)ethyl (10-epi);

Compound of Formula (I); R¹=methoxy; R²=H; W is —NH—; R=3-(4-chlorophenyl)propyl;

Compound of Formula (I); R¹=methoxy; R²=H; W is —NH—; R=3-(3-chlorophenyl)propyl;

Compound of Formula (I); R¹=methoxy; R²=H; W is —NH—; R=3-(2-chlorophenyl)propyl;

Compound of Formula (I); R¹=-methoxy; R²=H; W is —NH—; R=3-(2,4-dichlorophenyl)propyl;

Compound of Formula (I); R¹=methoxy; R²=H; W is —NH—; R=3-(4-hydroxyphenyl)propyl;

Compound of Formula (I); R¹=methoxy; R²=H; W is —NH—; R=3-(3-hydroxyphenyl)propyl;

Compound of Formula (I); R¹=methoxy; R²=H; W is —NH—; R=3-(2-hydroxyphenyl)propyl;

Compound of Formula (I); R¹=methoxy; R²=H; W is —NH—; R=3-(4-methoxyphenyl)propyl;

Compound of Formula (I); R¹=methoxy; R²=H; W is —NH—; R=3-(4-nitrophenyl)propyl;

Compound of Formula (I); R¹=methoxy; R²=H; W is —NH—; R=3-(3-nitrophenyl)propyl;

Compound of Formula (I); R¹=methoxy; R²=H; W is —NH—; R=3-(2-nitrophenyl)propyl;

Compound of Formula (I); R¹=methoxy; R²=H; W is —NH—; R=3-((4-(acetylamino)phenyl)propyl;

Compound of Formula (I); R¹=methoxy; R²=H; W is —NH—; R=trans-3-phenylprop-2-enyl;

Compound of Formula (I); R¹=methoxy; R²=H; W is —NH—; R=2-phenylethyl;

Compound of Formula (I); R¹=methoxy; R²=H; W is —NH—; R=phenylmethyl;

Compound of Formula (I); R¹=methoxy; R²=H; W is —NH—; R=(3-indolyl)methyl;

Compound of Formula (I); R¹=methoxy; R²=H; W is —NH—; R=(4-methoxyphenyl)methyl;

Compound of Formula (I); R¹=methoxy; R²=H; W is —NH—; R=(4-acetylaminophenyl)methyl;

Compound of Formula (I); R¹=methoxy; R²=H; W is —NH—; R=(4-chlorophenyl)methyl;

Compound of Formula (I); R¹=methoxy; R²=H; W is —NH—; R=(4-dimethylaminophenyl)methyl;

Compound of Formula (I); R¹=methoxy; R²=H; W is —NH—; R=trans-3-(4-nitrophenyl)prop-2-enyl;

Compound of Formula (I); R¹=methoxy; R²=H; W is —NH—; R=(4-nitrophenyl)methyl;

Compound of Formula (I); R¹=methoxy; R²=H; W is —NH—; R=(3,4-dihydroxyphenyl)methyl;

Compound of Formula (I); R¹=methoxy; R²=H; W is —NH—; R=(2,5-dihydroxyphenyl)methyl;

Compound of Formula (I); R¹=methoxy; R²=H; W is —NH—; R=(2-hydroxy-5-nitrophenyl)methyl;

Compound of Formula (I); R¹=methoxy; R²=H; W is —NH—; R=(4-hydroxymethylphenyl)methyl;

Compound of Formula (I); R¹=methoxy; R²=H; W is —NH—; R=trans-3-(5-nitro-2-furanyl)prop-2-enyl;

Compound of Formula (I); R¹=methoxy; R²=H; W is —NH—; R=(4-hydroxyphenyl)methyl;

Compound of Formula (I); R¹=methoxy; R²=H; W is —NH—; R=(3-hydroxyphenyl)methyl;

Compound of Formula (I); R¹=methoxy; R²=H; W is —NH—; R=(2-hydroxyphenyl)methyl;

Compound of Formula (I); R¹=methoxy; R²=H; W is —NH—; R=(4-trifluoromethylphenyl)methyl;

Compound of Formula (I); R¹=methoxy; R²=H; W is —NH—; R=(4-cyanophenyl)methyl;

Compound of Formula (I); R¹=methoxy; R²=H; W is —NH—; R=(2-pyridyl)methyl;

Compound of Formula (I); R¹=methoxy; R²=H; W is —NH—; R=(3-pyridyl)methyl;

Compound of Formula (I); R¹=methoxy; R²=H; W is —NH—; R=(4-pyridyl)methyl;

Compound of Formula (I); R¹=methoxy; R²=H; W is —NH—; R=(2-hydroxy-1-naphthyl)methyl;

Compound of Formula (I); R¹=methoxy; R²=H; W is —NH—; R=(4-dimethylamino-1-naphthyl)methyl;

Compound of Formula (I); R¹=methoxy; R²=H; W is —NH—; R=(4-(methylthio)phenyl)methyl;

Compound of Formula (I); R¹=methoxy; R²=H; W is —NH—; R=(4-phenoxyphenyl)methyl;

Compound of Formula (I); R¹=methoxy; R²=H; W is —NH—; R=3-(4-fluorophenyl)propyl;

Compound of Formula (I); R¹=methoxy; R²=H; W is —NH—; R=(trans-3-(4-nitrophenyl)prop-2-enyl;

Compound of Formula (I); R¹=methoxy; R²=H; W is —NH—; R=(4-aminophenyl)methyl;

Compound of Formula (I); R¹=methoxy; R²=H; W is —NH—; R=3-(4-amino-phenyl)propyl;

Compound of Formula (I); R¹=methoxy; R²=H; W is —NH—; R=3-(3-amino-phenyl)propyl;

Compound of Formula (I); R¹=methoxy; R²=H; W is —NH—; R=3-(2-amino-phenyl)propyl;

Compound of Formula (I); R¹=methoxy; R²=H; W is —NH—; R=trans-3-(4-acetylaminophenyl)prop-2-enyl;

Compound of Formula (I); R¹=methoxy; R²=H; W is —NH—; R=trans-3-(4-(4-nitrobenzoylamino)phenyl)prop-2-enyl;

Compound of Formula (I); R¹=methoxy; R²=H; W is —NH—; R=3-(2-benztriazolyl)propyl;

Compound of Formula (I); R¹=methoxy; R²=H; W is —NH—; R=3-(1-benztriazolyl)propyl;

Compound of Formula (I); R¹=methoxy; R²=H; W is —NH—; R=3-(4-phenylimidazolyl)propyl;

Compound of Formula (I); R¹=methoxy; R²=H; W is —NH—; R=3-(1-anhydro-1-cladinosyl)propyl;

Compound of Formula (I); R¹=methoxy; R²=H; W is —NH—; R=3-phenylpropyl (10-epi);

Compound of Formula (I); R¹=methoxy; R²=H; W is —NH—; R=isopropyl;

Compound of Formula (I); R¹=methoxy; R²=H; W is —NH—; R=1,3-diphenyl-2-propyl; or Compound of Formula (I); R¹=methoxy; R²=H; W is —NH—; R=3-pentyl.

8. A process for the preparation of a compound having the Formula (I):

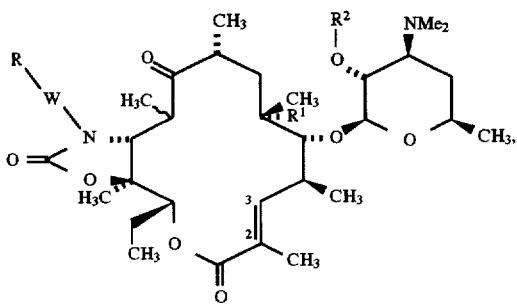

(I)

wherein
R¹ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl;

R² is hydrogen or a hydroxy protecting group;
R is selected from the group consisting of:
(a) hydrogen;
(b) $C_1$–$C_6$-alkyl optionally substituted with one or more substituents selected from the group consisting of:
(i) aryl;
(ii) substituted-aryl;
(iii) heteroaryl;
(iv) substituted-heteroaryl;
(v) hydroxy;
(vi) $C_1$–$C_6$-alkoxy;
(vii) NR³R⁴, where R³ and R⁴ are independently selected from hydrogen and $C_1$–$C_6$-alkyl, or R³ and R⁴ are taken with the nitrogen atom to which they are connected to form a 3- to 7-membered ring optionally containing a hetero function consisting of —O—, —NH—, —N($C_1$–$C_6$-alkyl-)-, —N(aryl-$C_1$–$C_6$-alkyl-)-, —N(substituted-aryl-$C_1$–$C_6$-alkyl-)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;
(viii) —$CH_2$-M-R⁵, wherein M is selected from the group consisting of:
(aa) —C(O)—NH—;
(bb) —NH—C(O)—;
(cc) —NH—
(dd) —N=;
(ee) —N($CH_3$)—
(ff) —O—
(gg) —S(O)$_n$—, wherein n is 0, 1 or 2;
(hh) —CO—O—
(ii) —O—CO—
(jj) —CO—; and
R⁵ is selected from the group consisting of:
(aaa) $C_1$–$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;

(eee) substituted-heteroaryl; and
(fff) heterocycloalkyl; and
(c) $C_3$–$C_7$-cycloalkyl;
(d) aryl;
(e) substituted-aryl;
(f) heteroaryl;
(g) substituted-heteroaryl; and
W is absent;
the method comprising:
(a) treating a compound having the formula:

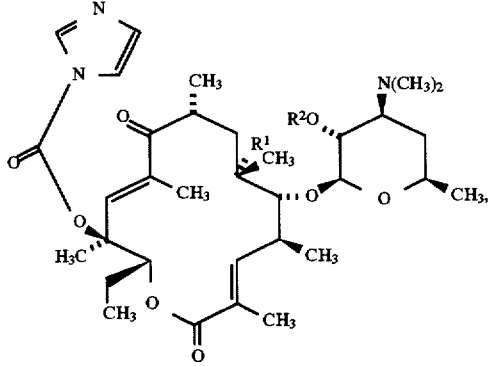

wherein R¹ is selected from the group consisting of hydrogen, protected hydroxy, O—CO—$C_1$–$C_6$-alkyl, O—$C_1$–$C_{12}$-alkyl, O—CO—$NH_2$, O—CO—NH—CO—$C_1$–$C_{12}$-alkyl, and O—CO—NH—$SO_2$—$C_1$–$C_{12}$-alkyl; and R² is a hydroxy protecting group, with a primary amine $RNH_2$, wherein R is as defined above, in a suitable organic solvent at room temperature to reflux temperature for about 4 to about 48 hours, extracting, optionally deprotecting, and isolating the desired compound.

9. A process according to claim 8 wherein R is hydrogen, $C_1$–$C_6$-alkyl, $C_3$–$C_7$-cycloalkyl, aryl, substituted-aryl, heteroaryl or substituted-heteroaryl, and the solvent is selected from the group consisting of methylene chloride, tetrahydrofuran, N-methylpyrrolidinone, diethyl ether, bis-methoxymethyl ether, dimethyl formamide, acetonitrile, acetone and aqueous mixtures thereof.

10. A process for the preparation of a compound having the Formula (I):

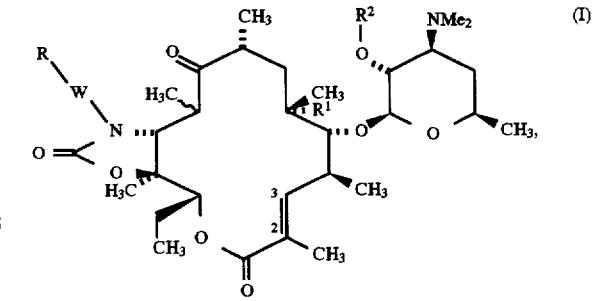

(I)

wherein
R¹ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl;

$R^2$ is hydrogen or a hydroxy protecting group;

R is selected from the group consisting of:
- (a) hydrogen;
- (b) $C_1$–$C_6$-alkyl optionally substituted with one or more substituents selected from the group consisting of:
  - (i) aryl;
  - (ii) substituted-aryl;
  - (iii) heteroaryl;
  - (iv) substituted-heteroaryl;
  - (v) hydroxy;
  - (vi) $C_1$–$C_6$-alkoxy;
  - (vii) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)-, —N(aryl)-, —N(aryl-$C_1$–$C_6$-alkyl-)-, —N(substituted-aryl-$C_1$–$C_6$-alkyl-)-, —N(heteroaryl)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;
  - (viii) —$CH_2$-M-$R^5$, wherein M is selected from the group consisting of:
    - (aa) —C(O)—NH—;
    - (bb) —NH—C(O)—;
    - (cc) —NH—
    - (dd) —N=;
    - (ee) —N($CH_3$)—
    - (ff) —O—
    - (gg) —S(O)$_n$—, wherein n is 0, 1 or 2;
    - (hh) —CO—O—
    - (ii) —O—CO—
    - (jj) —CO—; and $R^5$ is selected from the group consisting of:
  - (aaa) $C_1$–$C_6$-alkyl, optionally substituted with a substituent selected from the group consisting of:
    - (i) aryl;
    - (ii) substituted-aryl;
    - (iii) heteroaryl; and
    - (iv) substituted-heteroaryl;
  - (bbb) aryl;
  - (ccc) substituted-aryl;
  - (ddd) heteroaryl;
  - (eee) substituted-heteroaryl; and
  - (fff) heterocycloalkyl; and
- (c) $C_3$–$C_7$-cycloalkyl;
- (d) aryl;
- (e) substituted-aryl;
- (f) heteroaryl;
- (g) substituted-heteroaryl; and W is selected from the group consisting of —NH—CO—, —N=CH—, —NH— and —N($C_1$–$C_6$-alkyl)-;

the method comprising:

(a) treating a compound having the formula:

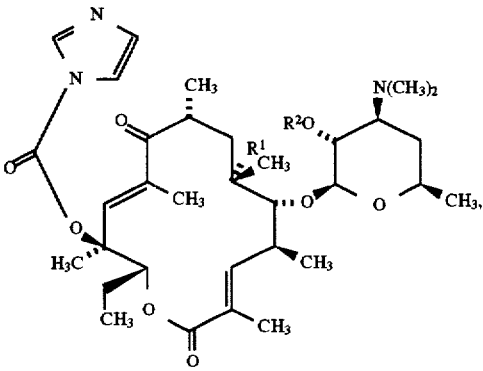

wherein $R^1$ is selected from the group consisting of hydrogen, protected hydroxy, O—CO—$C_1$–$C_6$-alkyl, O—$C_1$–$C_{12}$-alkyl, O—CO—$NH_2$, O—CO—NH—CO—$C_1$–$C_{12}$-alkyl, or O—CO—NH—$SO_2$—$C_1$–$C_{12}$-alkyl; and $R^2$ is a hydroxy protecting group, with a reagent selected from the group consisting of hydrazine, a substituted hydrazine, hydroxylamine and O-substituted hydroxylamine in a suitable organic solvent at room temperature to reflux for about 4 to about 48 hours to afford the desired compound;

(b) optionally acylating the compound of Formula (I) obtained in step (a) wherein W is —NH— and R is H with an acylating agent to afford a compound of Formula (I) wherein W is —NH—CO—;

(c) optionally condensing the compound of Formula (I) obtained in step (a) wherein W is —NH— and R is H with an aldehyde to afford a compound of Formula (I) wherein W is —N=CH—;

(d) optionally reducing the compound of Formula (I) obtained in step (c) wherein W is —N=CH— with a reducing agent to afford a compound of Formula (I) wherein W is —NH—;

(e) and extracting, optionally deprotecting, and isolating the desired compound.

11. A process according to claim 10 wherein the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF, and aqueous acetone.

12. A process according to claim 10 wherein the product is a compound of Formula (I) wherein W is —NH— and R is H, and the hydrazine reagent is hydrazine.

13. A process according to claim 10 wherein the product is a compound of Formula (I) wherein W is —N($C_1$–$C_6$-alkyl)-, the hydrazine reagent is a substituted hydrazine $RR^4NNH_2$, wherein R is as defined for Formula (I) and $R^4$ is $C_1$–$C_6$-alkyl.

14. A process according to claim 10 wherein the product is a compound of Formula (I) wherein W is —NH—CO—, the hydrazine reagent is hydrazine, and the product obtained in step (a) having the Formula (I) wherein W is —NH— and R is H is treated with an R-acyl acylating agent, wherein R is as defined for Formula (I).

15. A process according to claim 10 wherein the acylating agent is selected from the group consisting of an acid chloride, an acid fluoride, an acid anhydride, a carboxylic acid in the presence of carbonyldiimidazole, and a carboxylic acid in the presence of 1-(3-dimethylaminopropyl)-3-ethylcarbodiimide hydrochloride.

16. A process according to claim 10 wherein the product is a compound of Formula (I) wherein W is —N=CH—, the hydrazine reagent is hydrazine, and the product obtained in step (a) having the Formula (I) wherein W is —NH— and R is H is treated with an aldehyde having the formula R—CHO, wherein R is as defined for Formula (I).

17. A process according to claim 10 wherein the product is a compound of Formula (I) wherein W is —NH— and R is not H, the hydrazine reagent is hydrazine, the product obtained in step (a) having the Formula (I) wherein W is —NH— and R is H is treated with an aldehyde having the formula R—CHO, wherein R is as defined for Formula (I), and the product obtained in step (c) having the Formula (I) wherein W is —N=CH— is treated with a reducing agent.

18. A process according to claim 17 wherein the reducing agent is selected from the group consisting of sodium cyanoborohydride, sodium borohydride, sodium triacetoxyborohydride, borane-tetrahydrofuran complex, and borane-piperidine complex.

19. A process for the preparation of a compound having the Formula (I):

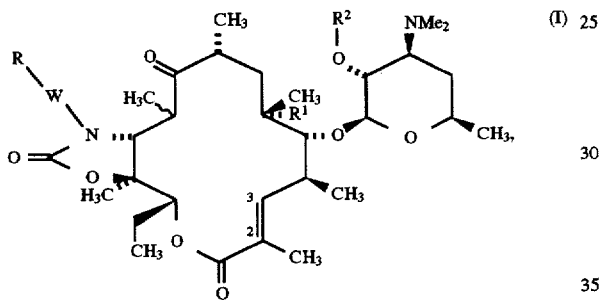

wherein
R$^1$ is selected from the group consisting of:
  (a) hydrogen;
  (b) hydroxy;
  (c) O—C$_1$–C$_{12}$-alkyl;
  (d) O—CO—C$_1$–C$_6$-alkyl;
  (e) O—CO—NH$_2$;
  (f) O—CO—NH—CO—C$_1$–C$_{12}$-alkyl; and
  (g) O—CO—NH—SO$_2$—C$_1$–C$_{12}$-alkyl;
R$^2$ is hydrogen or a hydroxy protecting group;
R is selected from the group consisting of:
  (a) hydrogen;
  (b) C$_1$–C$_6$-alkyl optionally substituted with one or more substituents selected from the group consisting of:
    (i) aryl;
    (ii) substituted-aryl;
    (iii) heteroaryl;
    (iv) substituted-heteroaryl;
    (v) hydroxy;
    (vi) C$_1$–C$_6$-alkoxy;
    (vii) NR$^3$R$^4$, where R$^3$ and R$^4$ are independently selected from hydrogen and C$_1$–C$_6$-alkyl, or R$^3$ and R$^4$ are taken with the nitrogen atom to which they are connected to form a 3- to 7-membered ring which, when the ring is a 5- to 7-membered ring, may optionally contain a hetero function consisting of —O—, —NH—, —N(C$_1$–C$_6$-alkyl-)-, —N(aryl)-, —N(aryl-C$_1$–C$_6$-alkyl-)-, —N(substituted-aryl-C$_1$–C$_6$-alkyl-)-, (—N(heteroaryl)-, —N(heteroaryl-C$_1$–C$_6$-alkyl-)-, —N(substituted-heteroaryl-C$_1$–C$_6$-alkyl-)-,
—S— or —S(O)$_n$—, wherein n is 1 or 2;
  (viii) —CH$_2$-M-R$^5$, wherein M is selected from the group consisting of:
    (aa) —C(O)—NH—;
    (bb) —NH—C(O)—;
    (cc) —NH—
    (dd) —N=;
    (ee) —N(CH$_3$)—
    (ff) —O—
    (gg) —S(O)$_n$—, wherein n is 0, 1 or 2;
    (hh) —CO—O—
    (ii) —O—CO—
    (jj) —CO—; and
  R$^5$ is selected from the group consisting of:
    (aaa) C$_1$–C$_6$-alkyl, optionally substituted with a substituent selected from the group consisting of:
      (i) aryl;
      (ii) substituted-aryl;
      (iii) heteroaryl; and
      (iv) substituted-heteroaryl;
    (bbb) aryl;
    (ccc) substituted-aryl;
    (ddd) heteroaryl;
    (eee) substituted-heteroaryl; and
    (fff) heterocycloalkyl; and
  (c) C$_3$–C$_7$-cycloalkyl;
  (d) aryl;
  (e) substituted-aryl;
  (f) heteroaryl;
  (g) substituted-heteroaryl; and
W is —O—;
the method comprising:
(a) treating a compound having the formula:

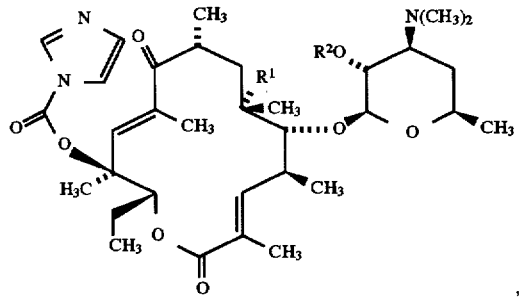

wherein R$^1$ is selected from the group consisting of hydrogen, protected hydroxy, O—C$_1$–C$_{12}$-alkyl, O—CO—C$_1$–C$_6$-alkyl, O—CO—NH$_2$, O—CO—NH—CO—C$_1$–C$_{12}$-alkyl, or O—CO—NH—SO$_2$—C$_1$–C$_{12}$-alkyl; and R$^2$ is a hydroxy protecting group, with a hydroxylamine reagent selected from the group consisting of unsubstituted hydroxylamine and an O—C$_1$–C$_6$-alkylated hydroxylamine in a suitable organic solvent at room temperature to reflux for about 4 to about 48 hours, to give the desired compound;

(b) optionally treating the product obtained in step (a) having the Formula (I) wherein W is —O— and R is H with base and an appropriate electrophile having the formula R-L, wherein R is selected from the group consisting of C$_1$–C$_6$-alkyl, C$_3$–C$_7$-cycloalkyl, aryl, substituted-aryl, heteroaryl and a substituted-heteroaryl group, as defined for compounds of Formula (I) above, and L is suitable leaving group, to give the desired compound of formula (I) wherein W is —O— and R is selected from the group consisting of $C_1$–$C_6$-alkyl, $C_3$–$C_7$-cycloalkyl, aryl, substituted-aryl, heteroaryl and a substituted-heteroaryl group; and (c) extracting, optionally deprotecting, and isolating the desired compound.

20. A process according to claim 19 wherein the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF, and aqueous acetone.

21. A process according to claim 20 wherein the product is a compound of Formula (I) wherein W is —O— and R is H and the hydroxylamine reagent is unsubstituted hydroxylamine.

22. A process according to claim 20 wherein the product is a compound of Formula (I) wherein W is —O— and R is O—$C_1$–$C_6$-alkyl and the hydroxylamine reagent is an O—$C_1$–$C_6$-alkylated hydroxylamine.

23. A process according to claim 20 wherein the final product is a compound of Formula (I) wherein W is —O— and R is selected from the group consisting of $C_1$–$C_6$-alkyl, $C_3$–$C_7$-cycloalkyl, aryl, substituted-aryl, heteroaryl or a substituted-heteroaryl group, and the product obtained in step (a) having the Formula (I) wherein W is —O— and R is H is treated with a suitable base and an electrophile having the formula R-L, wherein R is as defined above and L is a suitable leaving group.

24. A process according to claim 22 wherein in the base is selected from the group consisting of sodium hydride, potassium hydride, lithium hydride, lithium diethylamide, and butyllithium, and L is selected from the group consisting of halide, methanesulfonyl and p-toluenesulfonyl.

25. A process for the preparation of a compound having the Formula (II):

wherein
$R^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—$NH_2$;
(f) O—CO—NH—CO—$C_1$–$C_{12}$-alkyl; and
(g) O—CO—NH—$SO_2$—$C_1$–$C_{12}$-alkyl;

$R^2$ is hydrogen or a hydroxy protecting group;

A, B, D and E are independently selected from the group consisting of:
(a) hydrogen;
(b) $C_1$–$C_6$-alkyl, optionally substituted with one or more substituents selected from the group consisting of:
(i) aryl;
(ii) substituted-aryl;
(iii) heteroaryl;
(iv) substituted-heteroaryl;
(v) heterocycloalkyl;
(vi) hydroxy;
(vii) $C_1$–$C_6$-alkoxy;
(viii) halogen consisting of Br, Cl, F or I; and
(ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)-, —N(aryl)-, —N(aryl-$C_1$–$C_6$-alkyl-)-, —N(substituted-aryl-$C_1$–$C_6$-alkyl-)-, —N(heteroaryl)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;

(c) $C_3$–$C_7$-cycloalkyl;
(d) aryl;
(e) substituted-aryl;
(f) heteroaryl;
(g) substituted-heteroaryl;
(h) heterocycloalkyl;
and
(i) a group selected from option (b) above further substituted with -M-$R^5$, wherein M is selected from the group consisting of:
(aa) —C(O)—NH—;
(bb) —NH—C(O)—;
(cc) —NH—
(dd) —N($CH_3$)—
(ee) —O—
(ff) —S(O)$_n$—, wherein n is 0, 1 or 2;
(gg) —C(=NH)—NH—;
(hh) —CO—O—
(ii) —O—CO—
(jj) —CO—;

and $R^5$ is selected from the group consisting of:
(aaa) $C_1$–$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;
(eee) substituted-heteroaryl; and
(fff) heterocycloalkyl;

or any one pair of substituents, consisting of AB, AD, AE, BD, BE or DE, is taken together with the atom or atoms to which they are attached to form a 3- to 7-membered ring optionally containing a hetero function consisting of:
—O—,
—NH—,
—N($C_1$–$C_6$-alkyl-)-,
—N(aryl-$C_1$–$C_6$-alkyl-)-,
—N(substituted-aryl-$C_1$–$C_6$-alkyl-)-,
—N(heteroaryl-$C_1$–$C_6$-alkyl-)-,
—N(substituted-heteroaryl-$C_1$–$C_6$-alkyl-)-,
—S— or —S(O)$_n$—, wherein n is 1 or 2;
—C(O)—NH—;
—C(O)—$NR^5$-, wherein $R^5$ is as defined above;

—NH—C(O)—;
—NR⁵—C(O)—, wherein R⁵ is as defined above; and
—C(=NH)—NH—;

the method comprising:

(a) treating a compound having the formula:

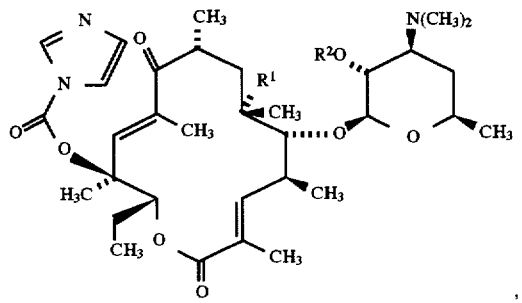

wherein R¹ is selected from the group consisting of hydrogen, protected hydroxy, O—$C_1$-$C_{12}$-alkyl, O—CO—$C_1$-$C_6$-alkyl, O—CO—$NH_2$, O—CO—NH—CO—$C_1$-$C_{12}$-alkyl, or O—CO—NH—$SO_2$—$C_1$-$C_{12}$-alkyl; and R² is a hydroxy protecting group, with a compound having the formula:

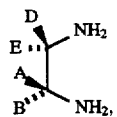

wherein A, B, D, and E are as defined for compounds of Formula (I) above, in a suitable solvent at room temperature to reflux temperature for about 4 to about 48 hours to give the bicyclic intermediate compound having the formula:

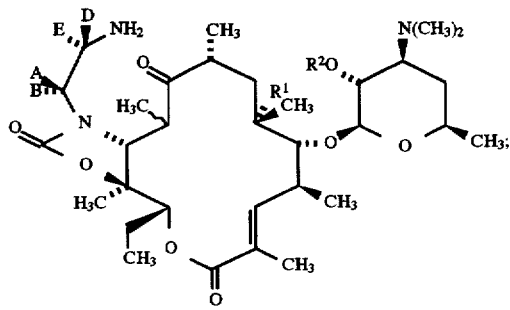

(b) deprotecting said bicyclic intermediate compounds to give the second intermediate compounds having the formula:

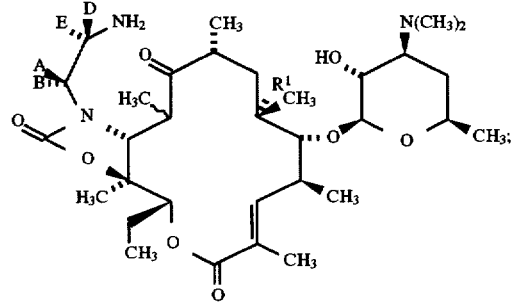

(c) cyclizing said second intermediate compounds by treatment with dilute concentration of a strong acid in a suitable organic solvent for a period of from about 4 hours to about 10 days at a temperature from ambient to reflux temperature of the solvent to give the desired compounds; and (d) extracting, optionally deprotecting, and isolating the desired compound.

26. A process according to claim 25 wherein in step (a) the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF, and aqueous acetone; and in step (c) the solvent is selected the group consisting of methanol, ethanol, propanol, isopropanol, butanol, iso-butanol and t-butanol.

27. A process for the preparation of a compound having the Formula (II):

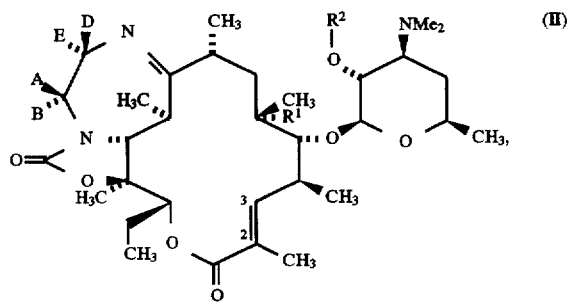

wherein
R¹ is selected from the group consisting of:
(a) hydrogen;
(b) hydroxy;
(c) O—$C_1$-$C_{12}$-alkyl;
(d) O—CO—$C_1$-$C_6$-alkyl;
(e) O—CO—$NH_2$;
(f) O—CO—NH—CO—$C_1$-$C_{12}$-alkyl; and
(g) O—CO—NH—$SO_2$—$C_1$-$C_{12}$-alkyl;
R² is hydrogen or a hydroxy protecting group;
A, B, D and E are independently selected from the group consisting of:
(a) hydrogen;
(b) $C_1$-$C_6$-alkyl, optionally substituted with one or more substituents selected from the group consisting of:

117

(i) aryl;
(ii) substituted-aryl;
(iii) heteroaryl;
(iv) substituted-heteroaryl;
(v) heterocycloalkyl;
(vi) hydroxy;
(vii) $C_1$-$C_6$-alkoxy;
(viii) halogen consisting of Br, Cl, F or I; and
(ix) $NR^3R^4$, where $R^3$ and $R^4$ are independently selected from hydrogen and $C_1$-$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$-$C_6$-alkyl-)-, —N(aryl)-, —N(aryl-$C_1$-$C_6$-alkyl-)-, —N(substituted-aryl-$C_1$-$C_6$-alkyl-)-, —N(heteroaryl)-, —N(heteroaryl-$C_1$-$C_6$-alkyl-)-, —N(substituted-heteroaryl-$C_1$-$C_6$-alkyl-)-, —S— or —S(O)$_n$—, wherein n is 1 or 2;

(c) $C_3$-$C_7$-cycloalkyl;
(d) aryl;
(e) substituted-aryl;
(f) heteroaryl;
(g) substituted-heteroaryl;
(h) heterocycloalkyl;
and
(i) a group selected from option (b) above further substituted with -M-$R^5$, wherein M is selected from the group consisting of:
(aa) —C(O)—NH—;
(bb) —NH—C(O)—;
(cc) —NH—
(dd) —N($CH_3$)—
(ee) —O—
(ff) —S(O)$_n$—, wherein n is 0, 1 or 2;
(gg) —C(=NH)—NH—;
(hh) —CO—O—
(ii) —O—CO—
(jj) —CO—;
and $R^5$ is selected from the group consisting of:
(aaa) $C_1$-$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;
(eee) substituted-heteroaryl; and
(fff) heterocycloalkyl;
or
any one pair of substituents, consisting of AB, AD, AE, BD, BE or DE, is taken together with the atom or atoms to which they are attached to form a 3- to 7-membered ring optionally containing a hetero function consisting of:
—O—,
—NH—,
—N($C_1$-$C_6$-alkyl-)-,
—N(aryl-$C_1$-$C_6$-alkyl-)-,

118

—N(substituted-aryl-$C_1$-$C_6$-alkyl-)-,
—N(heteroaryl-$C_1$-$C_6$-alkyl-)-,
—N(substituted-heteroaryl-$C_1$-$C_6$-alkyl-)-,
—S— or —S(O)$_n$—, wherein n is 1 or 2;
—C(O)—NH—;
—C(O)—$NR^5$-, wherein $R^5$ is as defined above;
—NH—C(O)—;
—$NR^5$—C(O)—, wherein $R^5$ is as defined above;
and
—C(=NH)—NH—;
the method comprising:
(a) treating a compound having the formula:

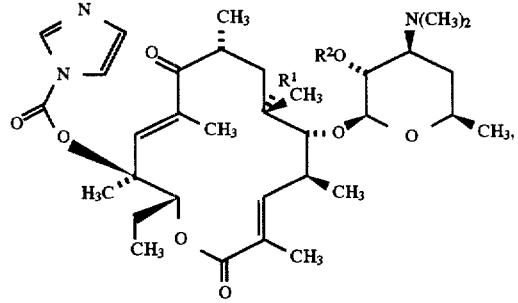

wherein $R^1$ is selected from the group consisting of hydrogen, protected hydroxy, O—$C_1$-$C_{12}$-alkyl, O—CO—$C_1$-$C_6$-alkyl, O—CO—$NH_2$, O—CO—NH—CO—$C_1$-$C_{12}$-alkyl, or O—CO—NH—$SO_2$—$C_1$-$C_{12}$-alkyl; and $R^2$ is a hydroxy protecting group, with a compound having the formula:

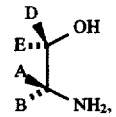

wherein A, B, D, and E are as defined above, in a suitable solvent at 0°–70° C. for about 4 to about 48 hours to give a bicyclic intermediate compound having the formula:

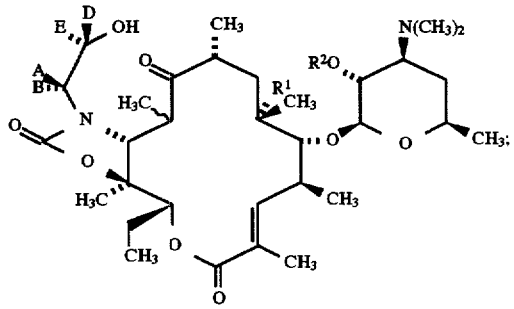

(b) treating the bicyclic intermediate compound from step (a) with triphenylphosphine and diphenylphosphoryl azide-diethylazodicarboxylate in tetrahydrofuran under Mitsunobu reaction conditions to prepare the second intermediate azide compound having the formula:

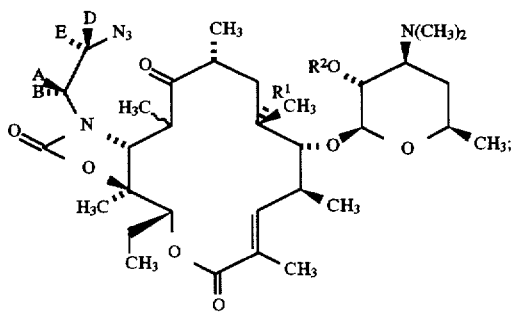

(c) reducing the second intermediate azide compound to prepare the third intermediate compound having the formula:

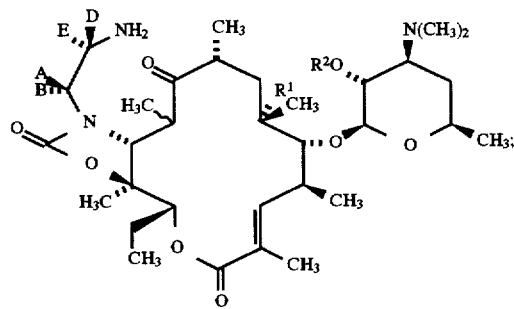

(d) cyclizing said third intermediate compound by treatment with a dilute concentration of a strong acid at ambient temperature to reflux temperature for about 4 hours to about 10 days in a aqueous alcohol solvent to give the desired compounds; and (e) extracting, optionally deprotecting, and isolating the desired compound.

28. A process as in claim 27 wherein in step (a) the solvent is selected from the group consisting of methanol, ethanol, propanol, isopropanol, butanol, t-butanol, methylene chloride, tetrahydrofuran, N-methyl-pyrrolidinone, diethyl ether, bis-methoxymethyl ether, dimethyl formamide, acetone, aqueous acetonitrile, aqueous DMF and aqueous acetone; in step (c) the reducing agent is selected from the group consisting of triphenylphosphine-water, hydrogen with a catalyst, sodium borohydride, and dialkylaluminum hydride; and in step (d) the solvent is selected the group consisting of methanol, ethanol, propanol, iso-propanol, butanol, iso-butanol and t-butanol.

29. A process as in claim 27 wherein step (b) thereof is replaced with two steps consisting of:

(b') reacting the hydroxy group of the bicyclic intermediate compound with a sulfonating agent selected from the group consisting of sulfonyl chloride, alkyl sulfonic anhydride, aryl sulfonic anhydride, and trifluoromethanesulfonic anhydride, in an aprotic solvent at −78° C. to room temperature to give an intermediate compound wherein the hydroxyl group has been replaced with a sulfonate ester moiety; and (b") reacting the sulfonate ester of step (b') with an alkali metal azide in an aprotic solvent at from about 0° C. to about 100° C. to give the second intermediate azide compound.

30. A process for the preparation of a compound having the Formula (III):

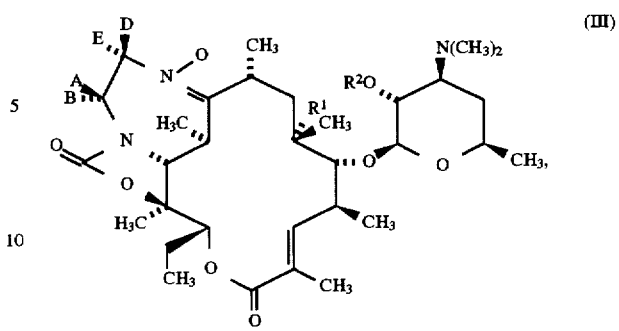

(III)

wherein
A, B, D and E are independently selected from the group consisting of:
(a) hydrogen;
(b) $C_1$–$C_6$-alkyl, optionally substituted with one or more substituents selected from the group consisting of:
(i) aryl;
(ii) substituted-aryl;
(iii) heteroaryl;
(iv) substituted-heteroaryl;
(v) heterocycloalkyl;
(vi) hydroxy;
(vii) $C_1$–$C_6$-alkoxy;
(viii) halogen consisting of Br, Cl, F or I; and
(ix) $NR^3R^4$, where $R^3$ and $R^4$ are independently selected from hydrogen and $C_1$–$C_6$-alkyl, or $R^3$ and $R^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)-, —N(aryl)-, —N(aryl-$C_1$–$C_6$-alkyl-)-, —N(substituted-aryl-$C_1$–$C_6$-alkyl-)-, —N(heteroaryl)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;

(c) $C_3$–$C_7$-cycloalkyl;
(d) aryl;
(e) substituted-aryl;
(f) heteroaryl;
(g) substituted-heteroaryl;
(h) heterocycloalkyl;
and
(i) a group selected from option (b) above further substituted with -M-$R^5$, wherein M is selected from the group consisting of
(aa) —C(O)—NH—;
(bb) —NH—C(O)—;
(cc) —NH—
(dd) —N(CH$_3$)—
(ee) —O—
(ff) —S(O)$_n$—, wherein n is 0, 1 or 2; and
(gg) —C(=NH)—NH—;
and $R^5$ is selected from the group consisting of:
(aaa) $C_1$–$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;
(ddd) heteroaryl;

(eee) substituted-heteroaryl; and
(fff) heterocycloalkyl;
or
any one pair of substituents, consisting of AB, AD, AE, BD, BE or DE, is taken together with the atom or atoms to which they are attached to form a 3- to 7-membered ring optionally containing a hetero function consisting of
—O—,
—NH—,
—N($C_1$–$C_6$-alkyl-)-,
—N(aryl-$C_1$–$C_6$-alkyl-)-,
—N(substituted-aryl-$C_1$–$C_6$-alkyl-)-,
—N(heteroaryl-$C_1$–$C_6$-alkyl-)-,
—N(substituted-heteroaryl-$C_1$–$C_6$-alkyl-)-,
—S— or —S(O)$_n$—, wherein n is 1 or 2;
—C(O)—NH—;
—C(O)—NR$^5$-, wherein R$^5$ is as defined above;
—NH—C(O)—;
—NR$^5$—C(O)—, wherein R$^5$ is as defined above; and
—C(=NH)—NH—;

R$^1$ is selected from the group consisting of:
(a) hydrogen;
(b) hydroxy;
(c) O—$C_1$–$C_{12}$-alkyl;
(d) O—CO—$C_1$–$C_6$-alkyl;
(e) O—CO—NH$_2$;
(f) O—CO—NH—CO—$C_1$–$C_{12}$-alkyl; and
(g) O—CO—NH—SO$_2$—$C_1$–$C_{12}$-alkyl; and R$^2$ is hydrogen or a hydroxy-protecting group;
the method comprising:

(a) reacting a compound having the formula (II):

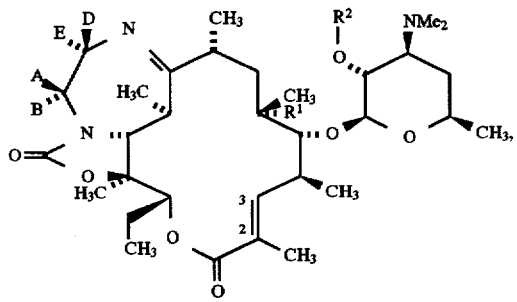

wherein R$^1$ is as above or is a hydroxy protecting group and R$^2$, A, B, D, and E are as defined above, with a suitable oxidizing agent to oxidize the imine nitrogen to the nitrone and the nitrogen atom on the desosamine moiety to the N-oxide to give an N-oxidized intermediate; and (b) treating the N-oxidized intermediate with a reducing agent to reduce the desosamine N-oxide, and extracting, optionally deprotecting, and isolating the desired compound.

31. A process according to claim 30 wherein in step (a) the oxidizing agent is selected from the group consisting of hydrogen peroxide and a carboxylic peracid; and in step (b) the reducing agent is selected from the group consisting of triphenylphosphine and hydrogen in the presence of a catalyst.

32. A process for the preparation of a compound having the Formula (IV):

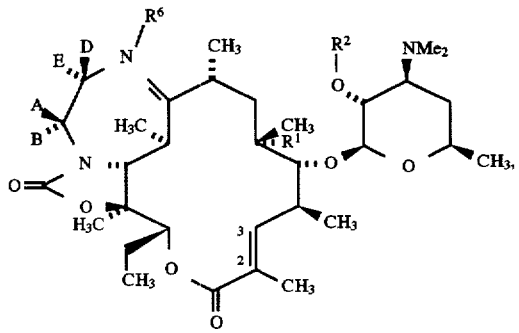

wherein
A, B, D and E are independently selected from the group consisting of:
(a) hydrogen;
(b) $C_1$–$C_6$-alkyl, optionally substituted with one or more substituents selected from the group consisting of:
(i) aryl;
(ii) substituted-aryl;
(iii) heteroaryl;
(iv) substituted-heteroaryl;
(v) heterocycloalkyl;
(vi) hydroxy;
(vii) $C_1$–$C_6$-alkoxy;
(viii) halogen consisting of Br, Cl, F or I; and
(ix) NR$^3$R$^4$, where R$^3$ and R$^4$ are independently selected from hydrogen and $C_1$–$C_6$-alkyl, or R$^3$ and R$^4$ are taken with the nitrogen atom to which they are connected to form a 3- to 7-membered ring which, when the ring is a 5- to 7-membered ring, may optionally contain a hetero function consisting of —O—, —NH—, —N($C_1$–$C_6$-alkyl-)-, —N(aryl)-, —N(aryl-$C_1$–$C_6$-alkyl-)-, —N(substituted-aryl-$C_1$–$C_6$-alkyl-)-, —N(heteroaryl)-, —N(heteroaryl-$C_1$–$C_6$-alkyl-)-, —N(substituted-heteroaryl-$C_1$–$C_6$-alkyl-)-, —S— or —S(O)$_n$—, wherein n is 1 or 2;
(c) $C_3$–$C_7$-cycloalkyl;
(d) aryl;
(e) substituted-aryl;
(f) heteroaryl;
(g) substituted-heteroaryl;
(h) heterocycloalkyl;
and
(i) a group selected from option (b) above further substituted with -M-R$^5$, wherein M is selected from the group consisting of
(aa) —C(O)—NH—;
(bb) —NH—C(O)—;
(cc) —NH—
(dd) —N(CH$_3$)—
(ee) —O—
(ff) —S(O)$_n$—, wherein n is 0, 1 or 2; and
(gg) —C(=NH)—NH—;
and R$^5$ is selected from the group consisting of:
(aaa) $C_1$–$C_6$-alkyl, optionally substituted with a substituent selected from the group consisting of:
(i) aryl;
(ii) substituted-aryl;
(iii) heteroaryl; and
(iv) substituted-heteroaryl;
(bbb) aryl;
(ccc) substituted-aryl;

(ddd) heteroaryl;
(eee) substituted-heteroaryl; and
(fff) heterocycloalkyl;

or any one pair of substituents, consisting of AB, AD, AE, BD, BE or DE, is taken together with the atom or atoms to which they are attached to form a 3- to 7-membered ring optionally containing a hetero function consisting of:

—O—,
—NH—,
—N($C_1$-$C_6$-alkyl-)-,
—N(aryl-$C_1$-$C_6$-alkyl-)-,
—N(substituted-aryl-$C_1$-$C_6$-alkyl-)-,
—N(heteroaryl-$C_1$-$C_6$-alkyl-)-,
—N(substituted-heteroaryl-$C_1$-$C_6$-alkyl-)-,
—S— or —S(O)$_n$—, wherein n is 1 or 2;
—C(O)—NH—;
—C(O)—NR$^5$-, wherein R$^5$ is as defined above;
—NH—C(O)—;
—NR$^5$—C(O)—, wherein R$^5$ is as defined above; and
—C(=NH)—NH—;

R$^1$ is selected from the group consisting of:
(a) hydrogen;
(b) hydroxy;
(c) O—$C_1$-$C_{12}$-alkyl;
(d) O—CO—$C_1$-$C_6$-alkyl;
(e) O—CO—NH$_2$;
(f) O—CO—NH—CO—$C_1$-$C_{12}$-alkyl; and
(g) O—CO—NH—SO$_2$—$C_1$-$C_{12}$-alkyl; and R$^2$ is hydrogen or a hydroxy-protecting group;
R$^6$ is hydrogen or $C_1$-$C_6$-alkyl;

the method comprising:

(a) reacting a compound having the formula:

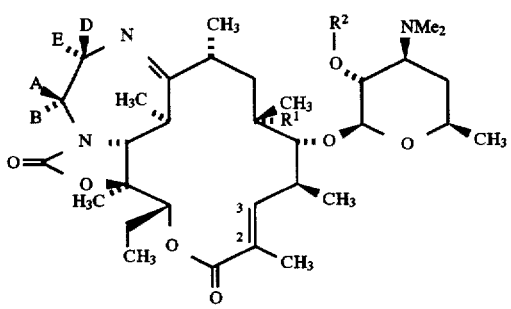

wherein R$^1$ is as above or is a hydroxy protecting group and R$^2$, A, B, D, and E are as defined above with a reducing agent in a suitable organic solvent to afford the desired compound wherein R$^6$ is H;

(b) optionally reductively alkylating the amino the product of step (a) with a reducing reagent in the presence of a $C_1$-$C_6$-alkyl-group precursor to afford the desired compound wherein R$^6$ is $C_1$-$C_6$-alkyl; and (c) extracting, optionally deprotecting, and isolating the desired compound.

33. A process according to claim 31 wherein in step (a) and in optional step (b) the reducing agent is selected from the group consisting of sodium cyanoborohydride, sodium borohydride, sodium triacetoxyborohydride, borane-tetrahydrofuran complex, and borane-piperidine complex.

34. A compound having the formula:

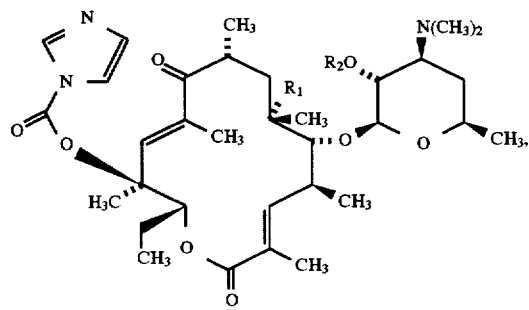

wherein

R$^1$ is selected from the group consisting of hydrogen, protected hydroxy, O—$C_1$-$C_{12}$-alkyl, O—CO—$C_1$-$C_6$-alkyl, O—CO—NH$_2$, O—CO—NH—CO—$C_1$-$C_{12}$-alkyl, or O—CO—NH—SO$_2$—$C_1$-$C_{12}$-alkyl; and R$^2$ is hydrogen or a hydroxy protecting group.

35. The compound according to claim 33 wherein R$^1$ is O—$C_1$-$C_{12}$-alkyl.

36. The compound according to claim 34 wherein R$^1$ is methoxy.

37. A process for the preparation of a compound having the formula:

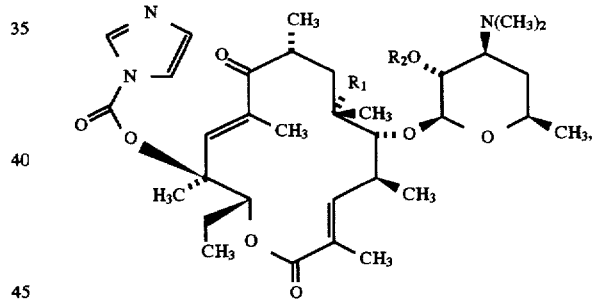

wherein

R$^1$ is selected from the group consisting of:
(a) hydrogen;
(b) protected hydroxy;
(c) O—$C_1$-$C_{12}$-alkyl;
(d) O—CO—$C_1$-$C_6$-alkyl;
(e) O—CO—NH$_2$;
(f) O—CO—NH—CO—$C_1$-$C_{12}$-alkyl; and
(g) O—CO—NH—SO$_2$—$C_1$-$C_{12}$-alkyl; and R$^2$ is hydrogen or a hydroxy-protecting group;

the method comprising:

(a) treating an erythromycin A compound having the formula:

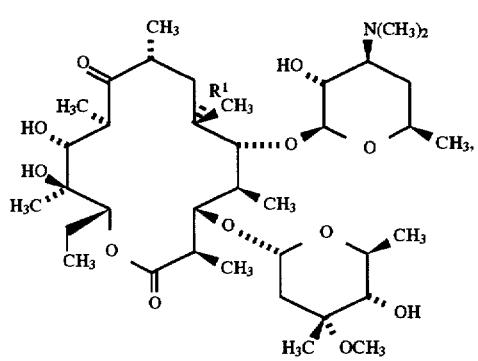

wherein R¹ is as defined above, with dehydrating reagents consisting of an organocarbonate in the presence of base at reflux temperature in an aprotic solvent to form an intermediate compound having the formula:

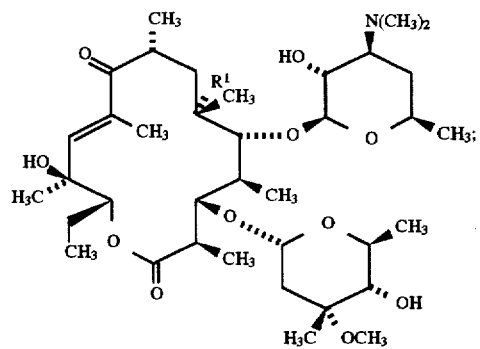

(b) hydrolytically removing the cladinose moiety from the intermediate compound of step (a) by treatment in an aqueous alcohol suspension with a dilute concentration of a strong acid at ambient temperature for about 0.5 to about 24 hours, extracting and optionally isolating the compound having the formula:

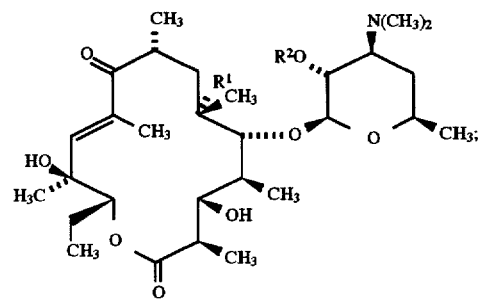

(c) treating the compound of step (b) with a suitable hydroxy group protecting reagent in an aprotic solvent, and extractively isolating the compound wherein R² is a hydroxy protecting group;

(d) treating a solution of the compound of step (c) with a sulfonylating agent at from about 0° C. to ambient temperature for about 1 to about 24 hours, and extractively isolating the compound having the formula:

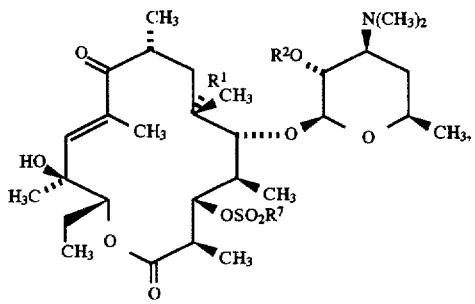

wherein R⁷ is alkyl or aryl;

(e) dehydrating the compound of step (d) with a hydride base in the presence of carbonyldiimidazole in an aprotic solvent at a temperature from about −20° C. to about 70° C. for from about 0.5 hours to about 10 days, and extracting, optionally deprotecting, and isolating the desired compound.

38. A process according to claim 36 wherein in step (a) the dehydrating reagents consist of an organocarbonate compound selected from the group consisting of ethylene carbonate, propylene carbonate, trimethylene carbonate, dipropyl carbonate, dibenzyl carbonate, isobutyl carbonate, dimethyl carbonate and diethyl carbonate, in the presence of a base selected from the group consisting of triethylamine, diisopropylethylamine, pyridine, 2,6-dimethylpyridne, 1,8-diazabicyclo[5.4.0]undec-7-ene, N-methylmorpholine, N-methylpyrrolidine, N-methylpiperidine, sodium carbonate, potassium carbonate, sodium bicarbonate and potassium carbonate; in step (b) the alcohol is chosen from the group consisting of methanol, ethanol, propanol, iso-propanol, butanol, iso-butanol and t-butanol, and the acid is selected from the group consisting of hydrochloric acid, sulfuric acid, dichloroacetic acid and trichloroacetic acid; in step (c) the hydroxy group protecting reagent is selected from the group consisting of acetyl chloride, acetic anhydride, benzoic anhydride, benzyl chloroformate, trimethylsilyl chloride and triethylsilyl chloride, and the aprotic solvent is selected from the group consisting of methylene chloride, chloroform, dimethylformamide, tetrahydrofuran, N-methylpyrrolidinone and mixtures thereof; in step (d) the sulfonylating agent is selected from the group consisting of methanesulfonyl anhydride, methanesulfonyl chloride, ethanesulfonyl chloride and p-toluenesulfonyl chloride, and the base is selected from the group defined in step (a) above; in step (e) the hydride base is selected from the group consisting of sodium hydride, potassium hydride and lithium hydride and the aprotic solvent is as defined for step (c).

39. A process according to claim 37 wherein R¹ is H and steps (d) and (e) are replaced with a single step (d') consisting of:

(d') treatment of the compound from step (c) with sodium hexamethyldisilazane at from about −50° to about −28° C. under an inert atmosphere followed by addition of carbonyldiimidazole at from about 0° C. to about ambient temperature for about 15 minutes to about 6 hours, and extracting, optionally deprotecting, and isolating the desired compound.

40. A process for the preparation of a compound having the formula:

127

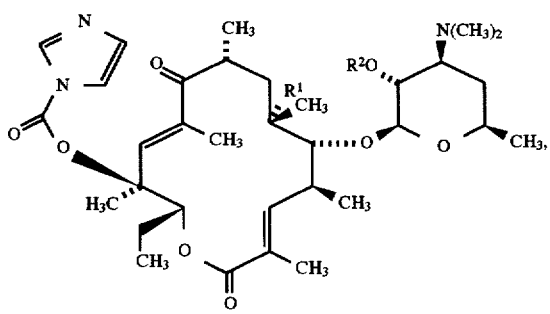

wherein
R¹ is selected from the group consisting of:
(a) hydrogen;
(b) protected hydroxy;
(c) O—$C_1$-$C_{12}$-alkyl;
(d) O—CO—$C_1$-$C_6$-alkyl;
(e) O—CO—$NH_2$;
(f) O—CO—NH—CO—$C_1$-$C_{12}$-alkyl; and
(g) O—CO—NH—$SO_2$—$C_1$-$C_{12}$-alkyl; and
R² is hydrogen or a hydroxy-protecting group;
the method comprising:
(a) hydrolytically removing the cladinose moiety from an erythromycin A compound having the formula:

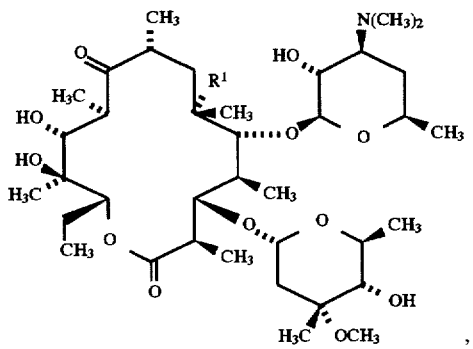

wherein R¹ is as described above by treatment in an aqueous alcohol suspension with a dilute concentration of a strong acid at ambient temperature for about 0.5 to about 24 hours, extracting and optionally isolating the first intermediate compound having the formula:

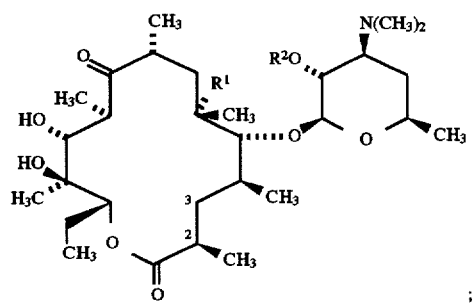

(b) optionally treating the first intermediate compound with a suitable hydroxy group protecting reagent, and extractively isolating the second intermediate compound having the formula of the compound of step (a) wherein R² is a hydroxy-protecting group;

(c) treating the second intermediate compound with an excess of a carbonylating reagent and isolating by

128 aqueous work up the third intermediate compound having the formula:

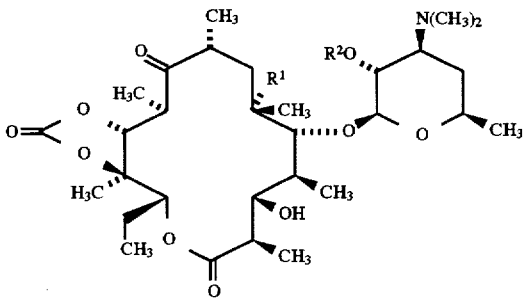

wherein R¹ may not be hydrogen but is otherwise as defined above;

(d) treating the third intermediate compound with a sulfonylating agent at from about 0° C. to ambient temperature for about 1 to about 24 hours, and extractively isolating the fourth intermediate compound having the formula:

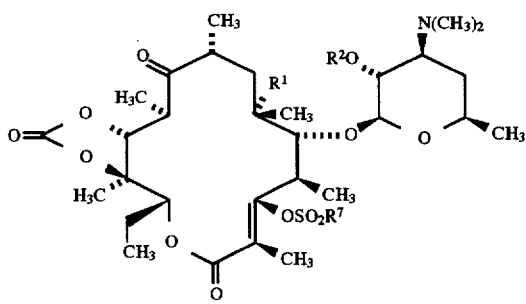

wherein R⁷ is alkyl or aryl;

(e) treating the fourth intermediate compound with a strong base, extracting and optionally isolating the to afford the fifth intermediate compound having the formula:

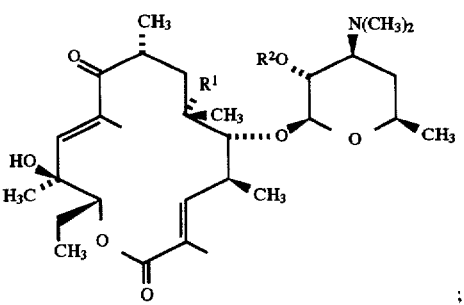

(f) treating the fifth intermediate compound with a hydride base and carbonyldiimidazole in an aprotic solvent at a temperature from about −20° C. to about 70° C. for from about 0.5 hours to about 10 days, and extracting, optionally deprotecting, and isolating the desired compound.

41. A process according to claim 40 wherein in step (a) the alcohol is chosen from the group consisting of methanol, ethanol, propanol, iso-propanol, butanol, iso-butanol and t-butanol, and the acid is selected from the group consisting of hydrochloric acid, sulfuric acid, dichloroacetic acid and trichloroacetic acid; in step (b) the hydroxy group protecting reagent is selected from the group consisting of acetyl chloride, acetic anhydride, benzoic anhydride, benzyl chloroformate, trimethylsilyl chloride and triethylsilyl chloride, and the aprotic solvent is selected from the group consisting of methylene chloride, chloroform, dimethylformamide, tetrahydrofuran, N-methylpyrrolidinone and mixtures thereof; in step (c) the carbonylating reagent is selected from the group consisting of phosgene, diphosgene and triphosgene; in step (d) the sulfonylating agent is selected from the group consisting of methanesulfonyl anhydride, methanesulfonyl chloride, ethanesulfonyl chloride and p-toluenesulfonyl chloride; in step (e) the base is selected from the group consisting of triethylamine, diisopropylethylamine, pyridine, 2,6-dimethylpyridne, 1,8-diazabicyclo[5.4.0]undec-7-ene, N-methylmorpholine, N-methylpyrrolidine, N-methylpiperidine, sodium carbonate, potassium carbonate, sodium bicarbonate and potassium carbonate; in step (f) the hydride base is selected from the group consisting of sodium hydride, potassium hydride and lithium hydride.

42. A process according to claim 40 wherein in step (b) the hydroxy protecting reagent is benzoic anhydride and $R^2$ is benzoyl, and steps (c), (d) and (e) are replaced with a single step (c') consisting of:

(c') treatment of the compound from step (b) with sodium hexamethyldisilazane at from about −50° to about −28° C. under an inert atmosphere followed by addition of carbonyldiimidazole at from about 0° C. to about ambient temperature for about 15 minutes to about 6 hours, and extracting, optionally deprotecting, and isolating the desired compound.

43. A pharmaceutical composition for treating bacterial infections comprising a therapeutically effective amount of a compound of claim 1 in combination with a pharmaceutically acceptable carrier.

44. A method for treating bacterial infections comprising administering to a mammal in need of such treatment a pharmaceutical composition containing a therapeutically-effective amount of a compound of claim 1.

\* \* \* \* \*